US012666866B2

(12) United States Patent
Jung et al.

(10) Patent No.: US 12,666,866 B2
(45) Date of Patent: Jun. 23, 2026

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: So-Young Jung, Gyeonggi-do (KR); Tae-Jun Han, Gyeonggi-do (KR); YeJin Jeon, Gyeonggi-do (KR); Dong-Gil Kim, Gyeonggi-do (KR); Young-Jae Kim, Gyeonggi-do (KR); Hyun-Ju Kang, Gyeonggi-do (KR); Sang-Hee Cho, Gyeonggi-do (KR); Bitnari Kim, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 376 days.

(21) Appl. No.: 18/433,577

(22) Filed: Feb. 6, 2024

(65) Prior Publication Data

US 2024/0298528 A1 Sep. 5, 2024

(30) Foreign Application Priority Data

Feb. 20, 2023 (KR) ........................ 10-2023-0022241
Dec. 20, 2023 (KR) ........................ 10-2023-0186737

(51) Int. Cl.

| | |
|---|---|
| ***H10K 85/60*** | (2023.01) |
| ***C07D 209/86*** | (2006.01) |
| ***C07D 405/14*** | (2006.01) |
| ***C07D 413/12*** | (2006.01) |
| ***C09K 11/06*** | (2006.01) |
| ***H10K 50/11*** | (2023.01) |
| ***H10K 85/30*** | (2023.01) |
| ***H10K 101/00*** | (2023.01) |
| ***H10K 101/10*** | (2023.01) |

(52) U.S. Cl.

CPC ......... *H10K 85/636* (2023.02); *C07D 413/12* (2013.01); *C09K 11/06* (2013.01); *H10K 85/622* (2023.02); *H10K 85/626* (2023.02); *H10K 85/654* (2023.02); *H10K 85/6574* (2023.02); *C09K 2211/1018* (2013.01); *H10K 50/11* (2023.02); *H10K 85/657* (2023.02); *H10K 85/6572* (2023.02); *H10K 2101/90* (2023.02)

(58) Field of Classification Search

CPC .. H10K 85/636; H10K 85/622; H10K 85/626; H10K 85/654; H10K 85/6574; H10K 85/342; H10K 85/6576; H10K 85/657; H10K 85/6572; H10K 50/11; H10K 2101/90; C07D 413/12; C07D 209/86; C07D 409/14; C09K 11/06; C09K 2211/1018

See application file for complete search history.

(56) References Cited

U.S. PATENT DOCUMENTS

| | | | | |
|---|---|---|---|---|
| 9,028,979 B2 * | 5/2015 | Schildknecht | C07D 235/02 | |
| | | | 428/917 | |
| 2012/0104941 A1 * | 5/2012 | Jung | H10K 85/6572 | |
| | | | 544/294 | |
| 2018/0208837 A1 | 7/2018 | Ahn | | |
| 2021/0265569 A1 * | 8/2021 | Kim | H10K 85/633 | |
| 2021/0336153 A1 * | 10/2021 | Kim | C07D 405/10 | |

* cited by examiner

*Primary Examiner* — Mohsen Ahmadi
(74) *Attorney, Agent, or Firm* — G. Creston Campbell

(57) ABSTRACT

The present disclosure relates to a plurality of host materials comprising a first host material comprising a compound represented by formula 1 and a second host material comprising a compound represented by formula 2, and an organic electroluminescent device comprising the same. By comprising a specific combination of compounds as a host material, an organic electroluminescent device having a lower driving voltage and/or higher luminous efficiency and/or improved lifespan properties compared to a conventional organic electroluminescent device may be provided.

10 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

The TPD/$Alq_3$ bilayer small molecule organic electroluminescent device (OLED) consisting of a light-emitting layer and a charge transport layer, was first developed by Tang, et al., of Eastman Kodak in 1987. Thereafter, the studies on an OLED have been rapidly effected, and OLEDs have been commercialized. At present, organic electroluminescent devices mainly use phosphorescent materials having excellent luminous efficiency in panel realization. In many applications such as TV, lighting, the problem of insufficient OLED life is encountered, and high efficiency of OLED is still required. In general, the higher the luminance of the OLED, the lifespan of the OLED become shorter. Therefore, for prolonged use of a display and high resolution, a OLED having high luminous efficiency and/or long lifespan is required.

Various materials or concepts have been proposed for the organic layer of the organic electroluminescent device in order to improve luminous efficiency, driving voltage and/or lifespan, but they have not been satisfactory for practical use.

Korean Patent Application Laid-open No. 10-2017-0022865 discloses an organic electroluminescent device using a phenanthrooxazole and a phenanthrothiazole compound as a host. However, said reference does not specifically disclose an organic electroluminescent device using a plurality of host materials of a specific combination claimed in the present disclosure, and it is still required to develop a host material for improving the performance of OLED.

PRIOR ART REFERENCES (Patent Document 1) Korean Patent Laid-open No. 10-2017-0022865 (2017 Mar. 2.)

DISCLOSURE OF THE INVENTION

Problems to be Solved

The object of the present disclosure is firstly, to provide a plurality of host materials capable of producing an organic electroluminescent device having a low driving voltage and/or high luminous efficiency and/or improved lifespan properties, and secondly, to provide an organic electroluminescent device having a low driving voltage and/or high luminous efficiency and/or improved lifespan properties by comprising a specific combination of compounds according to the present disclosure as a host material.

Solution to Problem

The present inventors paid attention to the fact that compounds with cores such as phenanthrooxazole, phenanthrothiazole, etc., unusually have a lower lowest unoccupied molecular orbital (LUMO) energy level than conventional hole-type hosts. They studied hole-type hosts capable of forming an appropriate energy gap with said compounds. As a result, it was found that when a combination of a compound represented by the following formula 1 and a compound represented by the following formula 2 is used in a light-emitting layer, hole and electron characteristics are balanced by appropriate HOMO and LUMO energy levels. Thus, an OLED with higher luminous efficiency and/or improved lifespan properties than a conventional OLED may be provided.

Specifically, the present inventors have completed the present disclosure by discovering that a plurality of host materials including a first host material including a compound represented by the following formula 1 and a second host material including a compound represented by the following formula 2 achieve the above-described objects.

(1)

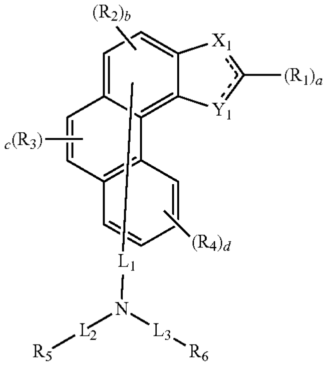

In formula 1, $X_1$ and $Y_1$ each independently represent, —N=, —$NR_{10}$—, —O— or —S—, provided that any one of $X_1$ and $Y_1$ is —N=, and the other of $X_1$ and $Y_1$ is —$NR_{10}$—, —O— or —S—;

$L_1$, $L_2$ and $L_3$ each independently represent, a single bond, a substituted or unsubstituted (C6-C30)arylene, or a substituted or unsubstituted (3- to 30-membered)heteroarylene;

$R_1$ represents a substituted or unsubstituted (C6-C30)aryl or a substituted or unsubstituted (3- to 30-membered) heteroaryl;

$R_5$ and $R_6$ each independently represent, a substituted or unsubstituted (C6-C30)aryl, or a substituted or unsubstituted (3- to 30-membered)heteroaryl; with a proviso that at least one of $R_5$ and $R_6$ is selected from carbazole derivatives represented by following formula 1-A or formula 1-B;

(1-A)

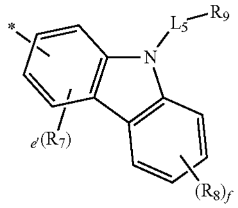

-continued (1-B)

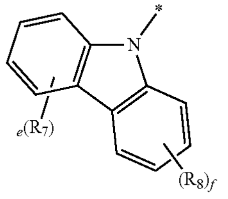

In formulas 1-A and 1-B, $L_5$ represents a single bond, a substituted or unsubstituted (C6-C30)arylene, or a substituted or unsubstituted (3- to 30-membered)heteroarylene;

$R_2$ to $R_4$ and $R_7$ to $R_{10}$ each independently represent, hydrogen, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or -$L_3$`` -N($Ar_3$`` )($Ar_4$`` ); or may be linked to the adjacent substituents to form a ring;

$L_3$`` represents a single bond, a substituted or unsubstituted (C6-C30)arylene, or a substituted or unsubstituted (3- to 30-membered)heteroarylene;

$Ar_3$`` and $Ar_4$`` each independently represent, hydrogen, deuterium, a substituted or unsubstituted (C1-C30) alkyl, a substituted or unsubstituted (C2-C30)alkenyl, a substituted or unsubstituted fused ring of (C3-C30) aliphatic ring and (C6-C30)aromatic ring, a substituted or unsubstituted (C6-C30)aryl, or a substituted or unsubstituted (3- to 30-membered)heteroaryl;

a represents 1, b and c each independently represent 1 or 2, d to f each independently represent an integer of 1 to 4, e` represents an integer of 1 to 3, when b to f and e ` are an integer of 2 or more, each of $R_2$ to $R_4$, $R_7$, and $R_8$ may be the same or different;

* indicates a binding site with $L_2$ or $L_3$, (2)

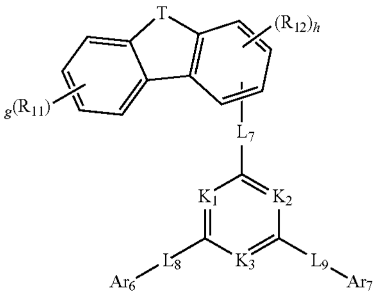

In formula 2,

T is O or S;

$K_1$ to $K_3$ each independently represent, N or CH, provided that at least one of $K_1$ to $K_3$ is N;

$L_7$ to $L_9$ each independently represent, a single bond, a substituted or unsubstituted (C6-C30)arylene, a substituted or unsubstituted (C3-C30)cycloalkylene, or a substituted or unsubstituted (3- to 30-membered)heteroarylene;

$R_{11}$, $R_{12}$, $Ar_6$ and $Ar_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or —N—(R` )(R`` ); or may be linked to the adjacent substituents to form a ring;

R` and R`` each independently represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl;

g represents an integer of 1 to 4, h represents an integer of 1 to 3, when g and h are an integer of 2 or more, each of $R_{11}$ and $R_{12}$ may be the same or different.

In addition, the present inventors have completed the present disclosure by discovering that an organic electroluminescent compound represented by the following formula 1` , an organic electroluminescent material comprising said organic electroluminescent compound, and an organic electroluminescent device comprising said organic electroluminescent material achieve the above-described objects.

(1′)

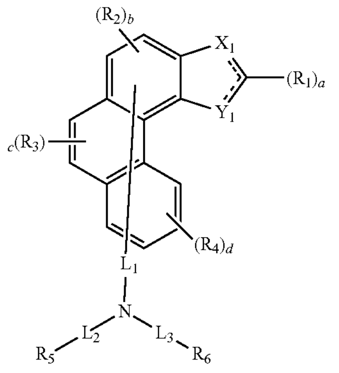

In formula 1` , $X_1$ and $Y_1$ each independently represent, —N═, —$NR_{10}$—, —O— or —S—, provided that any one of $X_1$ and $Y_1$ is —N═, and the other of $X_1$ and $Y_1$ is —$NR_{10}$—, —O— or —S—;

$L_1$, $L_2$, and $L_3$ each independently represent, a single bond, a substituted or unsubstituted (C6-C30)arylene, or a substituted or unsubstituted (3- to 30-membered) heteroarylene;

$R_5$ and $R_6$ each independently represent, a substituted or unsubstituted (C6-C30)aryl, or a substituted or unsubstituted (3- to 30-membered)heteroaryl; with a proviso that at least one of $R_5$ and $R_6$ is selected from carbazole derivatives represented by following formula 1-A or formula 1-B;

(1-A)

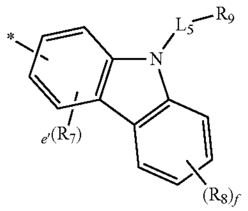

(1-B)

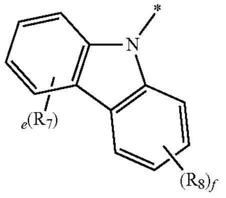

In formulas 1-A and 1-B, $L_5$ represents a single bond, a substituted or unsubstituted (C6-C30)arylene, or a substituted or unsubstituted (3- to 30-membered)heteroarylene;

$R_1$ represents a substituted or unsubstituted (C6-C30)aryl or a substituted or unsubstituted (3- to 30-membered) heteroaryl;

$R_2$ to $R_4$ and $R_7$ to $R_{10}$ each independently represent, hydrogen, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or -$L_3$`` -N($Ar_3$`` )($Ar_4$`` ); or may be linked to adjacent substituents to form a ring;

$L_3$`` represents a single bond, a substituted or unsubstituted (C6-C30)arylene, or a substituted or unsubstituted (3- to 30-membered)heteroarylene;

$Ar_3$`` and $Ar_4$`` each independently represent, hydrogen, deuterium, a substituted or unsubstituted (C1-C30) alkyl, a substituted or unsubstituted (C2-C30)alkenyl, a substituted or unsubstituted fused ring of (C3-C30) aliphatic ring and (C6-C30)aromatic ring, a substituted or unsubstituted (C6-C30)aryl, or a substituted or unsubstituted (3- to 30-membered)heteroaryl;

a represents 1, b and c each independently represent 1 or 2, d to f each independently represent an integer of 1 to 4, e` represents an integer of 1 to 3, when b to f and e ` are an integer of 2 or more, each of $R_2$ to $R_4$, $R_7$, and $R_8$ may be the same or different;

* indicates a binding site with $L_2$ or $L_3$,

Provided that the following compounds are excluded in formula 1` .

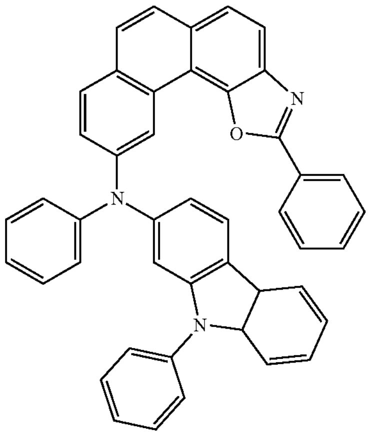

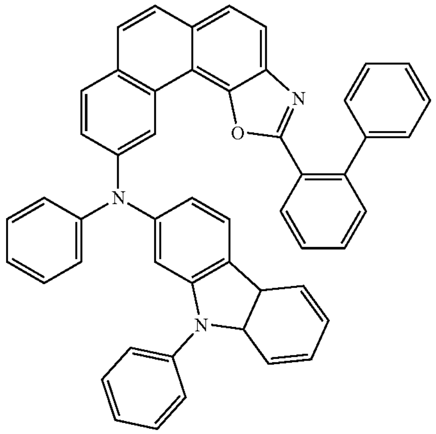

Advantageous Effects of Invention

By using compounds with the specific combination according to the present disclosure as a host material, an organic electroluminescent device having a low driving voltage and/or high luminous efficiency and/or improved lifespan properties could be manufactured.

EMBODIMENTS OF THE INVENTION

Hereinafter, the present disclosure will be described in detail. However, the following description is intended to explain the present disclosure, and is not meant to restrict the scope of the present disclosure.

The present disclosure relates to a plurality of host materials comprising a first host material comprising a compound represented by formula 1 and a second host material comprising a compound represented by formula 2, and an organic electroluminescent device comprising the host materials.

In addition, the present disclosure relates to an organic electroluminescent compound represented by the formula 1` , an organic electroluminescent material comprising said organic electroluminescent compound, and an organic electroluminescent device comprising said organic electroluminescent material.

Herein, the term “organic electroluminescent compound” in the present disclosure refers to a compound that may be used in an organic electroluminescent device, and may be comprised in any material layer consists the organic electroluminescent device, as needed.

Herein, the term "organic electroluminescent material" in the present disclosure refers to a material that may be used in an organic electroluminescent device, may comprise one or more compounds, and may be comprised in any layer consists an organic electroluminescent device, as needed. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

Herein, the term "a plurality of organic electroluminescent materials" in the present disclosure refers to an organic electroluminescent material comprising a combination of two or more compounds that may be comprised in any layer consisting an organic electroluminescent device, and may refer to materials before (e.g., before deposition) and after (e.g., after deposition) being included in the organic electroluminescent device. For example, the plurality of organic electroluminescent materials may be a combination of two or more compounds that may be comprised in one or more layers of a hole injection layer, a hole transport layer, a hole auxiliary layer, an light-emitting auxiliary layer, an electron blocking layer, a light-emitting layer, an electron buffer layer, a hole blocking layer, an electron transport layer, and an electron injection layer. The two or more types of compounds may be included in the same layer or different layers through methods used in the art, and may be, for example, mixed deposition, co-deposition, or individually deposited.

Herein, the term "a plurality of host materials" in the present disclosure refers to a host material comprising a combination of two or more compounds that may be comprised in any light-emitting layer consisting an organic electroluminescent device, and may refer to both materials before (e.g., before deposition) and after (e.g., after deposition) being comprised in the organic electroluminescent device. In one embodiment, the plurality of host materials of the present disclosure may be a combination of two or more host materials, and may optionally further include a conventional material comprised in the organic electroluminescent material. The plurality of host materials of the present disclosure may be included in any light-emitting layer consisting the organic electroluminescent device, and two or more types of compounds comprised in the plurality of host materials of the present disclosure may be comprised together in one light-emitting layer or may be included in different light-emitting layers through methods used in the art. For example, the two or more types of compounds may be mixed-deposited, co-deposited, or individually deposited.

Herein, the term "(C1-C30)alkyl(ene)" in the present disclosure refers to a linear or branched alkyl(ene) having 1 to 30 carbon atoms consisting the chain, in which the number of carbon atoms is preferably 1 to 20, more preferably 1 to 10. Specific examples of the alkyl may include methyl, ethyl, n-propyl, isopropyl, n-butyl, isobutyl, tert-butyl, sec-butyl, etc.

Herein, the term "(C2-C30)alkenyl" in the present disclosure refers to a straight-chain or branched-chain alkenyl having 2 to 30 carbon atoms consisting the chain, and the number of carbon atoms is preferably 2 to 20, more preferably 2 to 10. Specific examples of the alkenyl may include vinyl, 1-propenyl, 2-propenyl, 1-butenyl, 2-butenyl, 3-butenyl, 2-methylbut-2-enyl, etc.

Herein, the term "(C2-C30)alkynyl" in the present disclosure refers to a linear or branched alkynyl having 2 to 30 carbon atoms consisting the chain, and preferably has 2 to 20 carbon atoms, more preferably 2 to 10 carbon atoms. Examples of the alkynyl may include ethynyl, 1-propynyl, 2-propynyl, 1-butynyl, 2-butynyl, 3-butynyl, 1-methylpent-2-ynyl, etc.

Herein, the term "(C3-C30)cycloalkyl(ene)" in the present disclosure refers to a monocyclic or polycyclic hydrocarbon having 3 to 30 ring backbone carbon atoms, preferably having 3 to 20 carbon atoms, and more preferably having 3 to 7 carbon atoms. Examples of the cycloalkyl may include cyclopropyl, cyclobutyl, cyclopentyl, cyclohexyl, etc.

Herein, the term "(3- to 7-membered)heterocycloalkyl (ene)" in the present disclosure refers to a cycloalkyl(ene) having 3 to 7, preferably 5 to 7 ring backbone atoms and comprising at least one heteroatom selected from the group consisting of B, N, O, S, Si, and P, preferably O, S, and N, for example, tetrahydrofuran, pyrrolidine, thiolane, tetrahydropyran, etc.

Herein, "(C6-C60)aryl(ene)" in the present disclosure refers to a monocyclic or fused ring-based radical derived from an aromatic hydrocarbon having 6 to 60 ring backbone carbon atoms, and may be partially saturated. The number of ring backbone carbon atoms is preferably 6 to 30. The aryl includes those having a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. More specifically, phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, an o-terphenyl, m-terphenyl-4-yl, m-terphenyl-3-yl, m-terphenyl-2-yl, p-terphenyl-4-yl, p-carbazolyl, p-fluorenyl, 3-fluorenyl, 4-fluoranthenyl, 4-fluoranthenyl, 4-fluoranthenyl, 4-fluoranthenyl, 4-fluoranthenyl, 4-fluoranthenyl, 4-fluoranthenyl, 4-fluoranthenyl group m-tolyl, p-tolyl, 2,3-xylyl, 3,4-xylyl, 2,5-xylyl, mesityl, an o-cumenyl, m-cumenyl, p-cumenyl, p-t-butylphenyl, p-(2-phenylpropyl)phenyl, 4`-methylbiphenyl, 4`-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, and 9,9-diphenyl-4-fluorenyl.

Herein, the term "(3- to 30-membered)heteroaryl(ene)" refers to an aryl group having 3 to 30 ring backbone atoms and including at least one heteroatom selected from the group consisting of B, N, O, S, Si, P, Se, and Ge. The number of heteroatoms is preferably 1 to 4, and may be a single ring system or a fused ring system fused with one or more benzene rings, and may be partially saturated. In addition, the heteroaryl(ene) herein also includes a form in which one or more heteroaryl groups or aryl groups are linked to the heteroaryl group by a single bond, and also includes those having a spiro structure. Examples of the heteroaryl may include monocyclic heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc; fused heteroaryl such as benzofuranyl, benzothiophenyl, isobenzofuranyl, dibenzofuranyl, dibenzothiophenyl, benzonaphthofuranyl, benzonaphthothiophenyl, diazadibenzofuranyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, benzoquinolyl, isoquinolyl, benzoisoquinolyl, cinnolinyl, quinazolinyl, benzoquinazolinyl, quinoxalinyl, benzoquinoxalinyl, naphthyridinyl, triazanaphthyl, benzothienopyrimidinyl, carbazolyl, benzocarbazolyl, dibenzocarbazolyl, phenoxazinyl, phenothiazolyl, phenanolyl, phenanolyl, benzotridioxinyl, dihydrodifuranyl, etc. More specifically, 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazine-4-yl, 1,2,4-triazine-3-yl, 1,3,5-triazine-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, an 8-indolidinyl, 2-imidazopyridinyl, 3-imidazopyridinyl, 5-imidazopyridinyl, 6-imidazopyridinyl, 7-imidazopyridinyl, an 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, an isoindolyl, 3-isodolyl, 4-isodolyl, and 6-isodolyl group furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 2-carbazolyl, 3-carbazolyl, 4-carbazolyl, 9-carbazolyl, azacarbazolyl-2-yl, azacarbazazolyl-3-yl, azacarbazolyl, 5-carbazolyl, 6-azazolyl-azazolyl, 7-azazolyl, 8-azazolyl-azazolyl, 7-azazolyl-azazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-yl, 4-methyl-indolyl, 2-methyl-3-indolyl, 3-indolyl group t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germanfluorenyl, 2-germanfluorenyl, 3-germanfluorenyl, and 4-germanfluorenyl. In addition, "heteroaryl(ene)" may be classified into heteroaryl(ene) as having electron characteristics and heteroaryl(ene) having hole characteristics. The heteroaryl(ene) having electron characteristics is a substituent in which electrons are relatively abundant in the mother nucleus, and may be, for example, a substituted or unsubstituted pyridinyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted quinolyl, etc. The heteroaryl(ene) having hole characteristics may be a substituent having relatively insufficient electrons in the mother nucleus, and may be, for example, a substituted or unsubstituted carbazolyl, a substituted or unsubstituted dibenzofuranyl, or a substituted or unsubstituted dibenzothiophenyl.

In the formulas of the present disclosure, the heteroaryl or heteroarylene may each independently comprise at least one heteroatom selected from B, N, O, S, Si, and P. In addition, the heteroatom may be bonded to at least one selected from the group consisting of hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

Herein, the term "a fused ring of (C3-C30)aliphatic ring and (C6-C30)aromatic ring" in the present disclosure refers to a functional group of a ring fused with at least one aliphatic ring(s) having 3 to 30 ring backbone carbon atoms in which the number of carbon atoms is preferably 3 to 25, more preferably 3 to 18, and at least one aromatic ring(s) having 6 to 30 backbone carbon atoms in which the number of carbon atoms is preferably 6 to 25, and more preferably 6 to 18. For example, a fused ring of one or more benzene and one or more cyclohexane, or a fused ring of one or more naphthalene and one or more cyclopentane, etc. Herein, the carbon atoms of the fused ring of (C3-C30)aliphatic ring and (C6-C30)aromatic ring may be replaced by one or more heteroatoms selected from B, N, O, S, Si, and P, and preferably one or more heteroatoms selected from N, O, and S. Herein, the term "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other; for example, when two substituents in a benzene derivative occupy positions 1 and 2, it is called an ortho position. Meta indicates that two substituents are at positions 1 and 3; for example, when two substituents in a benzene derivative occupy positions 1 and 3, it is called a meta position. Para indicates that two substituents are at positions 1 and 4; for example, when two substituents in a benzene derivative occupy positions 1 and 4, it is called a para position.

In the formulas of the present disclosure, when a ring is formed by being linked with an adjacent substituent or when two adjacent substituents are linked with each other to form a ring, said ring may be a substituted or unsubstituted (3- to 30-membered) mono- or polycyclic, alicyclic or aromatic ring, or a combination thereof, formed by being linked with two or more adjacent substituents. In addition, the formed ring may comprise one or more heteroatoms selected from B, N, O, S, Si and P, preferably one or more heteroatoms selected from N, O and S. According to an embodiment of the present disclosure, the number of ring backbone atoms is (5-20 membered), and according to another embodiment of the present disclosure, the number of ring backbone atoms is (5-15 membered). For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In addition, “substituted” in the expression “substituted or unsubstituted” refers to a hydrogen atom in a functional group that is replaced with another atom or another functional group (i.e., a substituent). Unless otherwise specified, the substituents may not be limited to hydrogen at positions where the substituents may be substituted, and when two or more hydrogen atoms are each replaced with a substituent in a functional group, the substituents may be the same or different from each other. The maximum number of substituents that may be substituted with a certain functional group may be the total number of substituents that may be substituted with each atom constituting a functional group. The substituted alkyl, the substituted alkenyl, the substituted aryl, the substituted arylene, the substituted heteroaryl, the substituted heteroarylene, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted alkylarylamino, the substituted mono- or di-arylamino, the substituted mono- or di-heteroarylamino, the substituted arylheteroarylamino, and the substituted alicyclic and aromatic rings in the formulas of the present disclosure, may each be independently substituted with one or more selected from the group consisting of deuterium; halogen; acyano; carboxyl; nitro; hydroxy; (C1-C30)alkyl; halo(C1-C30)alkyl; (C2-C30)alkenyl; (C2-C30) alkynyl; (C1-C30)alkoxy; (C1-C30)alkylthio; (C3-C30)cycloalkyl; (C3-C30)cycloalkenyl; (3-7-membered) heterocycloalkyl; (C6-C30)aryloxy; (C6-C30)arylthio; or (C6-arylthio)heteroaryl unsubstituted in the formulas of the present disclosure (C6-C30)aryl unsubstituted or substituted with at least one of (C1-C30)alkyl and (3- to 30-membered) heteroaryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; mono- or di-(C1-C30)alkylamino; mono- or di-(C6-C30)arylamino; (C1-C30)alkyl(C6-C30) arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30) aryl, preferably, one or more selected from the group consisting of (C1-C10)alkyl; (C6-C20)aryl; (3- to 20-membered)heteroaryl substituted or unsubstituted with (C6-C20) aryl; and di(C6-C20)arylamino, more preferably, one or more selected from the group consisting of (C1-C6)alkyl; (C6-C12)aryl; (5- to 15-membered)heteroaryl substituted or unsubstituted with (C6-C12)aryl; and di(C6-C12)arylamino, for example, one or more selected from the group consisting of methyl, phenyl, naphthyl, carbazolyl, phenylquinoxalyl, and diphenylamino.

In the present disclosure, when a substituent is not shown in the formula or the compound structure, it may signify that all positions that may be present as substituents are hydrogen or deuterium. That is, in the case of deuterium, an isotope of hydrogen, some of the hydrogen atoms may be deuterium, which is an isotope; and in this case, the content of deuterium may be 0% to 100%. In the case where the substituent is not shown in the formula or the compound structure, when deuterium is not explicitly excluded, hydrogen and deuterium may be mixed and used in the compound, such as when the content of deuterium is 0%, the content of hydrogen is 100%, and all substituents are hydrogen. The deuterium is one of the isotopes of hydrogen and is an element that has a deuteron consisting of one proton and one neutron as its nucleus. It can be expressed as hydrogen-2, and the element symbol can be written as D or 2H. The isotopes refer to atoms with the same atomic number (Z) but different mass numbers (A). It can also be interpreted as an element that has the same number of protons but a different number of neutrons.

Herein, “combinations thereof” in the present disclosure refers to one or more components of the corresponding list are combined to form a known or chemically stable arrangement that a person skilled in the art could conceive of from the corresponding list. For example, alkyl and deuterium may be combined to form partially or entirely deuterated alkyl groups; halogen and alkyl may be combined to form halogenated alkyl substituents; and halogen, alkyl, and aryl may be combined to form halogenated arylalkyl. For example, preferred combinations of substituents may include up to 50 atoms excluding hydrogen and deuterium, or include up to 40 atoms excluding hydrogen and deuterium, or include up to 30 atoms excluding hydrogen and deuterium, or in many cases, preferred combinations of substituents may include up to 20 atoms excluding hydrogen and deuterium.

In the formula of the present disclosure, when multiple substituents are indicated by the same symbol, each of these substituents represented by the same symbol may be the identical or different from one another.

The compounds represented by formulas 1, 1`, and 2 may be described in more detail as follows.

In formulas 1 and 1`, $X_1$ and $Y_1$ are each independently represent, —N=, —$NR_{10}$—, —O— or —S—, provided that, one of $X_1$ and $Y_1$ is —N= and the other of $X_1$ and $Y_1$ is —$NR_{10}$—, —O— or —S—. For example, one of $X_1$ and $Y_1$ may be —N=, and the other of $X_1$ and $Y_1$ may be —O— or —S—.

In formulas 1 and 1`, $L_1$ represents a single bond, a substituted or unsubstituted (C6-C30)arylene, or a substituted or unsubstituted (3- to 30-membered)heteroarylene. According to an embodiment of the present disclosure, $L_1$ may represent a single bond, a substituted or unsubstituted (C6-C25)arylene, or a substituted or unsubstituted (3- to 25-membered)heteroarylene, and more preferably, a single bond, a substituted or unsubstituted (C6-C18)arylene, or a substituted or unsubstituted (3- to 18-membered)heteroarylene. For example, $L_1$ may be a single bond.

In formulas 1 and 1`, $L_2$ and $L_3$, each independently represent, a single bond, a substituted or unsubstituted (C6-C30)arylene, or a substituted or unsubstituted (3- to 30-membered)heteroarylene. According to an embodiment of the present disclosure, $L_2$ and $L_3$ may each be, independently, a single bond, a substituted or unsubstituted (C6-C25)arylene, or a substituted or unsubstituted (3- to 25-membered)heteroarylene, and more preferably a single bond, a substituted or unsubstituted (C6-C18)arylene, or a substituted or unsubstituted (3- to 18-membered)heteroarylene. For example, $L_2$ and $L_3$ may each be, independently, a single bond, a substituted or unsubstituted phenylene, a substituted or unsubstituted naphthylene, a substituted or unsubstituted phenanthrylene, a substituted or unsubstituted dibenzofuranylene, or a substituted or unsubstituted pyridinylene, and for example, the substituted phenylene may be substituted with a phenylamine.

In formulas 1 and 1`, $R_5$ and $R_6$, each independently represent a substituted or unsubstituted (C6-C30)aryl, or a substituted or unsubstituted (3- to 30-membered)heteroaryl, provided that at least one of $R_5$ and $R_6$ is selected from carbazole derivatives represented by formula 1-A or formula 1-B. According to an embodiment of the present disclosure, $R_5$ and $R_6$ may each be, independently, a substituted or unsubstituted (C6-C28)aryl, or a substituted or unsubstituted (3- to 28-membered)heteroaryl, and at least one of $R_5$ and $R_6$ may be selected from the carbazole derivatives represented by formula 1-A or formula 1-B, more preferably, selected from the substituted or unsubstituted (C6-C25)aryl, or a substituted or unsubstituted (3- to 25-membered)heteroaryl, where at least one of $R_5$ and $R_6$ is a carbazole derivative represented by formula 1-A or formula 1-B. For example, $R_5$ and $R_6$ may each independently be a substituted or unsubstituted phenyl, a substituted or unsubstituted naphthyl, a substituted or unsubstituted phenanthrenyl, a substituted or unsubstituted biphenyl, a substituted or unsubstituted p-terphenyl, a substituted or unsubstituted m-terphenyl, a substituted or unsubstituted o-terphenyl, a substituted or unsubstituted fluorenyl, a substituted or unsubstituted dibenzofuranyl, a substituted or unsubstituted dibenzothiophenyl, a substituted or unsubstituted carbazolyl, or a substituted or unsubstituted isoquinolinyl. For example, the substituted phenyl may be substituted with one or more selected from the group consisting of cyano, tert-butyl, diphenylamine, triphenylsilane, and carbazole, and the substituted fluorenyl may be substituted with methyl.

In formula 1-A, $L_5$ represents a single bond, a substituted or unsubstituted (C6-C30)arylene, or a substituted or unsubstituted (3- to 30-membered)heteroarylene. According to an embodiment of the present disclosure, $L_5$ may represent a single bond, a substituted or unsubstituted (C6-C25)arylene, or a substituted or unsubstituted (3- to 25-membered)heteroarylene, and more preferably, a single bond, a substituted or unsubstituted (C6-C18)arylene, or a substituted or unsubstituted (3- to 18-membered)heteroarylene. For example, $L_5$ may be a single bond.

In formulas 1 and 1`, $R_1$ represents a substituted or unsubstituted (C6-C30)aryl or a substituted or unsubstituted (3- to 30-membered)heteroaryl. According to an embodiment of the present disclosure, $R_1$ may represent a substituted or unsubstituted (C6-C25)aryl or a substituted or unsubstituted (3- to 25-membered)heteroaryl, and more preferably a substituted or unsubstituted (C6-C18)aryl or a substituted or unsubstituted (3- to 18-membered)heteroaryl. For example, $R_1$ may be a substituted or unsubstituted phenyl.

In formula 1, 1`, 1-A, and 1-B, $R_2$ to $R_4$ and $R_7$ to $R_{10}$ may be, independently, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or -$L_3$``-N($Ar_3$``)($Ar_4$``); —N(Ar3``); or may be linked to adjacent substituents to form a ring According to an embodiment of the present disclosure, $R_2$ to $R_4$ and $R_7$ to $R_{10}$ each independently represent, hydrogen, deuterium, a substituted or unsubstituted (C6-C25)aryl, a substituted or unsubstituted (3- to 25-membered)heteroaryl, a substituted or unsubstituted (C3-C25)cycloalkyl, or a substituted or unsubstituted fused ring of (C3-C25) aliphatic ring and (C6-C25) aromatic ring; or may be linked to an adjacent substituent(s) to form a ring(s), more preferably hydrogen, deuterium, a substituted or unsubstituted (C6-C18)aryl, a substituted or unsubstituted (3- to 18-membered)heteroaryl, or a substituted or unsubstituted (C3-C18)cycloalkyl, or a substituted or unsubstituted fused ring of (C3-C18) aliphatic ring and (C6-C18) aromatic ring; or may be linked to adjacent substituents to form a ring; For example, $R_2$ to $R_4$ and $R_7$ to $R_{10}$ may each be, independently, hydrogen, deuterium, a substituted or unsubstituted phenyl, a substituted or unsubstituted naphthyl, a substituted or unsubstituted biphenyl, a substituted or unsubstituted fluorenyl, a substituted or unsubstituted dibenzofuranyl, a substituted or unsubstituted dibenzothiophenyl, or a substituted or unsubstituted carbazolyl. For example, the substituted phenyl may be substituted with a carbazole, and the substituted fluorenyl may be substituted with a methyl.

In formulas 1 and 1`, $L_3$` represents a single bond, a substituted or unsubstituted (C6-C30)arylene, or a substituted or unsubstituted (3- to 30-membered)heteroarylene. For example, $L_3$` may be a substituted or unsubstituted phenylene.

In formulas 1 and 1`, $Ar_3$` and $Ar_4$` each independently represent, hydrogen, deuterium, a substituted or unsubstituted (C1-C30)alkyl, a substituted or unsubstituted (C2-C30)alkenyl, a substituted or unsubstituted fused ring of (C3-C30) aliphatic ring and (C6-C30) aromatic ring, a substituted or unsubstituted (C6-C30)aryl, or a substituted or unsubstituted (3- to 30-membered)heteroaryl. For example, $Ar_3$`` and $Ar_4$`` may each be, independently, a substituted or unsubstituted phenyl.

In formula 1, 1`, 1-A, and 1-B, a is 1, b and c each independently represent 1 or 2, and e and f each independently represent integers of 1 to 4, and e` represents integers of 1 to 3, and when b to f and e` represent integers of 2 or more, each of $R_2$ to $R_4$, $R_7$, and $R_8$ may be the same or different from each other.

According to an embodiment of the present disclosure, the compound represented by formulas 1 and 1` may be a compound represented by any one of the following formulas 1-1 to 1-5.

(1-1)

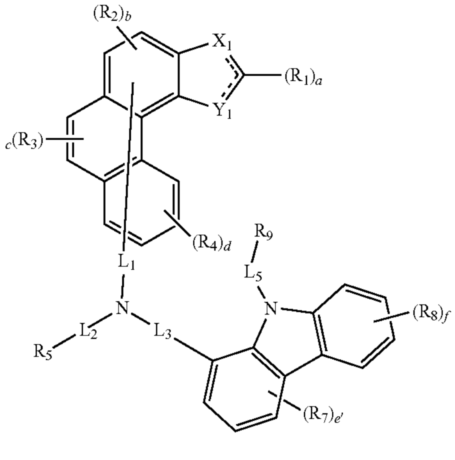

-continued (1-2)

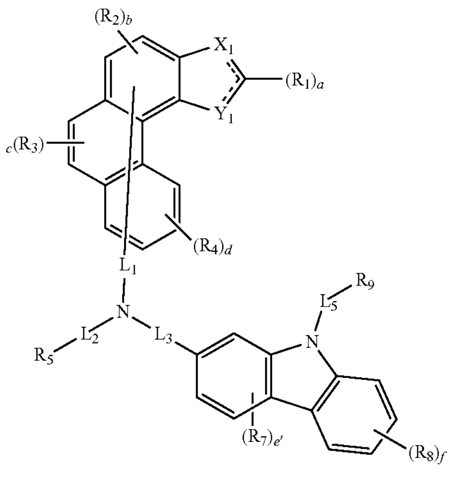

(1-3)

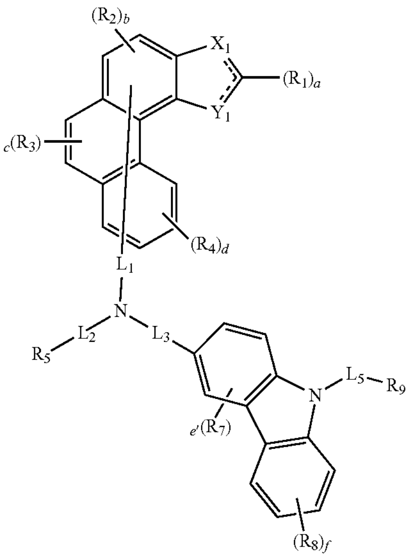

(1-4)

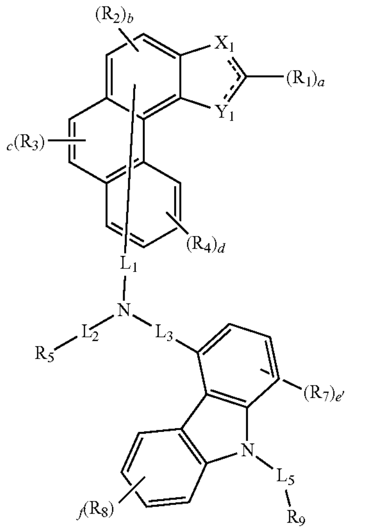

-continued (1-5)

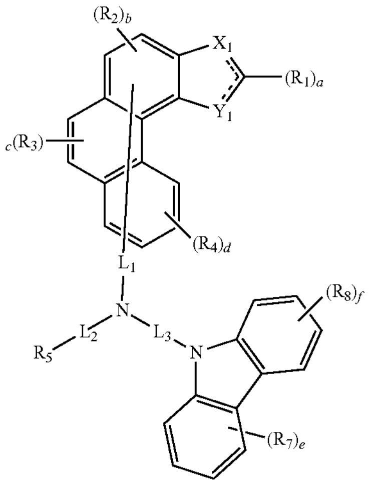

In formulas 1-1 to 1-5, $L_5$ represents a single bond, a substituted or unsubstituted (C6-C30)arylene, or a substituted or unsubstituted (3- to 30-membered)heteroarylene;

$X_1$, $Y_1$, $L_1$ to $L_3$, $R_1$ to $R_5$, $R_7$ to $R_{10}$, a to f, and e` are the same as defined in formulas 1, 1', 1-a, 1-a, and 1-B.

In formula 2, T represents O or S.

In formula 2, $K_1$ to $K_3$ each independently represent N or CH, provided that at least one of $K_1$ to $K_3$ is N. Specifically, at least two of $K_1$ to $K_3$ may be N, and the other one may be CH. For example, all of $K_1$ to $K_3$ may be N.

In formula 2, $L_7$ to $L_9$ each independently represent, a single bond, a substituted or unsubstituted (C6-C30)arylene, a substituted or unsubstituted (C3-C30)cycloalkylene, or a substituted or unsubstituted (3- to 30-membered)heteroarylene. Specifically, $L_7$ to $L_9$ each independently represent, a single bond or a substituted or unsubstituted (C6-C30)arylene. For example, $L_7$ to $L_9$ may independently be a single bond, phenylene unsubstituted or substituted with deuterium, phenylnaphthylene unsubstituted or substituted with deuterium, naphthylene unsubstituted or substituted with deuterium, naphthylphenylene unsubstituted or substituted with deuterium, or biphenylene unsubstituted or substituted with deuterium, and for example, the substituted phenylene, the substituted naphthylene, and the substituted biphenylene may be substituted with deuterium.

In formula 2, $R_{11}$ and $R_{12}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or —N—(R`)(R``); or may be adjacent substituent other to form a ring; According to an embodiment of the present disclosure, $R_{11}$ and $R_{12}$ may each be, independently, hydrogen, deuterium, or a substituted or unsubstituted (C6-C25)aryl, and more preferably, hydrogen or a substituted or unsubstituted (C6-C18)aryl. For example, $R_{11}$ and $R_{12}$ may each be, independently, hydrogen, deuterium, a substituted or unsubstituted phenyl, a substituted or unsubstituted phenylnaphthyl, a substituted or unsubstituted naphthyl, a substituted or unsubstituted naphthylphenyl, a substituted or unsubstituted phenanthrenyl, or a substituted or unsubstituted biphenyl.

In formula 2, $Ar_6$ and $Ar_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or —N—(R` )(R`` ); or may be linked to adjacent substituent to form a ring. According to one embodiment of the present disclosure, $Ar_6$ and $Ar_7$ may each be, independently, linked to a substituted or unsubstituted (C6-C25)aryl, a substituted or unsubstituted (3- to 25-membered)heteroaryl, a substituted or unsubstituted fused ring of (C3-C25) aliphatic ring and (C6-C25) aromatic ring, or an adjacent substituent to form a ring, and more preferably, may each be, independently, linked to a substituted or unsubstituted (C6-C18)aryl, a substituted or unsubstituted (3- to 18-membered)heteroaryl, or a substituted or unsubstituted fused ring of (C3-C18)aliphatic ring and (C6-C18)aromatic ring; or may be linked to adjacent substituent to form a ring. For example, $Ar_6$ and $Ar_7$ may each be, independently, a substituted or unsubstituted phenyl, a substituted or unsubstituted naphthyl, a substituted or unsubstituted phenanthrenyl, a substituted or unsubstituted chrysenyl, a substituted or unsubstituted benzophenanthrenyl, a substituted or unsubstituted biphenyl, a substituted or unsubstituted p-terphenyl, a substituted or unsubstituted o-terphenyl, a substituted or unsubstituted dibenzofuranyl, a substituted or unsubstituted dibenzothiophenyl, a substituted or unsubstituted naphthobenzofuranyl, a substituted or unsubstituted naphthobenzoxazolinyl, or a substituted or unsubstituted phenanthrobenzofuranyl. For example, the substituted phenyl, the substituted naphthyl, the substituted chrysenyl, and the substituted p-terphenyl may each be substituted with deuterium, and the substituted naphthobenzoxazolinyl may be substituted with phenyl.

In formula 2, R` and R`` each independently represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl.

g and h are an integer of 1 to 4, and when g and h are an integer of 2 or more, each of $R_{11}$ and $R_{12}$ may be the same or different.

According to one embodiment of the present disclosure, the compound represented by formula 2 may be a compound represented by any one of the following formulas 2-1 to 2-4.

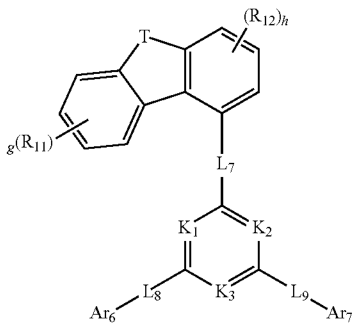
(2-1)

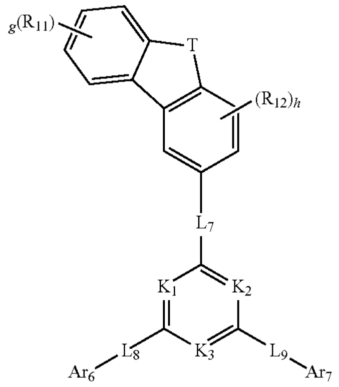
(2-2)

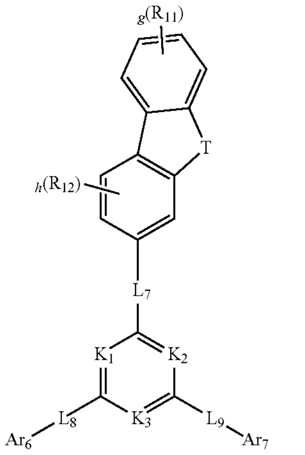
(2-3)

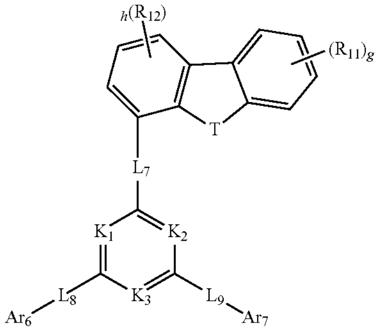
(2-4)

In formulas 2-1 to 2-4,

T, $K_1$ to $K_3$, $L_7$ to $L_9$, $R_{11}$, $R_{12}$, $Ar_6$, $Ar_7$, R` , R`` , g, and h are as defined in the formula 2.

The compounds represented by formulas 1 and 1` may be compounds selected from the following compounds, but are not limited thereto.
C-1
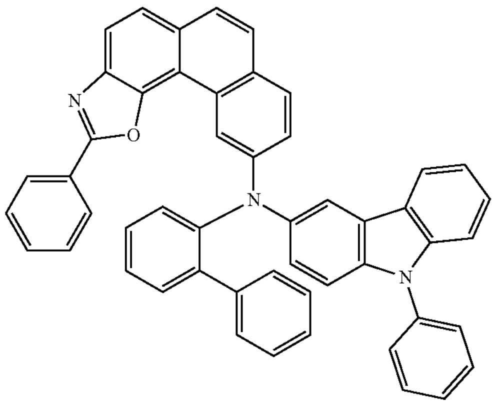
C-2
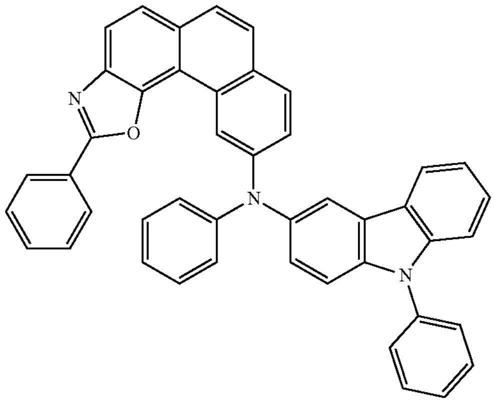
C-3
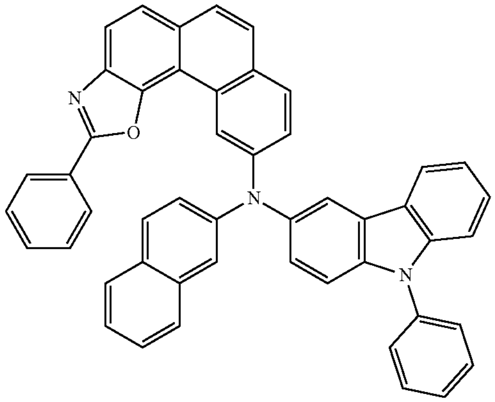
-continued
C-4
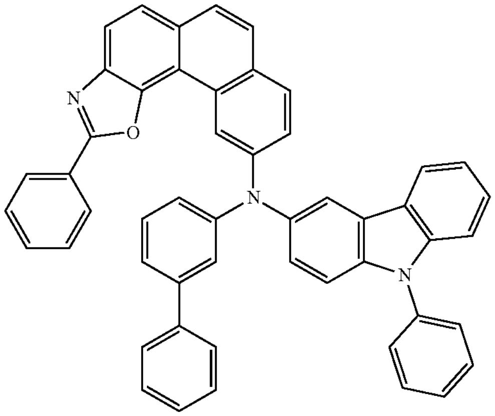
C-5
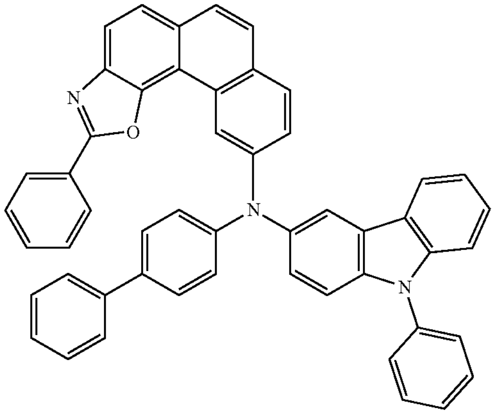
C-6
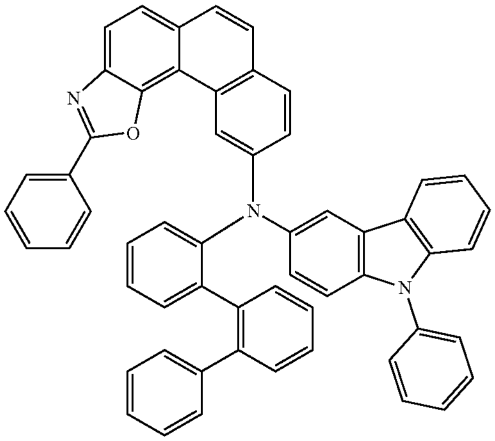

-continued
C-7
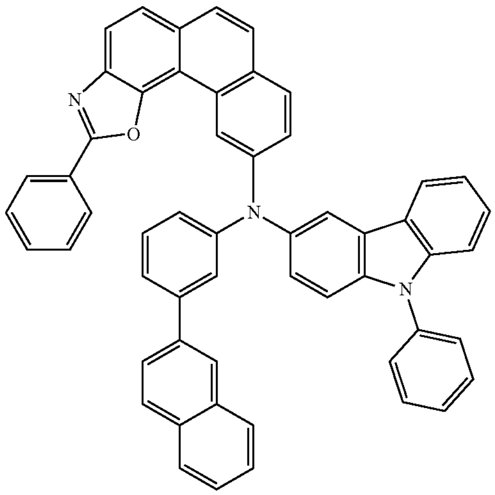
C-8
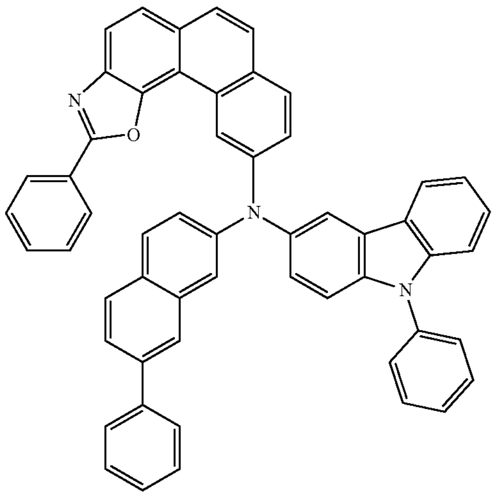
C-9
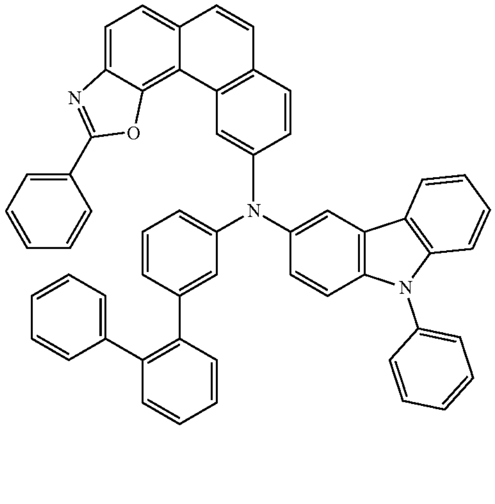
-continued
C-10
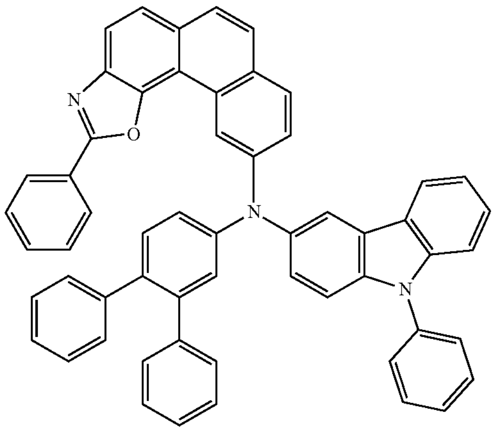
C-11
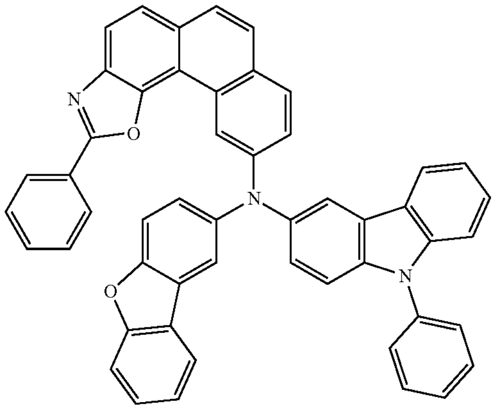
C-12
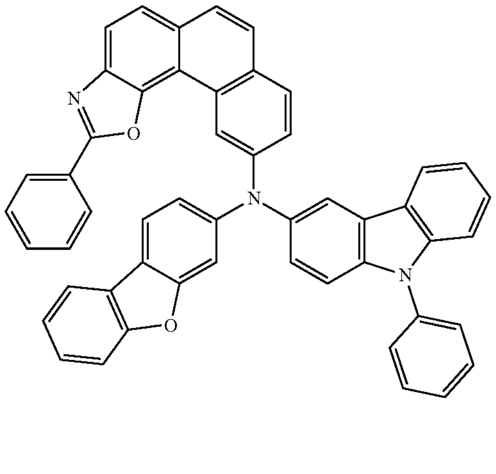

-continued
C-13
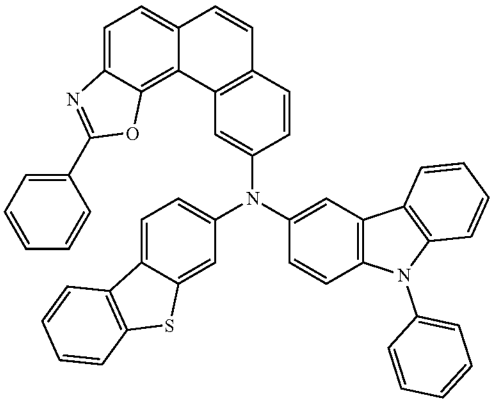
C-14
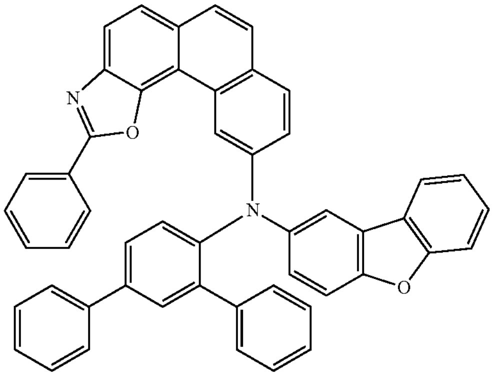
C-15
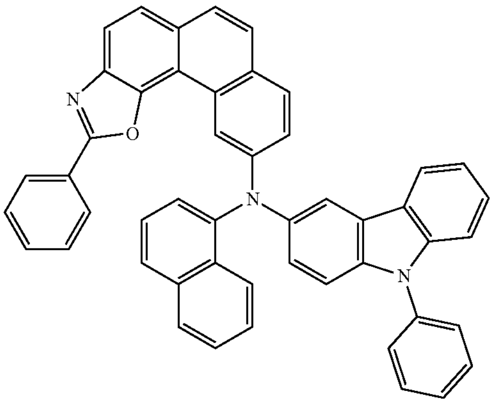
C-16
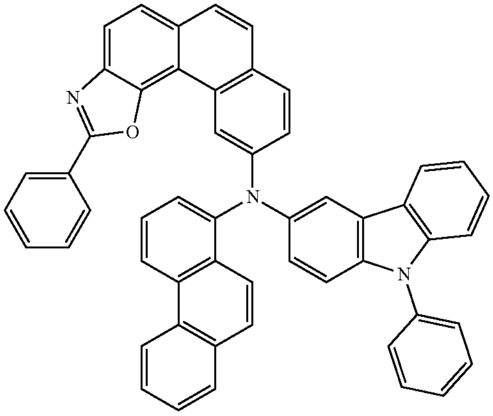
-continued
C-17
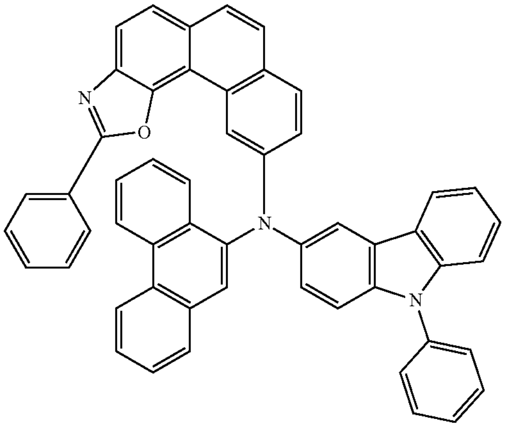
C-18
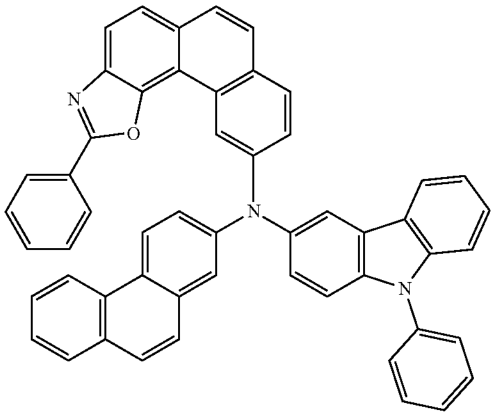
C-19
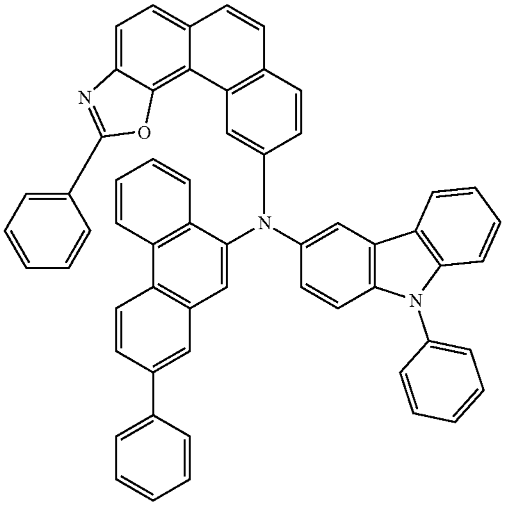

-continued
C-20
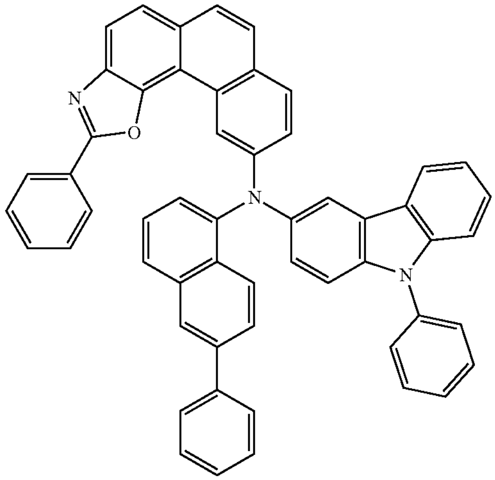
C-21
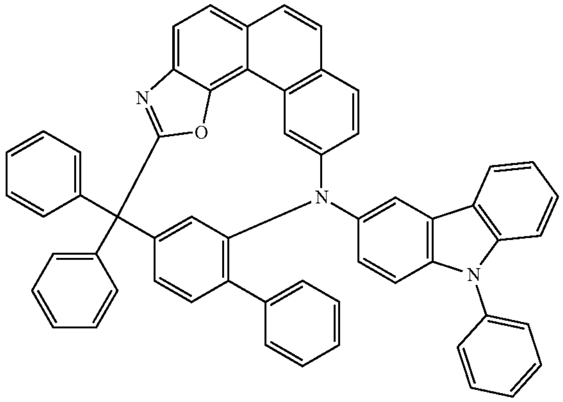
C-22
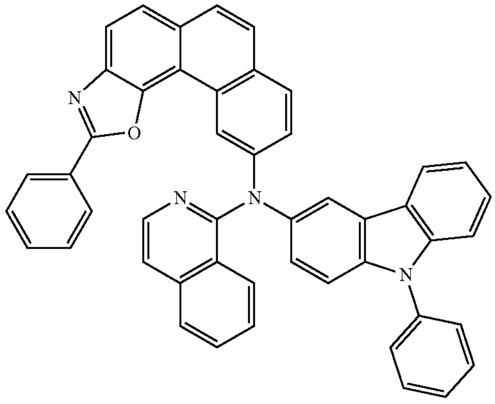
-continued
C-23
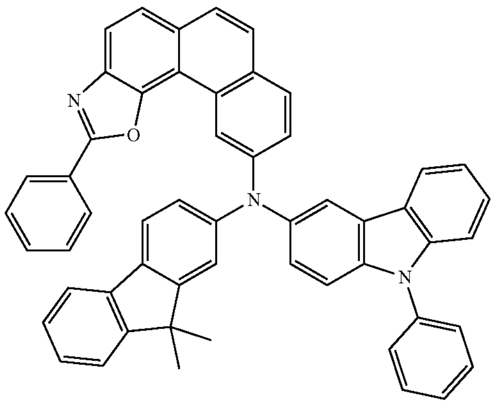
C-24
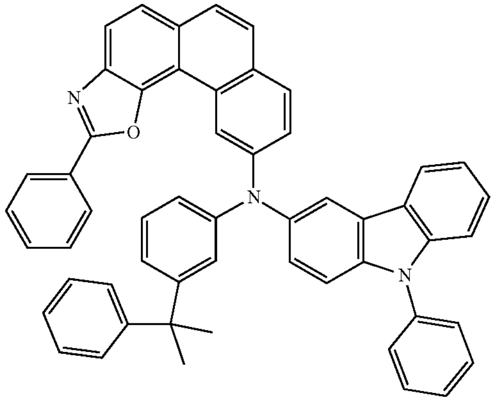
C-25
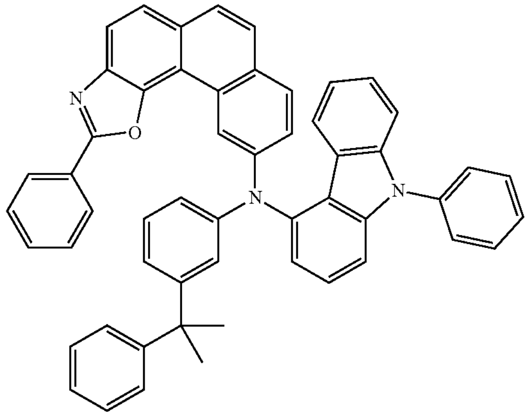
C-26
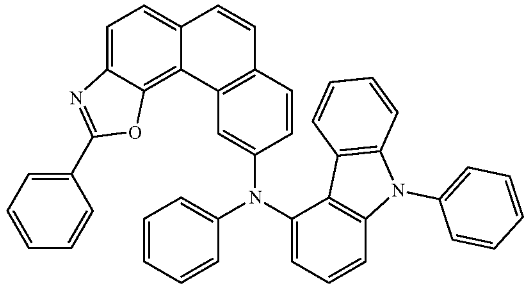

-continued
C-27
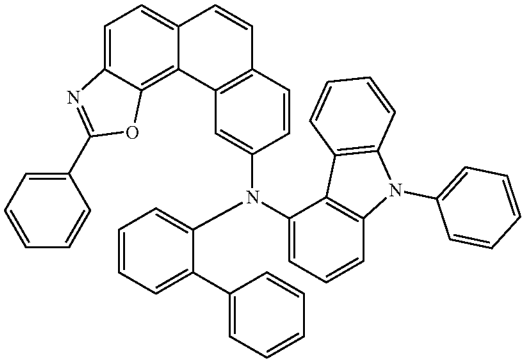
C-28
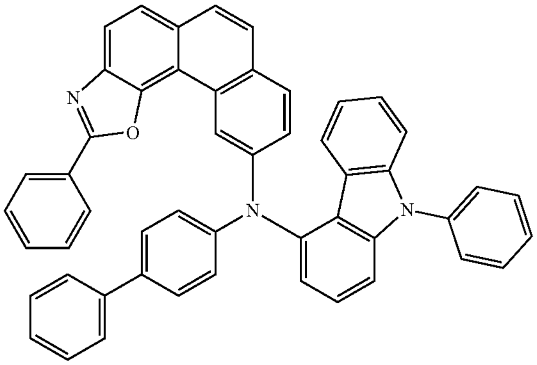
C-29
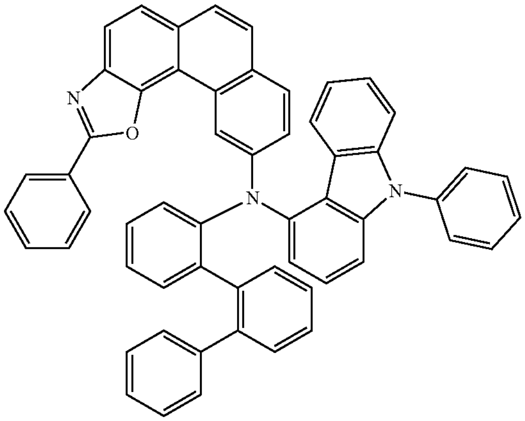
C-30
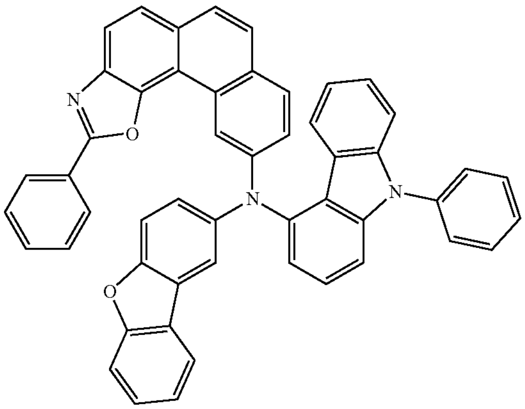
-continued
C-31
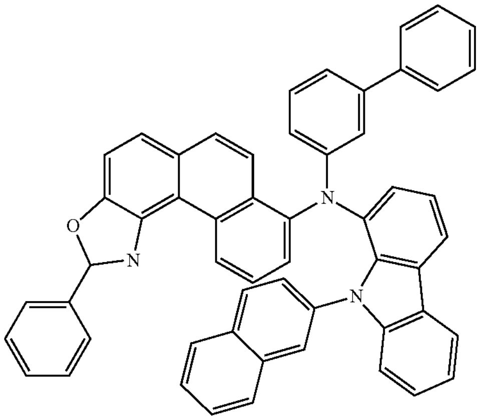
C-32
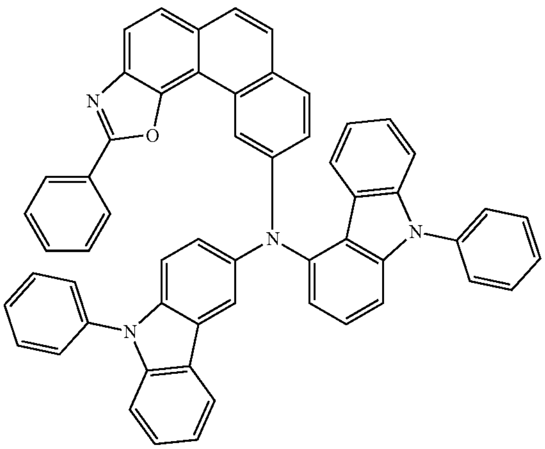
C-33
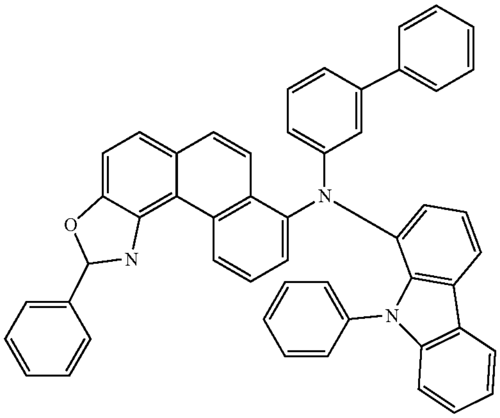

-continued
C-34
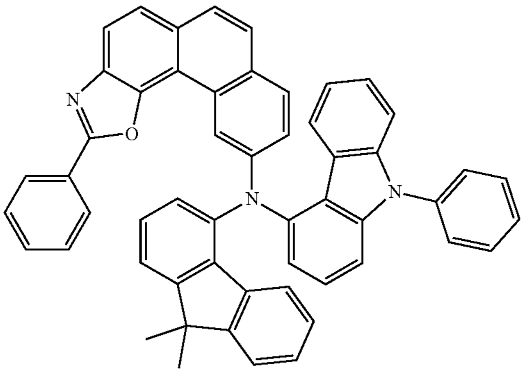
C-35
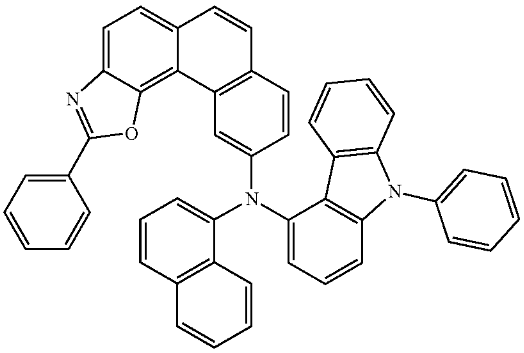
C-36
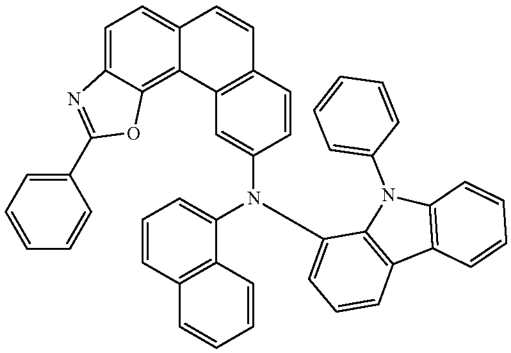
C-37
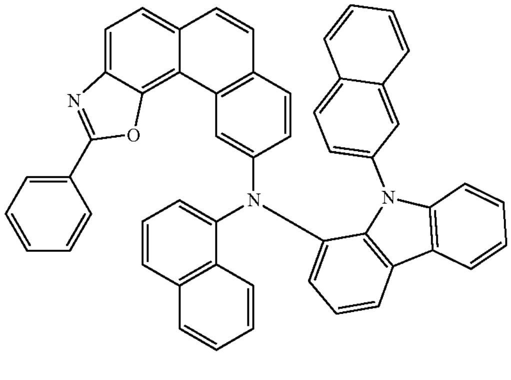
-continued
C-38
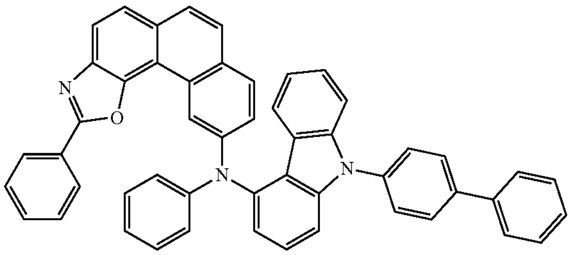
C-39
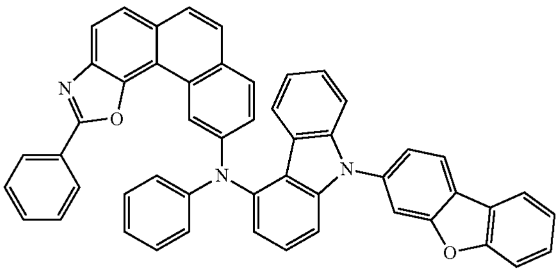
C-40
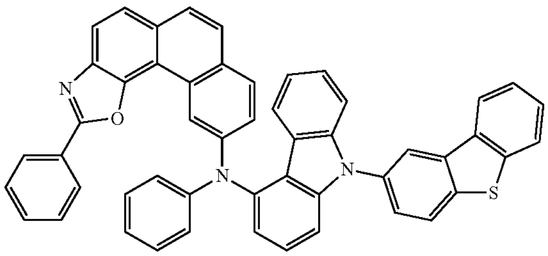
C-41
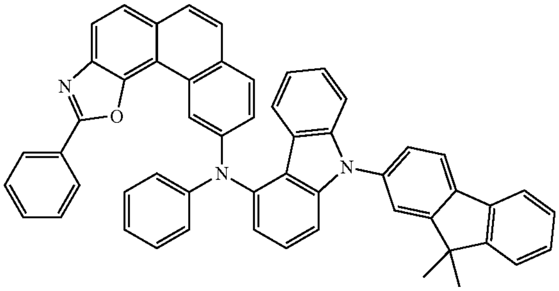
C-42
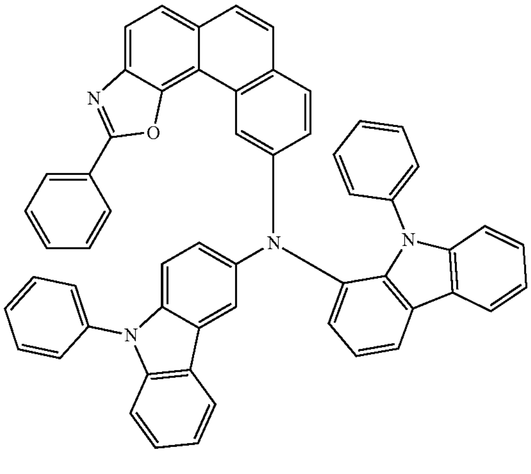

-continued
C-43
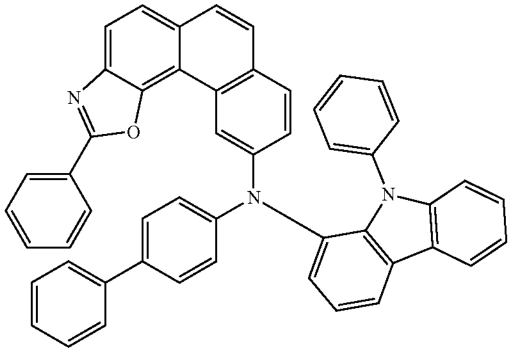
C-44
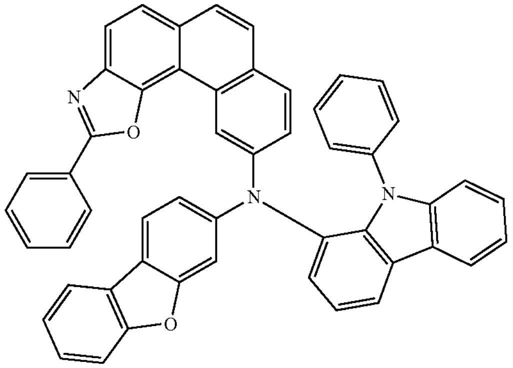
C-45
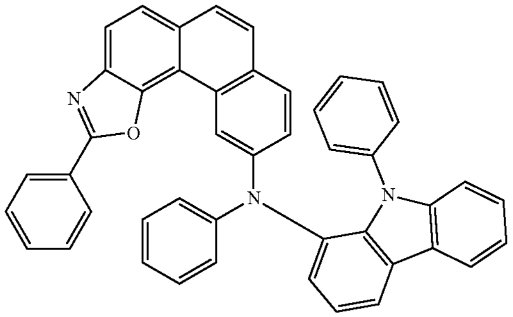
C-46
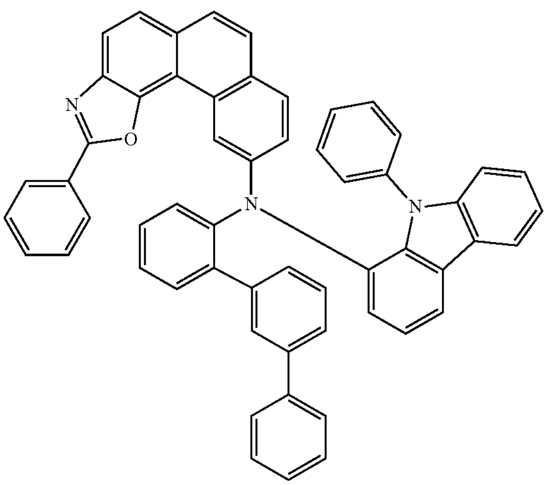
-continued
C-47
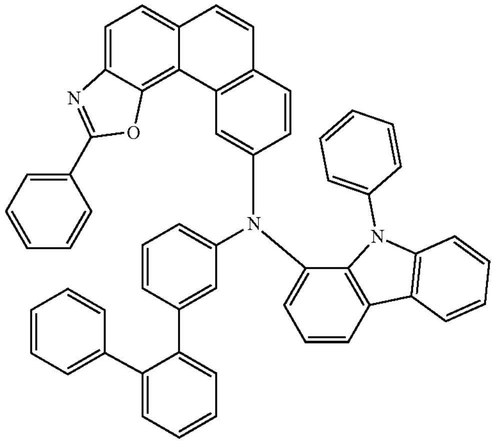
C-48
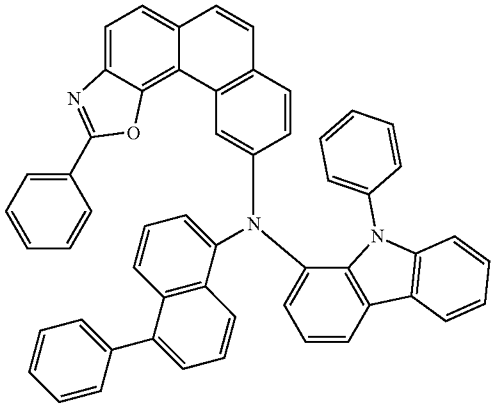
C-49
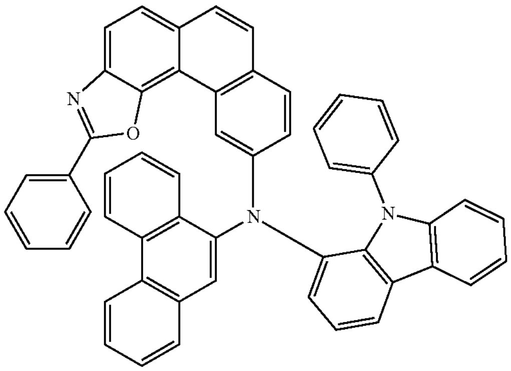

-continued
C-50
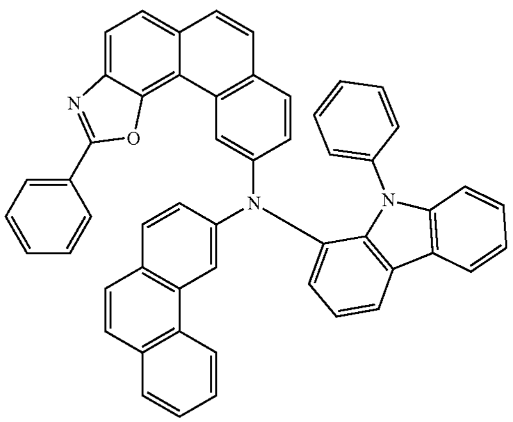
C-51
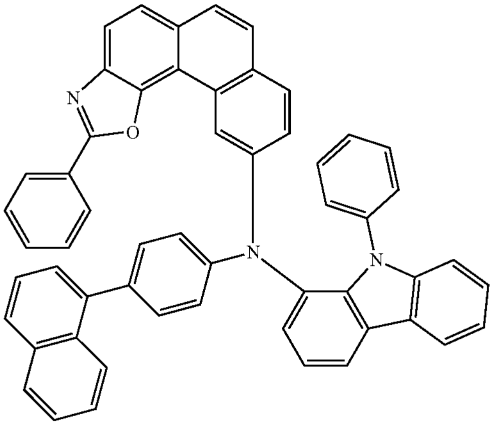
C-52
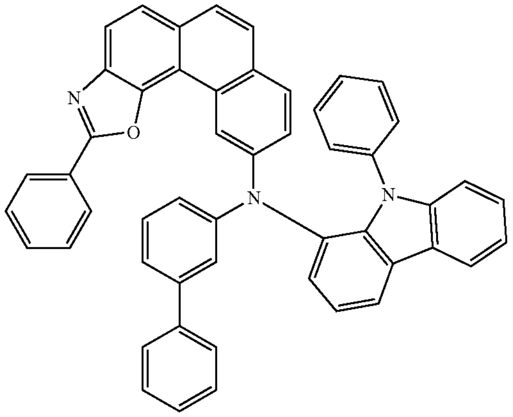
-continued
C-53
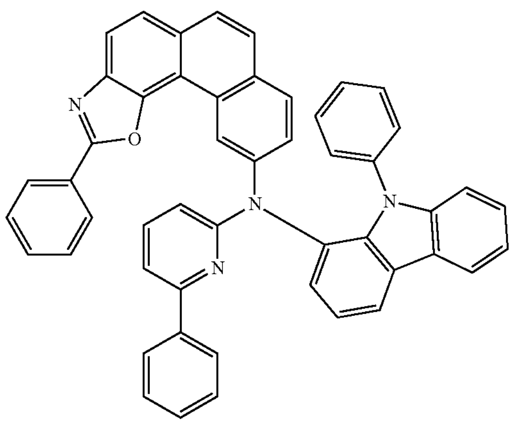
C-54
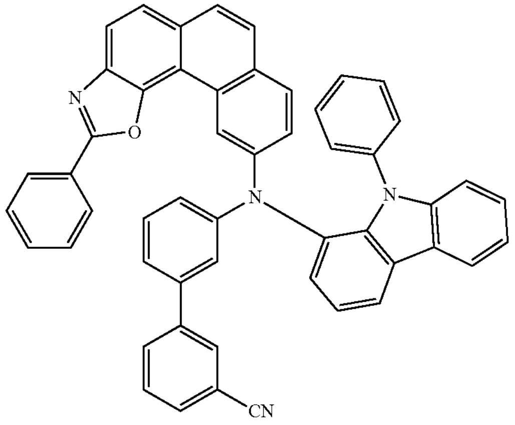
C-55
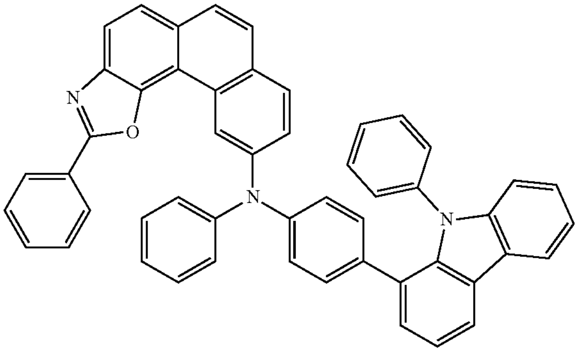
C-56
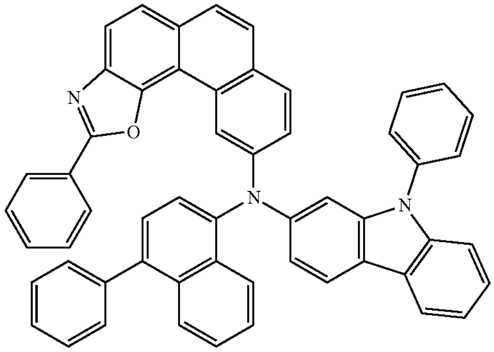

-continued
C-57
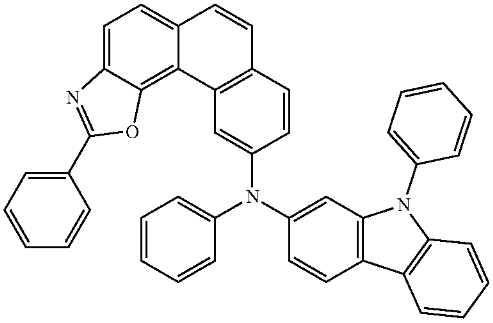
C-58
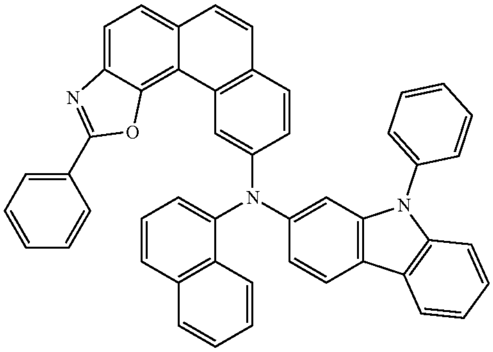
C-59
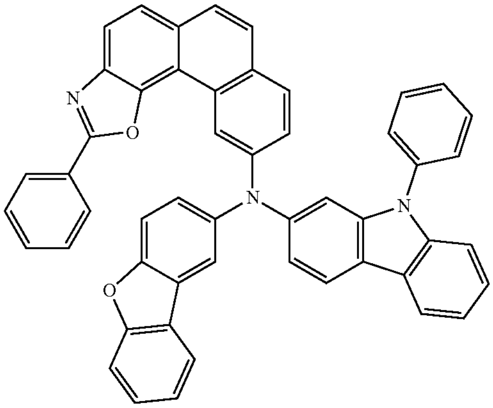
C-60
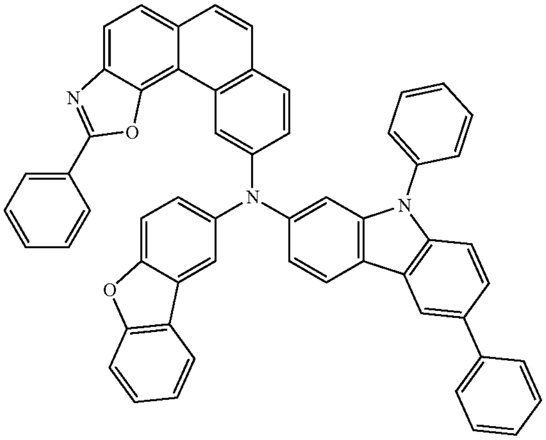
-continued
C-61
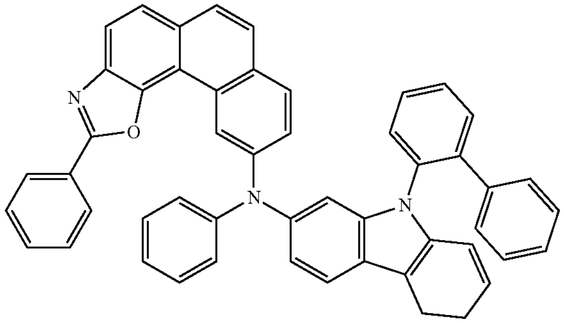
C-62
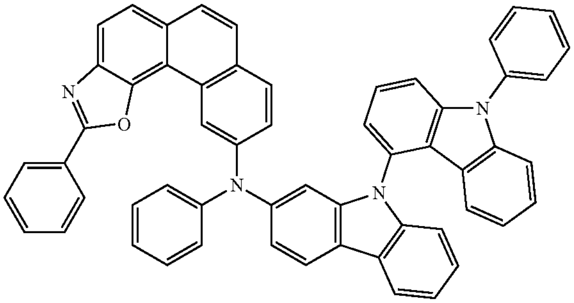
C-63
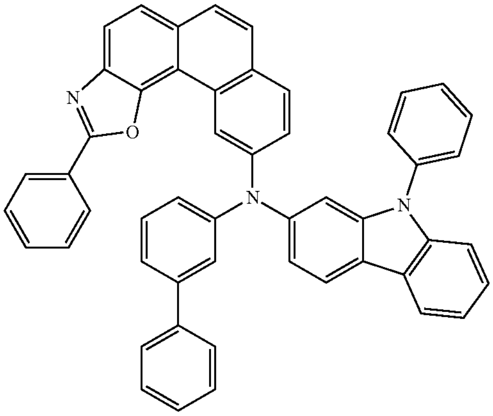
C-64
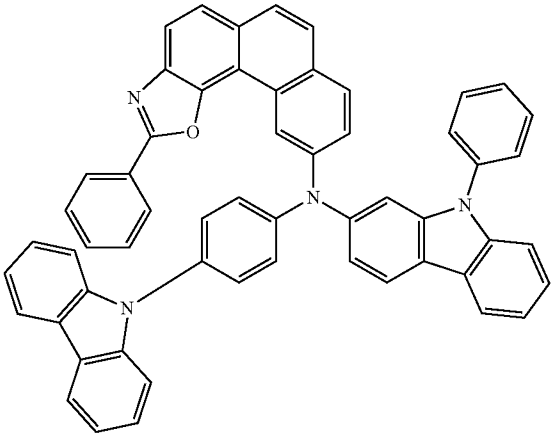

-continued
C-65
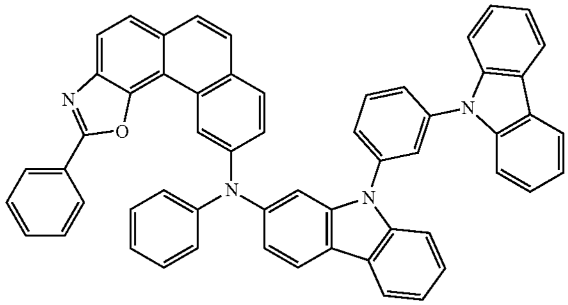
C-66
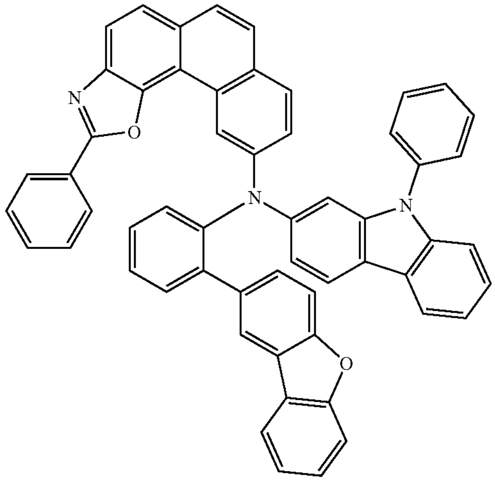
C-67
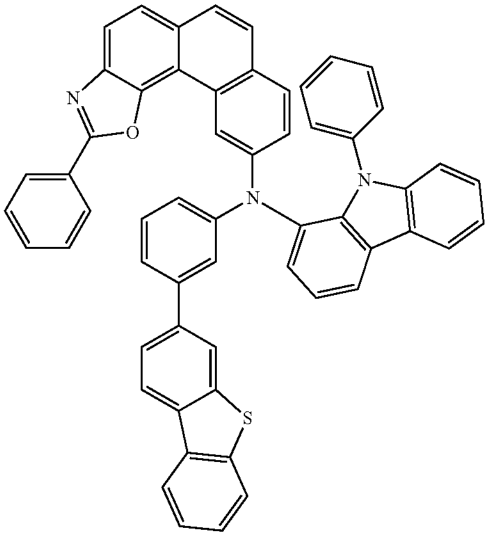
-continued
C-68
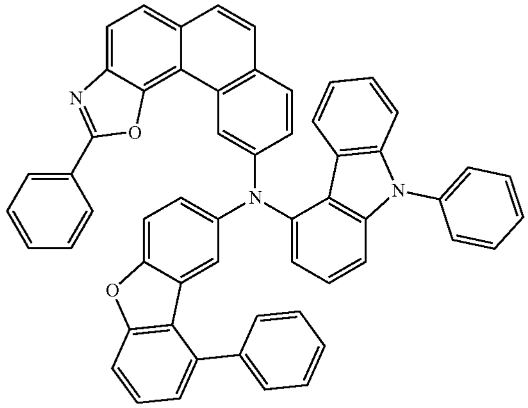
C-69
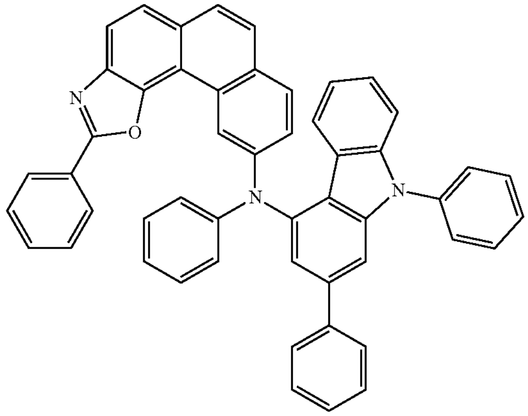
C-70
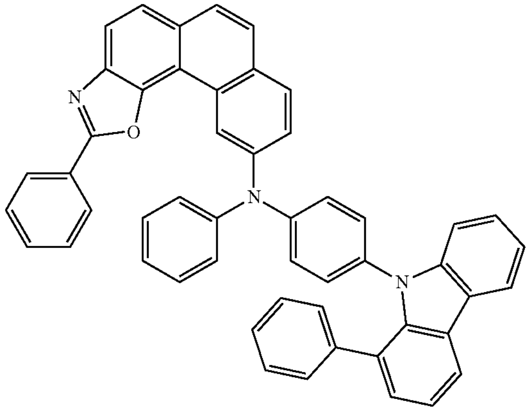

-continued
C-71
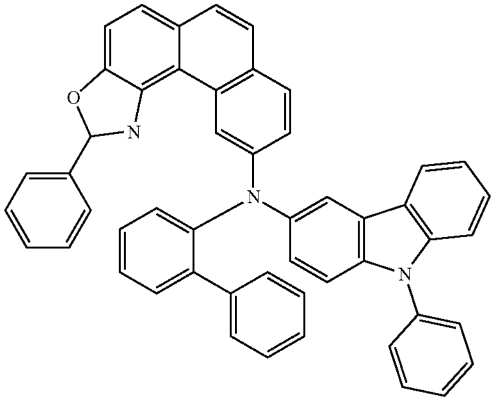
C-72
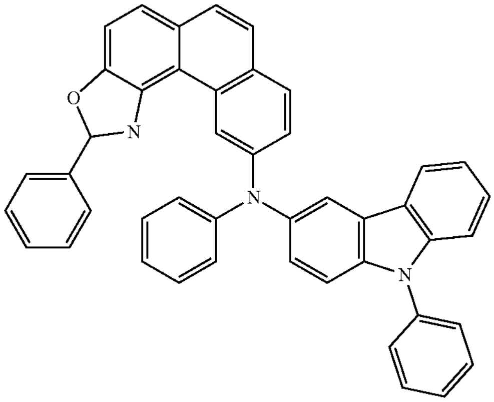
C-73
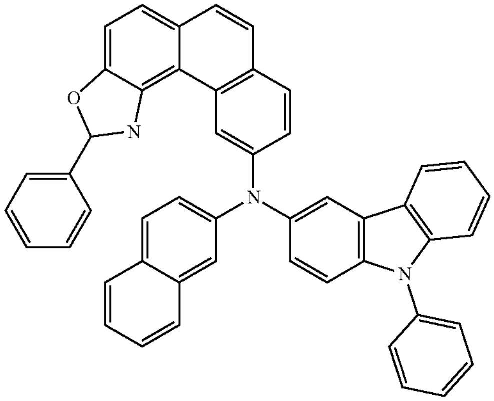
C-74
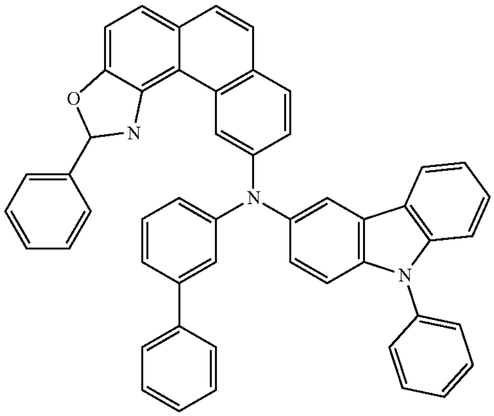
-continued
C-75
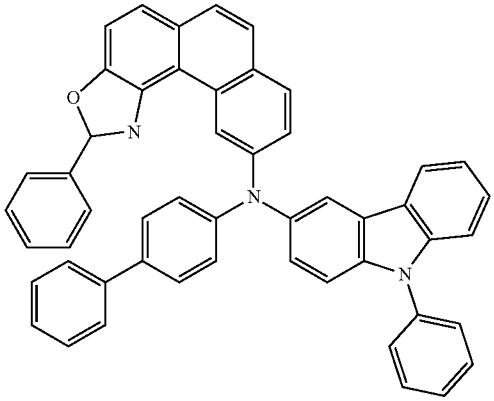
C-76
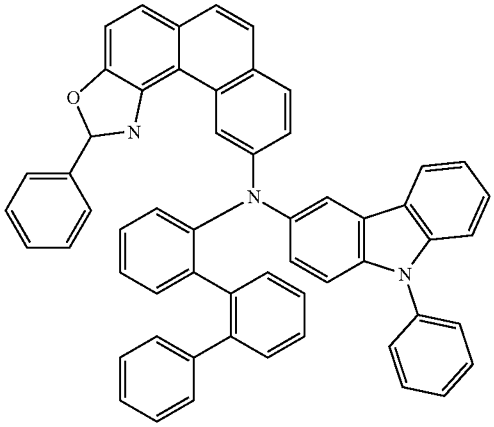
C-77
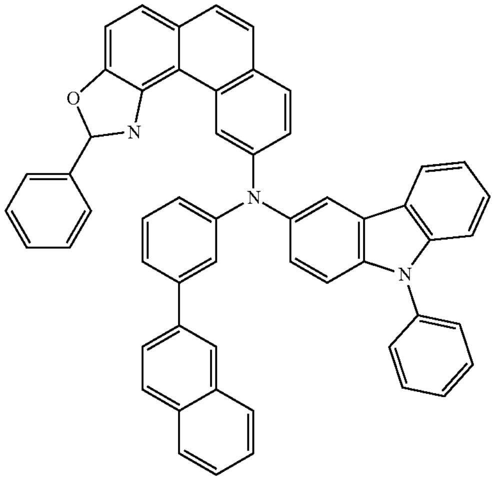

-continued
C-78
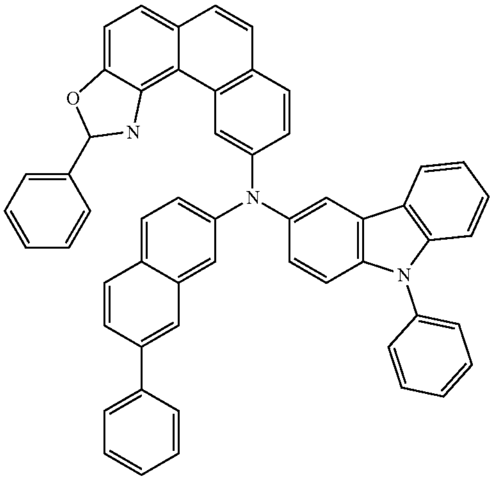
C-79
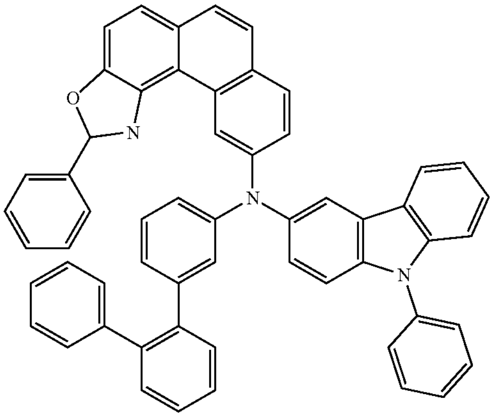
C-80
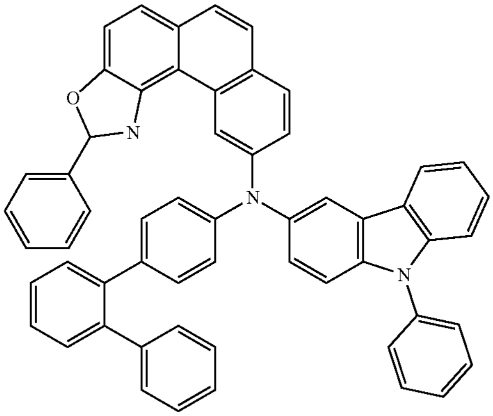
-continued
C-81
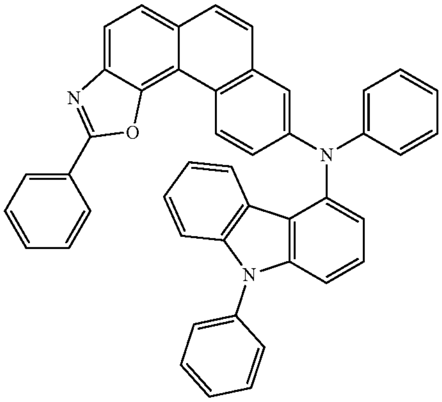
C-82
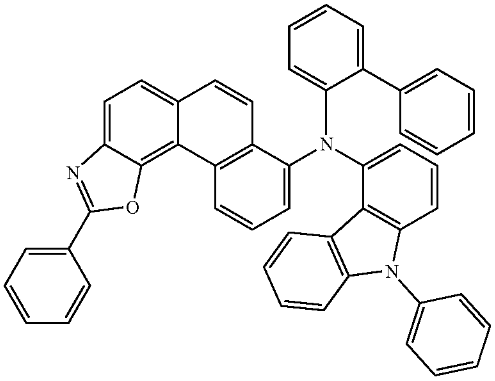
C-83
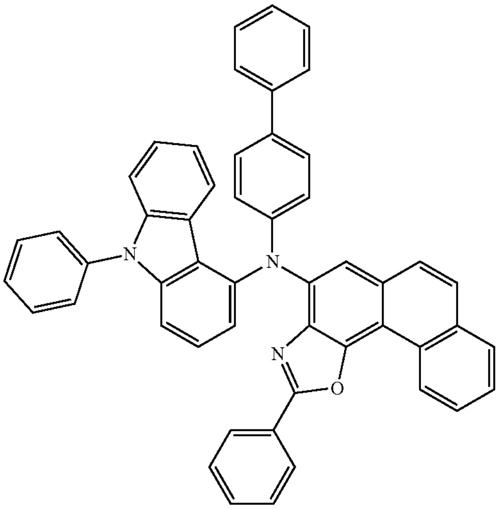

-continued
C-84
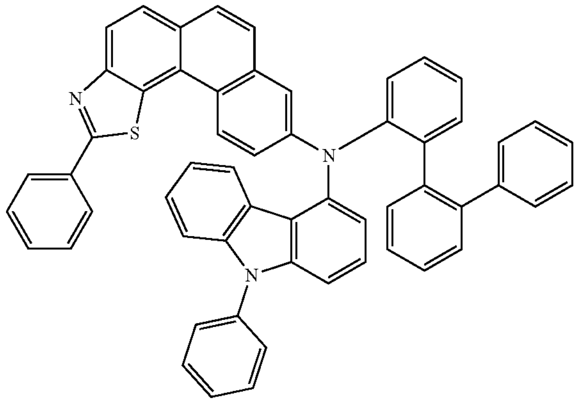
C-85
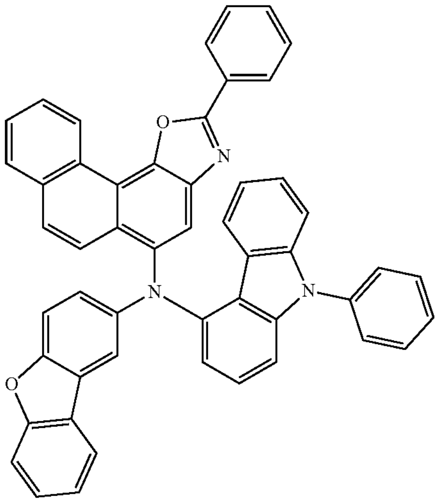
C-86
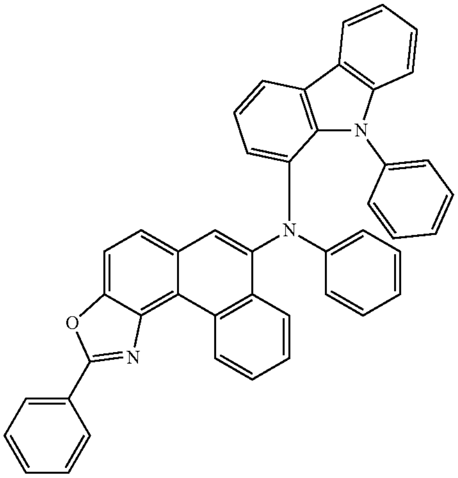
-continued
C-87
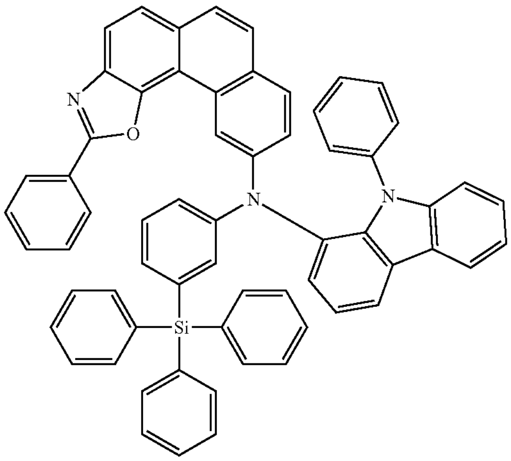
C-88
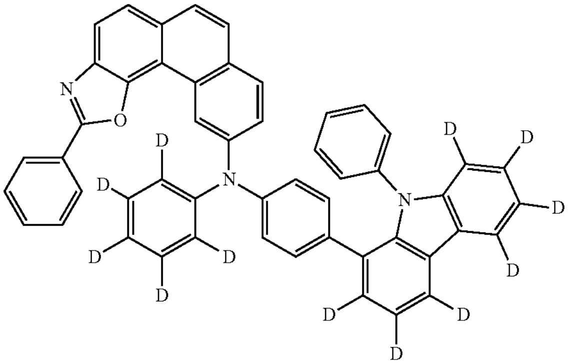
C-89
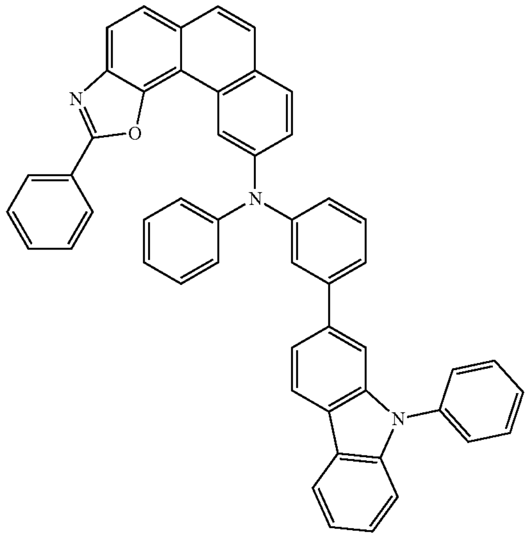

-continued
C-90
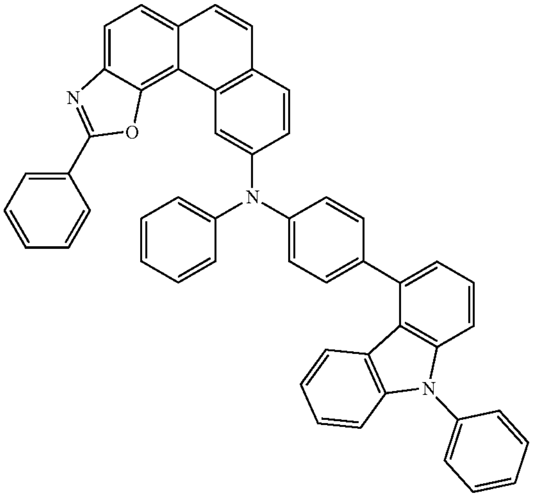
C-91
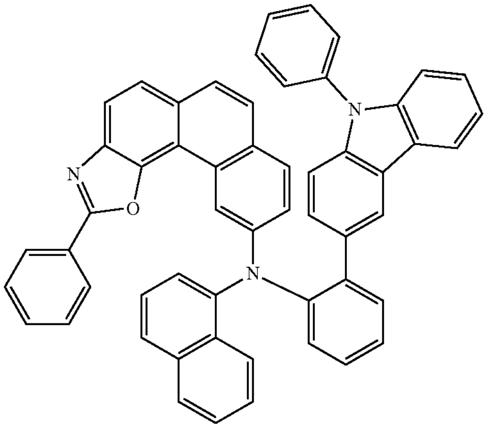
C-92
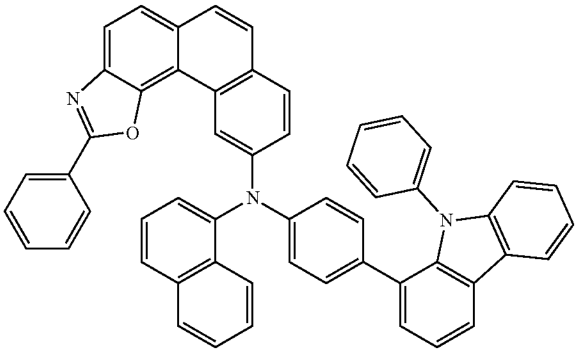
-continued
C-93
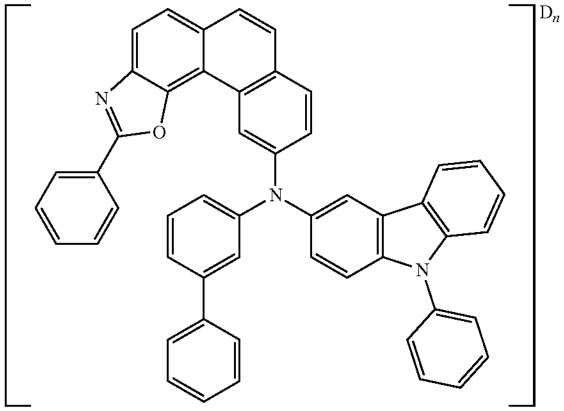
$D_n$: 1-33
C-94
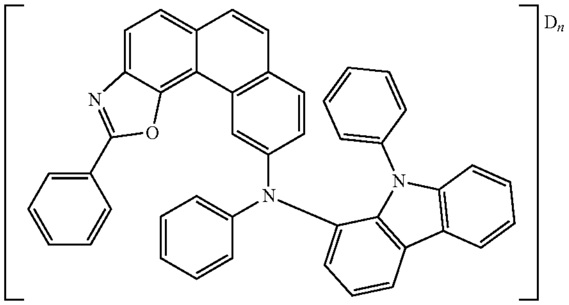
$D_n$: 1-29
C-95
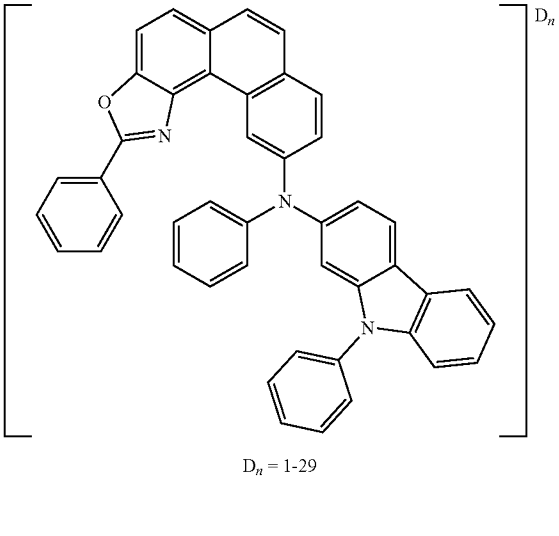
$D_n$ = 1-29

-continued
C-96
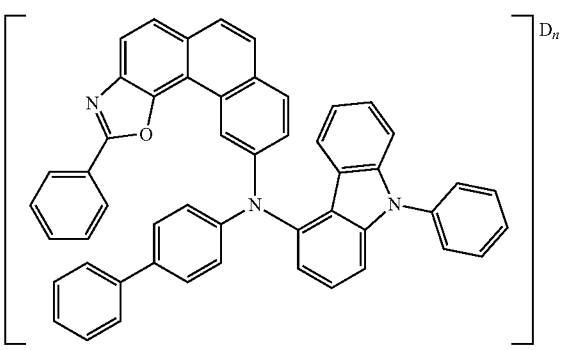
$D_n$ = 1-33
C-97
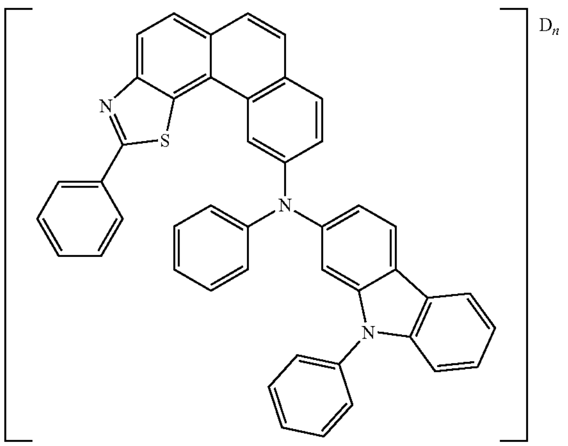
$D_n$ = 1-29
C-98
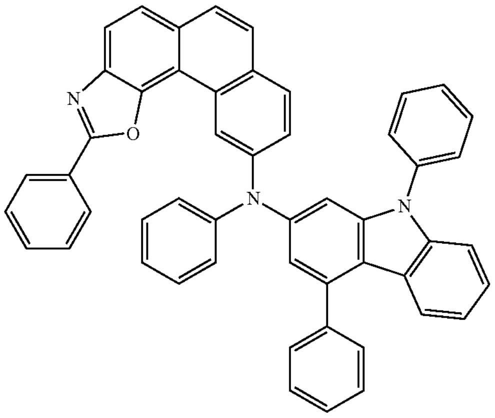
-continued
C-99
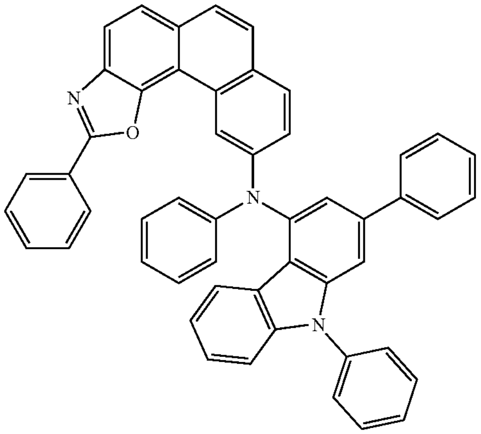
C-100
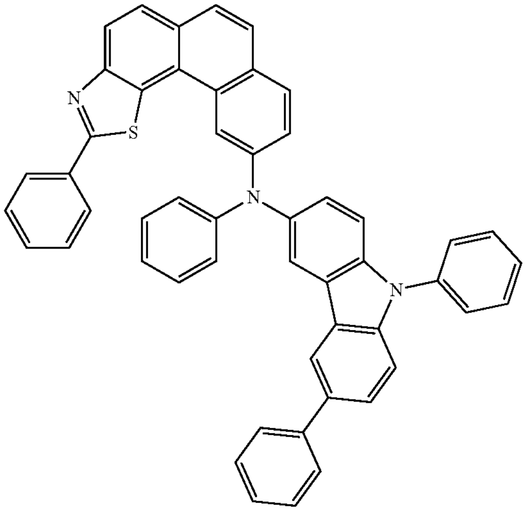
C-101
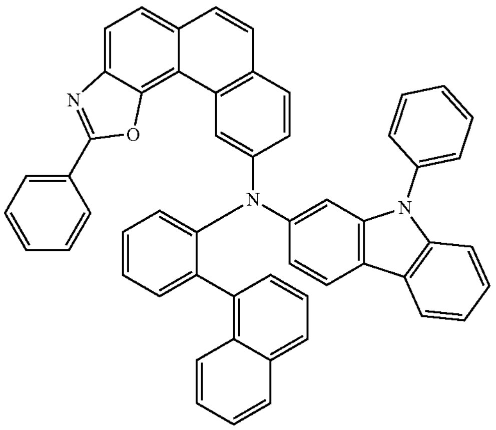

-continued
C-102
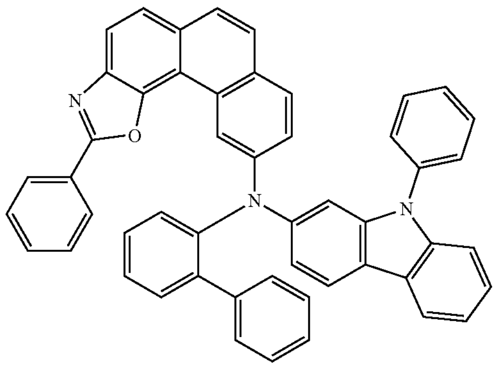
C-103
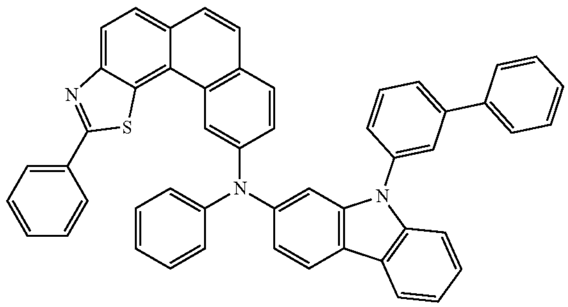
C-104
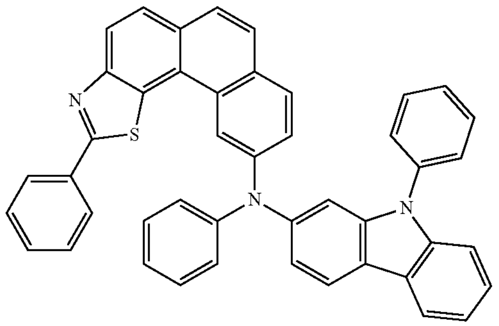
C-105
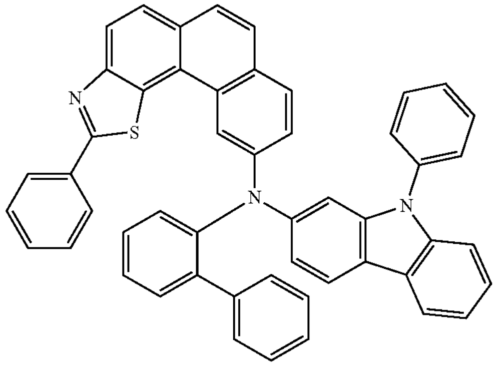
-continued
C-106
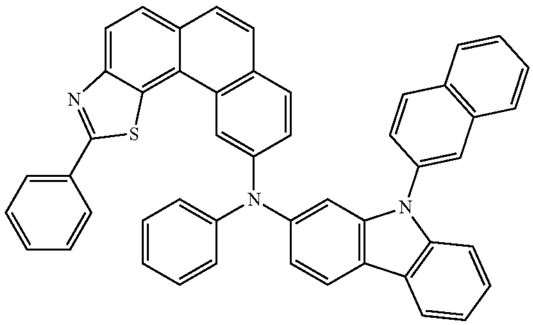
C-107
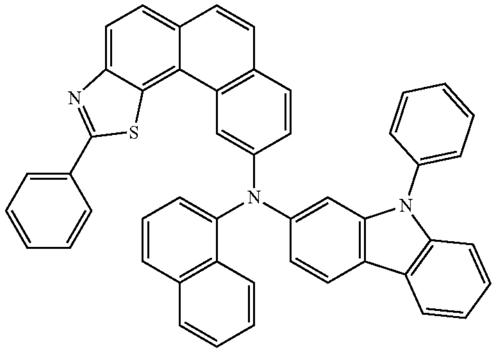
C-108
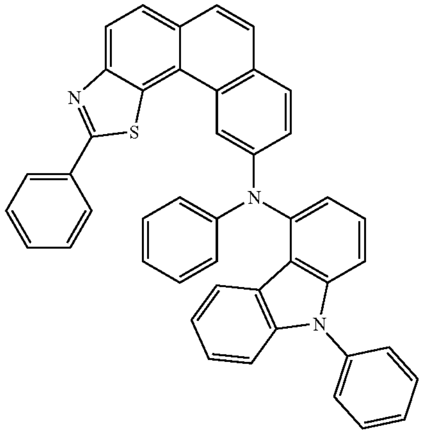

-continued
C-109
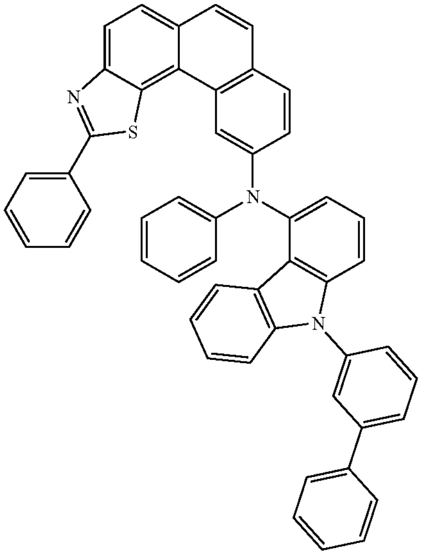
C-110
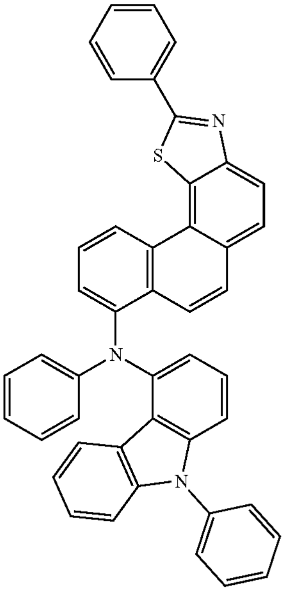
C-111
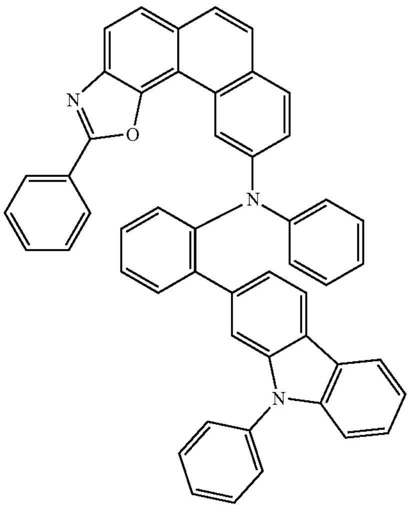
-continued
C-112
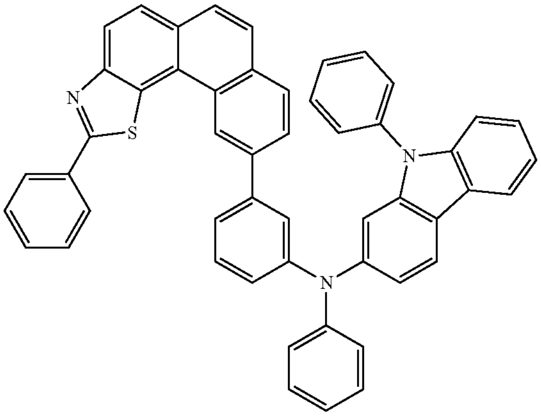
C-113
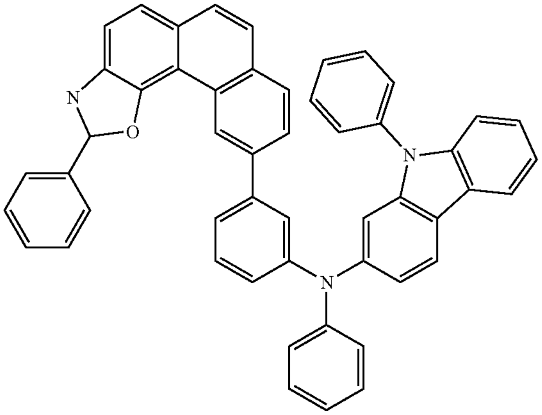
C-114
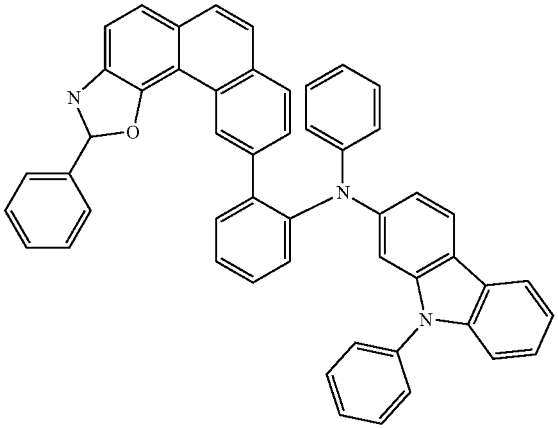

-continued
C-115
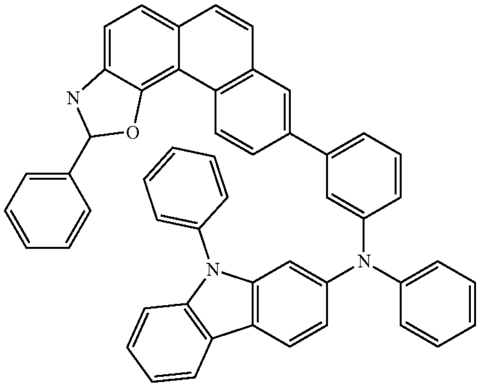
C-116
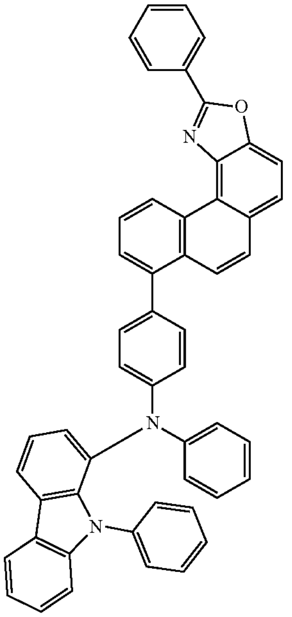
C-117
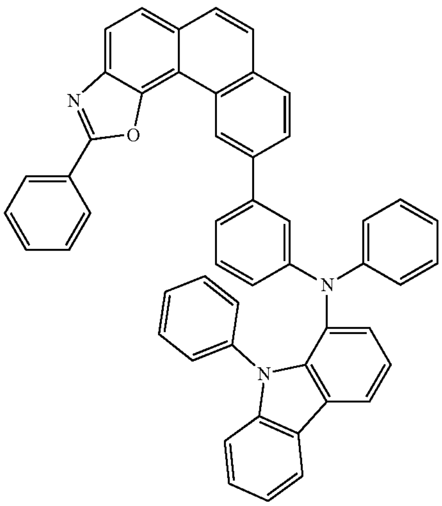
-continued
C-118
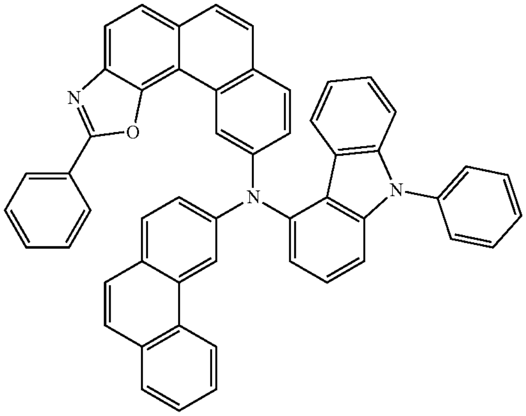
C-119
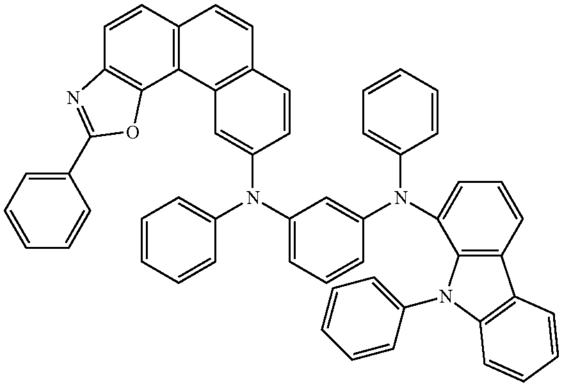
C-120
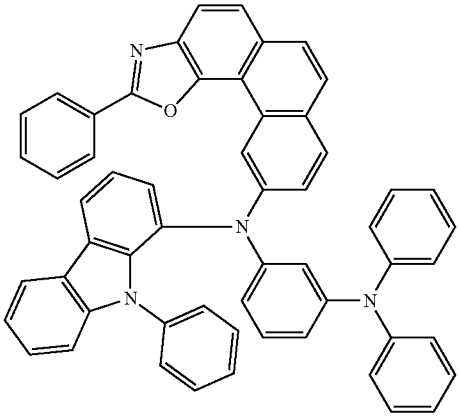
C-121
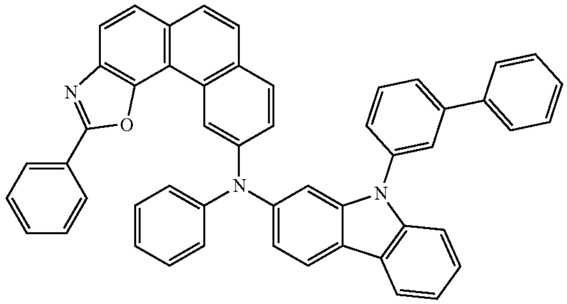

-continued
C-122
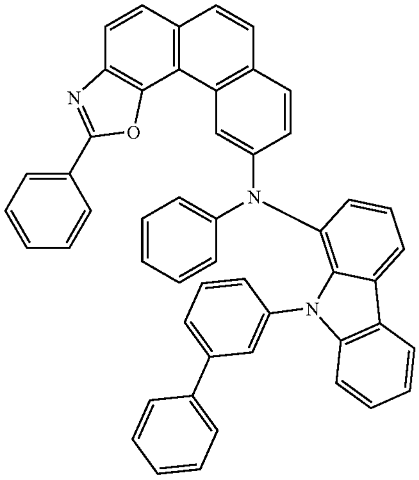
C-123
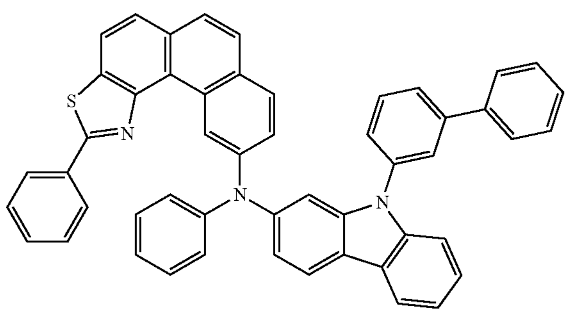
C-124
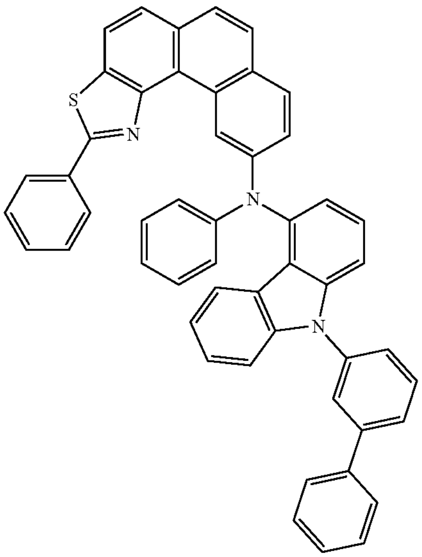
-continued
C-125
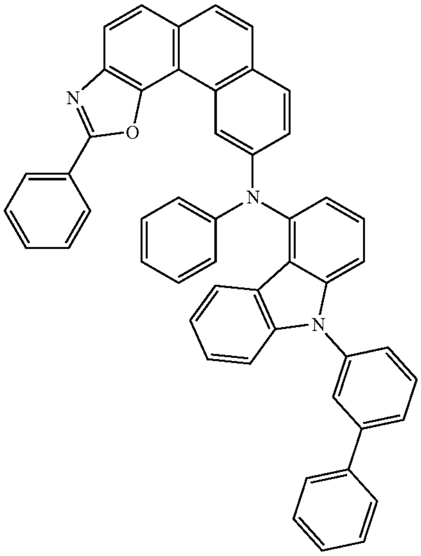
In compounds C-93 to C-97, $D_n$: 1-20 and $D_n$: 1-33 mean that 1 to 29 and 1 to 33 hydrogens may be replaced by deuterium, respectively.
The compound represented by formula 2 may be compounds selected from the following compounds, but are not limited thereto.
H2-1
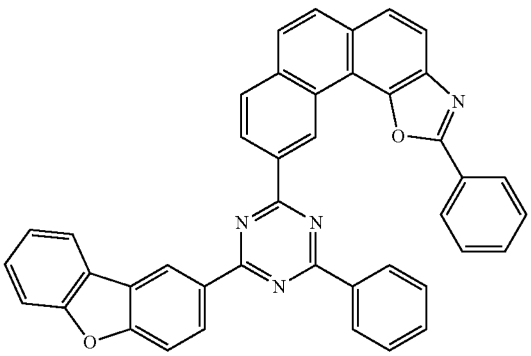
H2-2
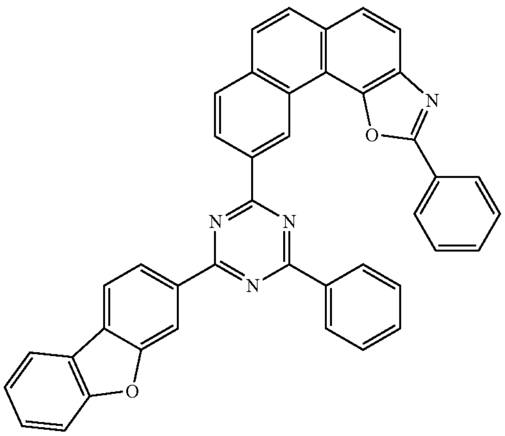

-continued
H2-3
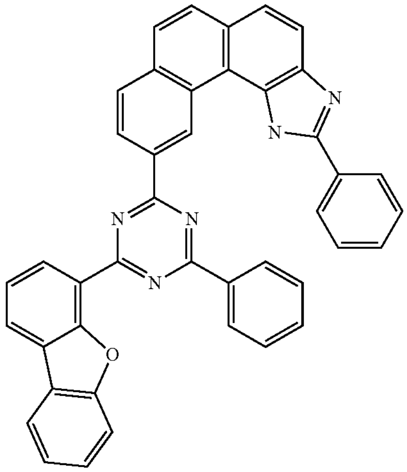
H2-4
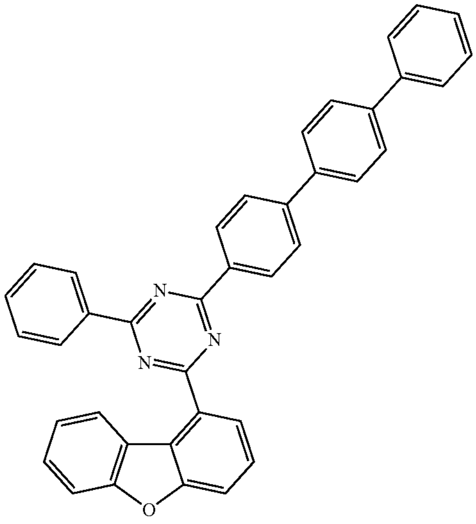
H2-5
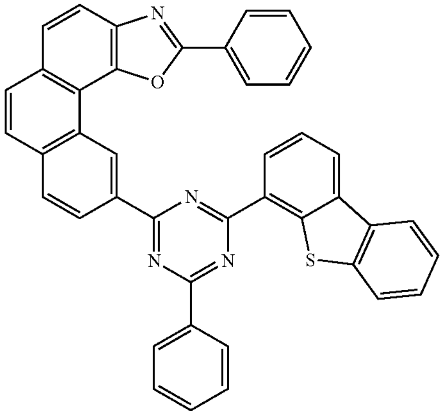
-continued
H2-6
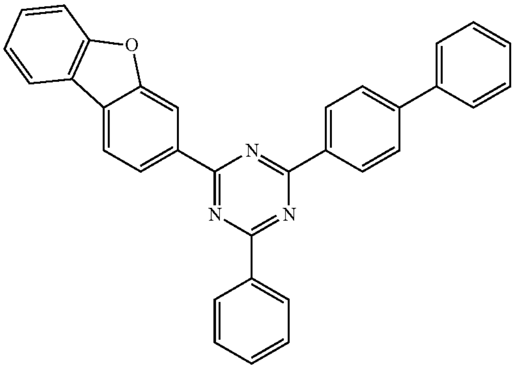
H2-7
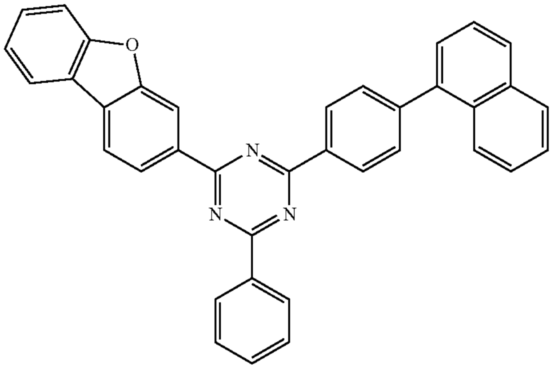
H2-8
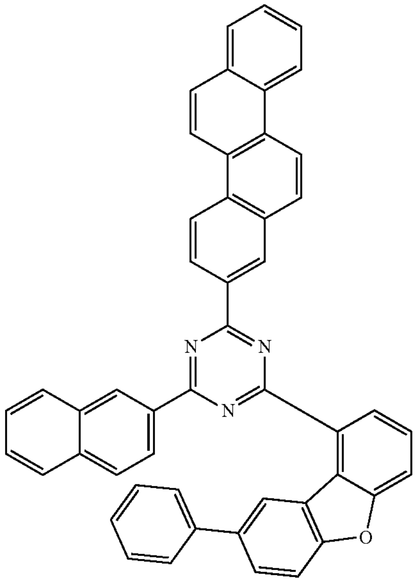

-continued
H2-9
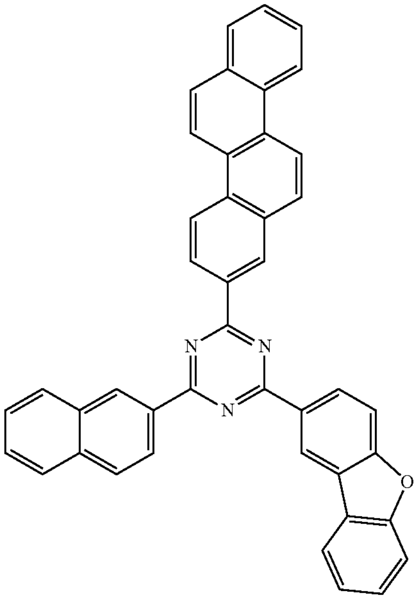
H2-10
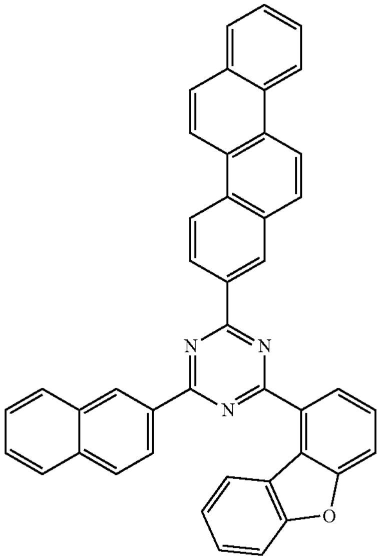
H2-11
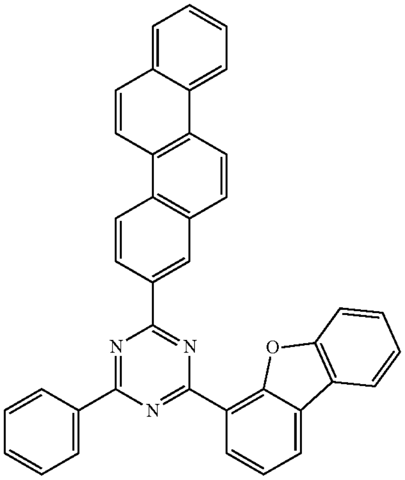
-continued
H2-12
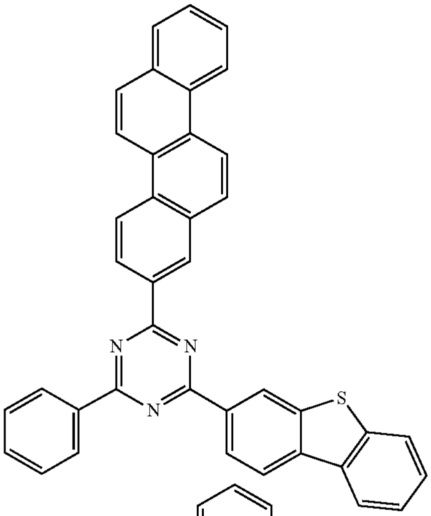
H2-13
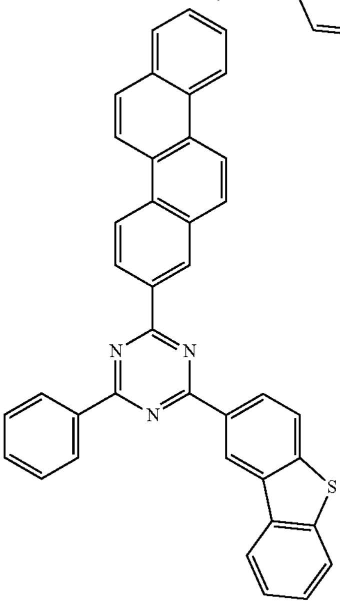
H2-14
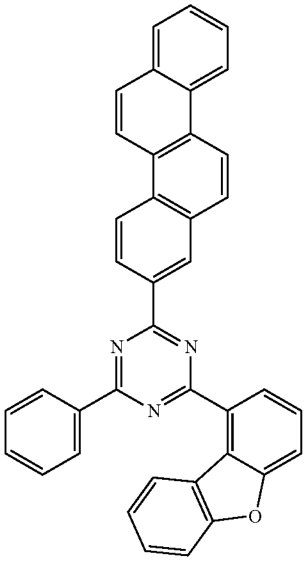

-continued
H2-15
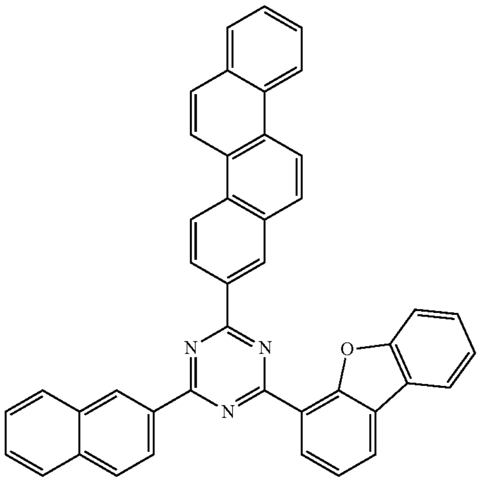
H2-16
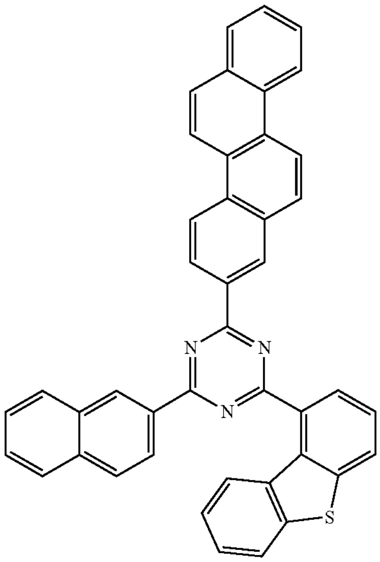
H2-17
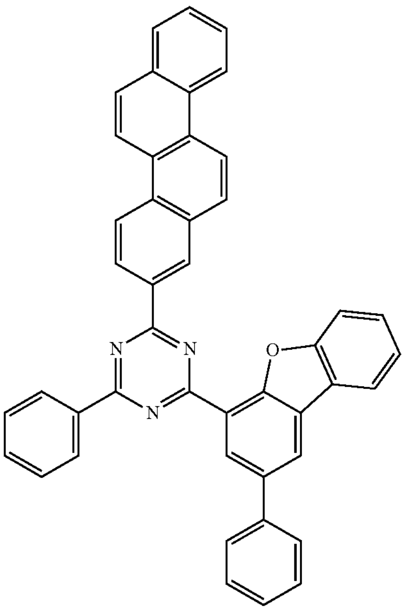
-continued
H2-18
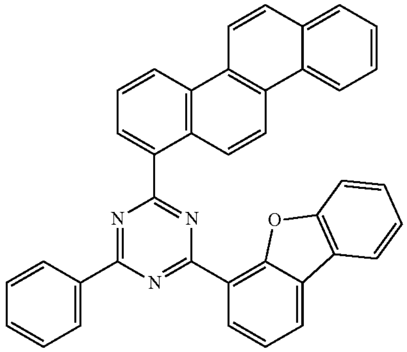
H2-19
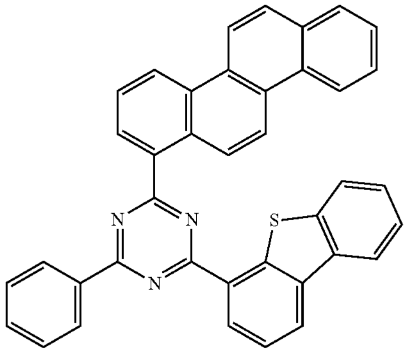
H2-20
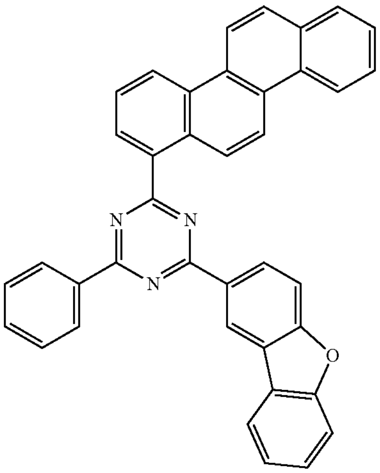
H2-21
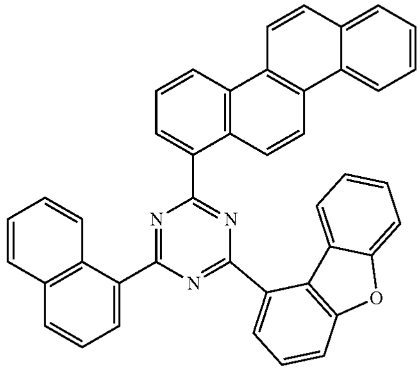

-continued
H2-22
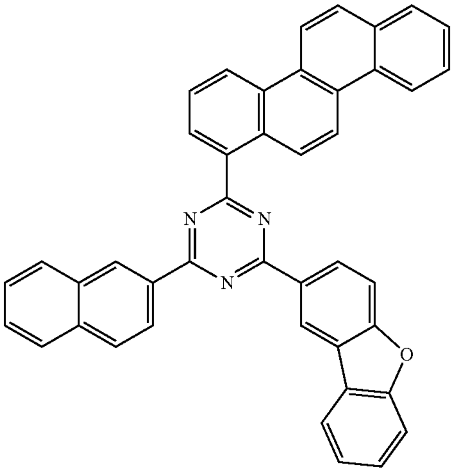
H2-23
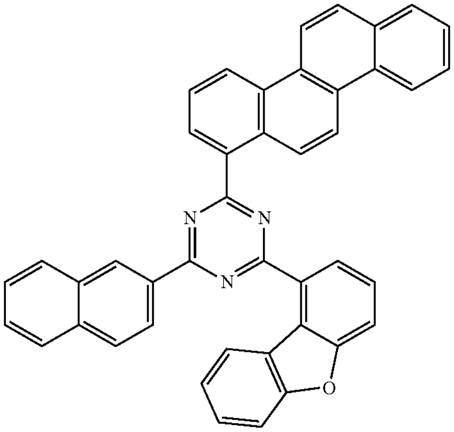
H2-24
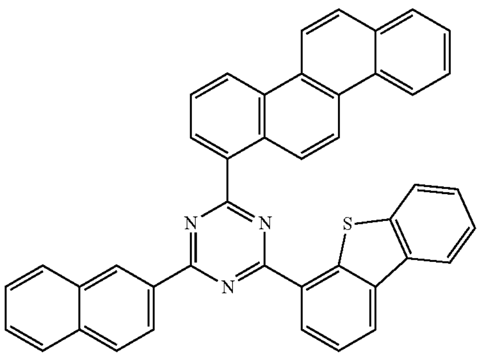
-continued
H2-25
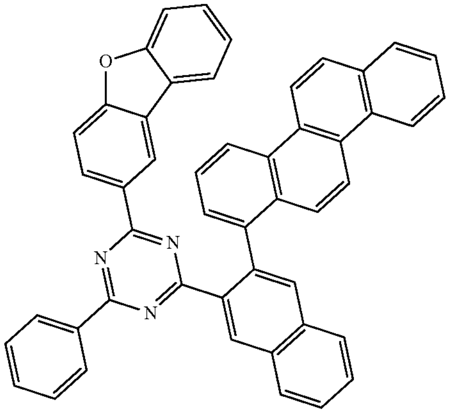
H2-26
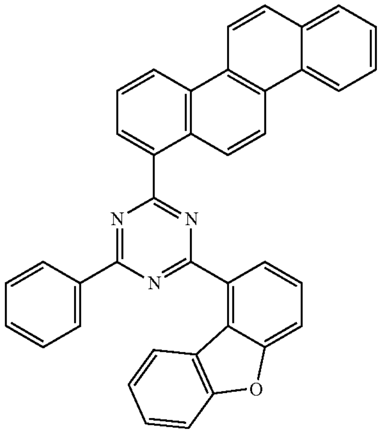
H2-27
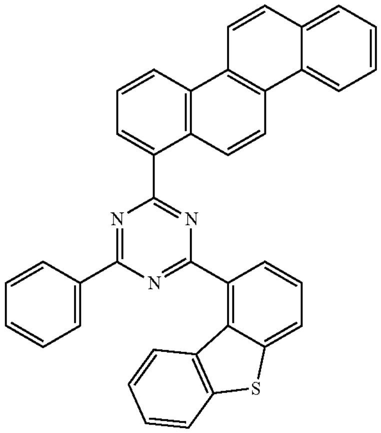

-continued
H2-28
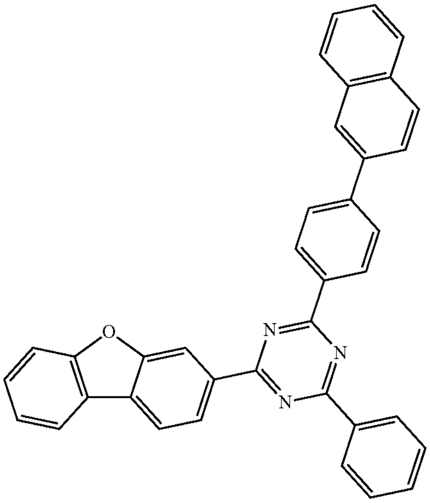
H2-29
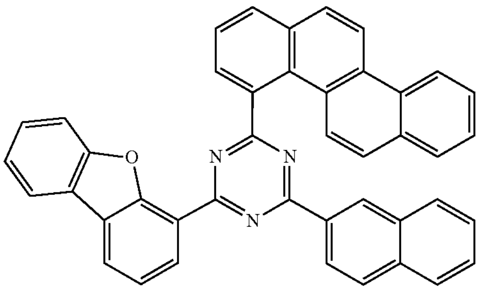
H2-30
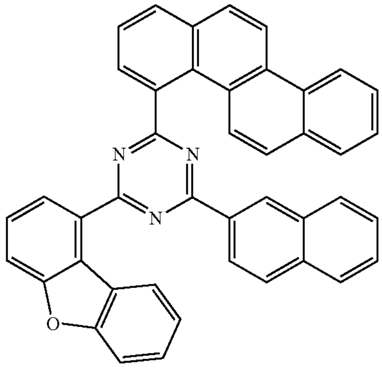
H2-31
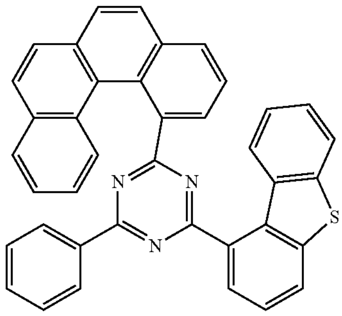
-continued
H2-32
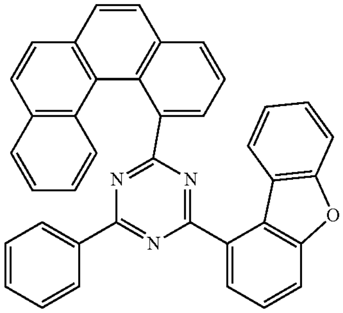
H2-33
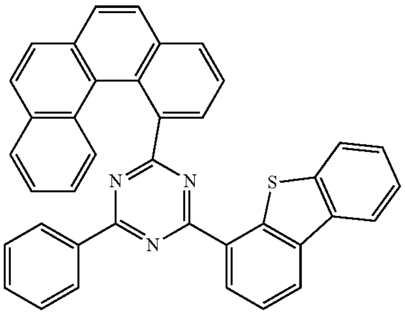
H2-34
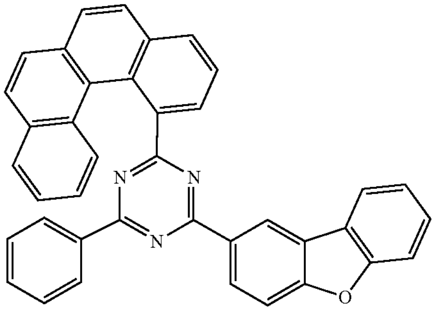
H2-35
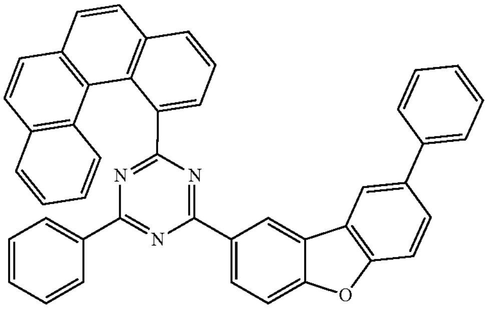
H2-36
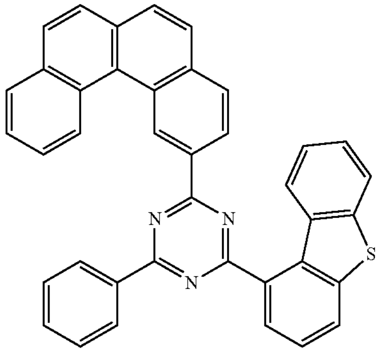

-continued
H2-37
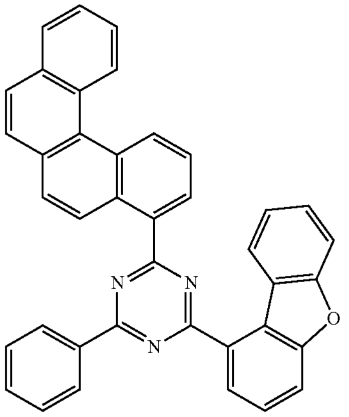
H2-38
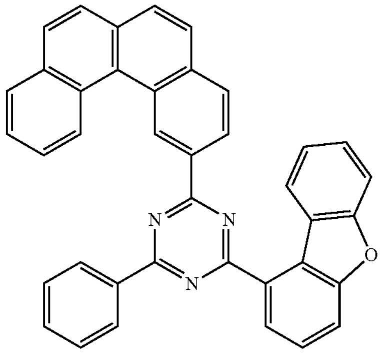
H2-39
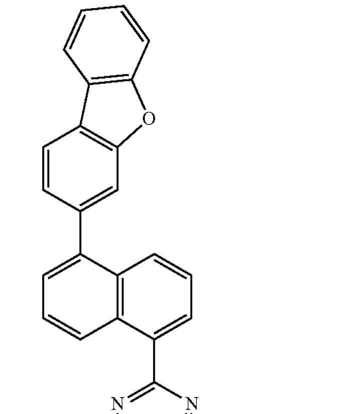
-continued
H2-40
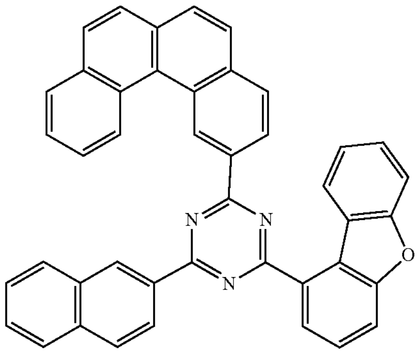
H2-41
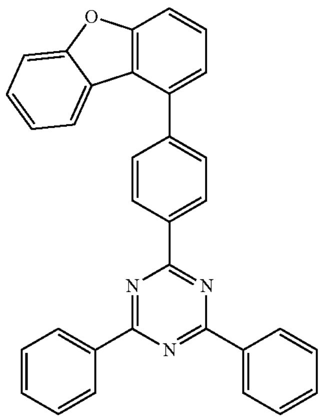
H2-42
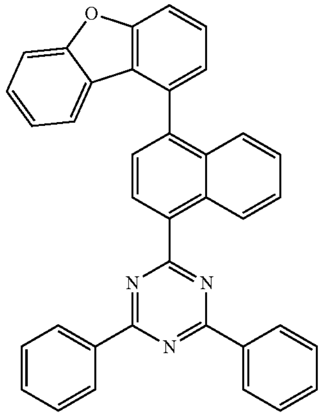
H2-43
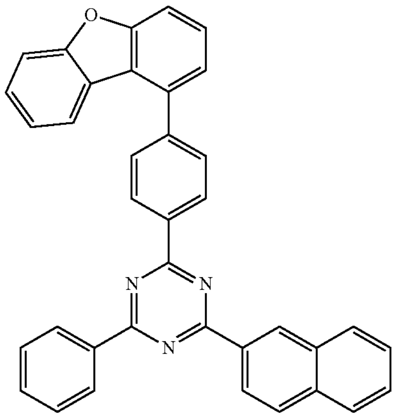

-continued
H2-44
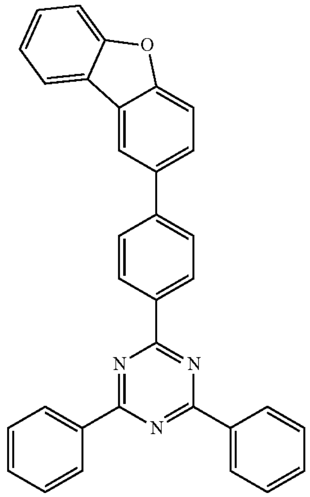
H2-45
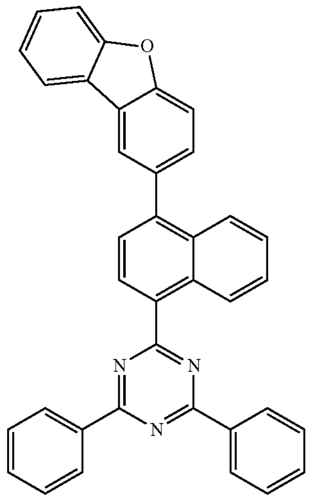
H2-46
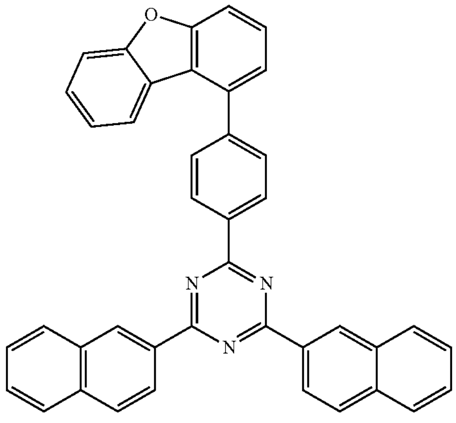
-continued
H2-47
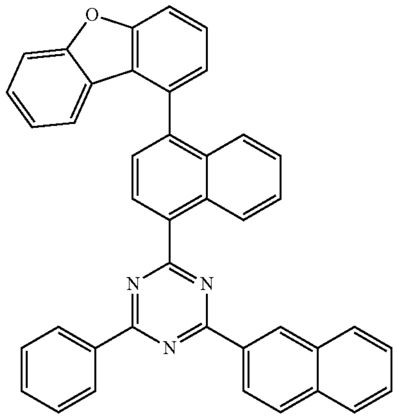
H2-48
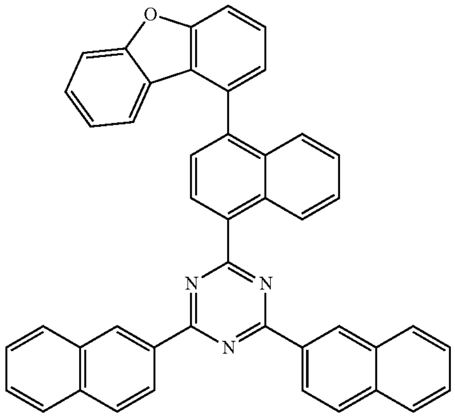
H2-49
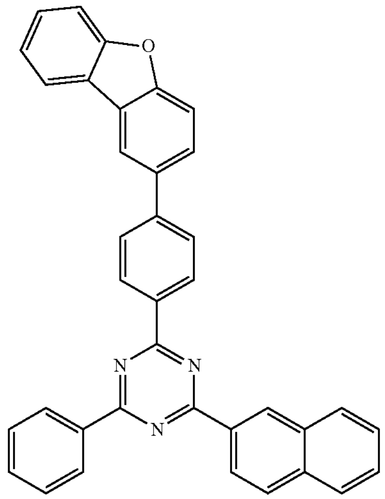

-continued
H2-50
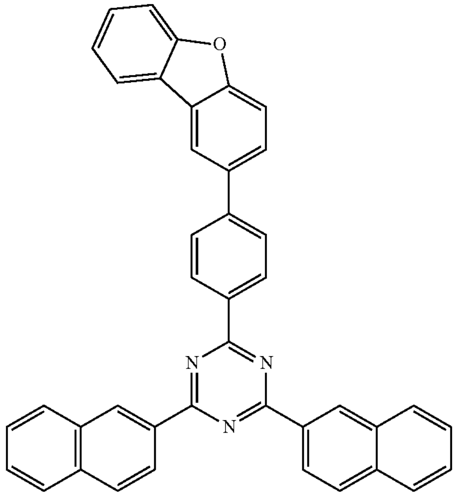
H2-51
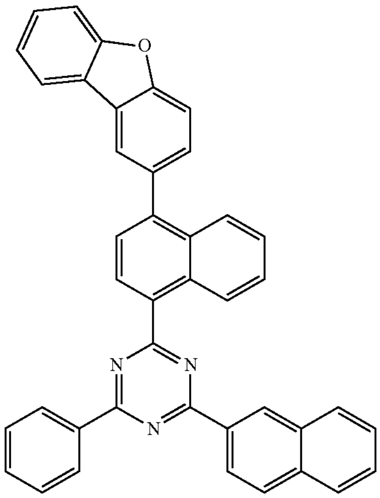
H2-52
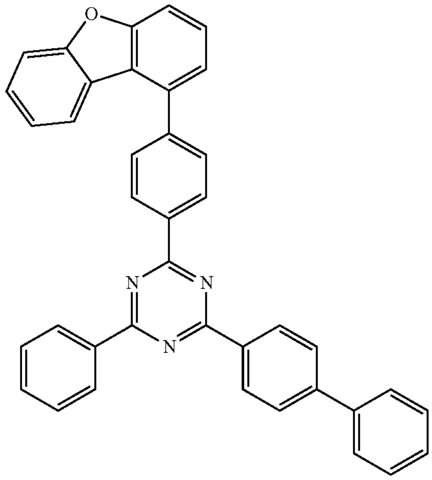
-continued
H2-53
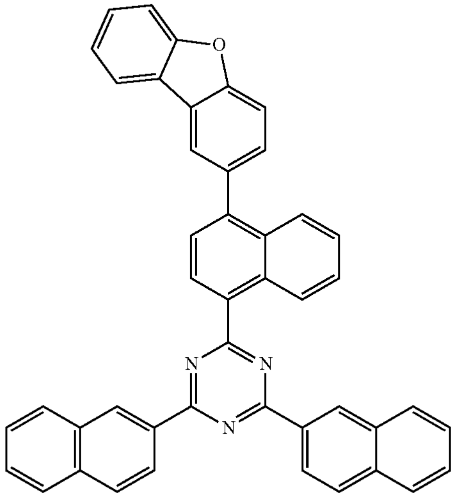
H2-54
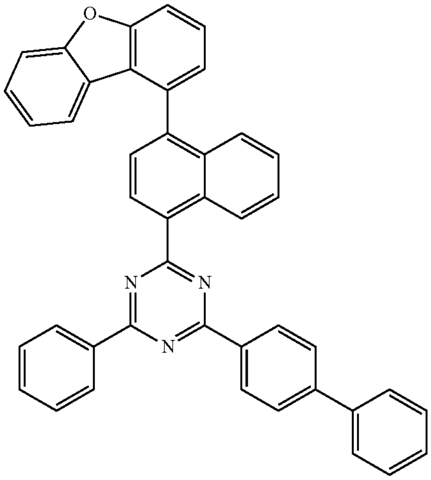
H2-55
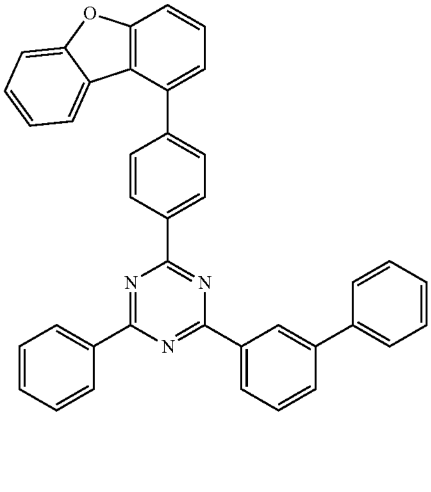

-continued
H2-56
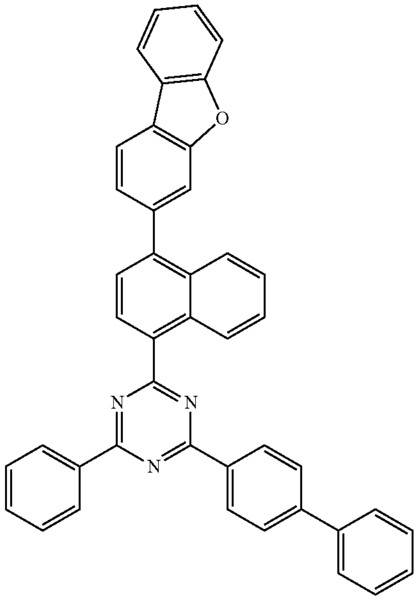
H2-57
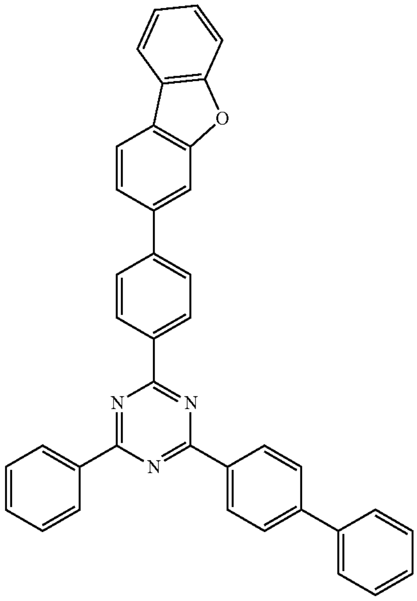
-continued
H2-58
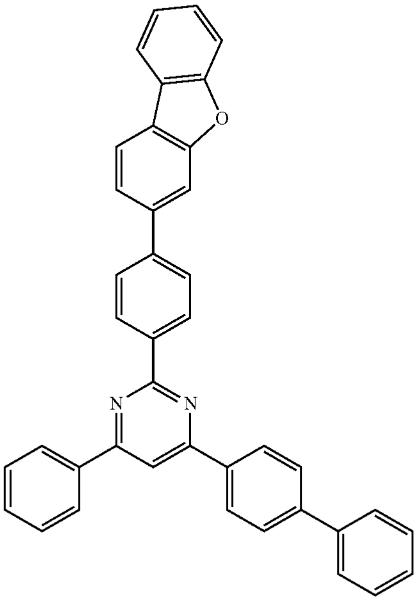
H2-59
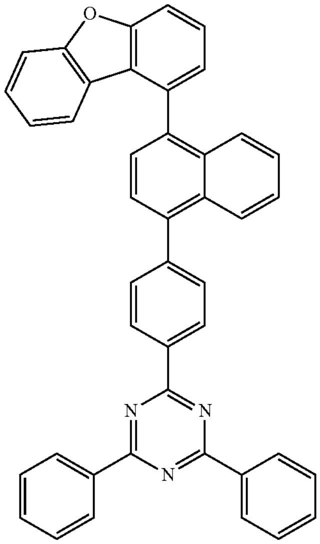
H2-60
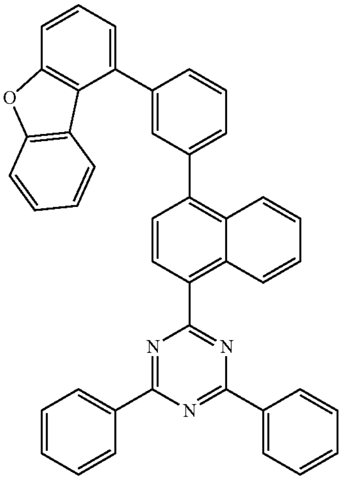

-continued
H2-61
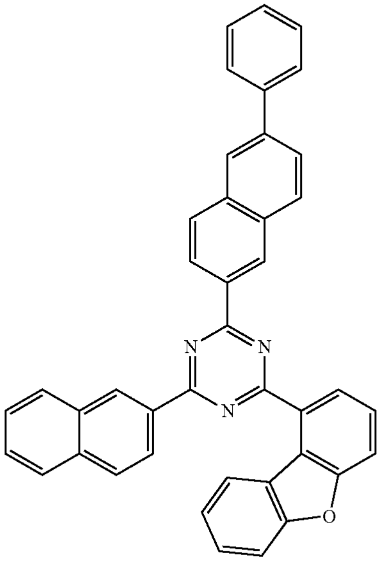
H2-62
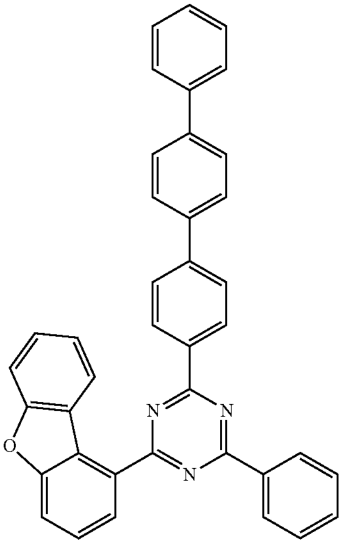
H2-63
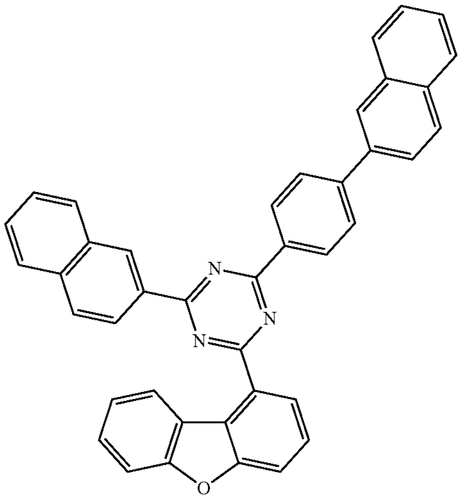
-continued
H2-64
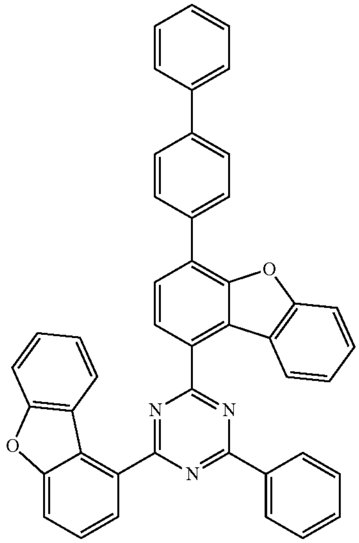
H2-65
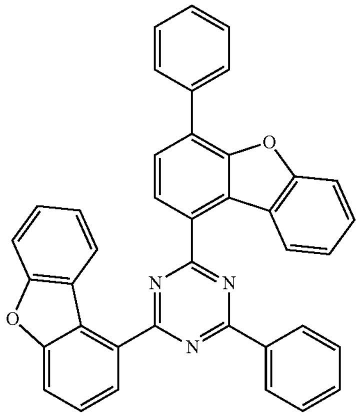
H2-66
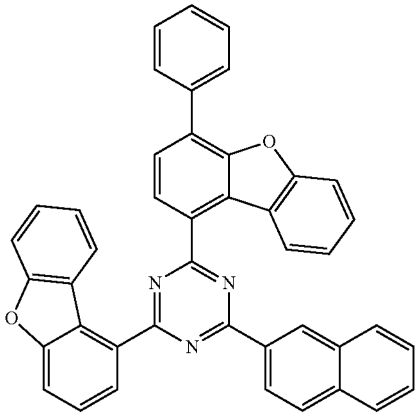

-continued
H2-67
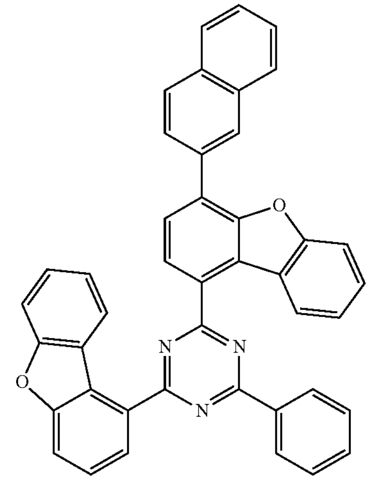
H2-68
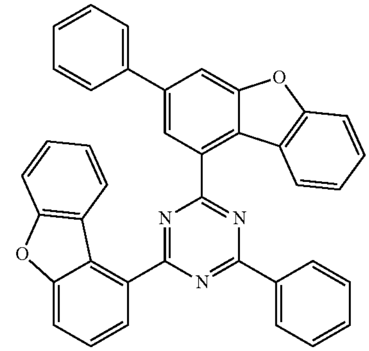
H2-69
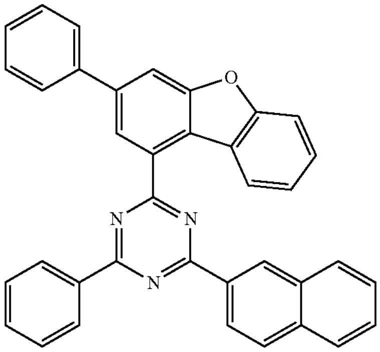
H2-70
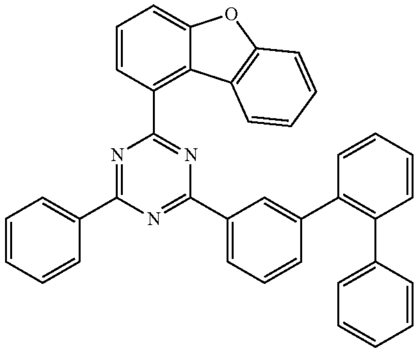
-continued
H2-71
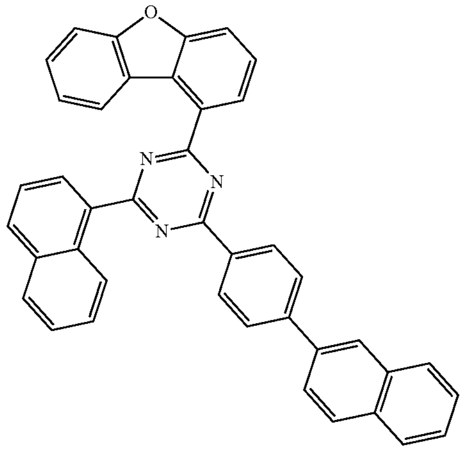
H2-72
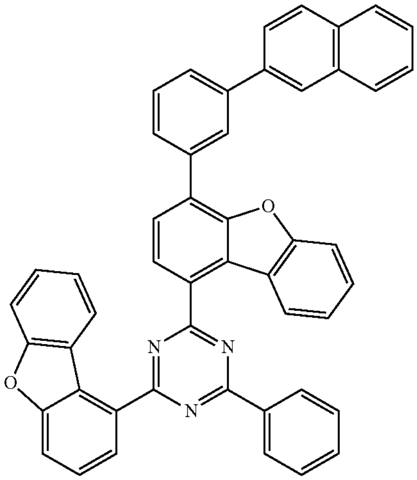
H2-73
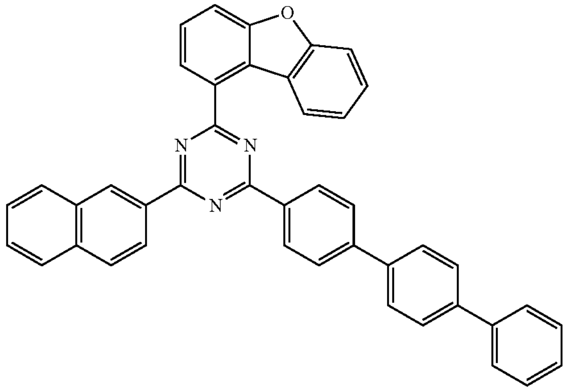

-continued
H2-74
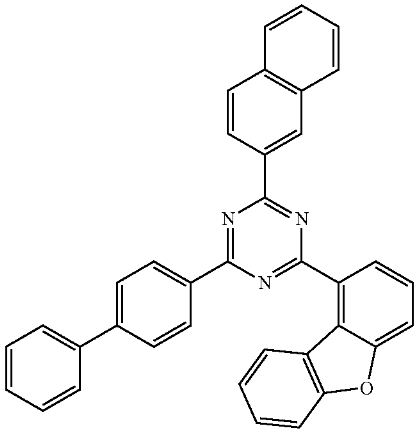
H2-75
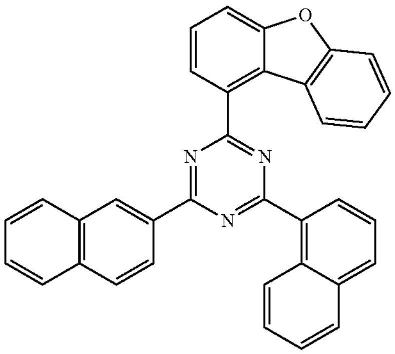
H2-76
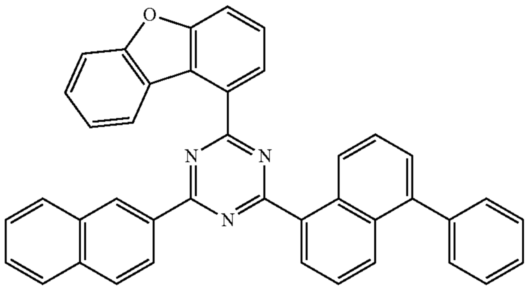
-continued
H2-77
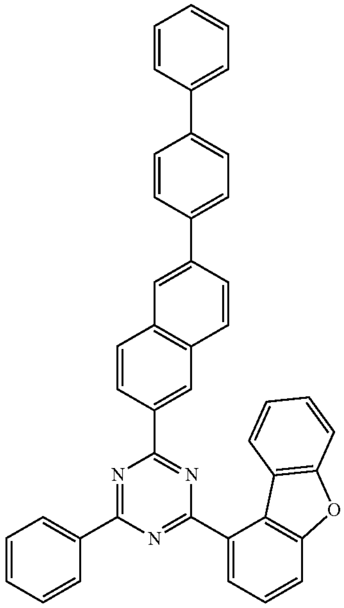
H2-78
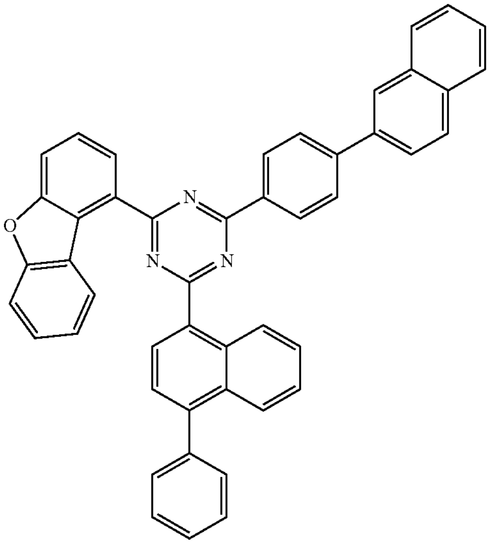
H2-79
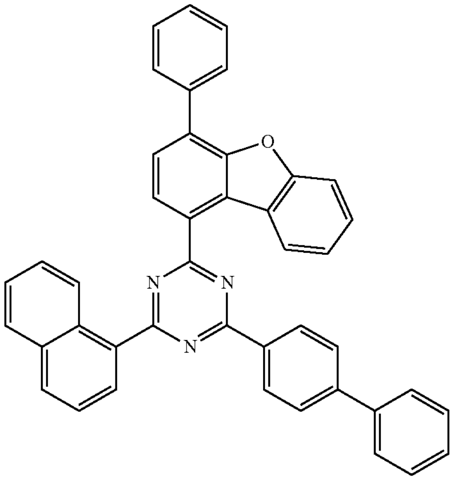

-continued
H2-80
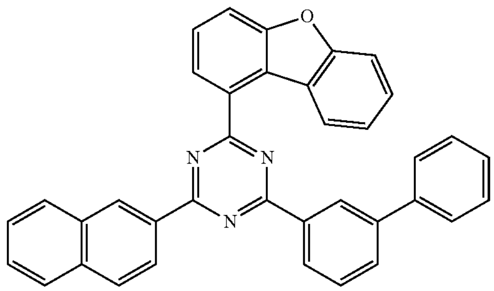
H2-81
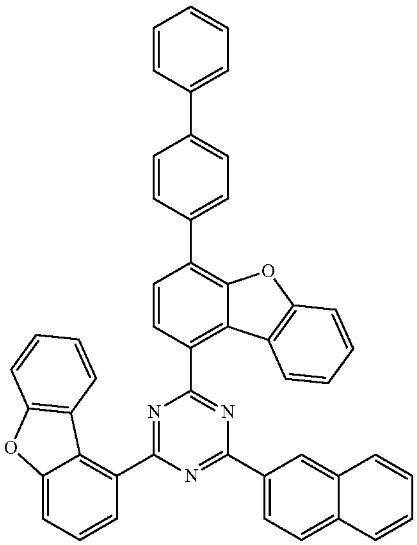
H2-82
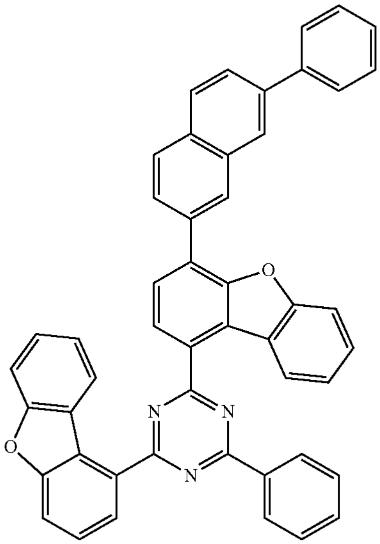
-continued
H2-83
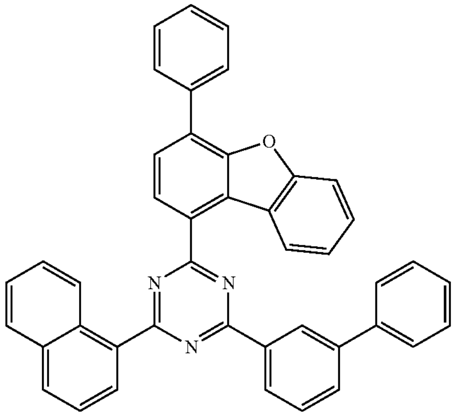
H2-84
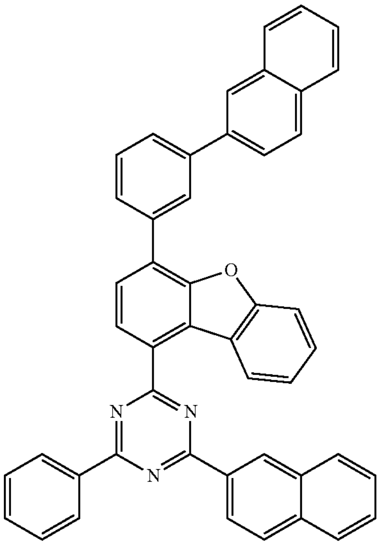
H2-85
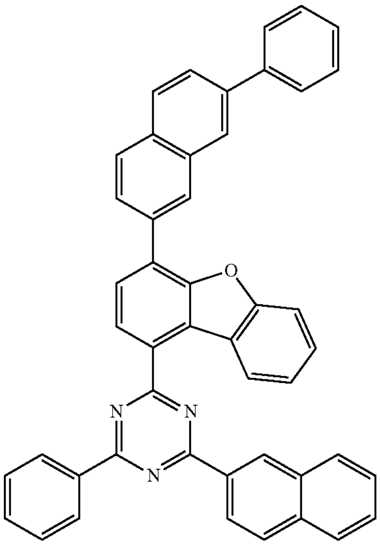

-continued
H2-86
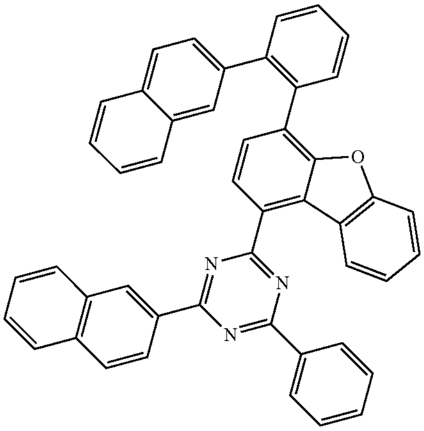
H2-87
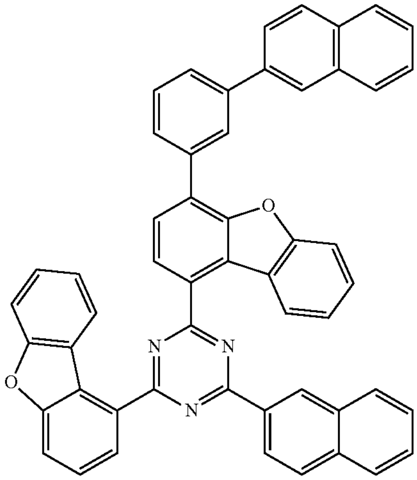
H2-88
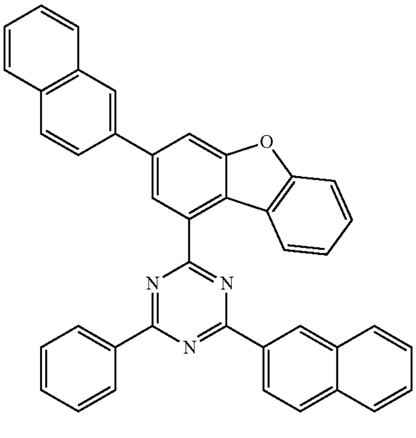
-continued
H2-89
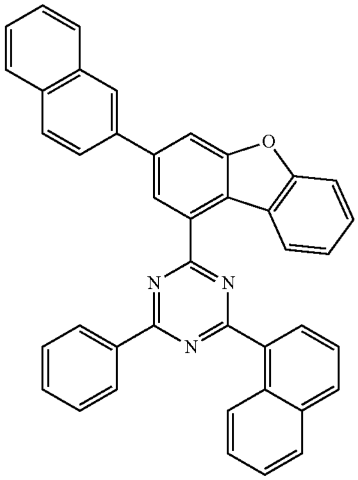
H2-90
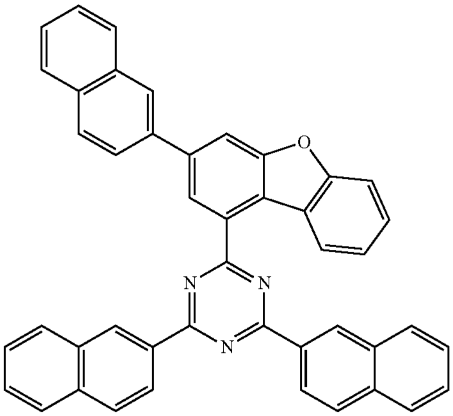
H2-91
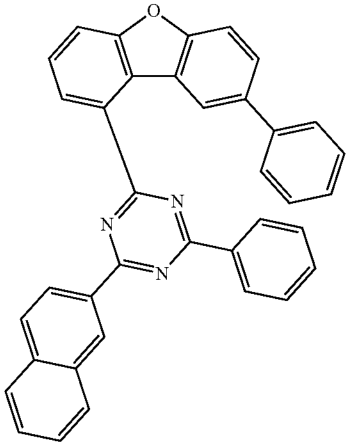

-continued
H2-92
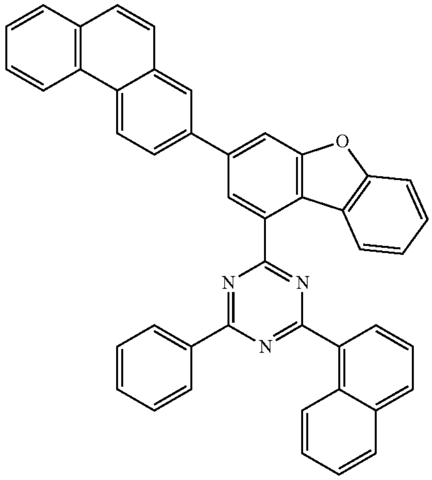
H2-93
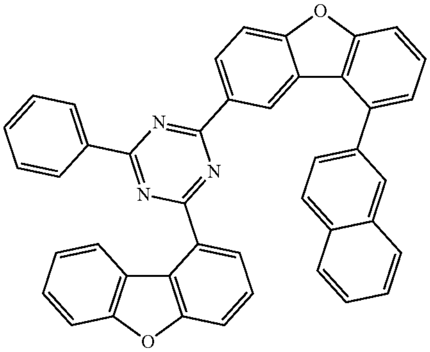
H2-94
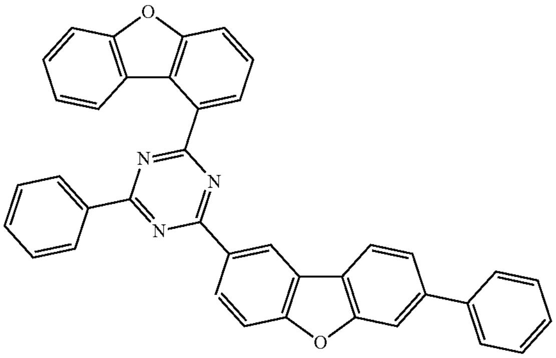
-continued
H2-95
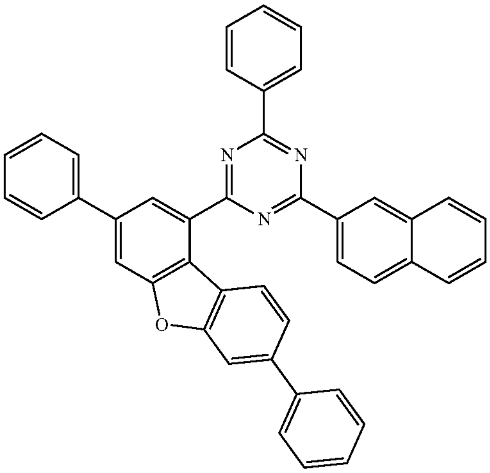
H2-96
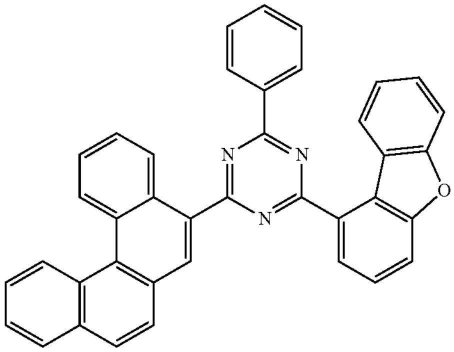
H2-97
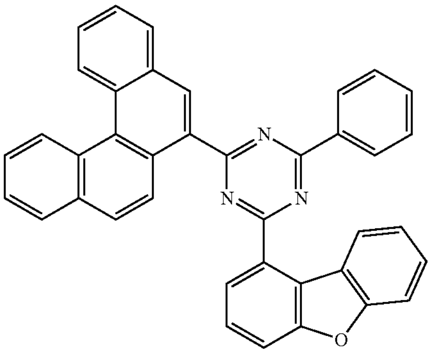
H2-98
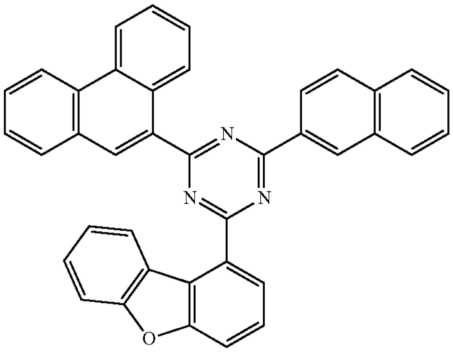

-continued
H2-99
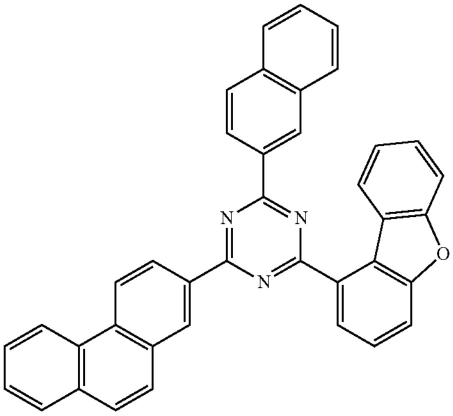
H2-100
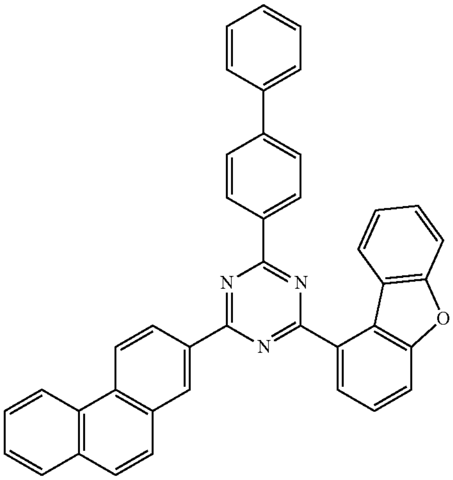
H2-101
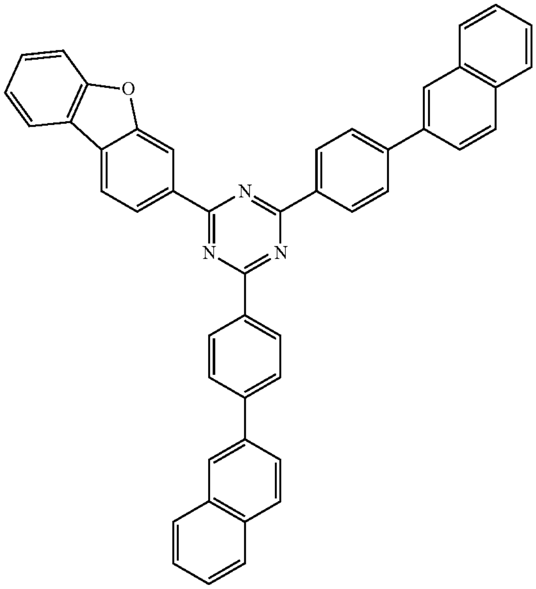
-continued
H2-102
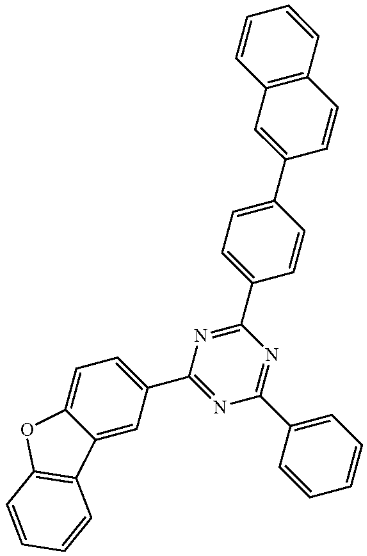
H2-103
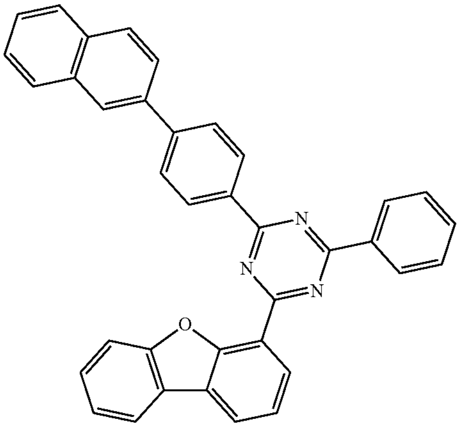
H2-104
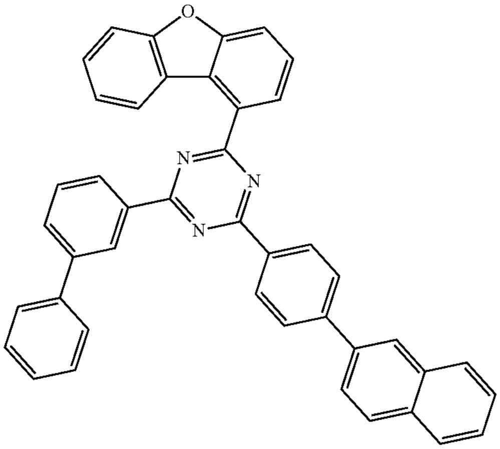

-continued
H2-105
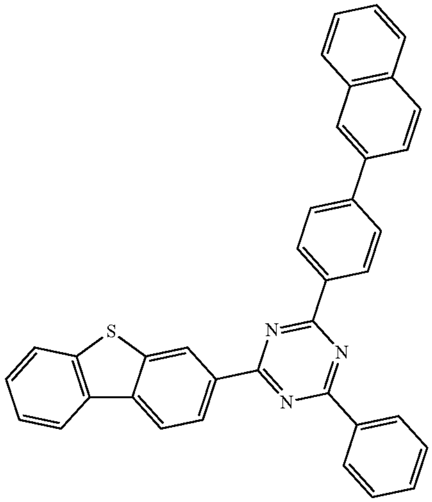
H2-106
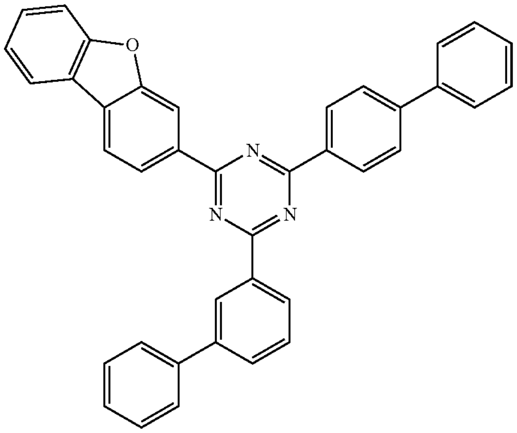
H2-107
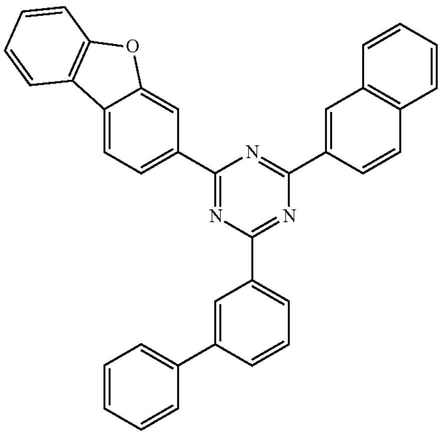
-continued
H2-108
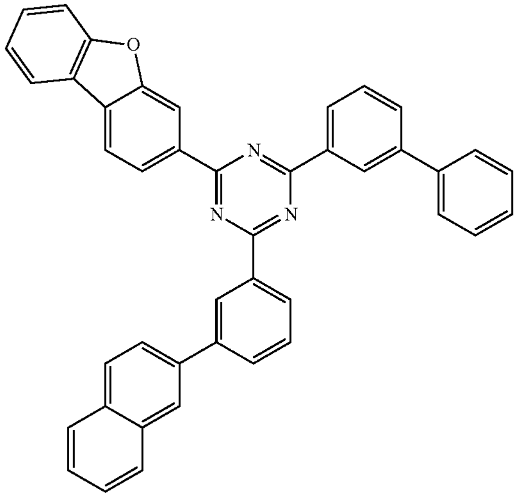
H2-109
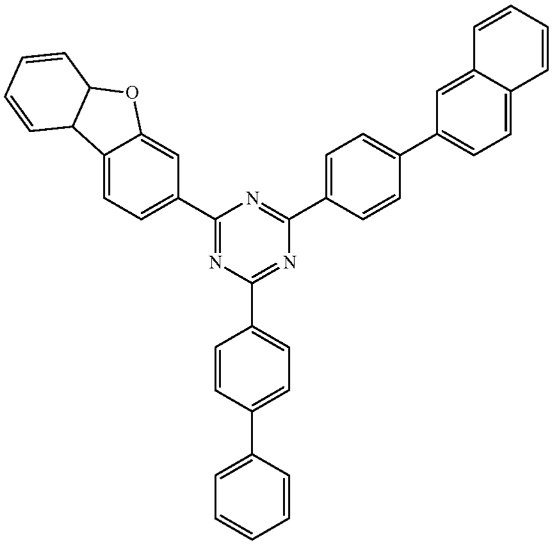
H2-110
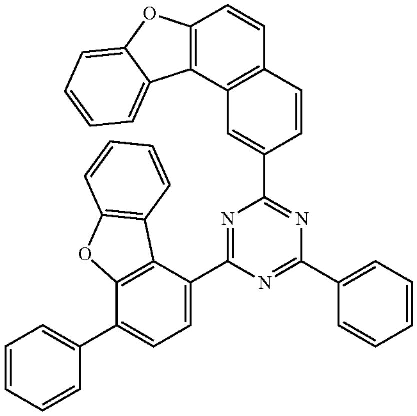

-continued
H2-111
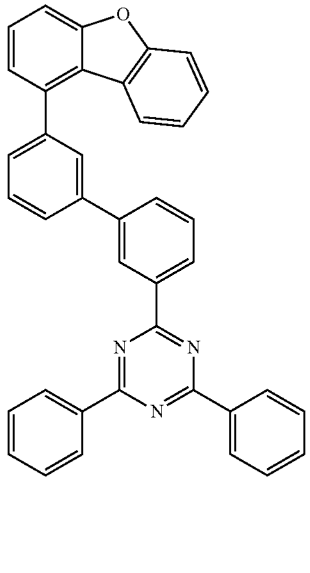
H2-112
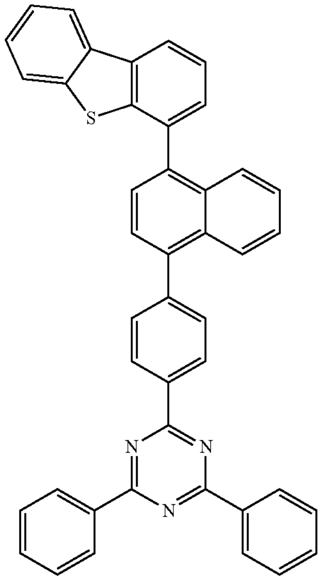
H2-113
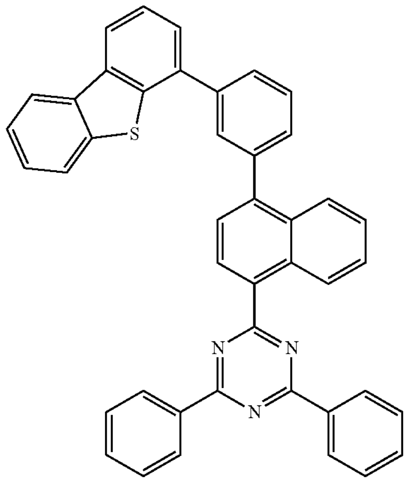
-continued
H2-114
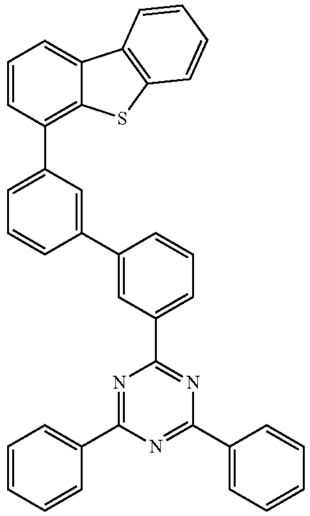
H2-115
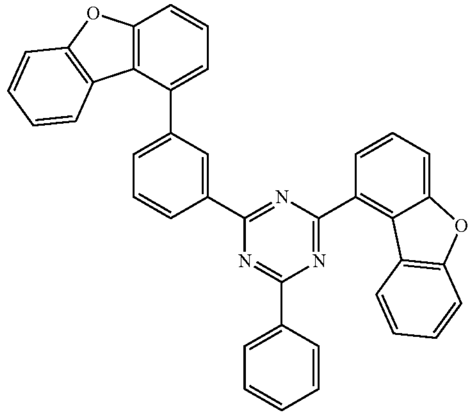
H2-116
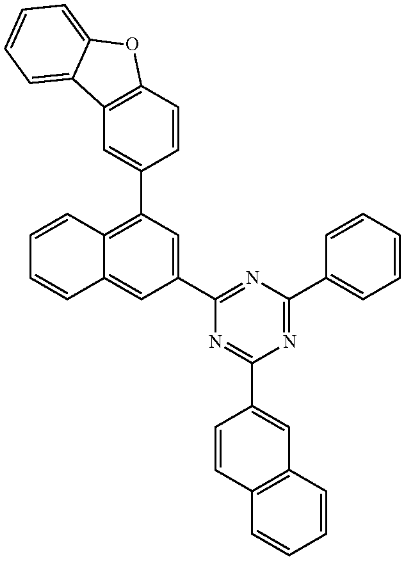

-continued
H2-117
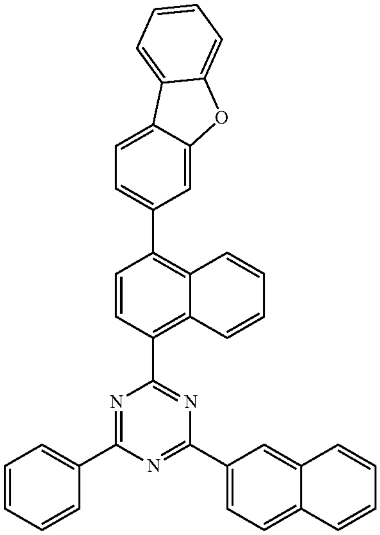
H2-118
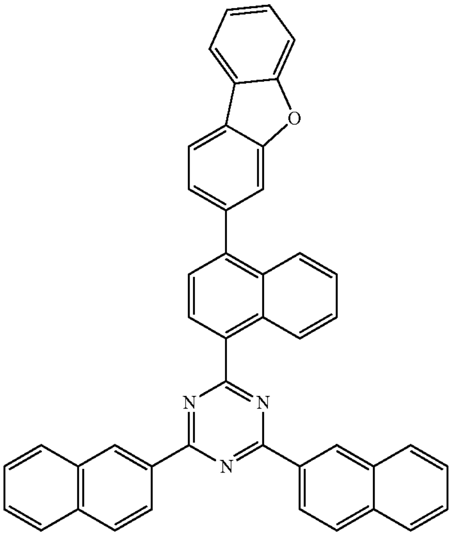
H2-119
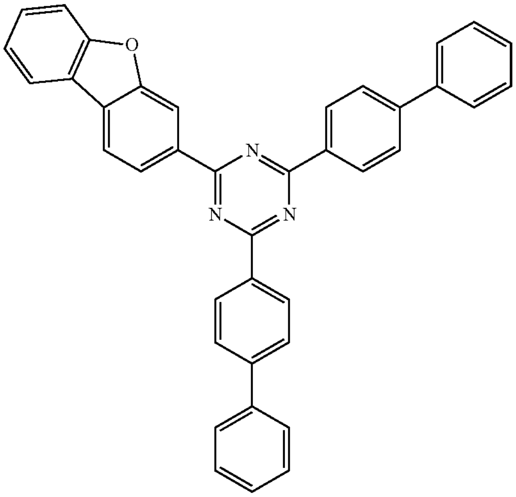
-continued
H2-120
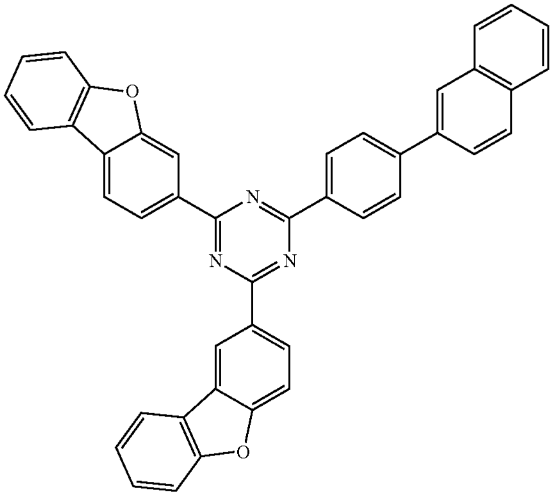
H2-121
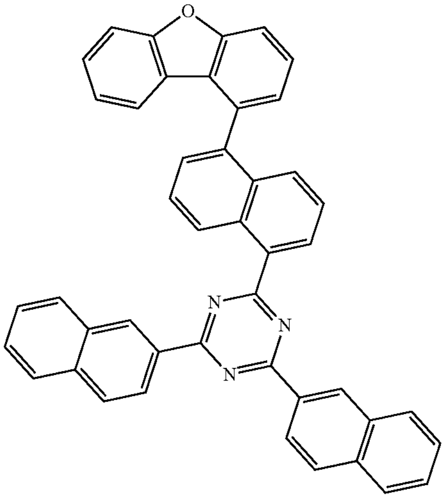
H2-122
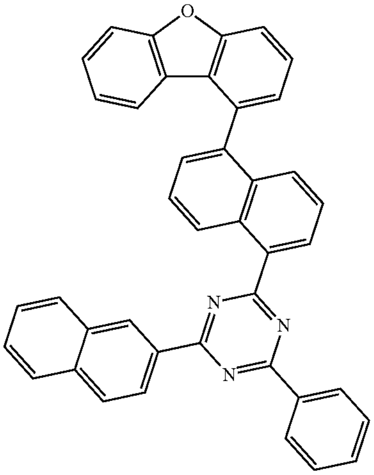

H2-123
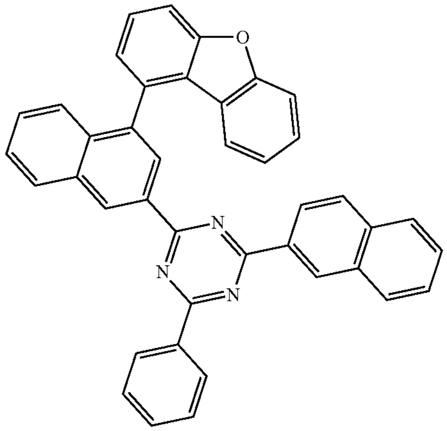
H2-124
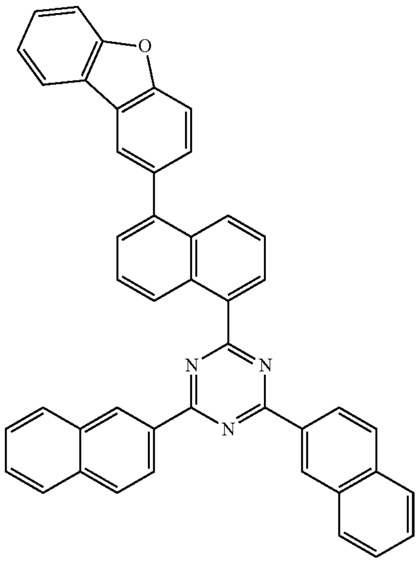
H2-125
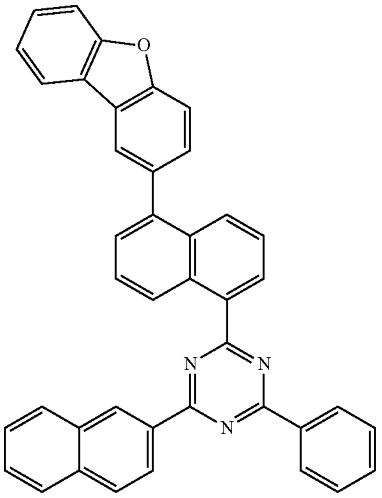
H2-126
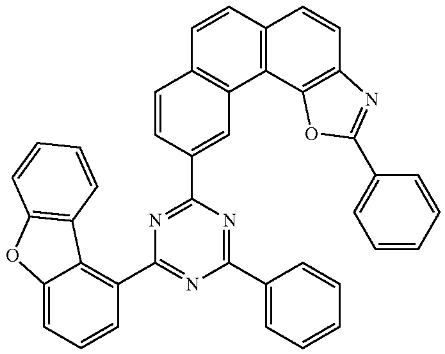
H2-127
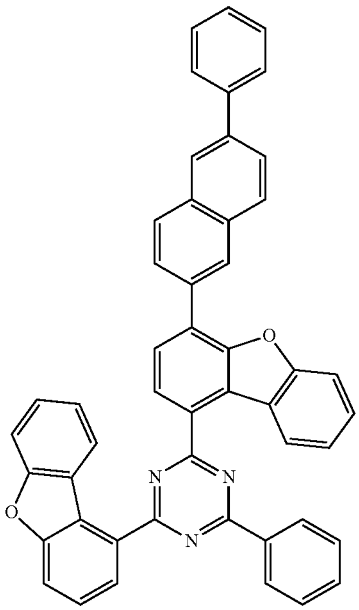
H2-128
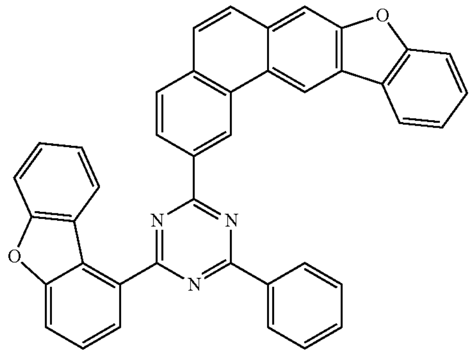

-continued
H2-129
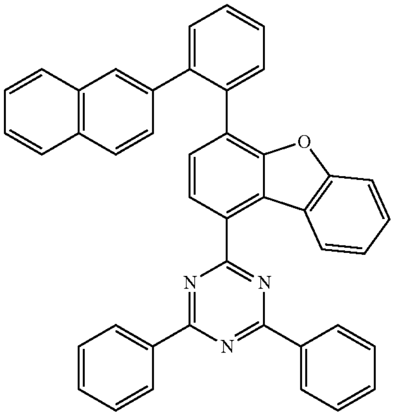
H2-130
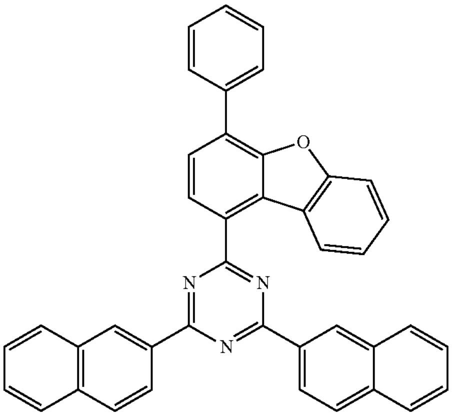
H2-131
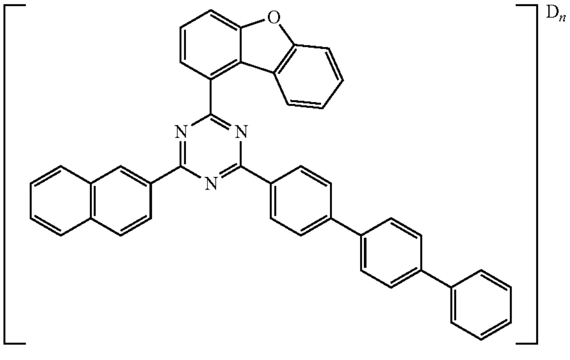
$D_n$: 1-27
-continued
H2-132
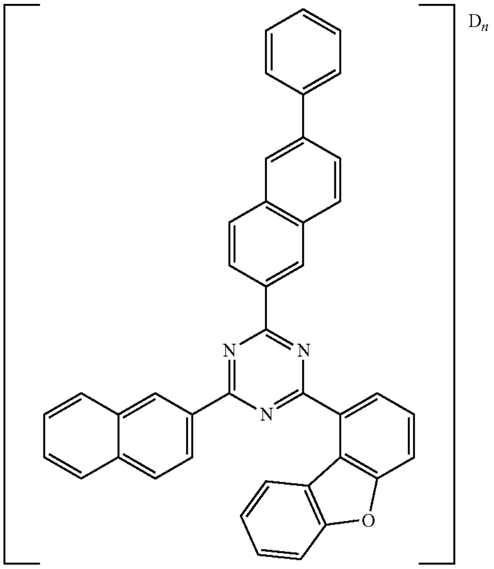
$D_n$: 1-25
H2-133
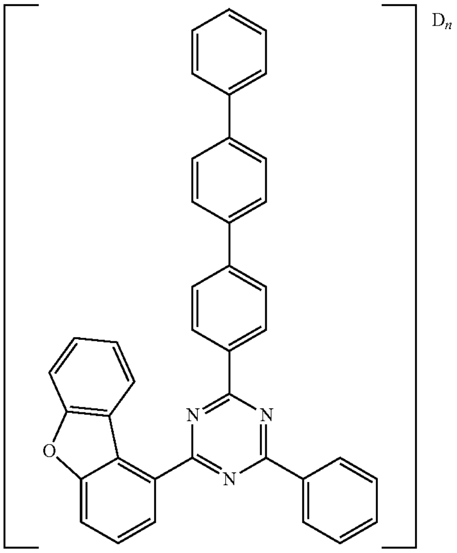
$D_n$: 1-25

-continued

H2-134

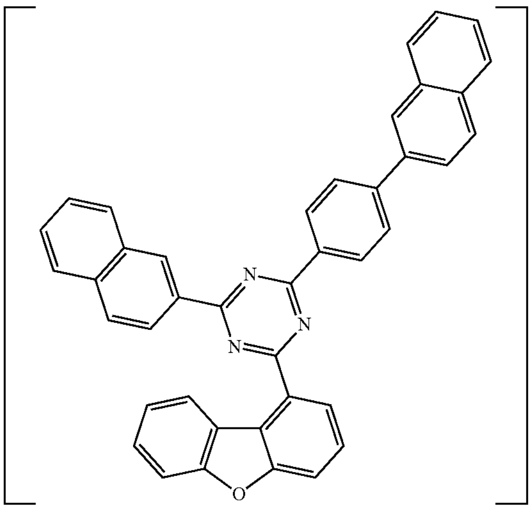

$D_n$: 1-25

H2-135

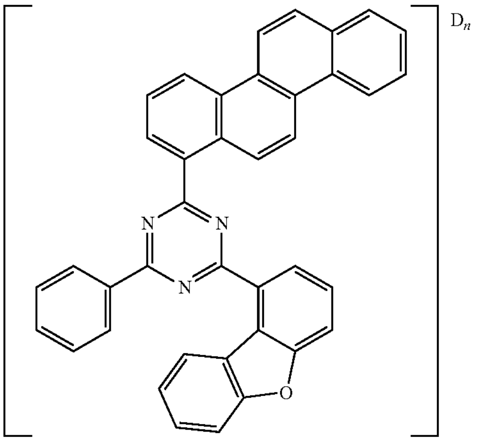

$D_n$: 1-23

H2-136

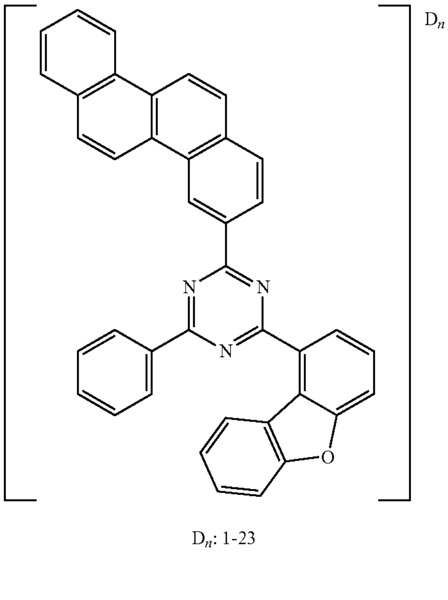

$D_n$: 1-23

In compounds H2-131 to H2-136, $D_n$: 1-23, $D_n$: 1-25, and $D_n$: 1-27 mean that 1 to 23, 1 to 25, and 1 to 27 hydrogens may be replaced by deuterium, respectively.

At least one of compounds C-1 to C-125 and at least one of compounds H2-1 to H2-136 may be combined and used in an organic electroluminescence device.

The compounds represented by formulas 1 and 1` according to the present disclosure may be prepared by a synthetic method known to a person skilled in the art, and for example, the compounds represented by formulas 1-1 to 1-5 may be prepared as shown in Reaction Scheme 1 or 2 below, but is not limited thereto.

[Reaction Scheme 1]

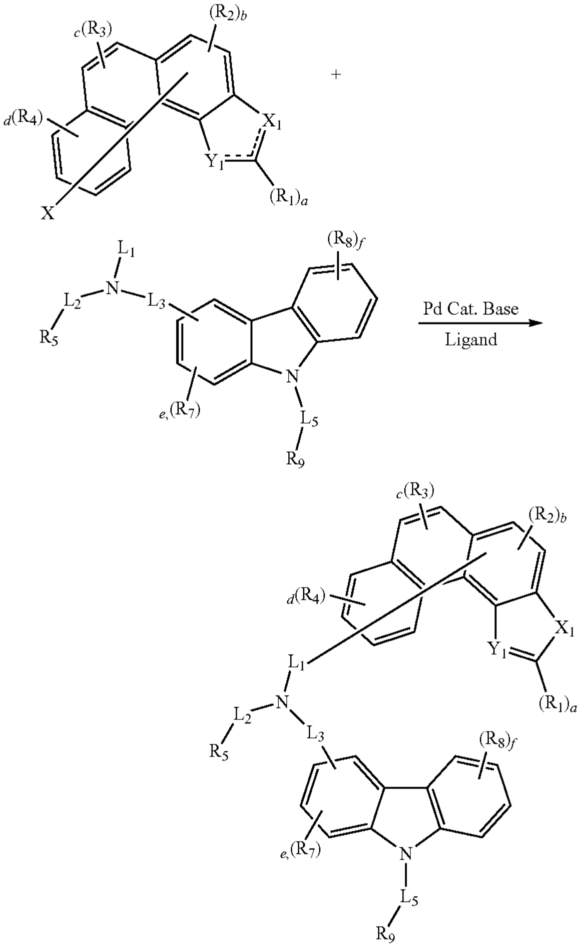

[Reaction Scheme 2]

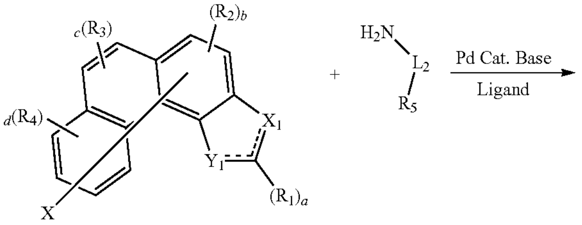

-continued

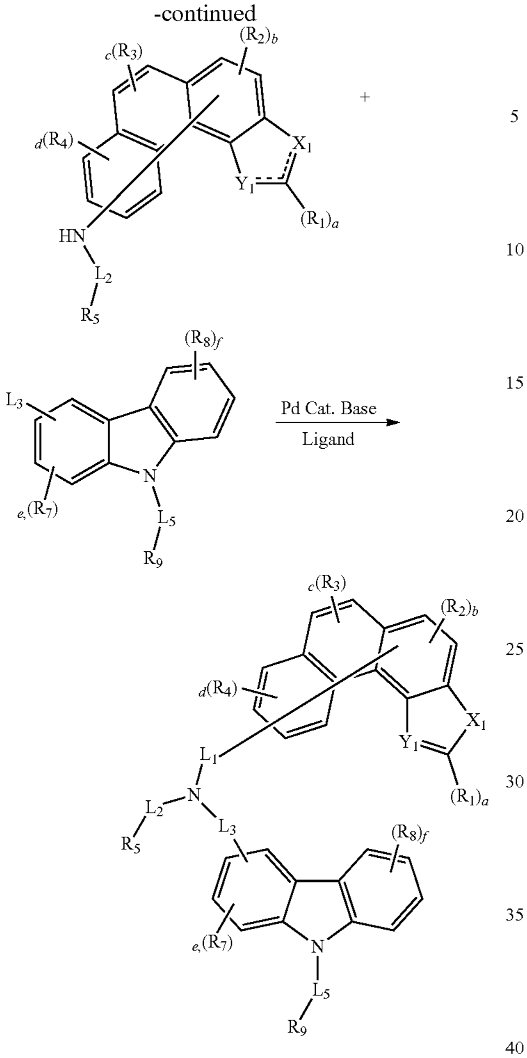

In Reaction Schemes 1 and 2, $X_1$, $Y_1$, $L_1$ to $L_3$, $R_1$ to $R_5$, $R_7$ to $R_{10}$, a to f, and e\` are the same as defined in formulas 1, 1\`, 1-A and 1-B, and $L_5$ is as defined in formulas 1-1 to 1-5.

The compound represented by formula 2 according to the present disclosure may be prepared by a synthetic method known to a skilled in the art, and for example, the compound represented by formula 2-1 or 2-2 may be prepared according to the synthetic methods described in KR 10-2020-0026079 A, KR 10-2020-0043269 A, and KR 10-2021-0109436 A.

The organic electroluminescent device according to the present disclosure comprises a first electrode; a second electrode; and one or more organic material layers interposed between the first electrode and the second electrode.

One of the first electrode and the second electrode may be an anode and the other may be a cathode. The organic layer may comprise a light-emitting layer and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Here, the second electrode may be a transflective electrode or a reflective electrode, and may be a front emission type, a rear emission type, or a both surface emission type according to a material. In addition, the hole injection layer may further be doped with a p-dopant, and the electron injection layer may further be doped with an n-dopant.

The organic electroluminescent device according to the present disclosure may comprise an anode, a cathode, and at least one organic material layer between the anode and the cathode, and the organic material layer may comprise a plurality of organic electroluminescent materials comprising a compound represented by formula 1 as a first organic electroluminescent material, and a compound represented by formula 2 as a second organic electroluminescent material. According to one embodiment of the present disclosure, the organic electroluminescent device according to the present disclosure may comprise an anode, a cathode, and at least one light-emitting layer between the anode and the cathode, wherein the light-emitting layer may comprise a compound represented by formula 1 and a compound represented by formula 2.

The light-emitting layer may include a host and a dopant, the host may include a plurality of host materials, the compound represented by formula 1 may be comprised as a first host compound among the plurality of host materials, and the compound represented by formula 2 may be comprised as a second host compound among the plurality of host materials. Here, the weight ratio of the first host compound and the second host compound is about 1:99 to about 99:1, preferably about 10:90 to about 90:10, more preferably about 30:70 to about 70:30, more preferably about 40:60 to about 60:40, and even more preferably about 50:50.

In the present disclosure, the light-emitting layer is a layer on which light is emitted, and may be a single layer, or may be a plurality of layers in which two or more layers are stacked. In the plurality of host materials of the present disclosure, both the first and second host materials may be comprised in one layer, or the first and second host materials may be comprised in different light-emitting layers. According to one embodiment of the present disclosure, a doping concentration of the dopant compound with respect to the host compound of the light-emitting layer may be less than 20 wt %.

According to one embodiment of the present disclosure, the organic electroluminescent device of the present disclosure may further comprise an an amine-based compound as at least one of a hole injection material, a hole transport material, a hole auxiliary material, a light-emitting material, a light-emitting auxiliary material, and an electron blocking material in addition to the plurality of host materials of the present disclosure. In addition, according to one embodiment of the present disclosure, the organic electroluminescent device of the present disclosure may further comprise an azine-based compound as at lease one of an electron transport material, an electron injection material, an electron buffer material, and a hole blocking material in addition to the plurality of host materials of the present disclosure.

In the organic electroluminescent device of the present disclosure, a hole-injection layer, a hole-transport layer, or an electron-blocking layer, or a combination thereof, may be used between the anode and the light-emitting layer For the hole-injection layer, a plurality of layers may be used for the purpose of lowering the hole-injection barrier (or hole-injection voltage) from the anode to the hole-transport layer or electron-blocking layer, and each layer may have two compounds used simultaneously. The hole transport layer or electron blocking layer may also have a plurality of layers.

In addition, a layer selected from an electron buffer layer, a hole blocking layer, an electron transport layer, or an electron injection layer or a combination thereof may be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. A plurality of layers may be used for the hole blocking layer or electron transport layer, and a plurality of compounds may be used for each layer.

In addition, the organic electroluminescent compound or the plurality of host materials according to one embodiment may also be applied to the organic electroluminescent device comprising a quantum dot (QD).

In addition, the plurality of host materials according to one embodiment may be used as light-emitting materials for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. In addition, the plurality of host materials according to one embodiment may also be applied to the organic electroluminescence device comprising a quantum dot (QD).

A hole injection layer, a hole transport layer, an electron blocking layer, or a combination thereof may be used between the anode and the light-emitting layer. For the hole-injection layer, a plurality of layers may be used for the purpose of lowering the hole-injection barrier (or hole-injection voltage) from the anode to the hole-transport layer or electron-blocking layer, and each layer may have two compounds used simultaneously. The hole injection layer may be doped with a p-dopant. The electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. As the hole transport layer or the electron blocking layer, a plurality of layers may be used, and a plurality of compounds may be used for each layer.

An electron buffer layer, a hole blocking layer, an electron transport layer, an electron injection layer or a combination thereof may be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. A plurality of layers may be used for the hole blocking layer or electron transport layer, and a plurality of compounds may be used for each layer. In addition, the electron injection layer may be doped with an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When the organic electroluminescent device includes two or more hole transport layers, the additional layers may be used for the hole auxiliary layer or the electron blocking layer. The light-emitting auxiliary layer, hole auxiliary layer or electron blocking layer has the effect of improving the efficiency and/or lifespan of the organic electroluminescent device.

In the organic electroluminescent device of the present disclosure, preferably, at least one inner surface layer selected from a chalcogenide layer, a metal halide layer, and a metal oxide layer (hereinafter referred to as "surface layers") may be placed on an inner surface(s) of at least one of the pair of electrodes. Specifically, a chalcogenide (including oxides) layer of silicon and aluminum is preferably placed on an anode surface of an electroluminescent medium layer, and a halogenated metal layer or a metal oxide layer is preferably placed on a cathode surface of a light-emitting medium layer. The operation stability for the organic electroluminescent device may be obtained by the surface layer. Preferred examples of the chalcogenide include SiOX ($1 \leq X \leq 2$), AlOX ($1 \leq X \leq 1.5$), SiON, SiAlON, etc; preferred examples of the metal halide include LiF, MgF2, CaF2, rare earth fluoride metal, etc; and preferred examples of the metal oxide include Cs2O, Li2O, MgO, SrO, BaO, CaO, etc.

The organic electroluminescence device according to one embodiment of the present disclosure may be an organic electroluminescence device having a tandem structure. In the case of the tandem organic electroluminescent device according to one embodiment, two or more single light-emitting units may be connected by a charge generation layer. The organic electroluminescent device may include two or more light-emitting units, for example, three or more light-emitting units, each having a first electrode and a second electrode facing each other on a substrate and a light-emitting layer stacked between the first and second electrodes and emitting light of a specific wavelength band, wherein each light-emitting unit may include a hole transport band, a light-emitting layer, and an electron transport band, wherein the hole transport band may include a hole injection layer and a hole transport layer, wherein the electron transport band may include an electron transport layer and an electron injection layer, and according to one embodiment, the light-emitting layer(s) included in the light-emitting unit may be three or more. The plurality of light-emitting units may emit the same color or emit different colors. In addition, one light-emitting unit may also include one or more light-emitting layer(s), and the plurality of light-emitting layers may be light-emitting layers of the same color or different colors. One or more charge generation layers may be included which is(are) positioned between each light-emitting unit. The charge generation layer refers to a layer in which holes and electrons are generated when a voltage is applied. When there are three or more light-emitting units, a charge generation layer may be positioned between the light-emitting units. In this case, the plurality of charge generation layers may be the same as each other and may be different from each other. Since the charge generation layer is positioned between the light-emitting units, current efficiency may be increased in each light-emitting unit, and charges may be smoothly distributed. Specifically, the charge generation layer may be provided between two adjacent stacks to serve to drive the tandem organic electroluminescent device only with a pair of anodes and cathodes without a separate internal electrode positioned between the stacks.

The organic electroluminescence device according to one embodiment may comprise two or more organic layers, and may further comprise one or more charge generation layers, wherein the charge generation layers may be disposed between the organic layers, and when two or more organic layers are comprised, the charge generation layers may be the same or different. As the charge generation layer is disposed between the organic layers, the organic electroluminescent device may be driven by only a pair of anodes and cathodes without a separate internal electrode disposed between the organic layers.

The charge generation layer may include an n-type charge generation layer and a p-type charge generation layer, the n-type charge generation layer may be doped with an alkali metal, an alkaline earth metal, or a compound of an alkali metal and an alkaline earth metal, the alkali metal may include one selected from the group consisting of Li, Na, K, Rb, Cs, Fr, Yb, and a combination thereof, and the alkaline earth metal may include one selected from the group consisting of Be, Mg, Ca, Sr, Ba, Ra, and a combination thereof.

In addition, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. In addition, a reductive dopant layer may be employed as a charge generating layer to prepare an organic electroluminescent device having two or more light-emitting layers and emitting white light.

The light-emitting layer of the organic electroluminescence device according to one embodiment may be a single layer as a layer on which light is emitted, or may be a plurality of layers in which two or more layers are stacked. The light-emitting layer may further include one or more dopants, and the doping concentration of the dopant compound with respect to the host compound of the light-emitting layer may be less than 20 wt %, preferably less than 10 wt %.

The dopants comprised in the organic electroluminescent device of the present disclosure may be at least one phosphorescent or fluorescent dopant, and are preferably a phosphorescent dopant. The phosphorescent dopant materials applied to the organic electroluminescent device of the present disclosure are not particularly limited, but may be a complex compound of a metal atom selected from iridium (Ir), osmium (Os), copper (Cu), and platinum (Pt), preferably ortho-metallated complex compounds of a metal atom selected from iridium (Ir), osmium (Os), copper (Cu), and platinum (Pt), and more preferably ortho-metallated iridium complex compounds.

A compound represented by the following formula 101 may be used as a dopant included in the organic electroluminescent device of the present disclosure, but is not limited thereto.

(101)

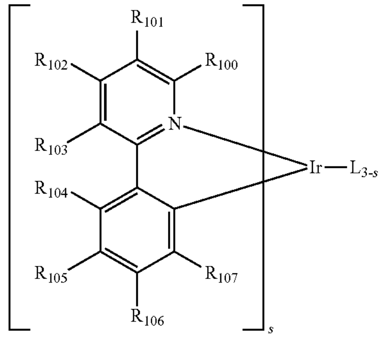

In formula 101,

L is any one selected from the following structures 1 to 3:

[Structure 1]

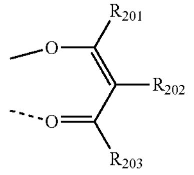

[Structure 2]

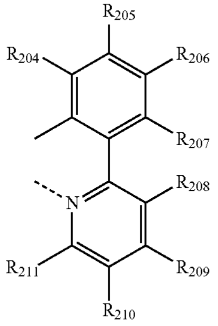

[Structure 3]

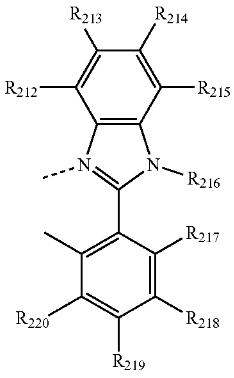

$R_{100}$ to $R_{103}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to an adjacent substituent(s) to form a ring, for example, a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or may be linked to an adjacent substituent(s) to form a ring, for example, a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{220}$ each independently represent hydrogen, deuterium, halogen, a (C1-C30)alkyl unsubstituted or substituted with deuterium and/or halogen, a substituted or unsubstituted (C3-C30)cycloalkyl, or a substituted or unsubstituted (C6-C30)aryl; or may be linked to an adjacent substituent(s) to form a substituted or unsubstituted ring; and s is an integer of 1 to 3.

The specific examples of the dopant compound are as follows, but are not limited thereto.

D-1

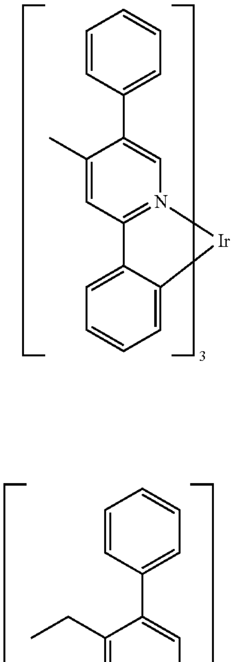

D-2

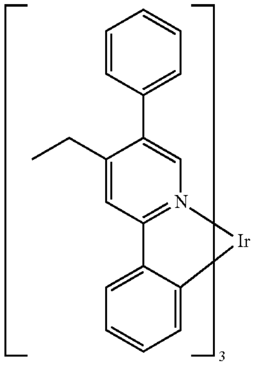

-continued

D-3

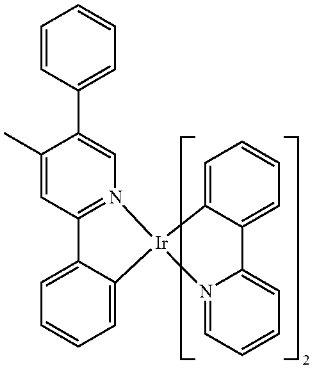

D-4

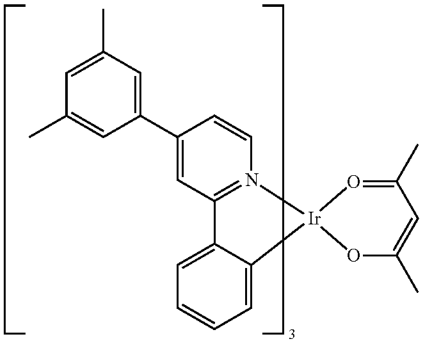

D-5

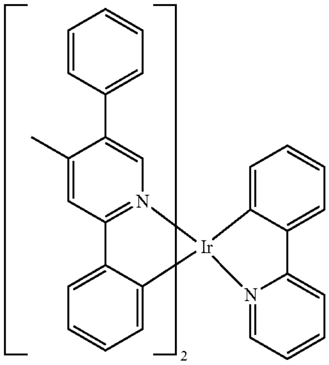

D-6

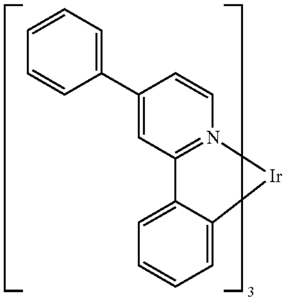

-continued
D-7
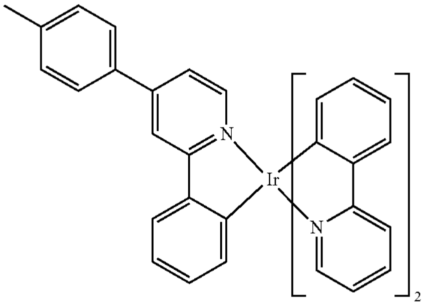
D-8
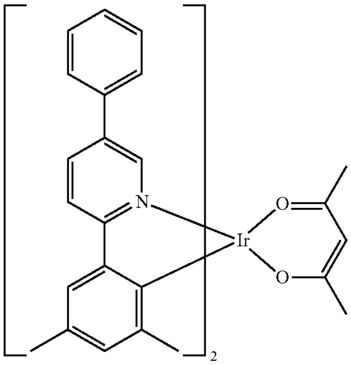
D-9
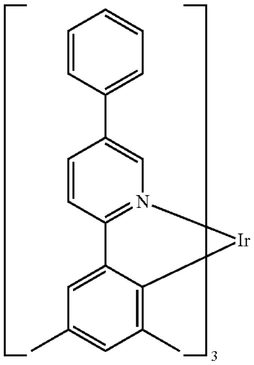
D-10
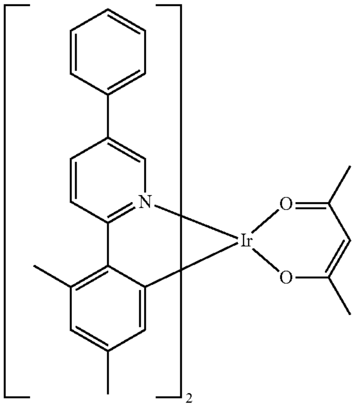
-continued
D-11
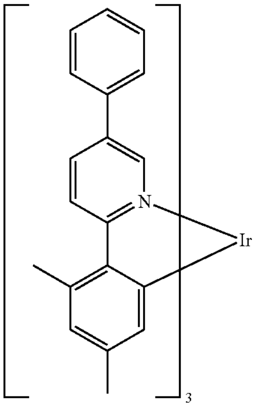
D-12
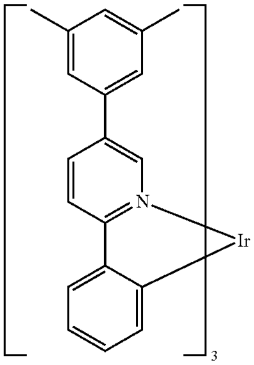
D-13
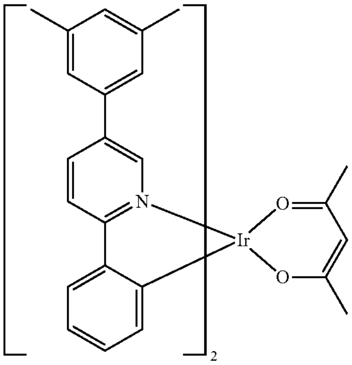
D-14
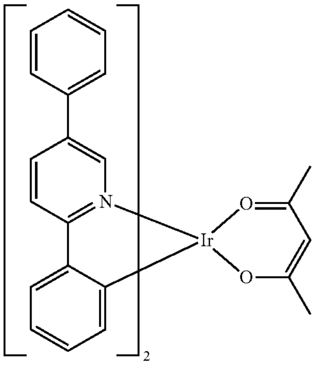

-continued
D-15
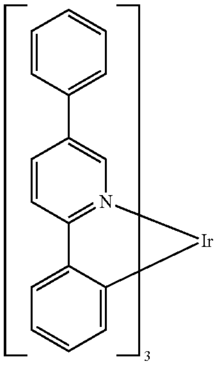
D-16
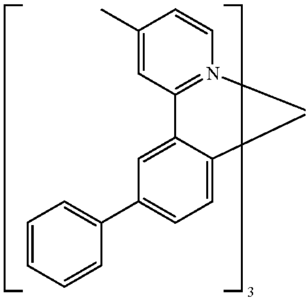
D-17
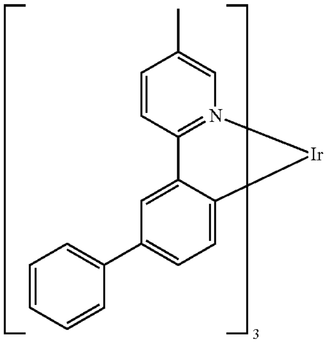
D-18
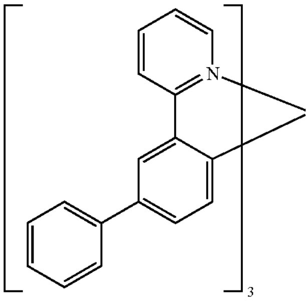
-continued
D-19
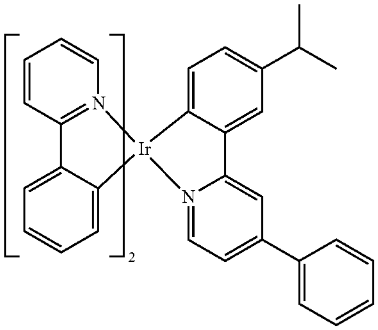
D-20
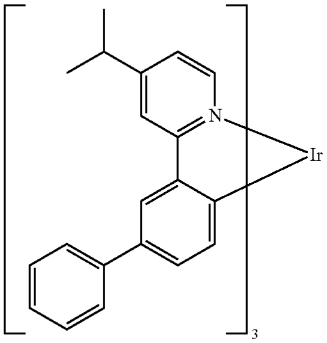
D-21
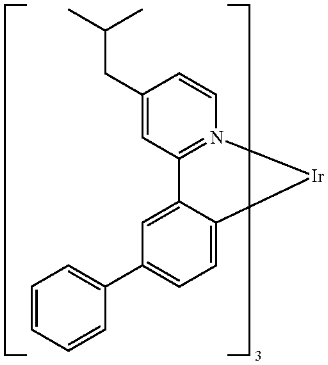
D-22
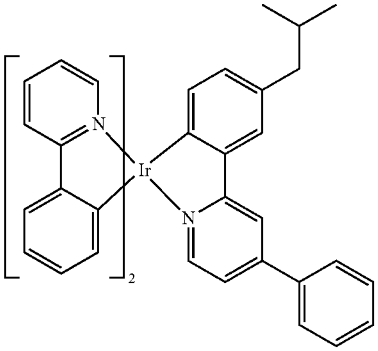

-continued
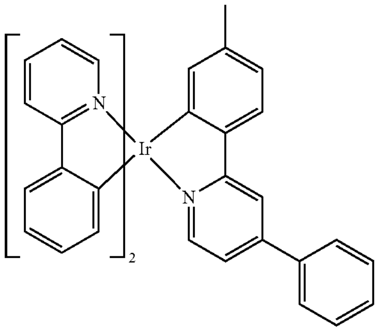
D-23
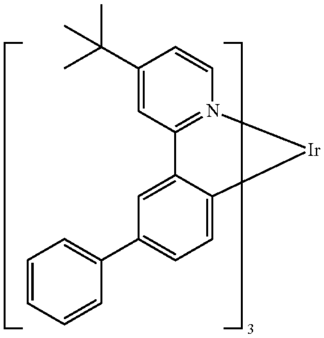
D-24
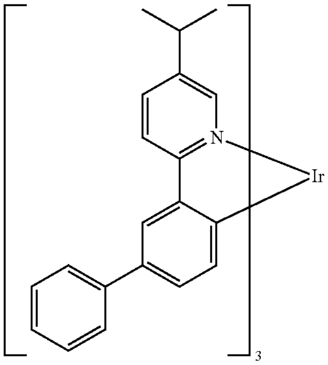
D-25
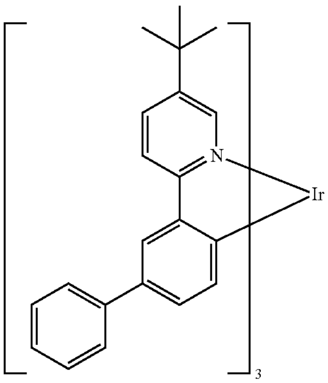
D-26
-continued
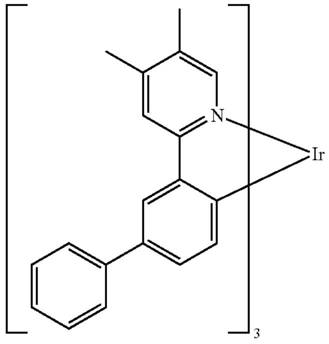
D-27
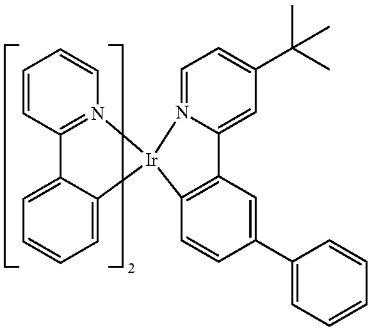
D-28
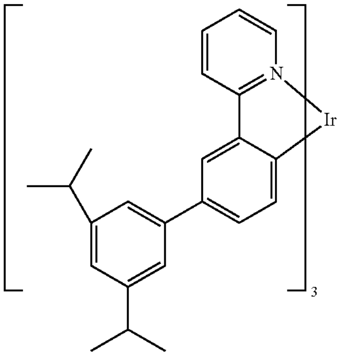
D-29
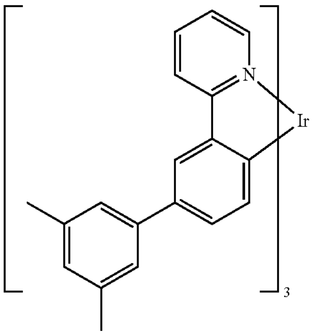
D-30

-continued
D-31
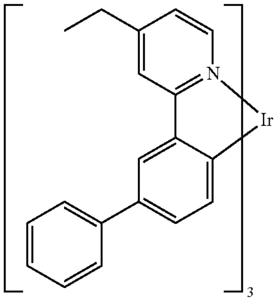
D-32
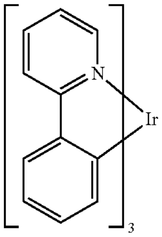
D-33
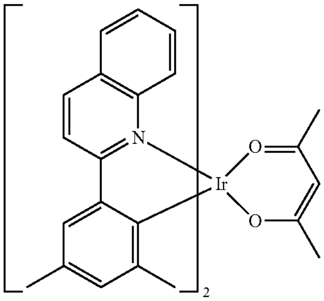
D-34
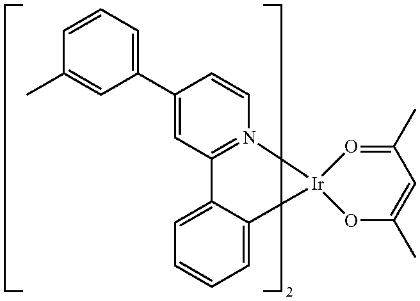
D-35
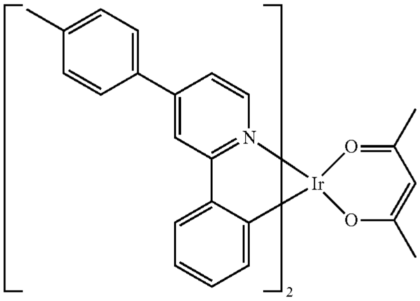
-continued
D-36
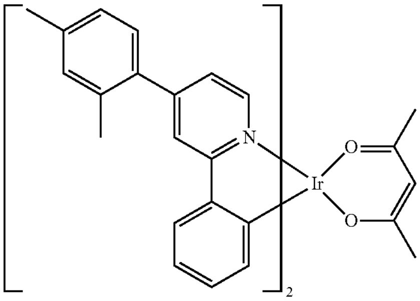
D-37
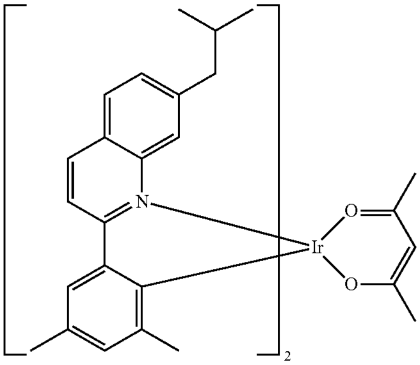
D-38
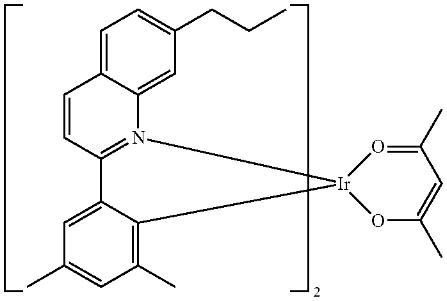
D-39
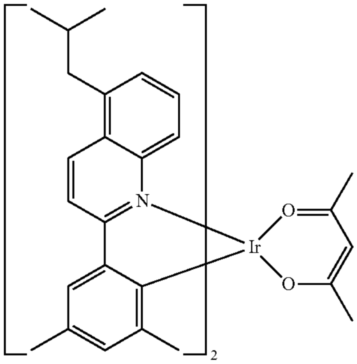

-continued
D-40
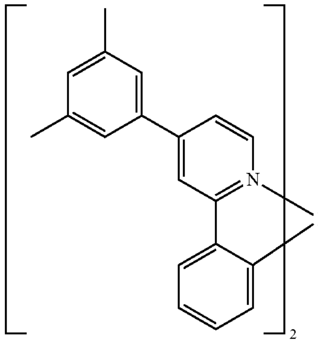
D-41
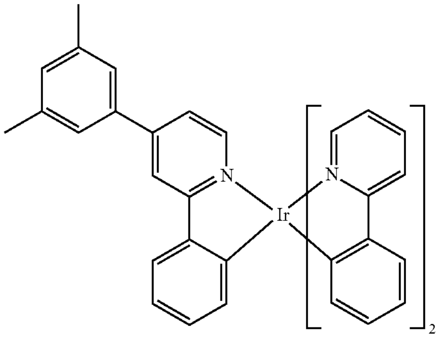
D-42
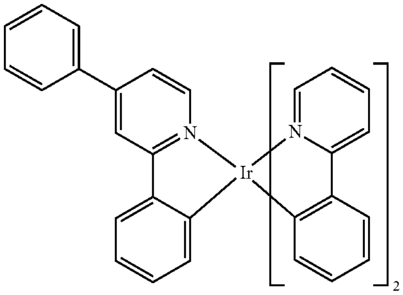
D-43
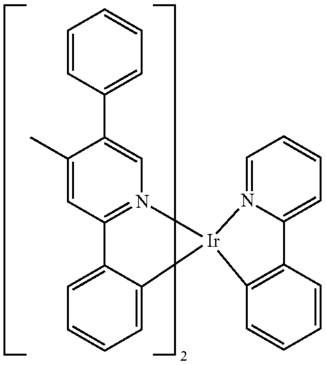
-continued
D-44
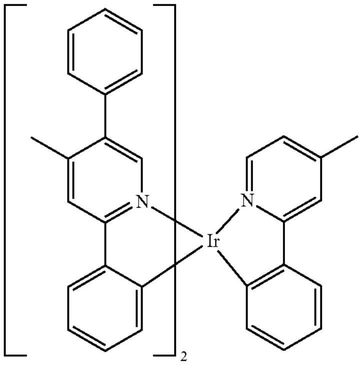
D-45
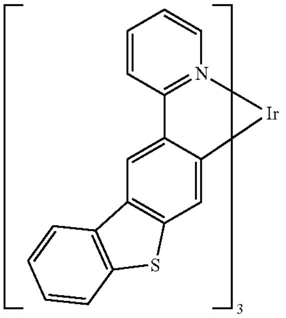
D-46
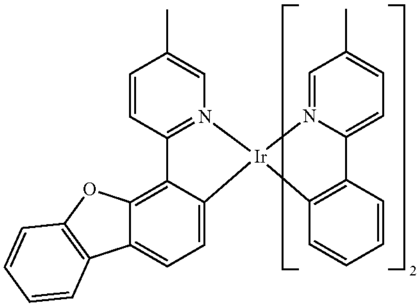
D-47
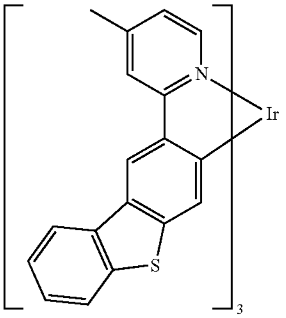
D-48
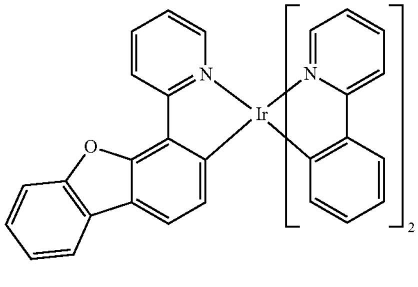

-continued
D-49
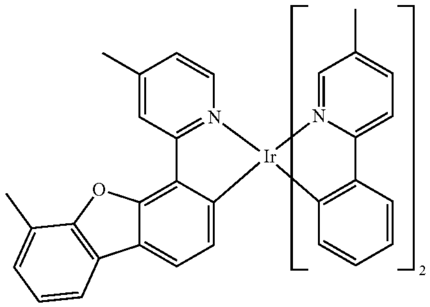
D-50
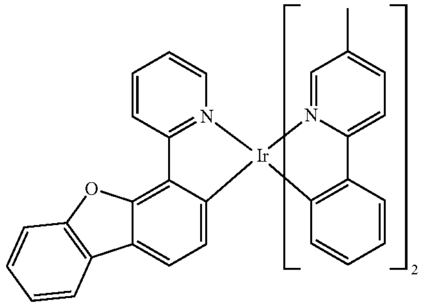
D-51
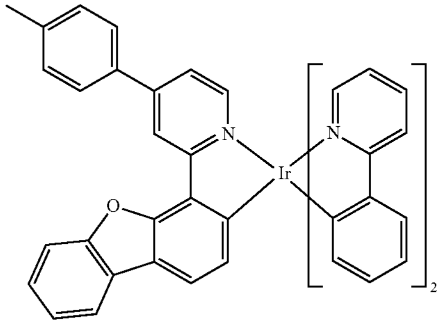
D-52
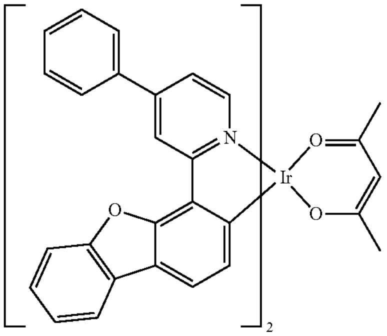
D-53
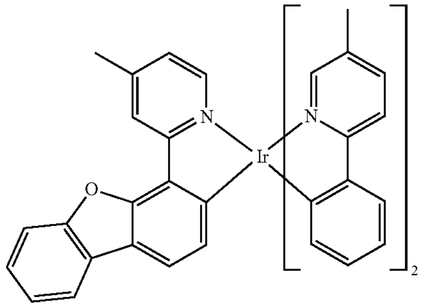
-continued
D-54
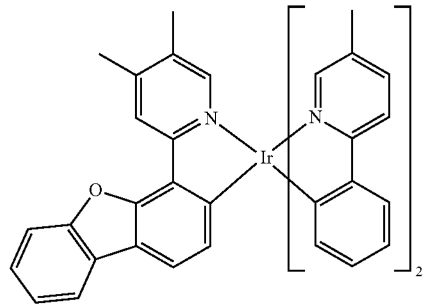
D-55
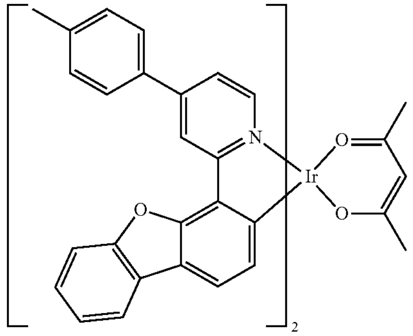
D-56
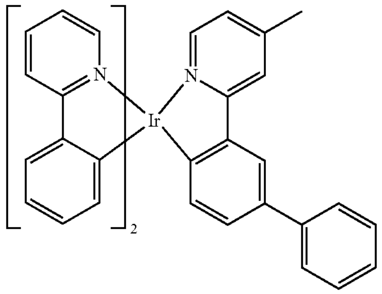
D-57
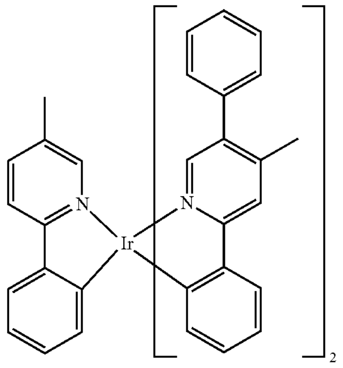

D-58
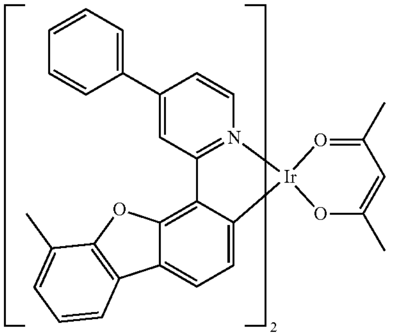
D-59
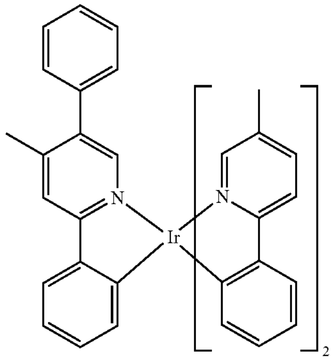
D-60
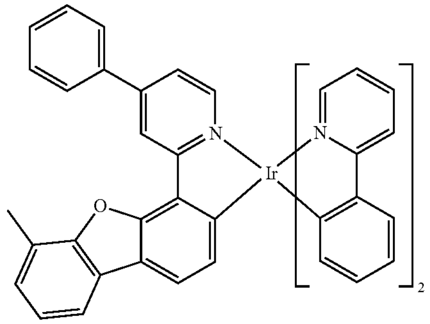
D-61
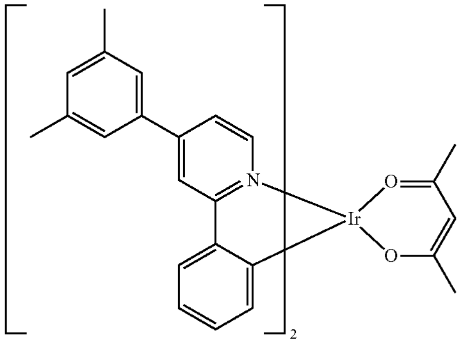
D-62
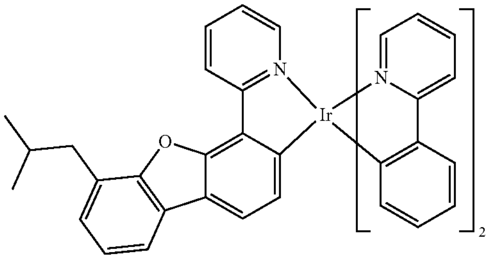
D-63
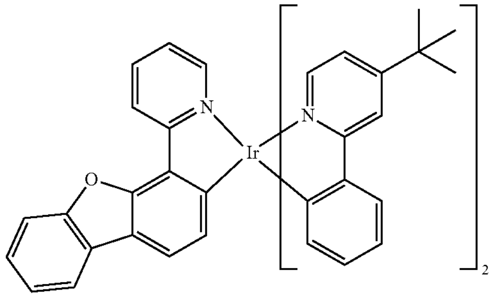
D-64
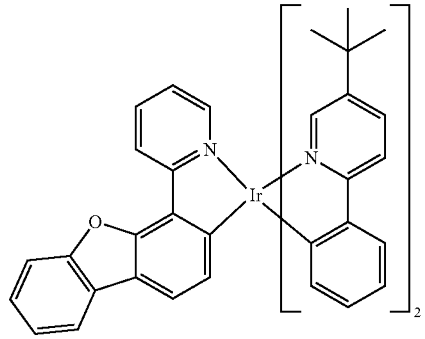
D-65
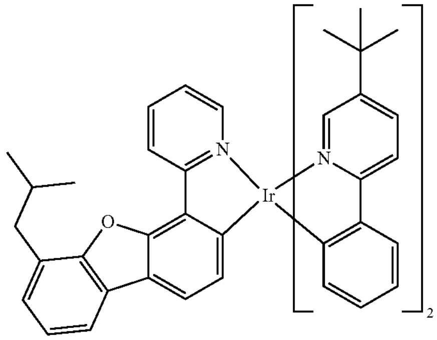
D-66
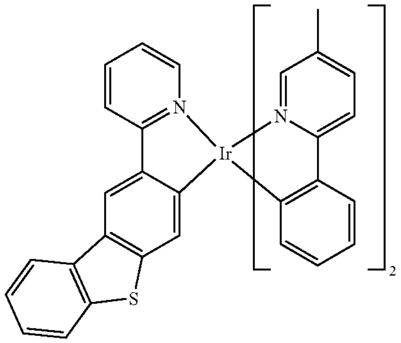

-continued
D-67
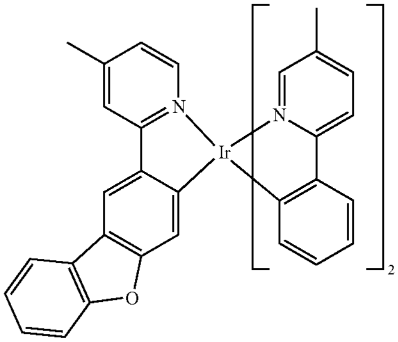
D-68
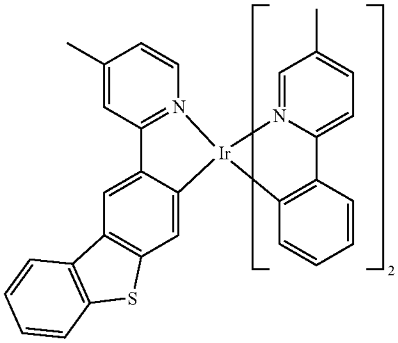
D-69
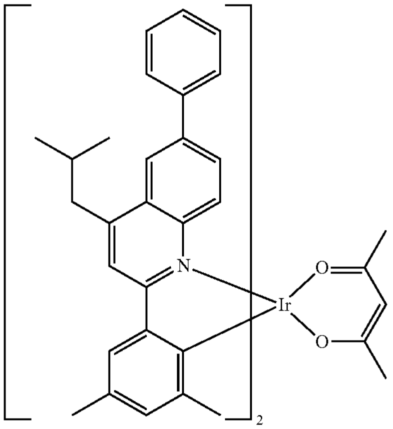
D-70
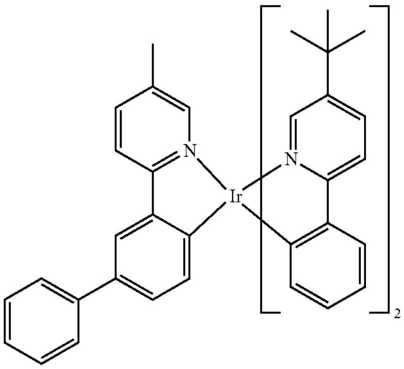
-continued
D-71
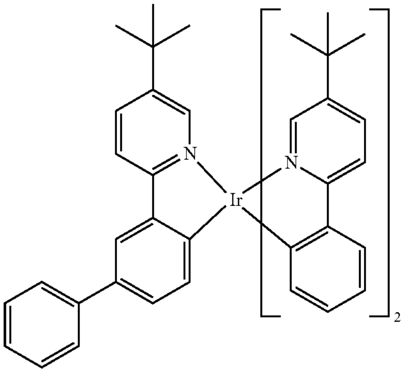
D-72
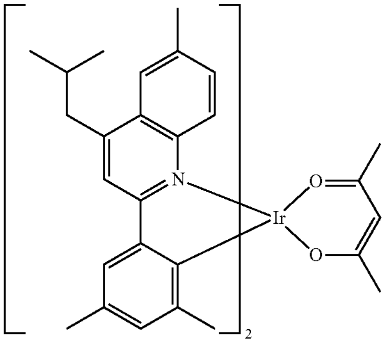
D-73
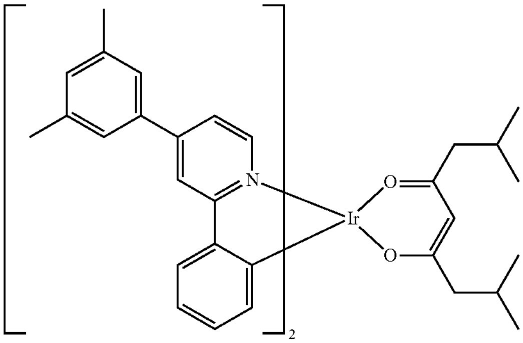
D-74
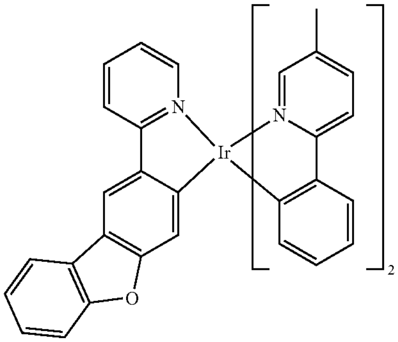

-continued
D-75
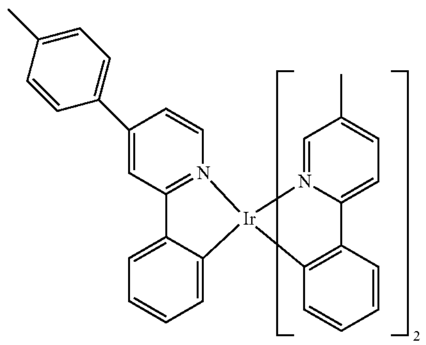
D-76
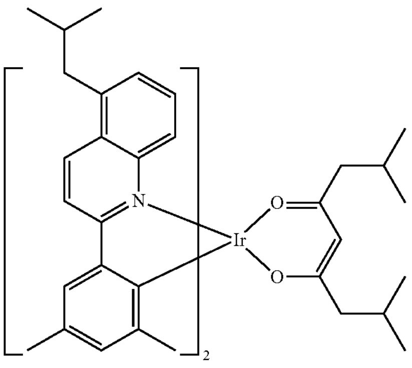
D-77
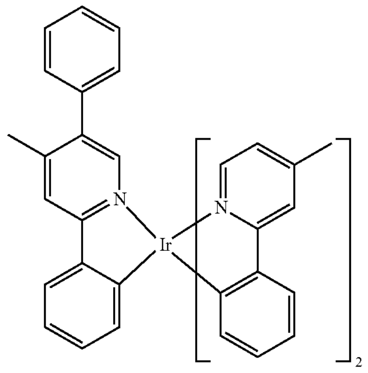
D-78
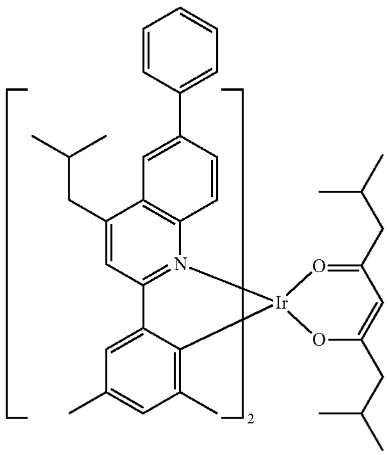
-continued
D-79
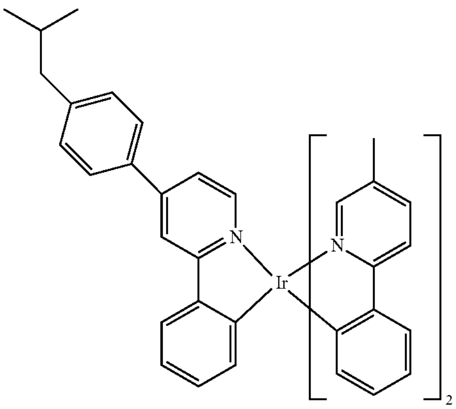
D-80
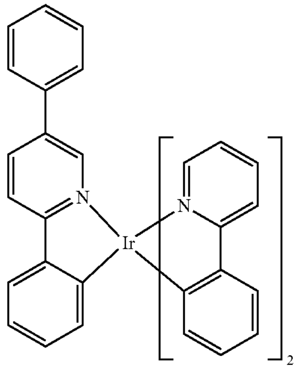
D-81
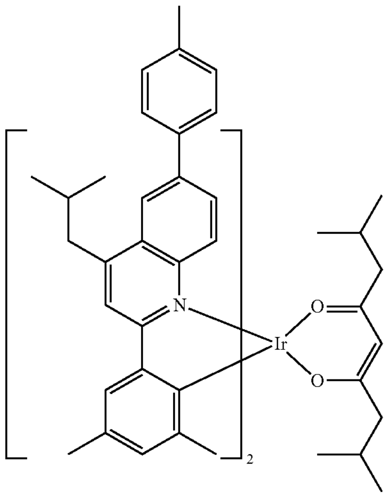

-continued
D-82
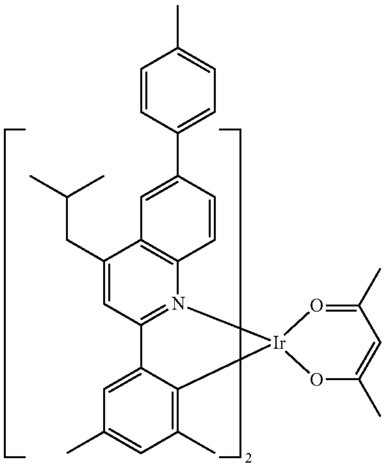
D-83
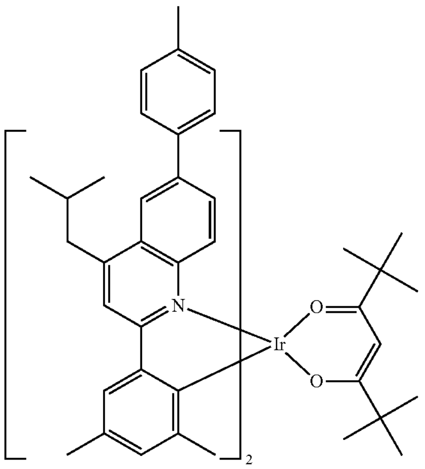
D-84
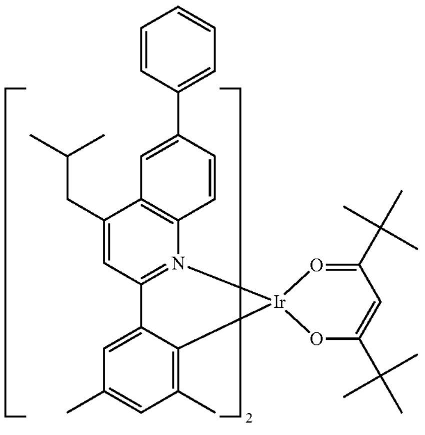
-continued
D-85
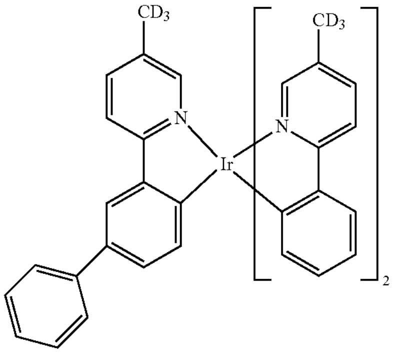
D-86
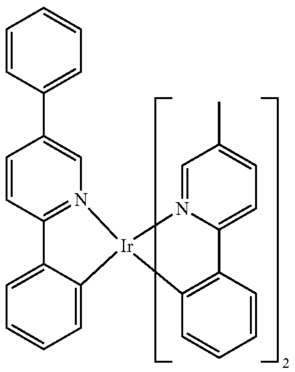
D-87
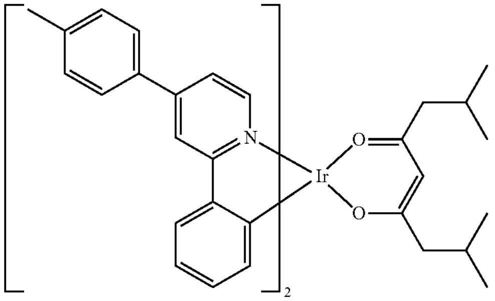
D-88
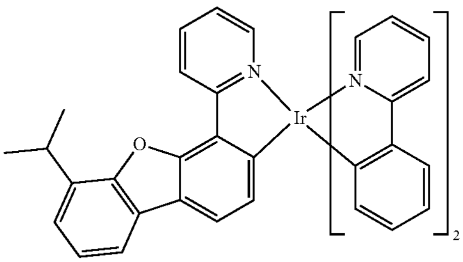
D-89
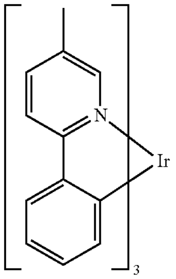

-continued
D-90
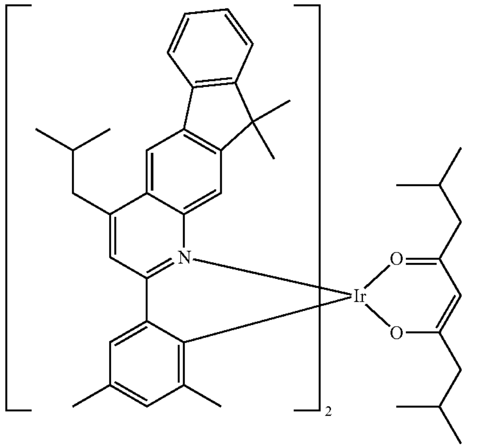
D-91
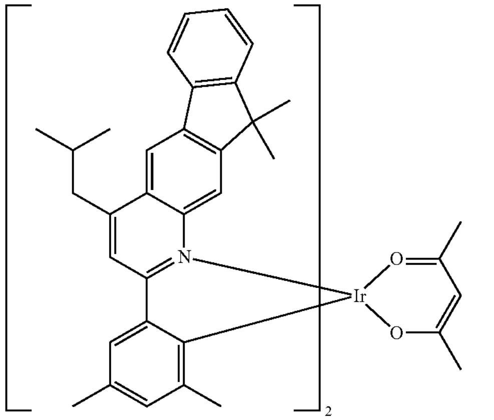
D-92
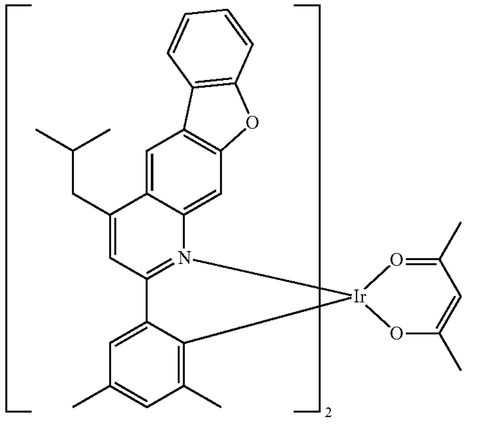
-continued
D-93
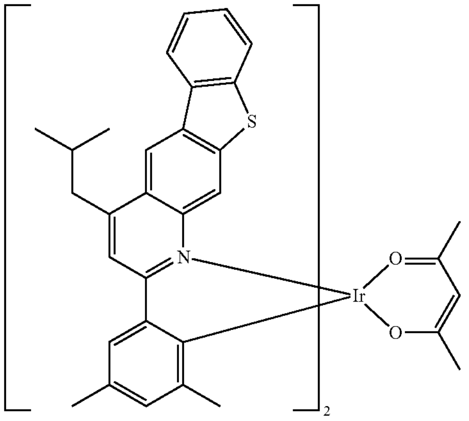
D-94
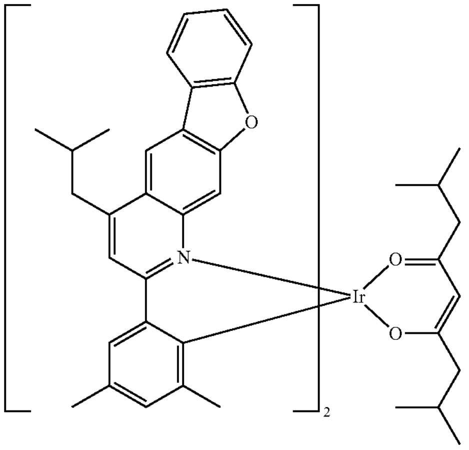
D-95
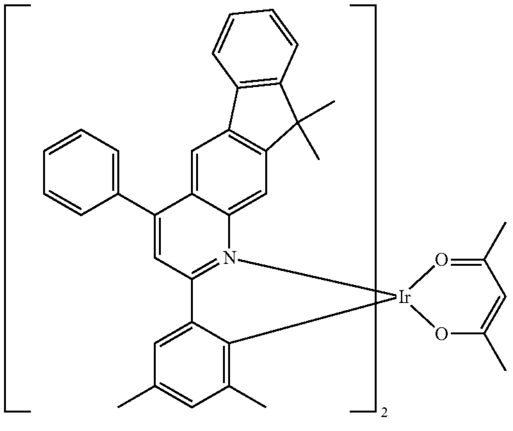

-continued
D-96
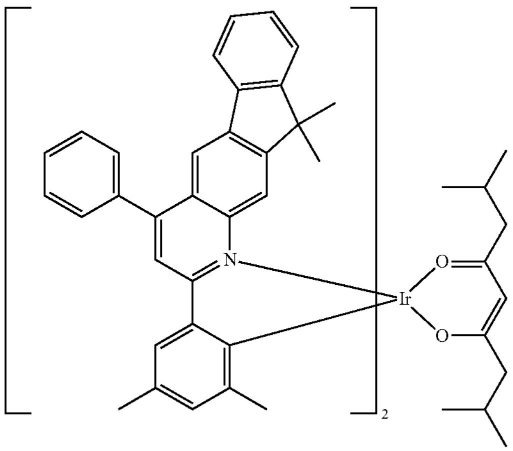
D-97
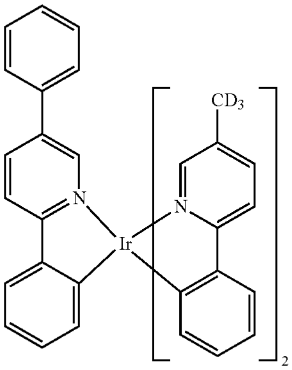
D-98
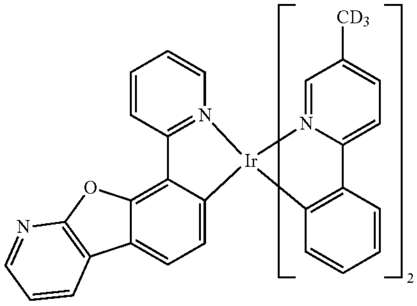
D-99
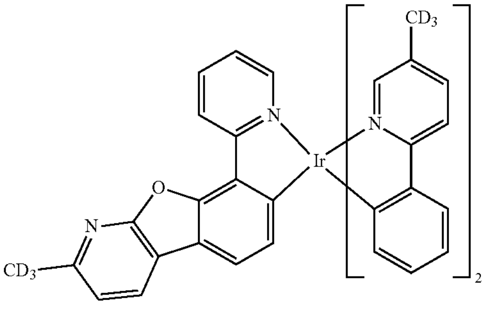
-continued
D-100
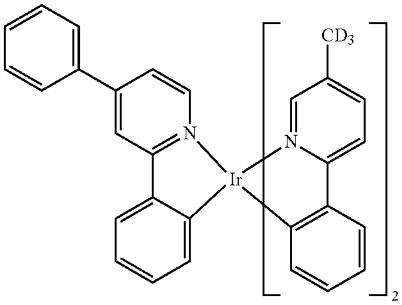
D-101
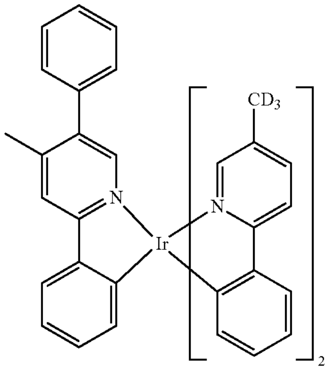
D-102
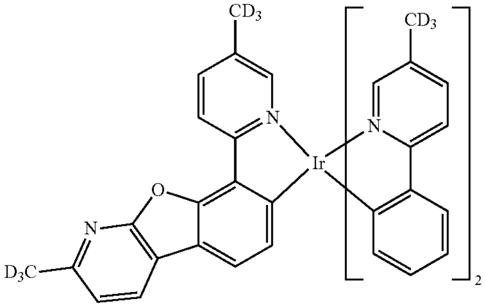
D-103
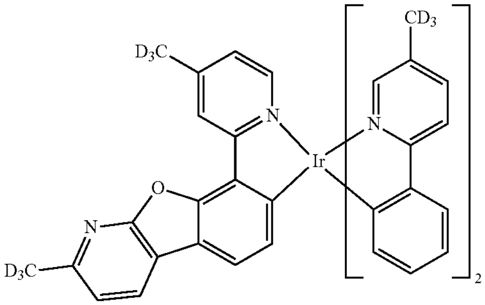
D-104
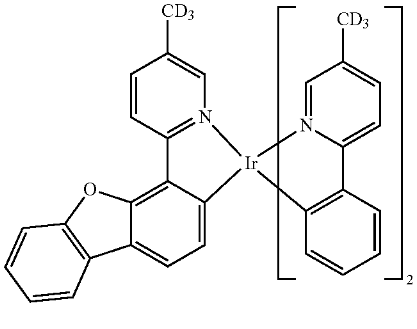

-continued
D-105
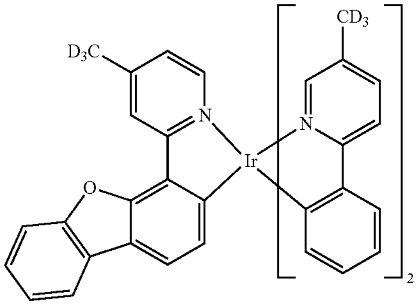
D-106
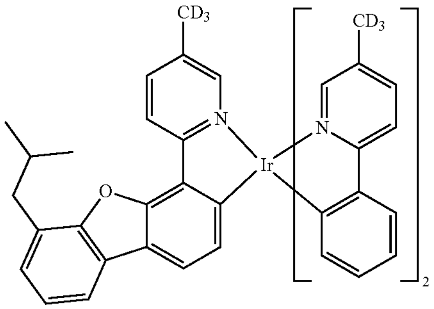
D-107
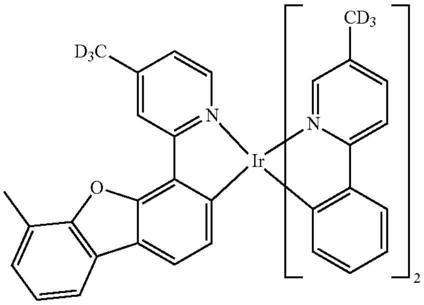
D-108
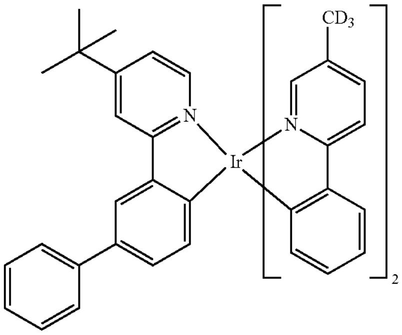
D-109
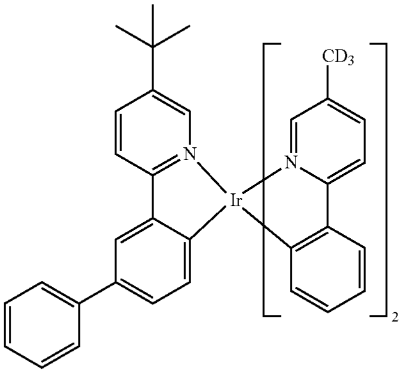
-continued
D-110
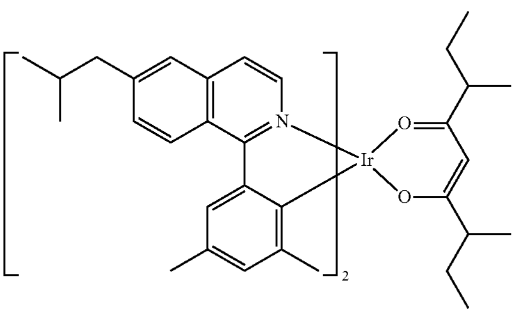
D-111
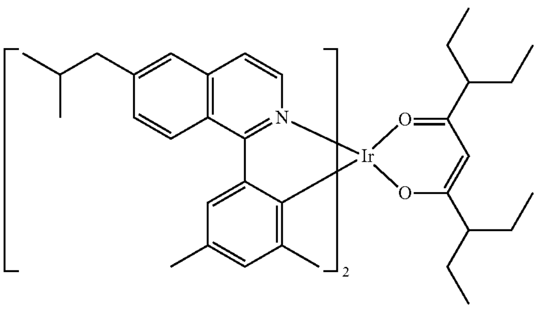
D-112
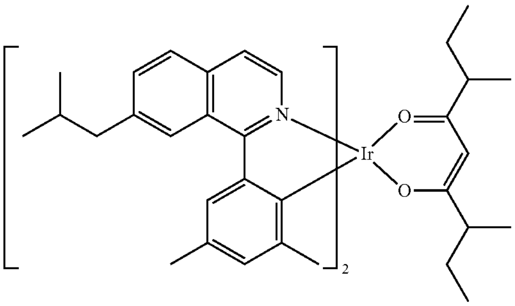
D-113
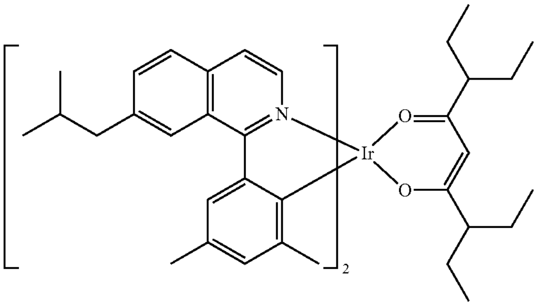
D-114
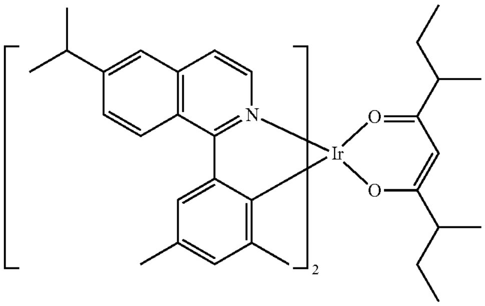

-continued
D-115
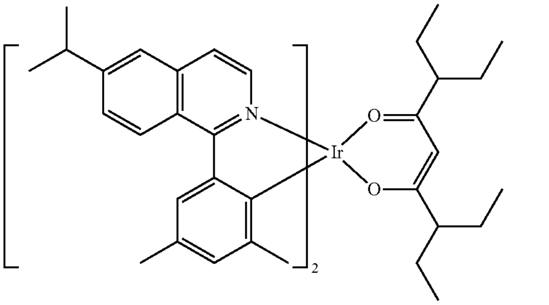
D-116
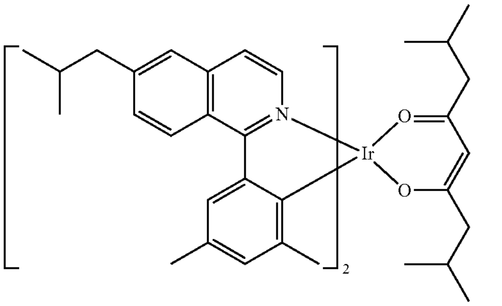
D-117
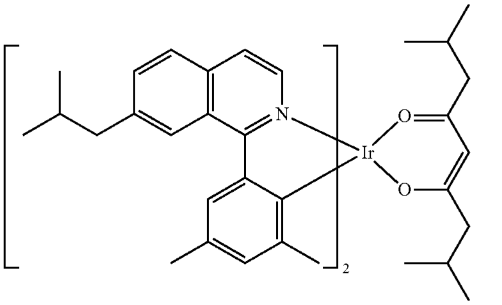
D-118
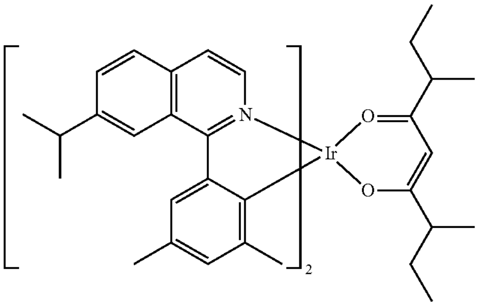
D-119
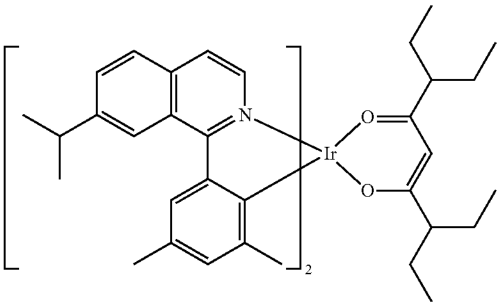
-continued
D-120
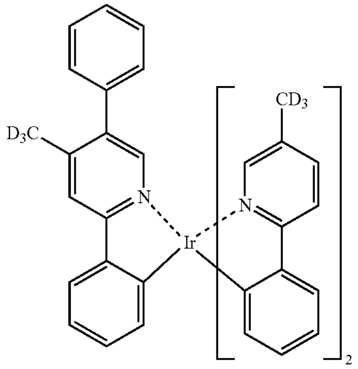
D-121
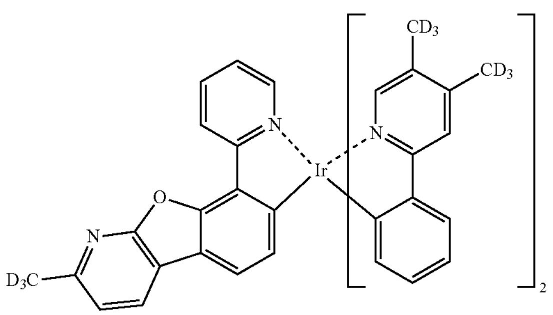
D-122
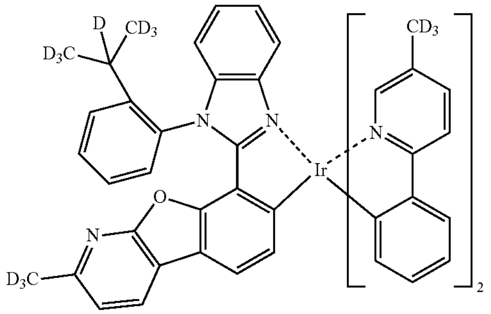
D-123
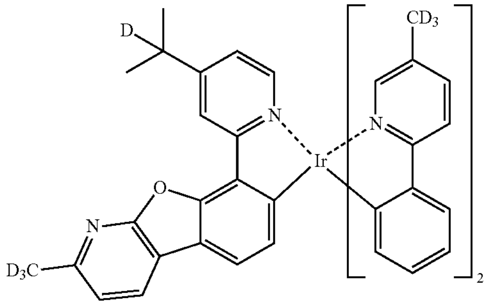
D-124
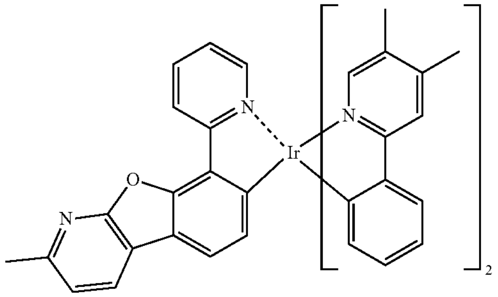

-continued
D-125
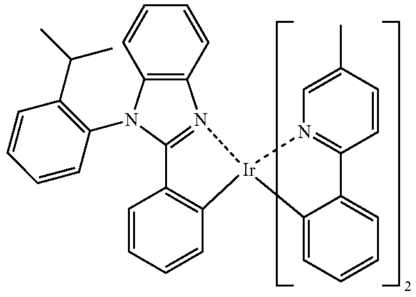
D-126
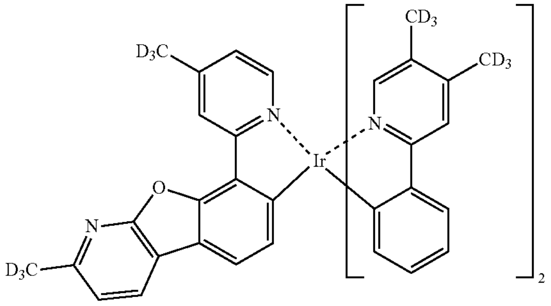
D-127
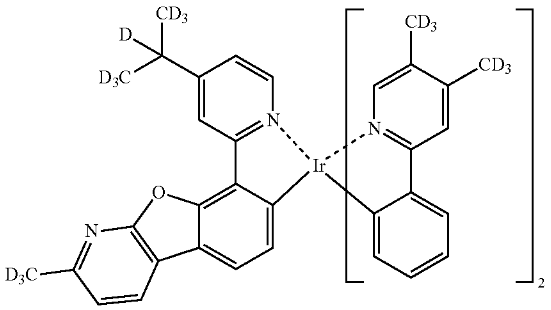
D-128
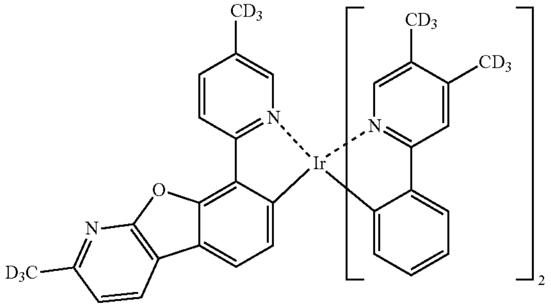
D-129
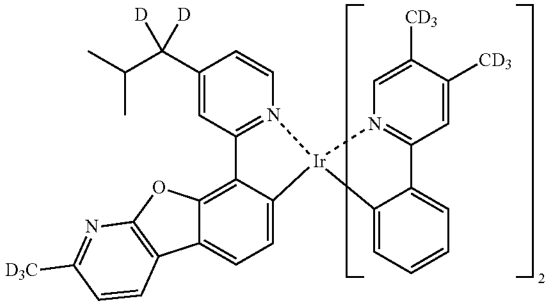
-continued
D-130
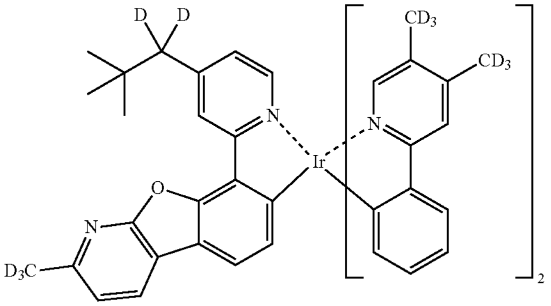
D-131
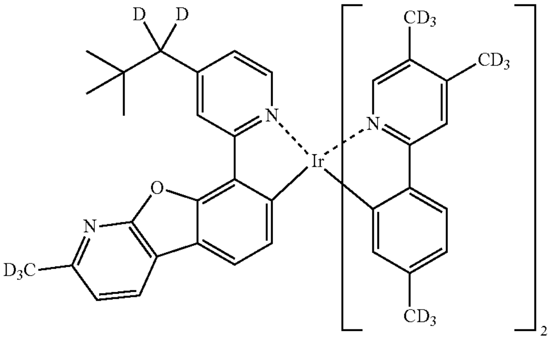
D-132
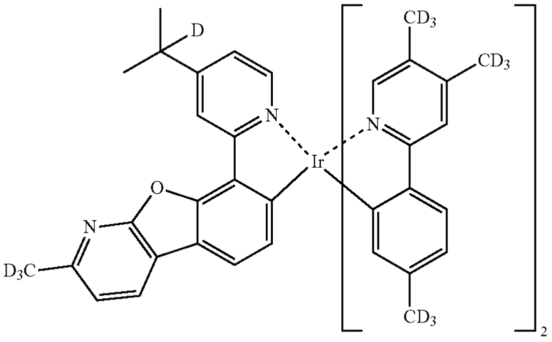
D-133
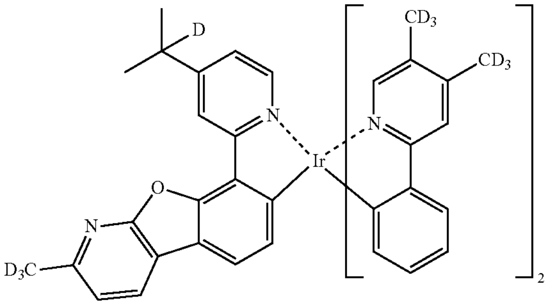

-continued
D-134
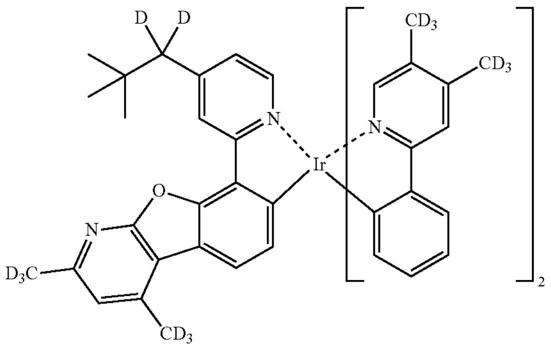
D-135
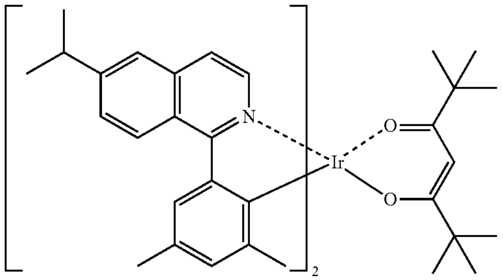
D-136
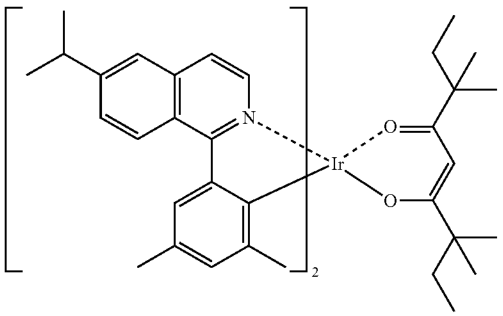
D-137
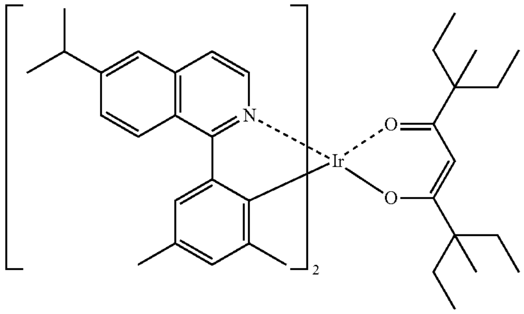
-continued
D-138
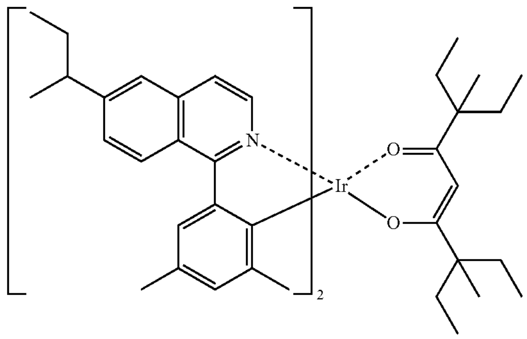
D-139
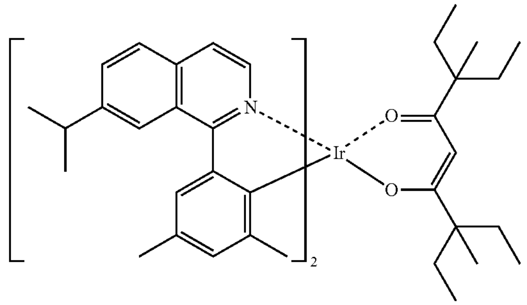
D-140
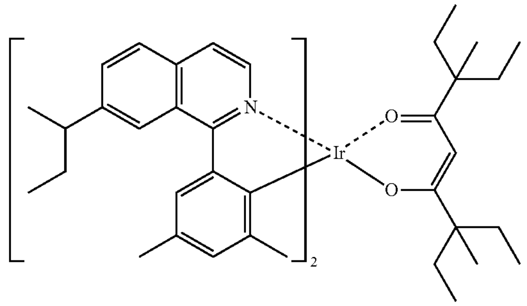
D-141
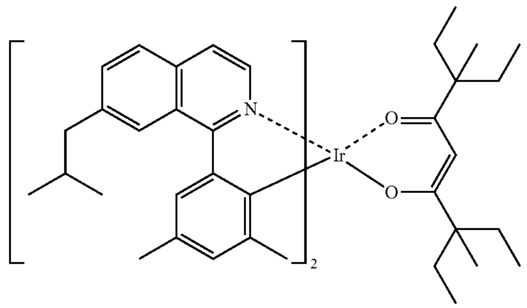

-continued
D-142
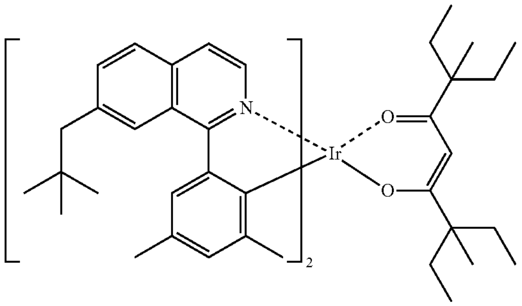
D-143
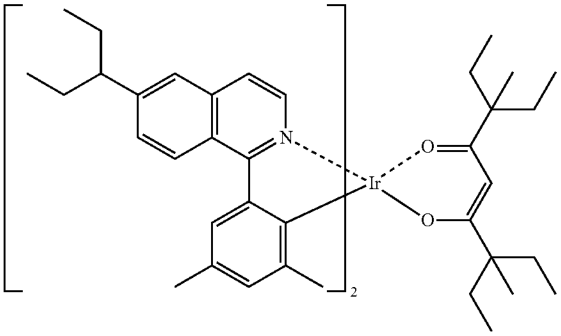
D-144
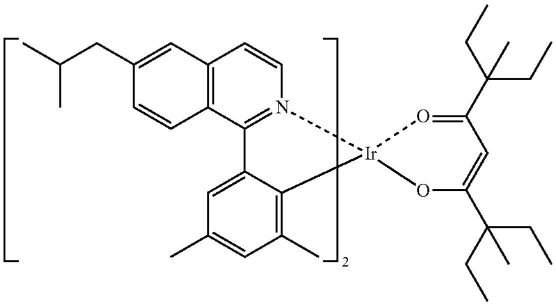
D-145
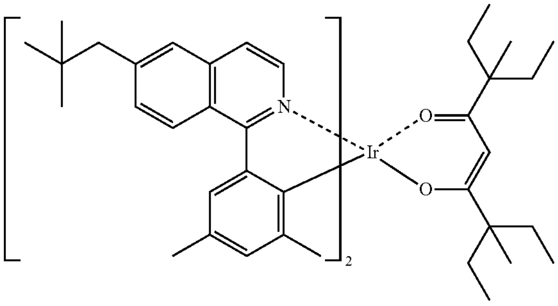
-continued
D-146
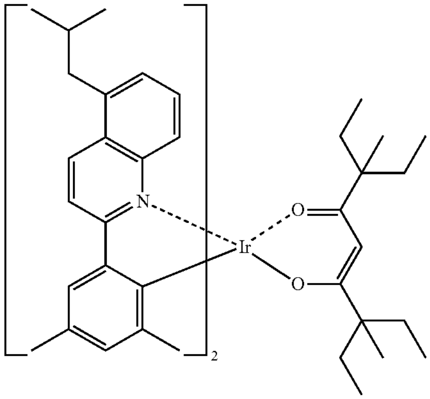
D-147
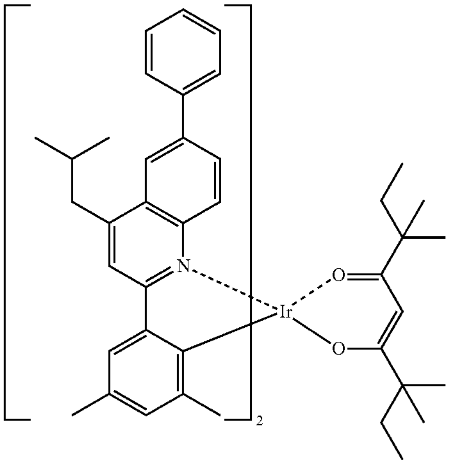
D-148
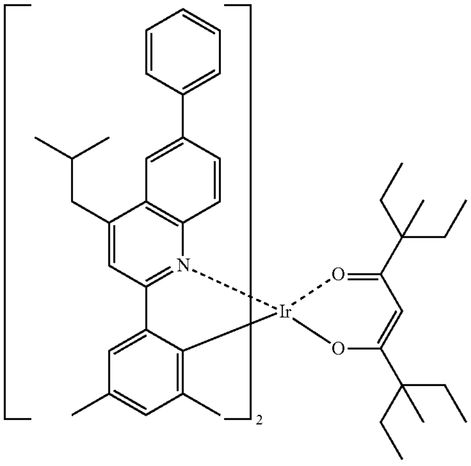

-continued

D-149

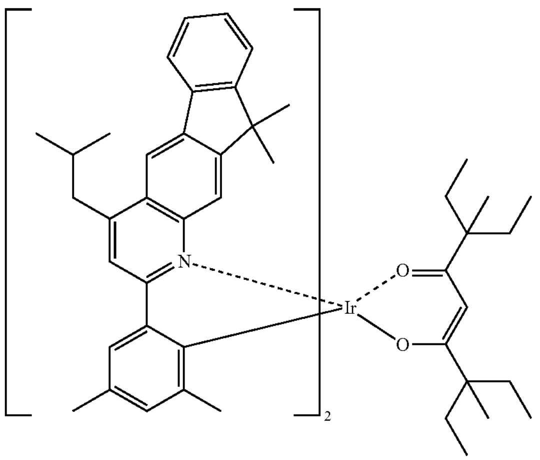

In order to form each layer of the organic electroluminescent device of the present disclosure, dry film-forming methods such as vacuum evaporation, sputtering, plasma, ion plating methods, etc., or wet film-forming methods such as inkjet printing, nozzle printing, slot coating, spin coating, dip coating, flow coating methods, etc., may be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

According to one embodiment, when the first host material and the second host material are present in the same layer or different layers in the organic electroluminescent device, the two host materials may be individually deposited. For example, the second host material may be deposited after depositing the first host material.

According to one embodiment, when each layer of the organic electroluminescent device is formed, the film may be formed by the above-described method, and the film may be formed in a co-deposition process, a mixed deposition process, and/or a process using the co-deposition process and the mixed deposition process together. For example, the co-deposition may be a method of depositing two or more isomeric materials by putting the isomeric materials into each individual vaporization source, for example, a crucible source, and simultaneously applying a current to two cells to evaporate the materials. In addition, for example, the mixed deposition may be a method of mixing two or more isomeric materials with one evaporation source, for example, a crucible source before deposition, and then evaporating and mixed by applying a current to one cell. In addition, for example, a process using co-deposition and mixed deposition may be a process of mixing the first host material and the second host material in one evaporation source, for example, a crucible source, putting another material in another evaporation source, for example, a crucible source, and then applying current to two cells at the same time to evaporate and deposit each material. When the film is formed by using the mixed deposition and/or the co-deposition and the mixed deposition, the number of evaporation sources used may be reduced.

According to one embodiment, the present disclosure may provide a compound obtained by depositing an organic layer in a manufacturing process of an organic electroluminescent device, and then recovering and purifying a material of the organic layer attached to deposition equipment. The recovered compound may be subjected to purification and/or recrystallization process, and the purity of the purified and/or recrystallized compound obtained therefrom may be 99.9% or more.

According to one embodiment, the present disclosure provides a method of recovering a plurality of host materials, the method comprising: depositing a plurality of host materials including at least one first host material comprising a compound represented by formula 1 and at least one second host material comprising a compound represented by formula 2; recovering the plurality of host materials attached to deposition equipment; and refining and/or recrystallizing the recovered plurality of host materials to obtain the plurality of host materials with a purity of 99.9% or higher.

The present disclosure may provide a display device using a plurality of host materials comprising the compound represented by formula 1 and the compound represented by formula 2. That is, it is possible to manufacture a display device or a lighting device using a plurality of host materials of the present disclosure. Specifically, it is possible to manufacture a display system, for example, a display device for a smartphone, tablet, laptop, PCs, TVs, or vehicle, or a lighting system, such as an outdoor or indoor lighting system, using the plurality of host materials of the present application.

Hereinafter, for a detailed understanding of the present disclosure, a method for preparing the compound according to the present disclosure will be described by taking a preparation method of a representative compound or an intermediate compound of the present disclosure as an example.

Example 1: Synthesis of Compound C-63

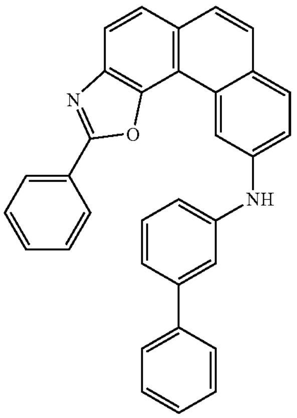

1-1

+

-continued

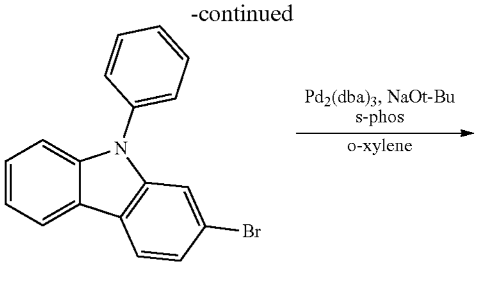

1-2

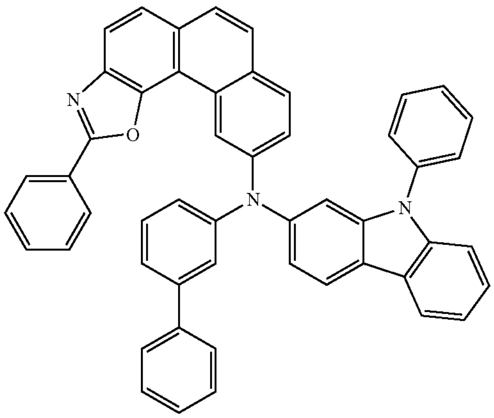

C-63

110 mL of o-xylene was added to Compound 1-1 (12 g, 26.07 mmol), Compound 1-2 (7 g, 21.72 mmol), tris(dibenzylideneacetone)dipalladium(0) ("$Pd_2(dba)_3$") (1 g, 1.086 mmol), sodium tert-butoxide ("NaOt-Bu") (3.1 g, 32.58 mmol), and S-Phos (0.9 g, 2.172 mmol), and then the mixture was stirred under reflux at 160° C. for 2 hours. After completion of the reaction, the reaction mixture was cooled to room temperature, and then filtered with Celite. The residue was distilled under reduced pressure, and separated by column chromatography to obtain compound C-63 (12.3 g, yield: 80%).

| | MW | M.P |
|---|---|---|
| C-63 | 703.8 | 114° C. |

Example 2: Synthesis of Compound C-2

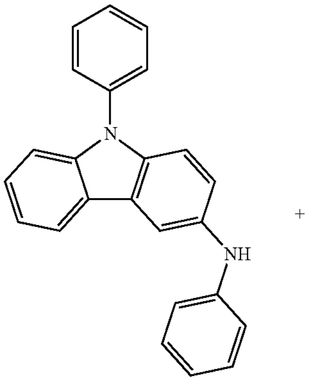

2-1

-continued

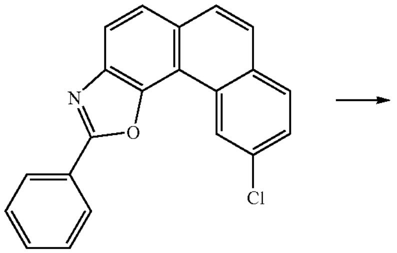

2-2

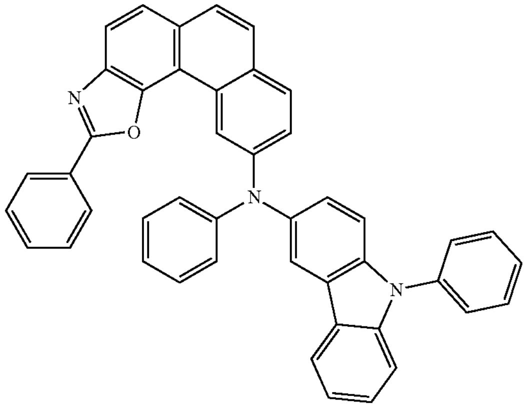

C-2

Compound 2-1 (20 g, 59.8 mmol), Compound 2-2 (18.8 g, 57.0 mmol), $Pd_2(dba)_3$ (0.26 g, 1.1 mmol), S-Phos (0.233 g, 2.3 mmol), and NaOt-Bu (8.2 g, 167.5 mmol) were dissolved in 400 mL of xylene, and then the mixture was stirred at a temperature of 135° C. for 20 hours. After cooling to room temperature and filtering with Celite to make a solid, the solid was separated by column chromatography to obtain Compound C-2 (15.3 g, yield: 43%).

| | MW | M.P |
|---|---|---|
| C-2 | 627.75 | 226.5° C. |

Example 3: Synthesis of Compound C-26

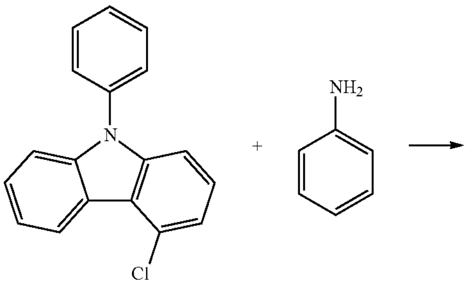

-continued

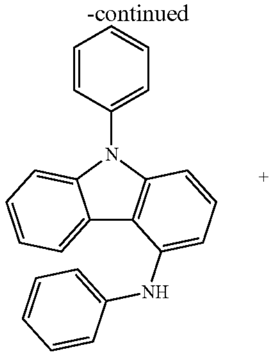

3-1

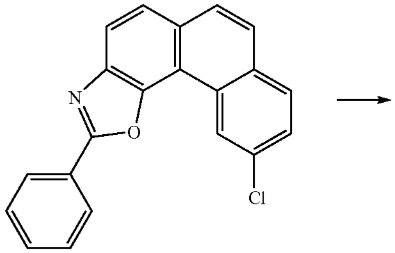

2-2

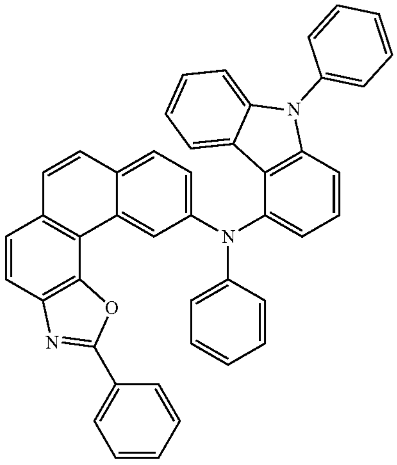

C-26

1) Synthesis of Compound 3-1

4-chloro-9-phenyl-9H-carbazole (68 g, 244 mmol), aniline (25.1 g, 269.5 mmol), $Pd(OAc)_2$ (0.549 g, 2.4 mmol), S-Phos (2.01 g, 4.8 mmol), and NaOt-Bu (35.3 g, 367.3 mmol) were dissolved in 640 mL of toluene, and then the mixture was stirred at a temperature of 95° C. for 10 hours. After cooling to room temperature and filtering with Celite to make a solid, the solid was separated by column chromatography to obtain Compound 3-1 (77.6 g, yield: 95.2%).

2) Synthesis of Compound C-26

Compound 3-1 (45.0 g, 134.5 mmol), Compound 2-2 (36.8 g, 111.6 mmol), $Pd(OAc)_2$ (0.25 g, 1.1 mmol), S-Phos (0.916 g, 2.3 mmol), and NaOt-Bu (16.1 g, 167.5 mmol) were dissolved in 1.73 L of toluene, and then the mixture was stirred at 100° C. for 18 hours. After cooling to room temperature and filtering with Celite to make a solid, the solid was separated by column chromatography to obtain Compound C-26 (17 g, yield: 24.3%).

| | MW | M.P |
|---|---|---|
| C-26 | 627.75 | 306.4° C. |

Example 4: Preparation of Compound C-45

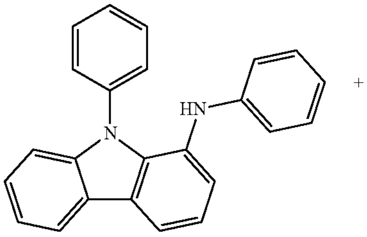

4-1

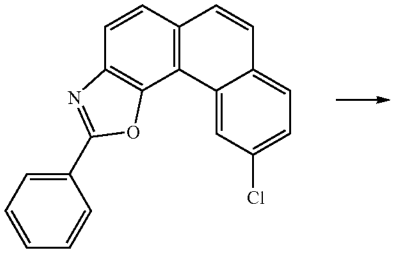

2-2

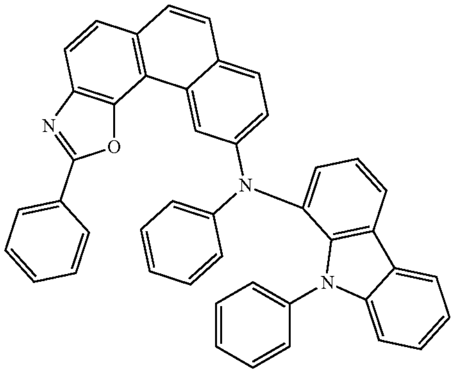

C-45

Compound 4-1 (23 g, 68.7 mmol), Compound 2-2 (20 g, 60.6 mmol), $Pd(OAc)_2$ (0.25 g, 1.1 mmol), S-Phos (0.916 g, 2.23 mmol), and NaOt-Bu (10 g, 104.0 mmol) were dissolved in 600 mL of toluene, and then the mixture was stirred at 100° C. for 5 hours. After cooling to room temperature and filtering with Celite to make a solid, the solid was separated by column chromatography to obtain Compound C-45 (26.6 g, yield: 70%).

| | MW | M.P |
|---|---|---|
| C-45 | 627.75 | 258° C. |

Example 5: Synthesis of Compound C-4

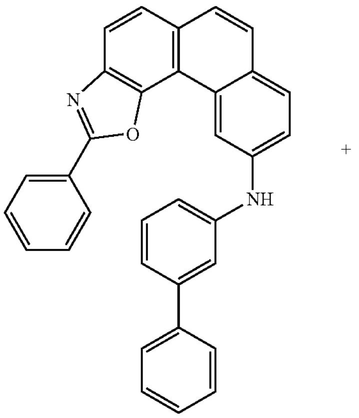

1-1

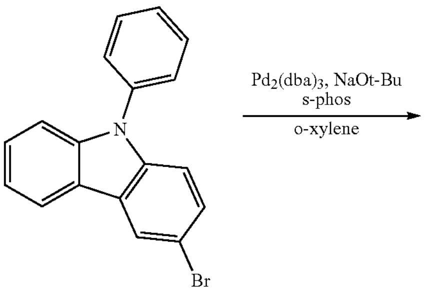

5-1

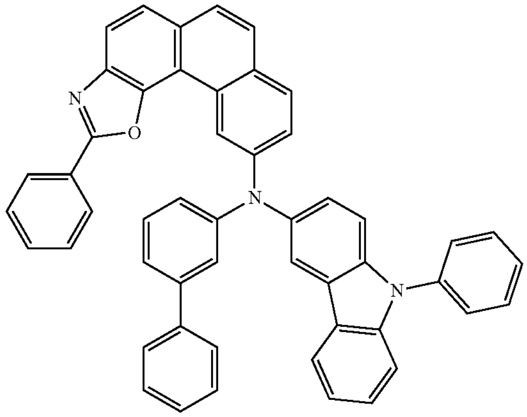

C-4

110 mL of o-xylene was added to Compound 1-1 (12 g, 26.07 mmol), Compound 5-1 (7 g, 21.72 mmol), $Pd_2(dba)_3$ (1 g, 1.086 mmol), NaOt-Bu (3.1 g, 32.58 mmol), and S-Phos (0.9 g, 2.172 mmol), and then the mixture was stirred under reflux at 160° C. for 2 hours. After completion of the reaction, the reaction mixture was cooled to room temperature, and then filtered with Celite. The residue was distilled under reduced pressure, and separated by column chromatography to obtain compound C-4 (7.9 g, yield: 51%).

Example 6: Synthesis of Compound C-119

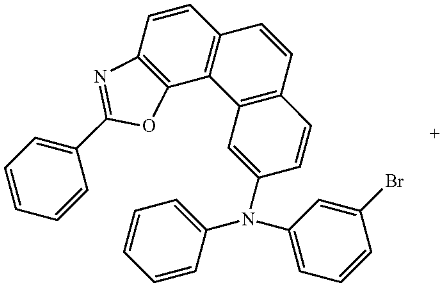

6-1

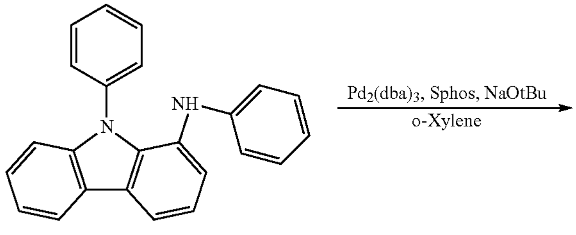

6-2

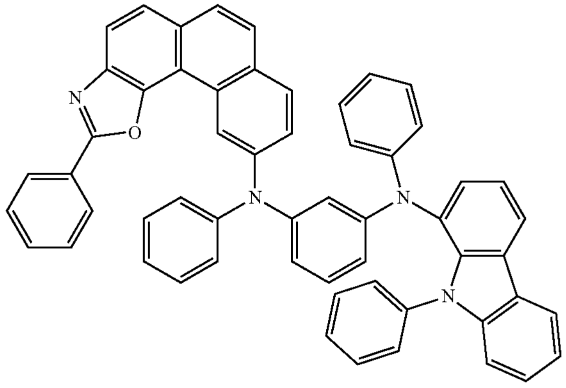

C-119

75 mL of o-xylene was added to Compound 6-1 (8 g, 14.7 mmol), Compound 6-2 (4.9 g, 14.7 mol), $Pd_2(dba)_3$ (0.7 g, 0.73 mmol), NaOt-Bu (2.1 g, 22.1 mmol), and S-Phos (0.6 g, 1.47 mmol), and then the mixture was refluxed and stirred for 3.5 hours. After completion of the reaction, the reaction mixture was cooled to room temperature, and then filtered with Celite. The residue was distilled under reduced pressure, and separated by column chromatography to obtain compound C-119 (7.5 g, 63.8%).

| | MW | M.P |
|---|---|---|
| C-119 | 794.9 | 185.6° C. |

Example 7: Synthesis of Compound C-120

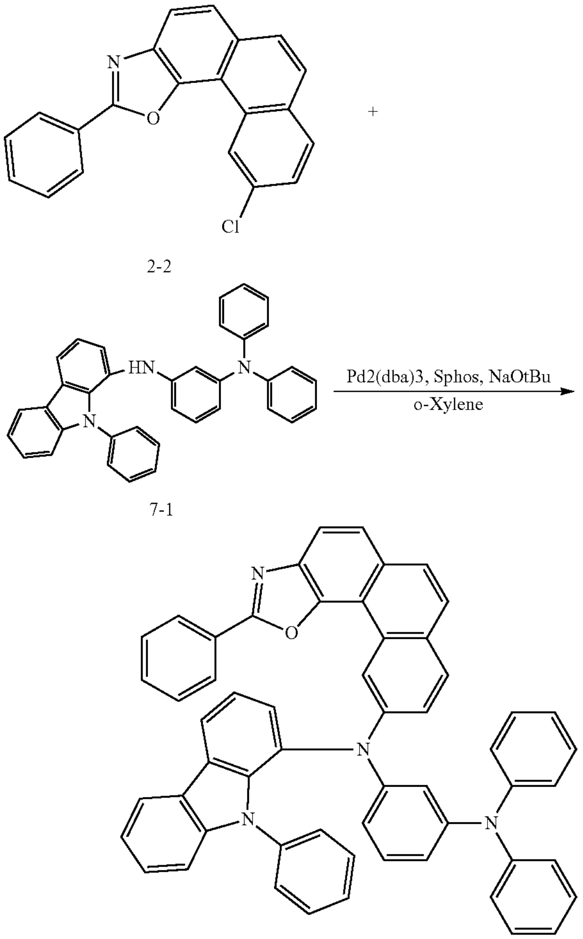

2-2

7-1

35 mL of o-xylene was added to Compound 2-2 (2.3 g, 6.97 mmol), Compound 7-1 (4.5 g, 9.07 mmol), $Pd_2(dba)_3$ (0.32 g, 0.35 mmol), NaOt-Bu (1.01 g, 10.46 mmol), and S-Phos (0.29 g, 0.70 mmol), and then the mixture was stirred under reflux for 24 hours. After completion of the reaction, the reaction mixture was cooled to room temperature, and then filtered with Celite. The residue was distilled under reduced pressure, and separated by column chromatography to obtain compound C-120 (3.3 g, 59.5%).

| | MW | M.P |
|---|---|---|
| C-120 | 794.9 | 232.8° C. |

Hereinafter, for a detailed understanding of the present disclosure, properties of an OLED device comprising a plurality of host materials of the present disclosure may be described with reference to the representative compound of the present disclosure. However, the following examples are merely for explaining the characteristics of the OLED device comprising the compound according to the present disclosure and a plurality of host materials according to the present disclosure for a detailed understanding of the present disclosure, and the present disclosure is not limited to the following examples.

Device Examples 1 to 10: Preparation of OLEDs by Co-Depositing a First Host Compound and a Second Host Compound According to the Present Disclosure OLEDs according to the present disclosure were prepared. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was mounted on a substrate holder of a vacuum vapor deposition apparatus. Compound HI-1 was introduced into a cell of the vacuum vapor deposition apparatus, and compound HT-1 was introduced into another cell. The two materials were evaporated at different rates, and compound HI-1 was deposited in a doping amount of 3 wt % based to the total amount of compound HI-1 and compound HT-1 to form a hole injection layer with a thickness of 10 nm. Subsequently, compound HT-1 was deposited on the hole injection layer to form a first hole transport layer with a thickness of 80 nm. Next, compound HT-2 was introduced into another cell of the vacuum vapor deposition apparatus and was evaporated by applying an electric current to the cell, thereby depositing a second hole transport layer with a thickness of 60 nm on the first hole transport layer. After forming the hole injection layer and the hole transport layers, a first light-emitting layer was deposited thereon as follows: A first host compound and a second host compound, which are listed in Table 1 below, were added as hosts to two cells in a vacuum deposition equipment, respectively, compound D-39 was added as a dopant in another cell, the two host materials were evaporated at a rate of 1:1 and simultaneously, the dopant material was evaporated at a different rate to dope the dopant in an amount of 3 wt % with respect to the total amount of the host and dopant, thereby depositing a light-emitting layer having a thickness of 40 nm on the second hole transport layer. Next, compounds ET-1 and EI-1 as electron transport materials were deposited on the light-emitting layer at a weight ratio of 50:50 to form an electron transport layer having a thickness of 35 nm. Then, compound EI-1 was deposited on the electron transport layer as an electron injection layer to a thickness of 2 nm, and then an Al cathode was deposited on the electron injection layer by using another vacuum deposition equipment to a thickness of 80 nm, thereby completing the manufacture of OLED. Each compounds used for all the materials were purified by vacuum sublimation under 10-6 torr.

Device Comparative Examples 1 and 2: Preparation of OLEDs Comprising Comparative Compound as a Host OLEDs were prepared in the same manner as in Device Example 1, except that the second host compound listed in Table 1 below was used alone as a host of the light-emitting layer.

The driving voltage, current efficiency, emission color at a luminance of 5,000 nits, and a time taken until the intensity decreases form 100% to 95% (lifespan; T95) at a luminance of 10,000 nits of the OLED devices of Device Examples 1 to 10 and Device Comparative Examples 1 and 2 prepared as described above, were measured and the results thereof are shown in the following Table 1.

TABLE 1

| | Host 1 | Host 2 | Driving Voltage (V) | Current Efficiency (cd/A) | luminous color | Lifespan T95 (hr) |
|---|---|---|---|---|---|---|
| Device Example 1 | C-2 | H2-26 | 3.8 | 30.2 | red | 375 |
| Device Example 2 | C-2 | H2-61 | 3.8 | 30.8 | red | 274 |
| Device Example 3 | C-26 | H2-26 | 4.0 | 32.5 | red | 310 |
| Device Example 4 | C-26 | H2-61 | 3.8 | 30.0 | red | 171 |
| Device Example 5 | C-45 | H2-26 | 3.7 | 32.3 | red | 312 |
| Device Example 6 | C-45 | H2-61 | 3.6 | 29.1 | red | 243 |
| Device Example 7 | C-63 | H2-26 | 3.7 | 32.3 | red | 315 |
| Device Example 8 | C-63 | H2-61 | 3.6 | 30.0 | red | 252 |
| Device Example 9 | C-4 | H2-26 | 3.8 | 32.1 | red | 300 |
| Device Example 10 | C-4 | H2-61 | 3.7 | 32.6 | red | 284 |
| Device Comparative Example 1 | — | H2-26 | 4.5 | 31.8 | red | 17.7 |
| Device Comparative Example 2 | — | H2-61 | 4.1 | 20.6 | red | 15.3 |

From Table 1, it can be confirmed that the organic electroluminescent devices comprising a plurality of host materials comprising the compounds with a specific combination according to the present disclosure have a low driving voltage and/or high luminous efficiency and/or significantly improved lifespan properties compared to the conventional organic electroluminescent device.

The compounds used in the Device Examples and the Device Comparative Examples are shown in Table 2 below.

TABLE 2

| | |
|---|---|
| Hole Injection Layer/ Hole Transport Layer | 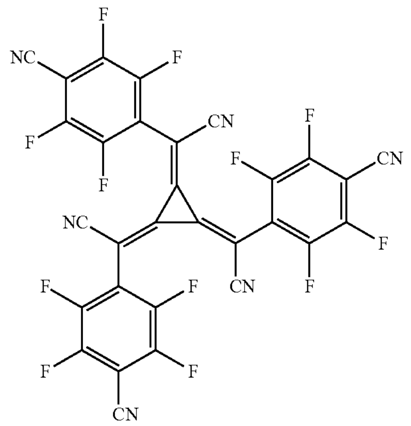 HI-1 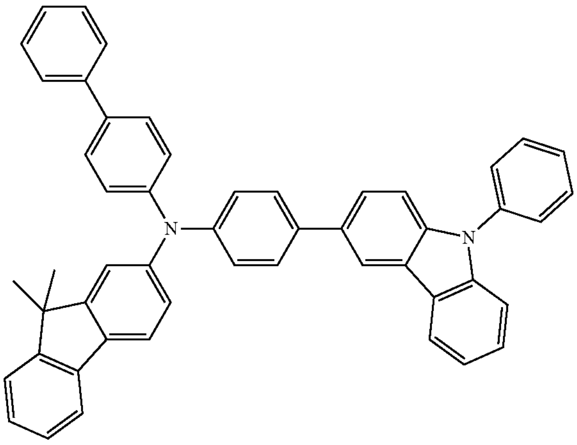 HT-1 |

TABLE 2-continued
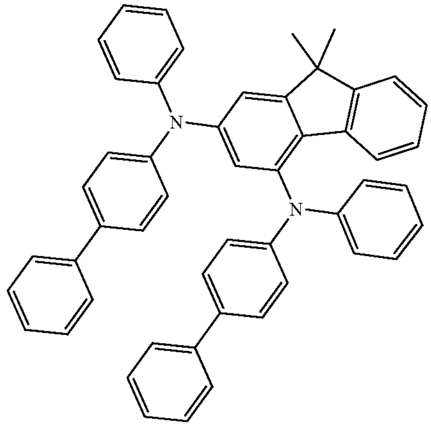
HT-2
Light-emitting
Layer
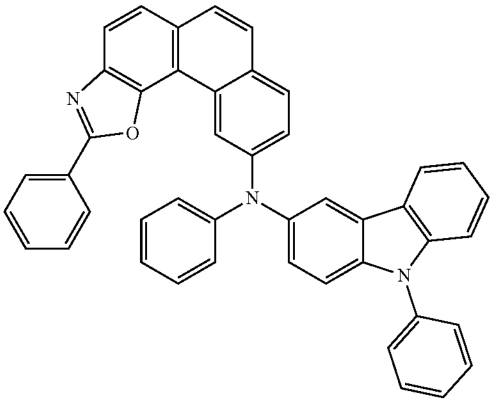
C-2
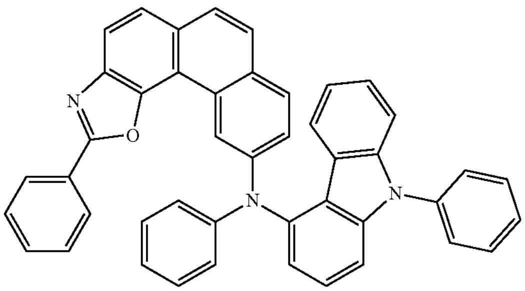
C-26

TABLE 2-continued
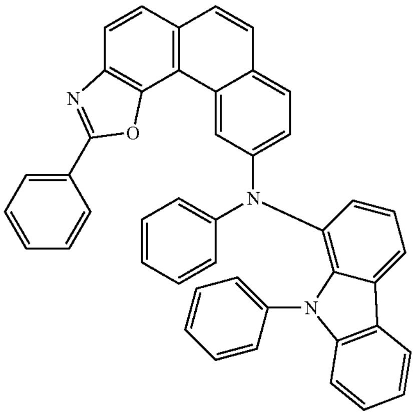
C-45
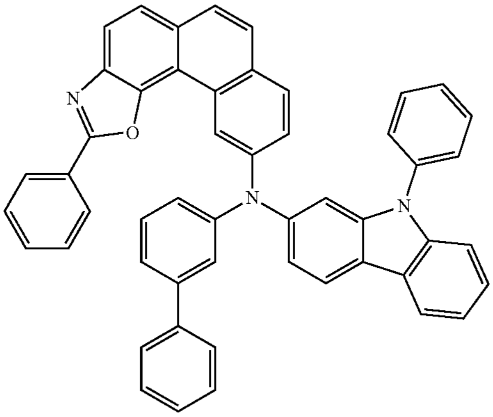
C-63
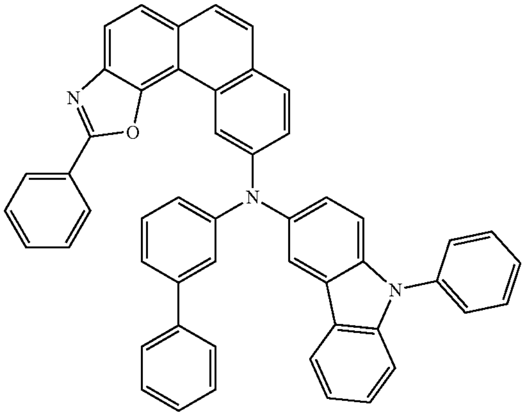
C-4

TABLE 2-continued
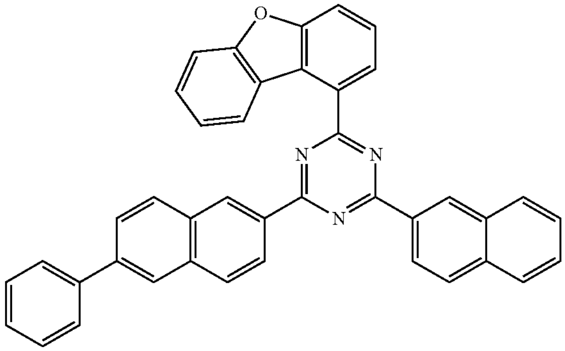
H2-61
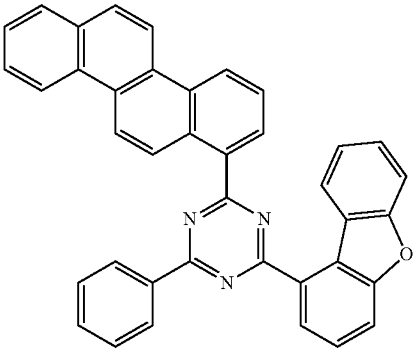
H2-26
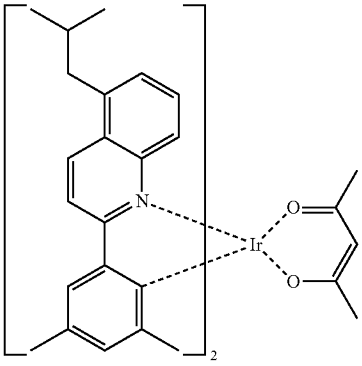
D-39
Electron Transport Layer/ Electron Injection Layer
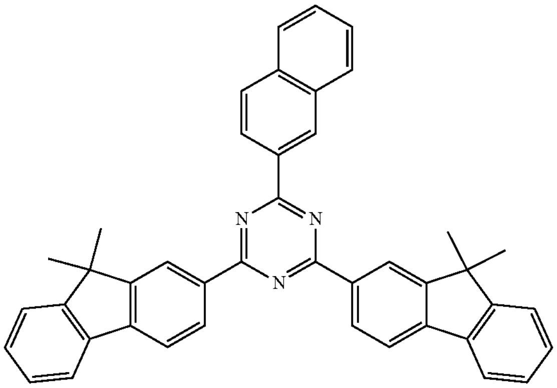
ET-1

TABLE 2-continued

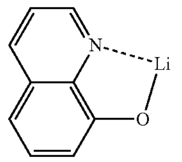

EI-1

The invention claimed is:

1. A plurality of host materials, comprising a first host material comprising a compound represented by following formula 1 and a second host material including a compound represented by following formula 2:

(1)

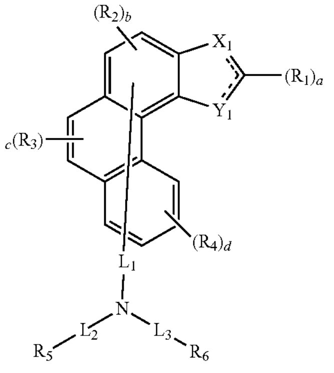

wherein, $X_1$ and $Y_1$ each independently represent, —N═, —$NR_{10}$—, —O— or —S—, provided that any one of $X_1$ and $Y_1$ is —N═, and the other of $X_1$ and $Y_1$ is —$NR_{10}$—, —O— or —S—;

$L_1$, $L_2$ and $L_3$ each independently represent, a single bond, a substituted or unsubstituted (C6-C30)arylene, or a substituted or unsubstituted (3- to 30-membered)heteroarylene;

$R_1$ represents a substituted or unsubstituted (C6-C30)aryl or a substituted or unsubstituted (3- to 30-membered) heteroaryl;

$R_5$ and $R_6$ each independently represent, a substituted or unsubstituted (C6-C30)aryl, or a substituted or unsubstituted (3- to 30-membered)heteroaryl; with a proviso that at least one of $R_5$ and $R_6$ is selected from carbazole derivatives represented by following formula 1-A or formula 1-B;

(1-A)

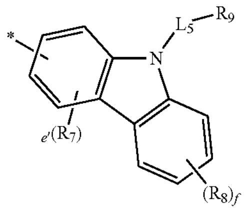

-continued (1-B)

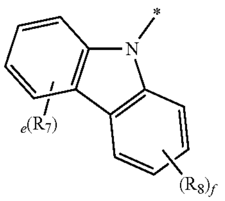

wherein, $L_5$ represents a single bond, a substituted or unsubstituted (C6-C30)arylene, or a substituted or unsubstituted (3- to 30-membered)heteroarylene;

$R_2$ to $R_4$ and $R_7$ to $R_{10}$ each independently represent, hydrogen, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or -$L_3$`` -N($Ar_3$`` )($Ar_4$`` ); or may be linked to the adjacent substituents to form a ring;

$L_3$`` represents a single bond, a substituted or unsubstituted (C6-C30)arylene, or a substituted or unsubstituted (3- to 30-membered)heteroarylene;

$Ar_3$`` and $Ar_4$`` each independently represent, hydrogen, deuterium, a substituted or unsubstituted (C1-C30) alkyl, a substituted or unsubstituted (C2-C30)alkenyl, a substituted or unsubstituted fused ring of a (C3-C30) aliphatic ring and a (C6-C30)aromatic ring, a substituted or unsubstituted (C6-C30)aryl, or a substituted or unsubstituted (3- to 30-membered)heteroaryl;

a represents 1, b and c each independently represent 1 or 2, d to f each independently represent an integer of 1 to 4, e` represents an integer of 1 to 3, when b to f and e ` are an integer of 2 or more, each of $R_2$ to $R_4$, $R_7$, and $R_8$ may be the same or different;

* indicates a binding site with $L_2$ or $L_3$, (2)

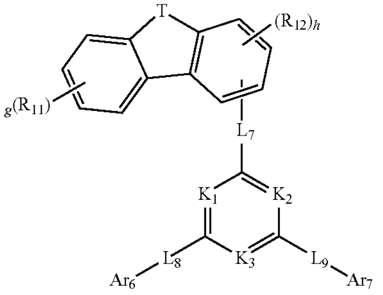

wherein,

T is O or S;

$K_1$ to $K_3$ each independently represent, N or CH, provided that at least one of $K_1$ to $K_3$ is N;

$L_7$ to $L_9$ each independently represent, a single bond, a substituted or unsubstituted (C6-C30)arylene, a substituted or unsubstituted (C3-C30)cycloalkylene, or a substituted or unsubstituted (3- to 30-membered)heteroarylene;

$R_{11}$, $R_{12}$, $Ar_6$ and $Ar_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring and a (C6-C30)aromatic ring, or —N—(R`)(R``); or may be linked to the adjacent substituents to form a ring;

R` and R`` each independently, represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl;

g represents an integer of 1 to 4, h represents an integer of 1 to 3, when g and h are an integer of 2 or more, each of $R_{11}$ and $R_{12}$ may be the same or different.

2. The plurality of host materials according to claim 1, wherein the substituted alkyl, the substituted alkenyl, the substituted aryl, the substituted arylene, the substituted heteroaryl, the substituted heteroarylene, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted alkylarylamino, the substituted mono- or di-arylamino, the substituted mono- or di-heteroarylamino, the substituted arylheteroarylamino, and the fused ring of the substituted aliphatic ring and aromatic ring are each independently substituted with one or more selected from the group consisting of deuterium; halogen; cyano; carboxyl; nitro; hydroxy; phosphine oxide group; (C1-C30)alkyl unsubstituted or substituted with at least one (C6-C30)aryl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered)heterocycloalkyl; (C6-C30)aryloxy; (C6-C30)arylthio; (3- to 30-membered)heteroaryl unsubstituted or substituted with at least one (C6-C30)aryl; (3- to 30-membered)aryl unsubstituted or substituted with deuterium, halogen, cyano, (C1-C30)alkyl, (C6-C30)aryl, (3- to 30-membered)heteroaryl, and tri(C6-C30)aryl; (C1-C30)alkylsilyl; tri(C6-C30)arylsilyl; di(C1-C30)alkyl(C6-C30)arylsilyl; (C1-C30)alkyldi(C6-C30)arylsilyl; (C6-C30)aryldi(3- to 30-membered)heteroarylsilyl; di(C6-C30)aryl(3- to 30-membered)heteroarylsilyl; tri(3- to 30-membered)heteroarylsilyl; amino; mono- or di-(C1-C30)alkylamino; mono- or di-(C2-C30)alkenylamino; mono- or di-(C6-C30)arylamino unsubstituted or substituted with (C1-C30)alkyl; mono- or di-(3- to 30-membered)heteroarylamino; (C1-C30)alkyl(C2-C30)alkenylamino; (C1-C30)alkyl(3- to 30-membered)heteroarylamino; (C2-C30)alkenyl(C6-C30)arylamino; (C2-C30)alkenyl(3- to 30-membered)heteroarylamino; (C6-C30)aryl(3- to 30-membered)heteroarylamino; (C1-C30)alkylcarbonyl; (C1-C30)alkoxycarbonyl; (C6-C30)arylcarbonyl; di(C6-C30)arylboronyl; (C6-C30)arylphosphine group; di(C1-C30)alkylboronyl; (C1-C30)alkyl(C6-C30)arylboronyl; (C6-C30)ar(C1-C30)alkyl; and (C1-C30)alkyl(C6-C30)aryl.

3. The plurality of host materials according to claim 1, wherein the compound represented by formula 1 is represented by any one of the following formulas 1-1 to 1-5:

(1-1)

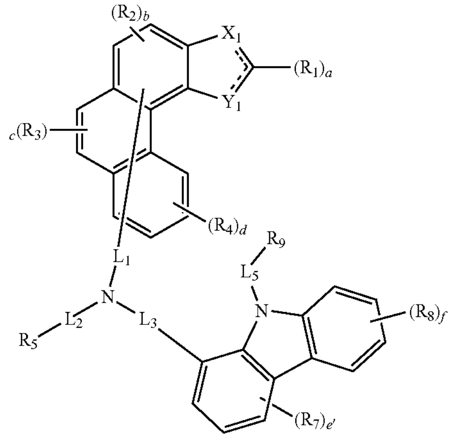

(1-2)

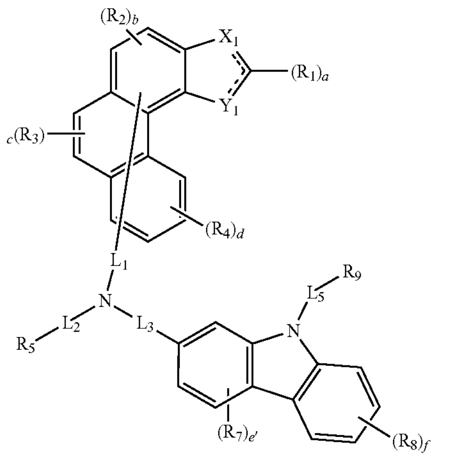

-continued
(1-3)
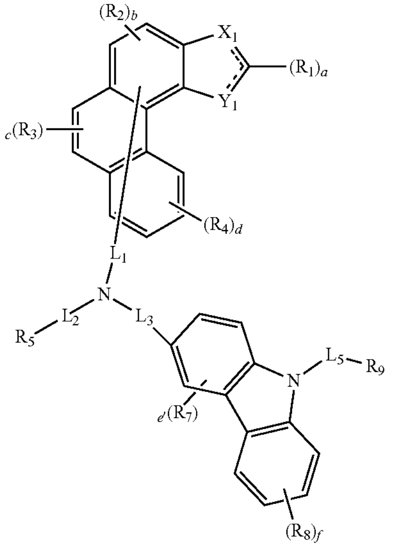
(1-4)
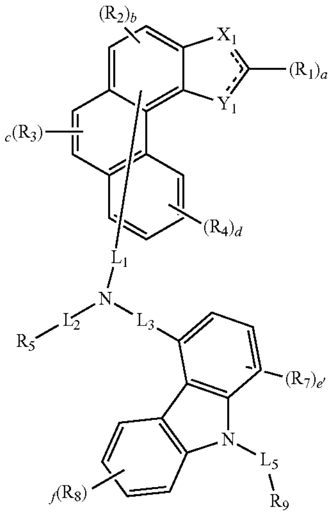
(1-5)
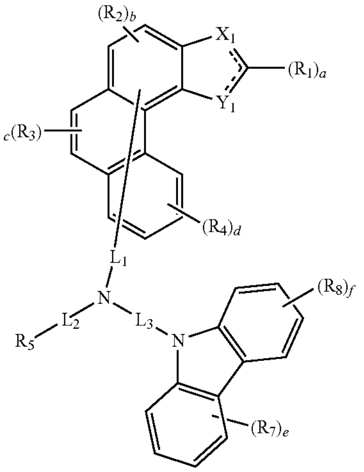
wherein,
$X_1$, $Y_1$, $L_1$ to $L_3$, $L_5$, $R_1$ to $R_5$, $R_7$ to $R_9$, a to f and e` are the same as defined in claim 1.
4. The plurality of host materials according to claim 1, wherein the compound represented by formula 2 is represented by any one of the following formulas 2-1 to 2-4:
(2-1)
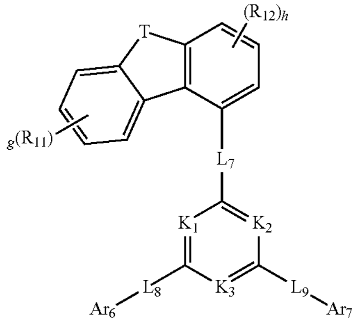
(2-2)
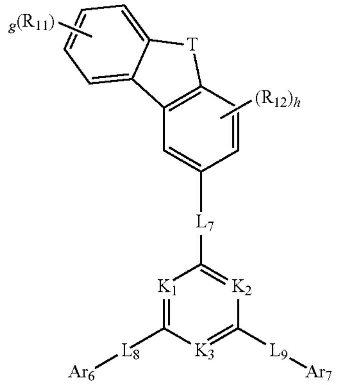
(2-3)
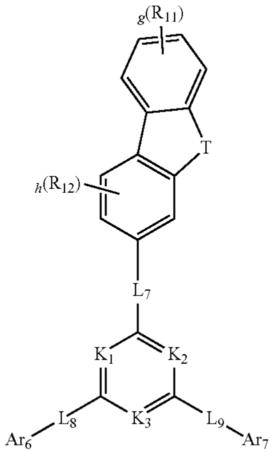
(2-4)
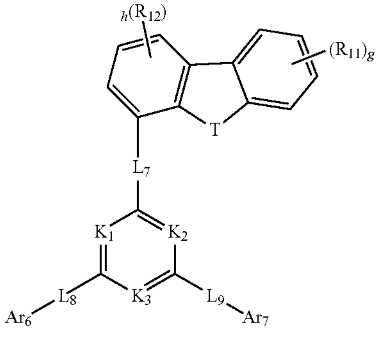

wherein,
T, $K_1$ to $K_3$, $L_7$ to $L_9$, $R_{11}$, $R_{12}$, $Ar_6$, $Ar_7$, g, and h are the same as defined in claim 1.
5. The plurality of host materials according to claim 1, wherein the compound represented by formula 1 is selected from the following compounds:
C-1
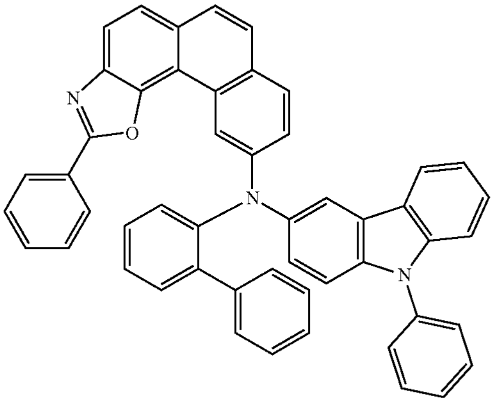
C-2
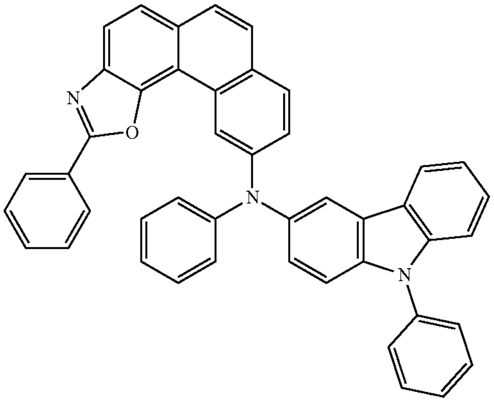
C-3
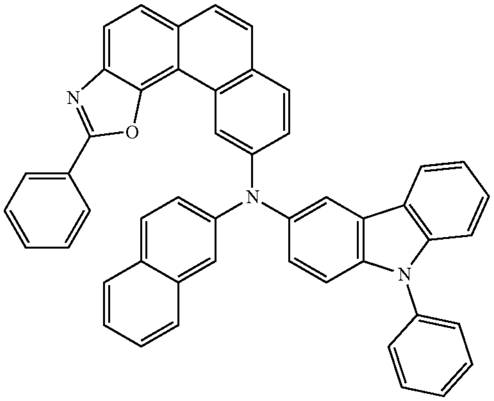
-continued
C-4
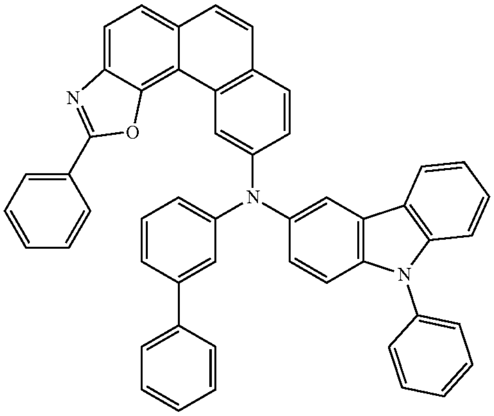
C-5
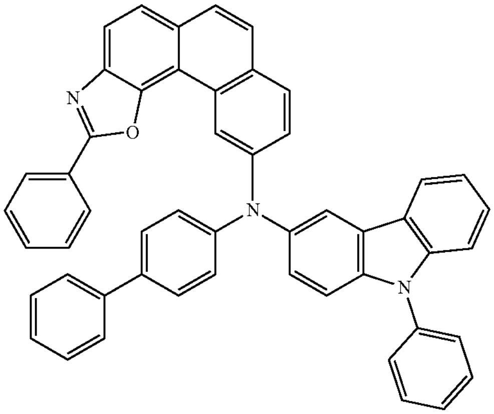
C-6
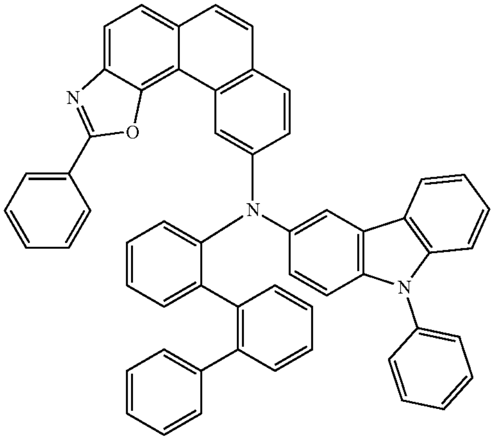

-continued
C-7
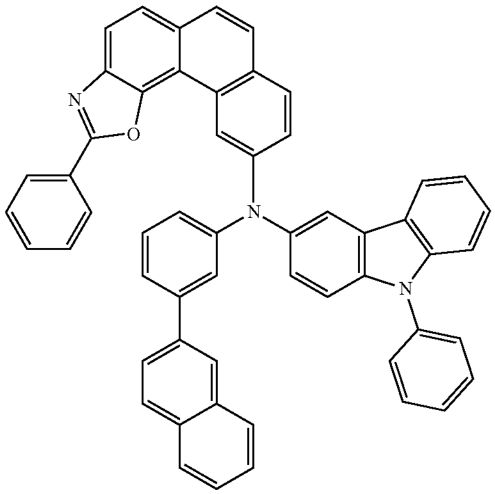
C-8
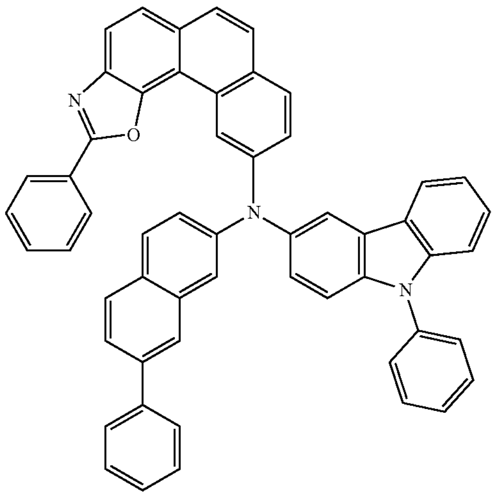
C-9
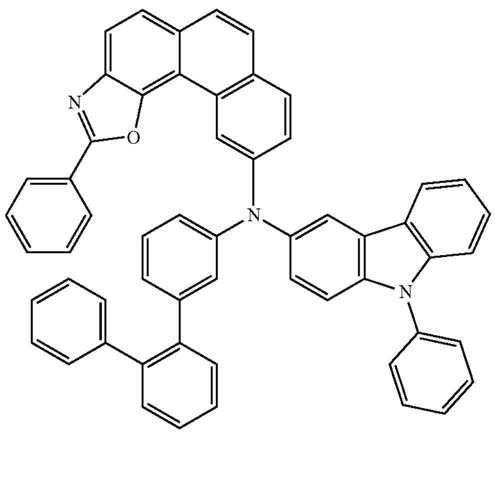
-continued
C-10
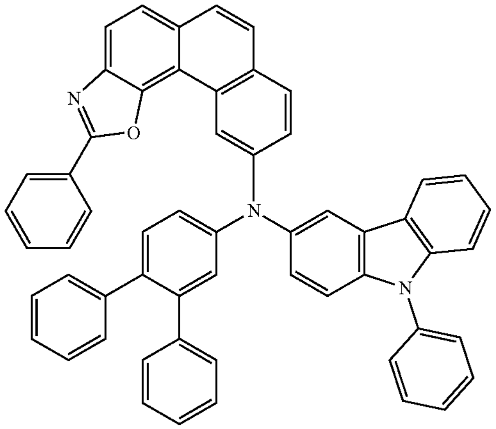
C-11
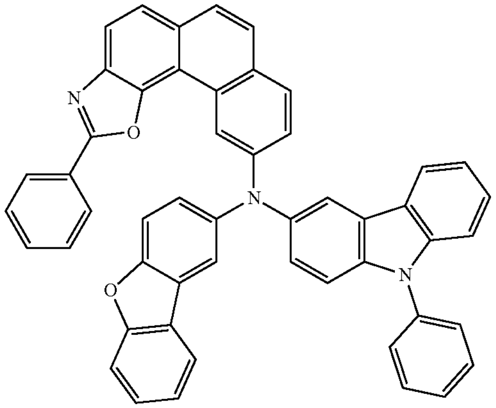
C-12
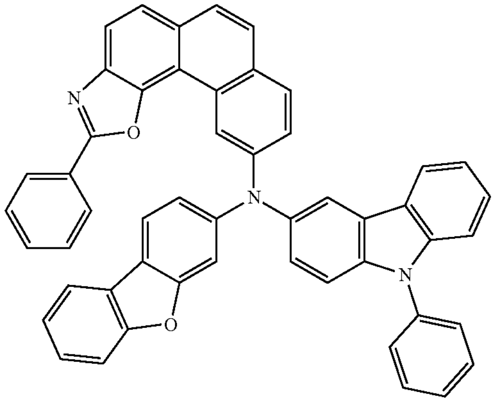
C-13
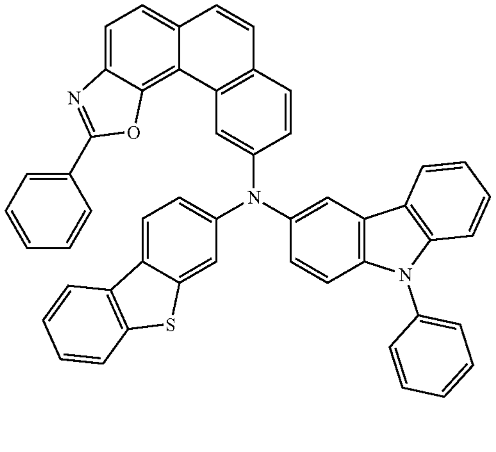

-continued
C-14
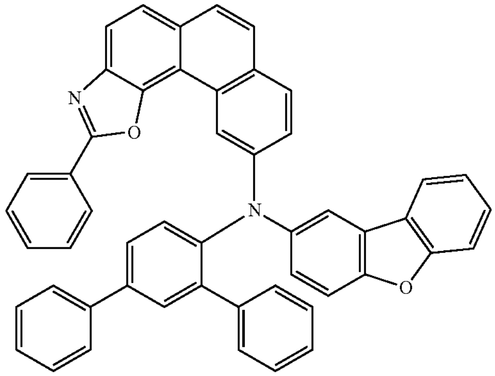
C-15
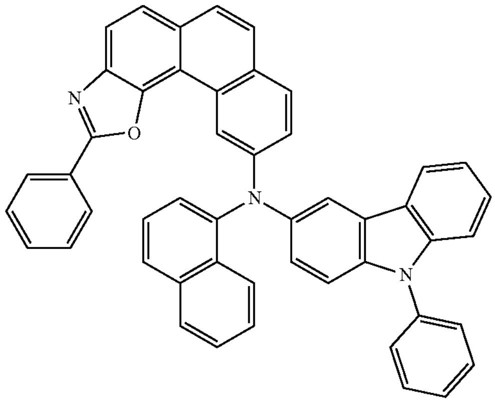
C-16
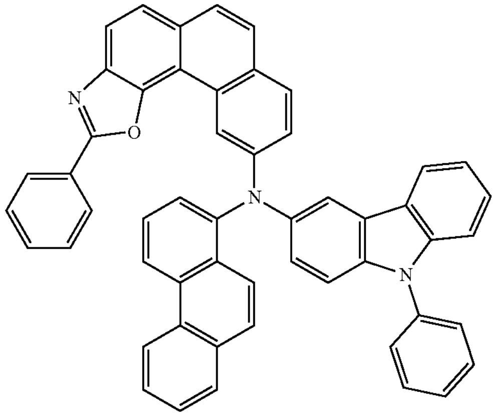
C-17
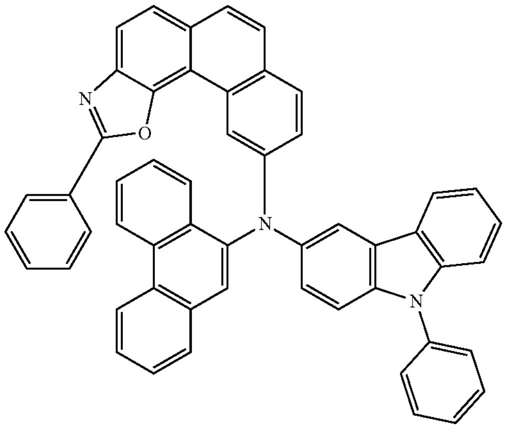
-continued
C-18
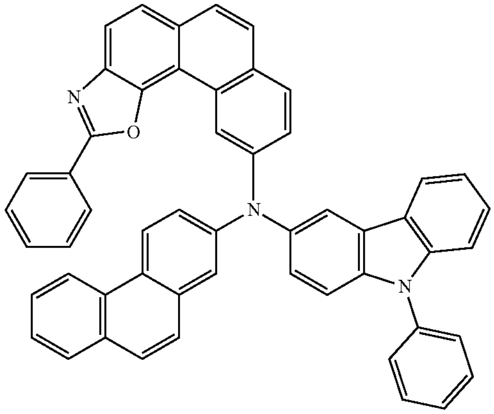
C-19
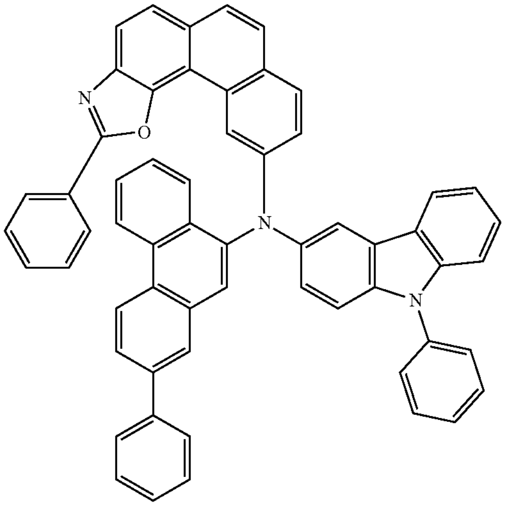
C-20
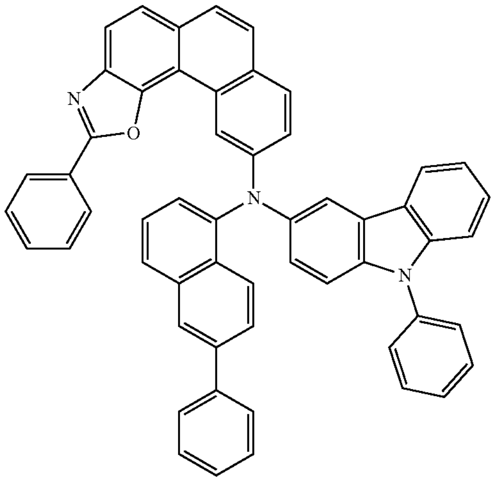

-continued
C-21
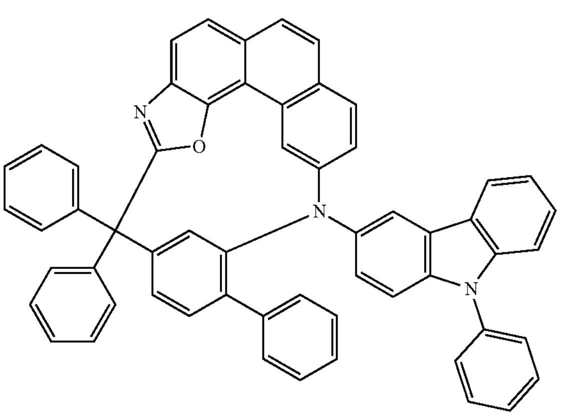
C-22
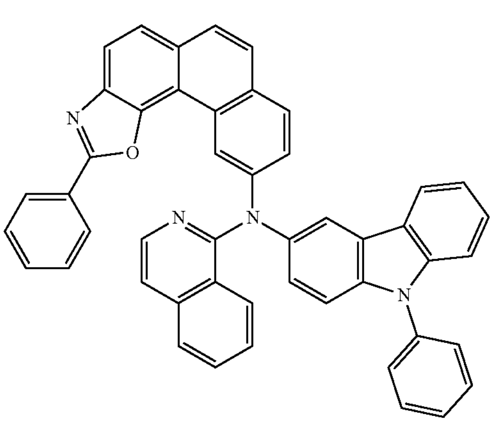
C-23
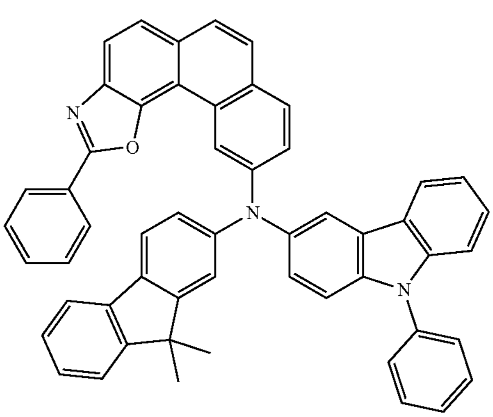
-continued
C-24
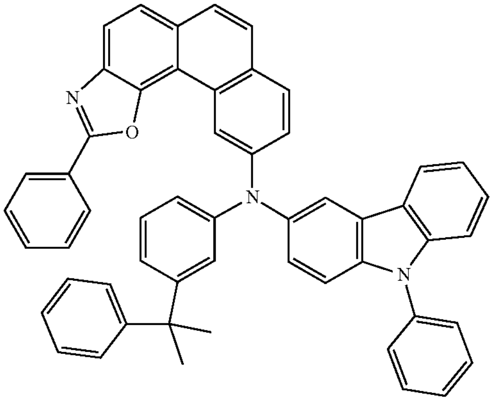
C-25
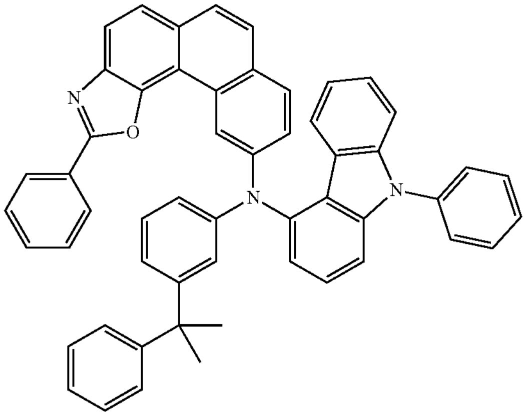
C-26
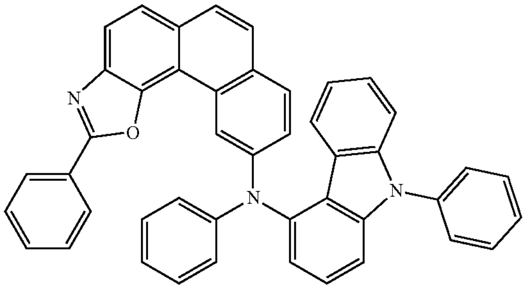
C-27
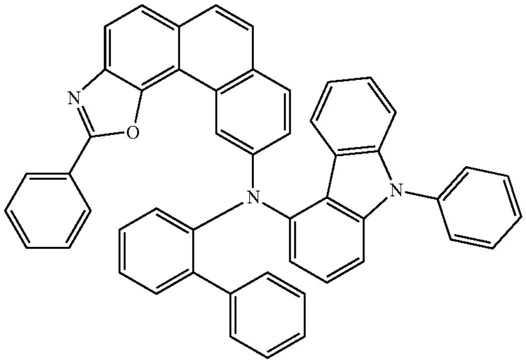

-continued
C-28
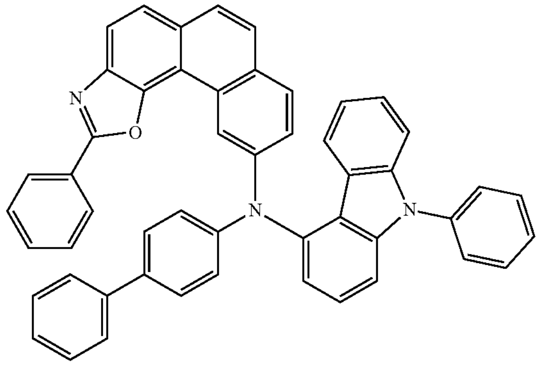
C-29
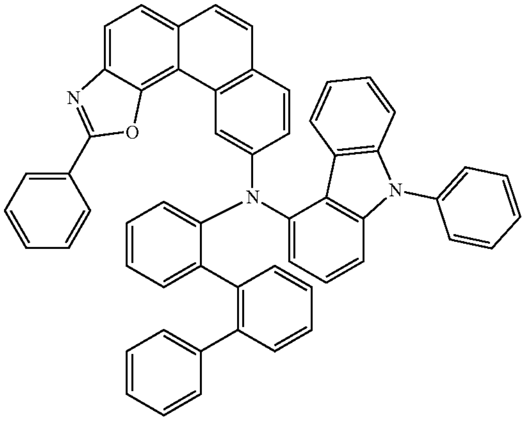
C-30
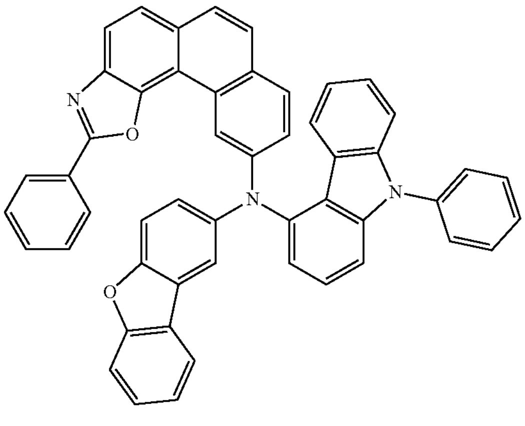
-continued
C-31
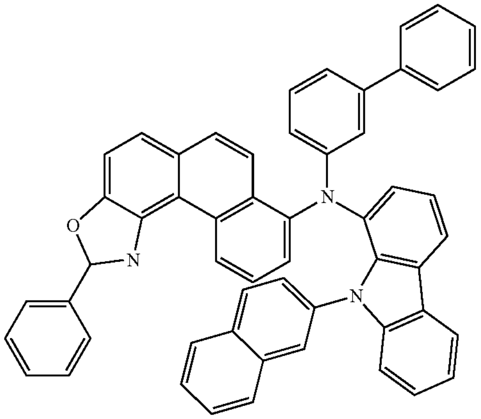
C-32
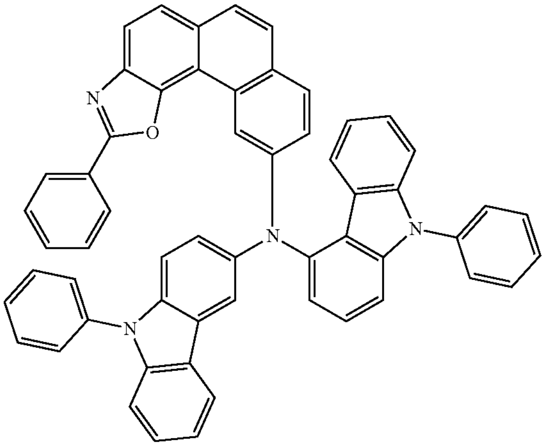
C-33
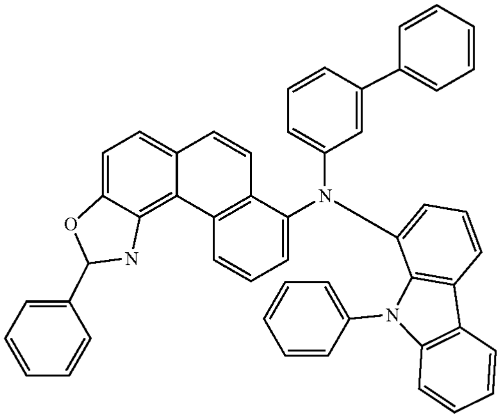

-continued
C-34
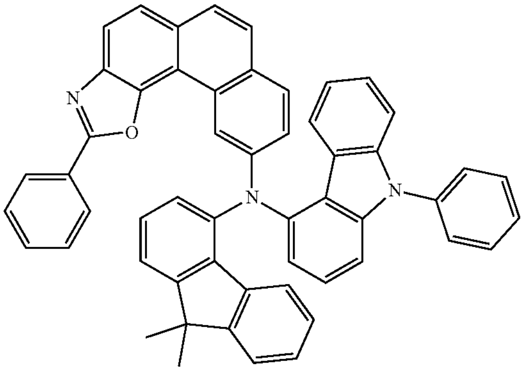
C-35
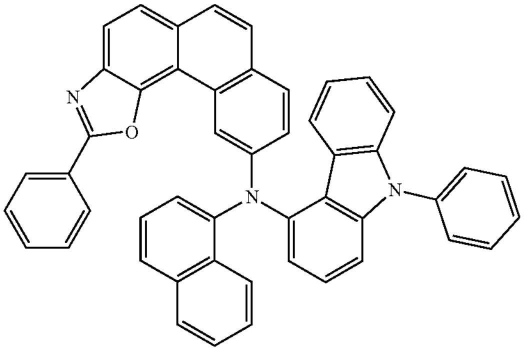
C-36
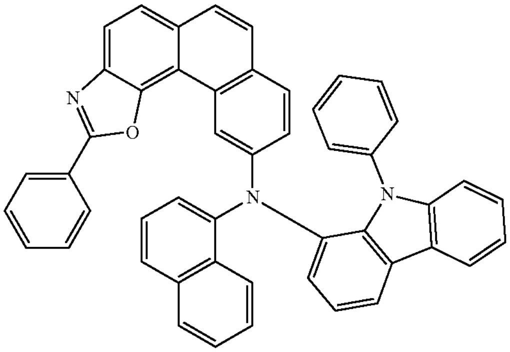
C-37
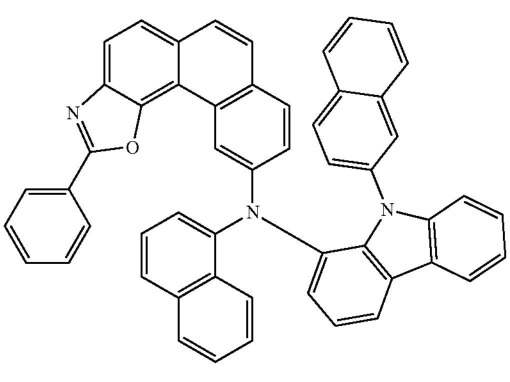
-continued
C-38
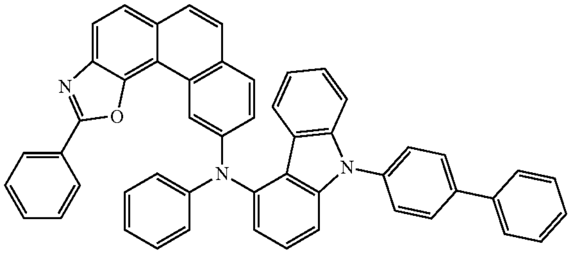
C-39
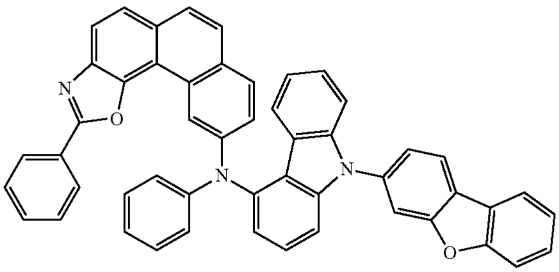
C-40
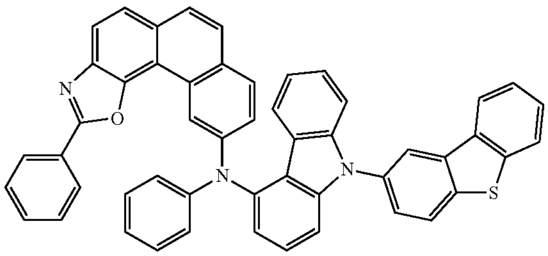
C-41
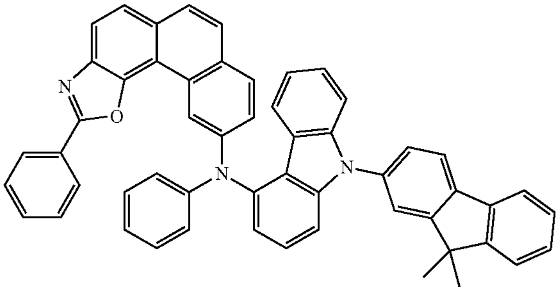
C-42
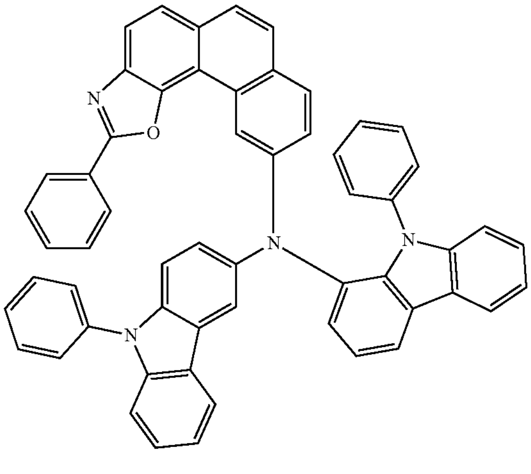

-continued
C-43
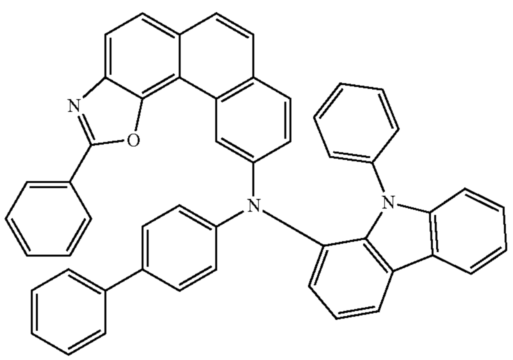
C-44
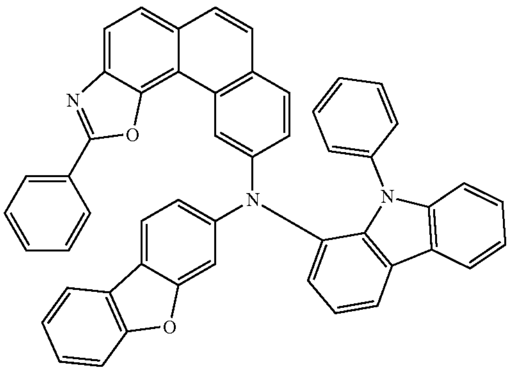
C-45
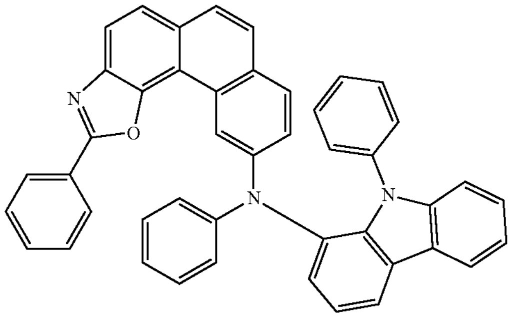
C-46
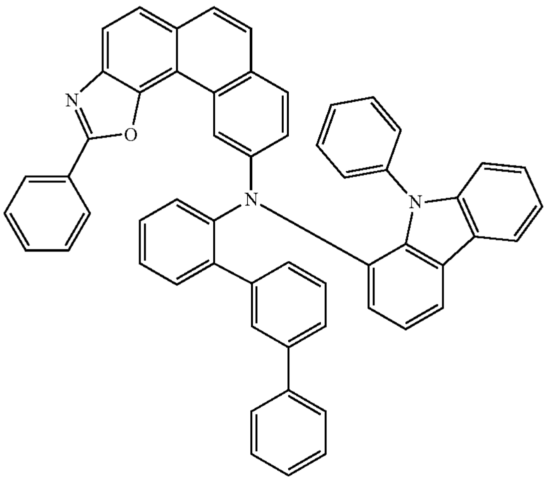
-continued
C-47
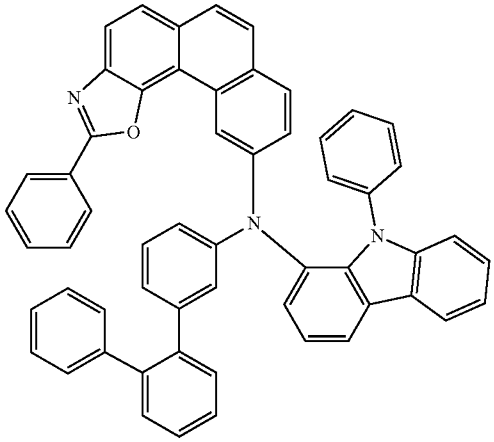
C-48
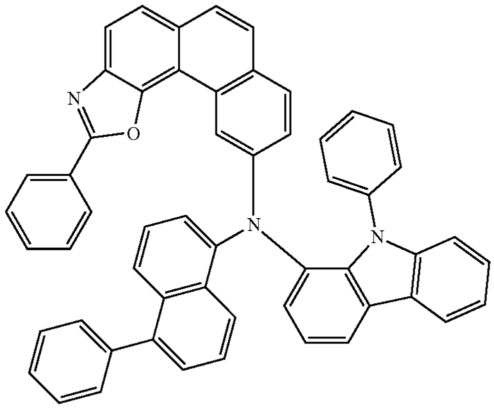
C-49
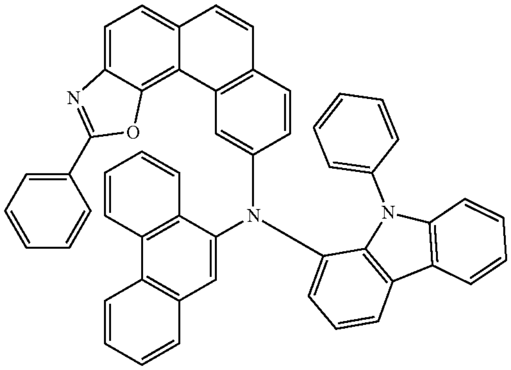

-continued
C-50
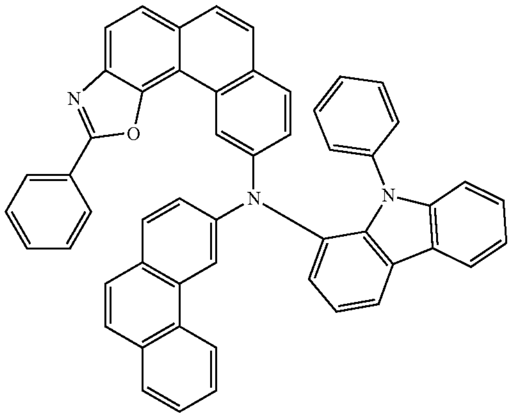
C-51
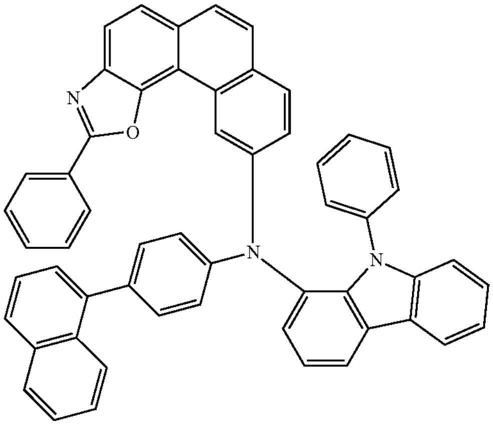
C-52
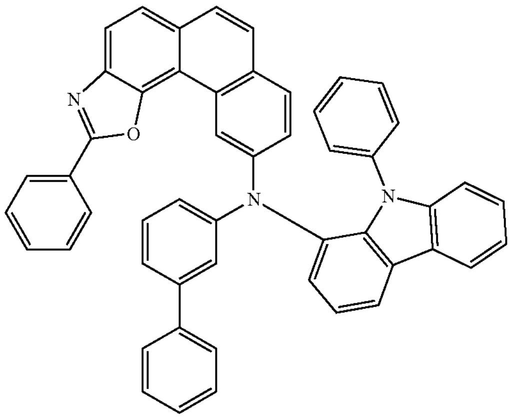
-continued
C-53
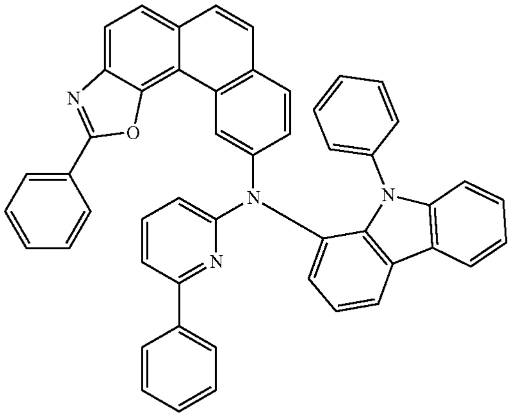
C-54
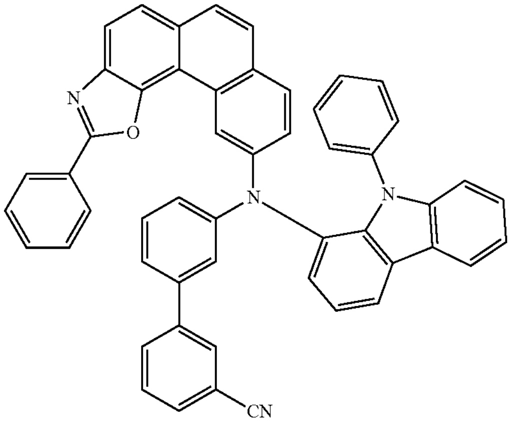
C-55
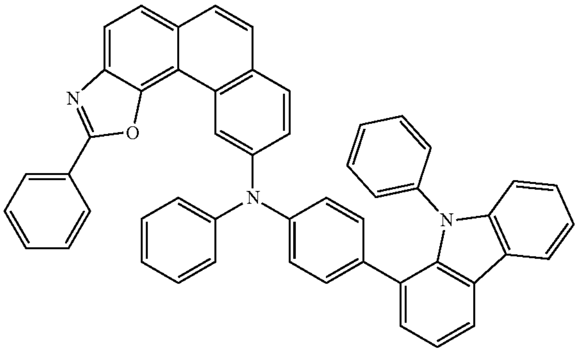
C-56
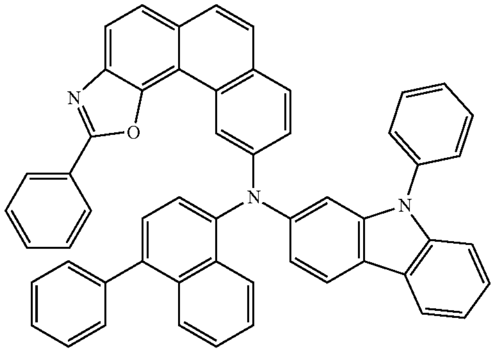

-continued
C-57
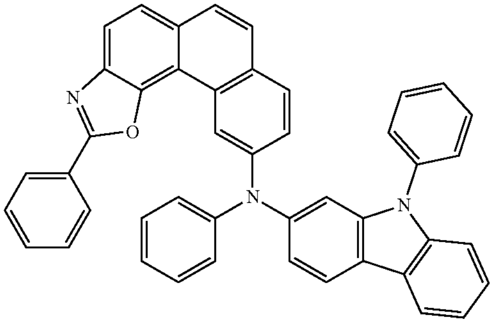
C-58
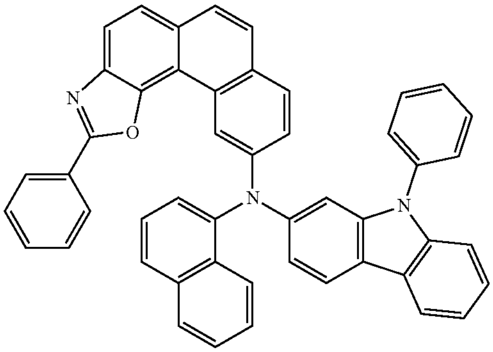
C-59
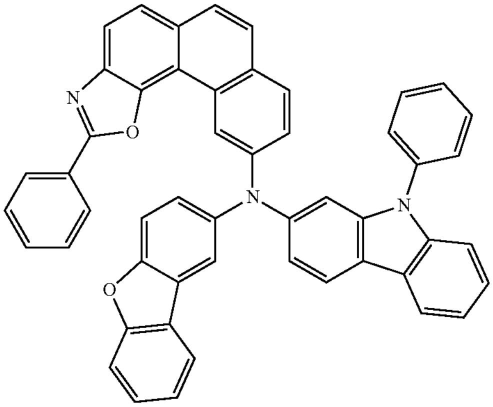
C-60
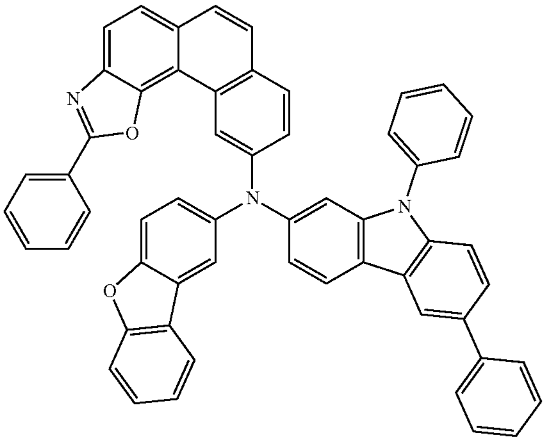
-continued
C-61
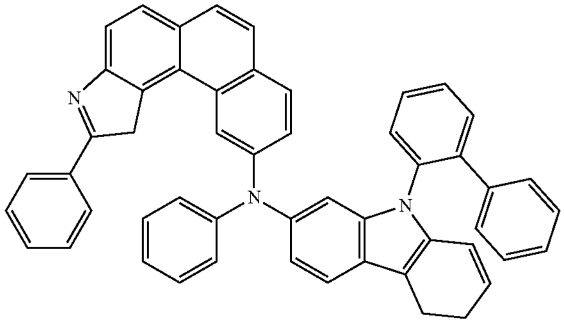
C-62
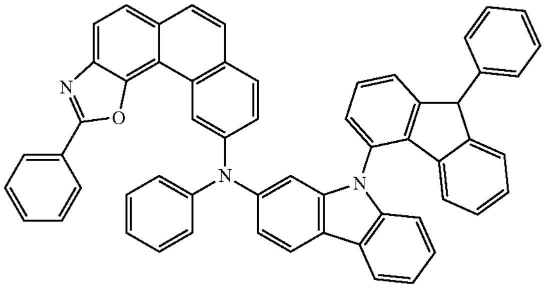
C-63
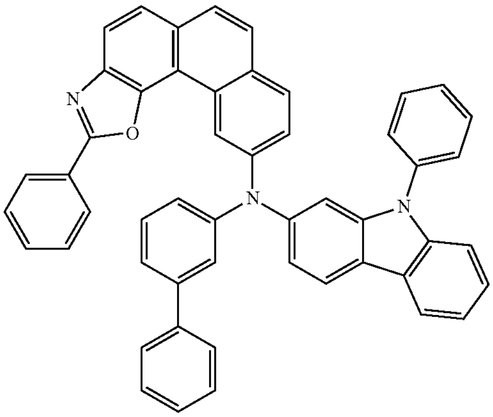
C-64
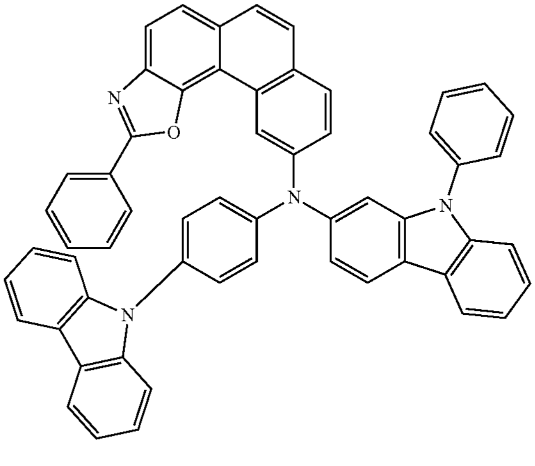

-continued
C-65
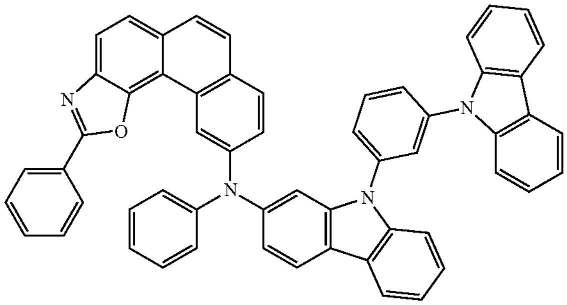
C-66
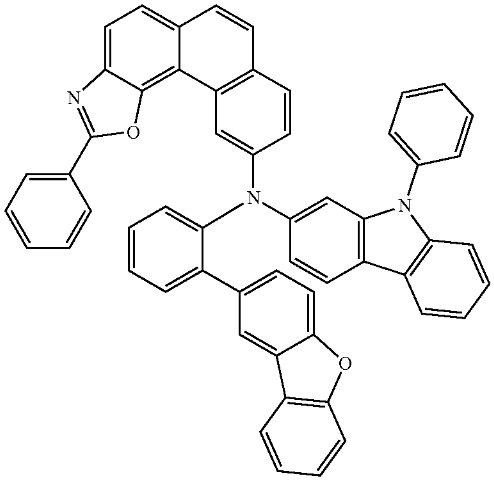
C-67
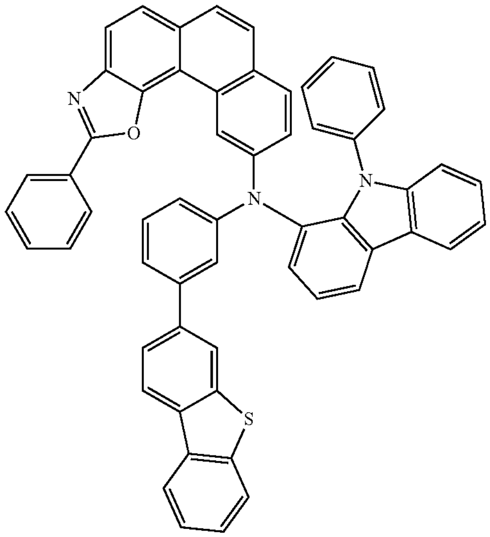
-continued
C-68
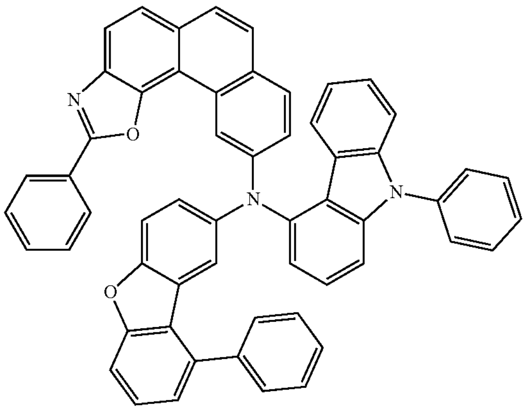
C-69
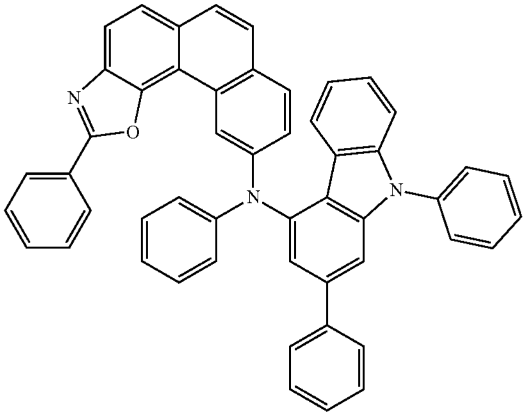
C-70
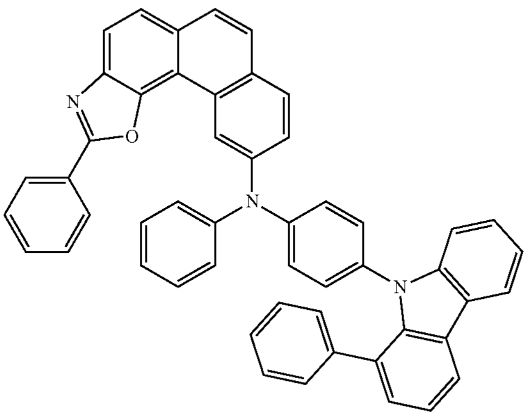

-continued
C-71
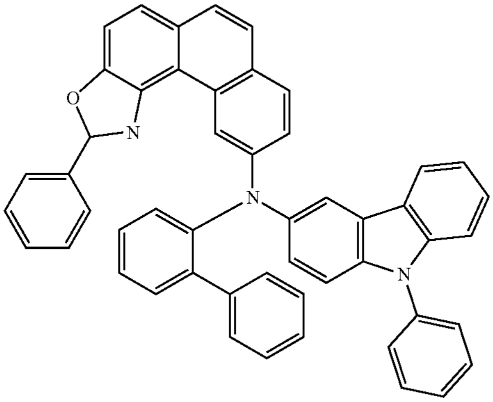
C-72
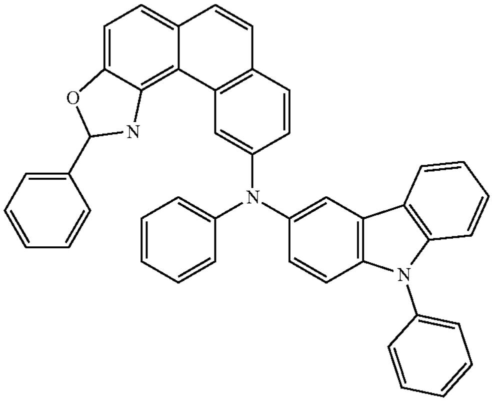
C-73
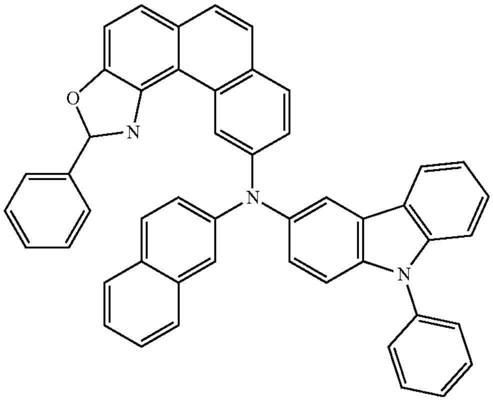
C-74
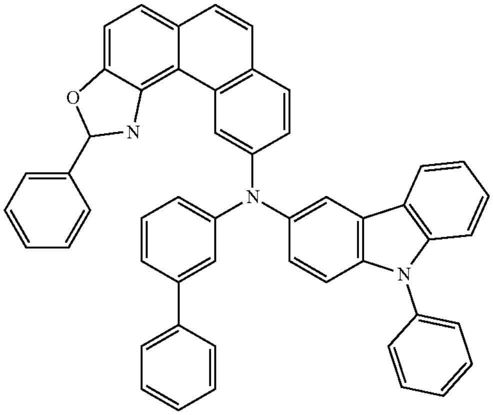
-continued
C-75
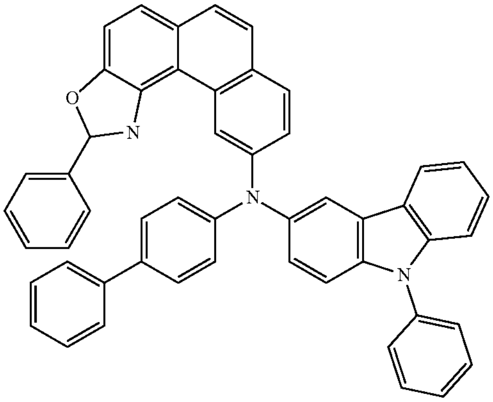
C-76
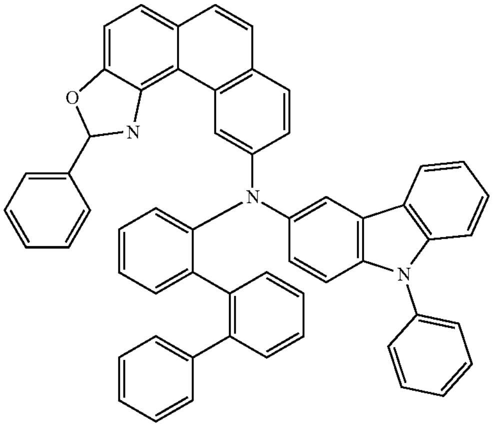
C-77
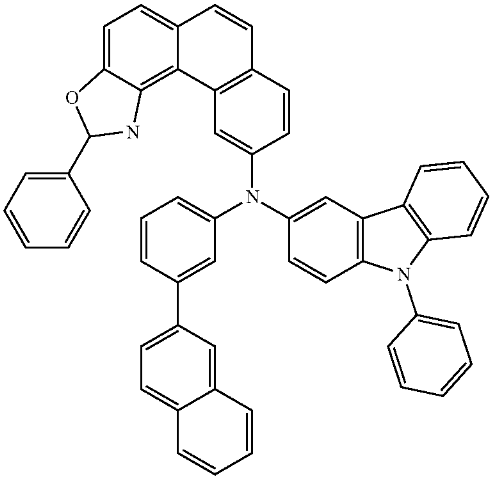

-continued
C-78
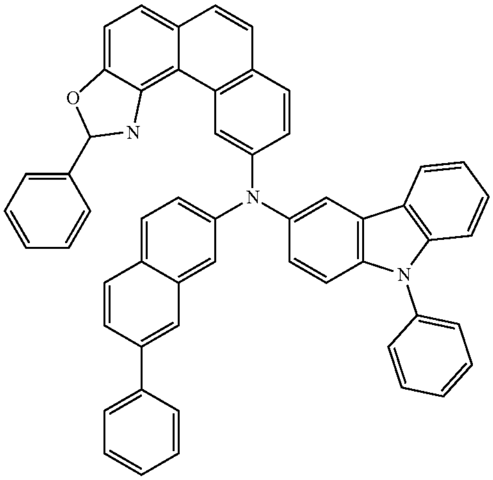
C-79
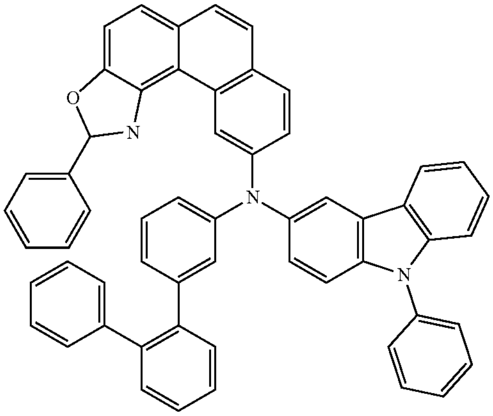
C-80
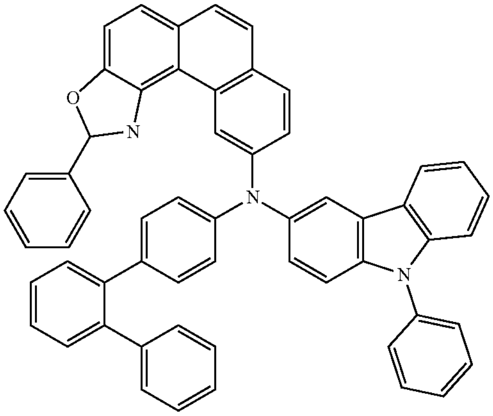
-continued
C-81
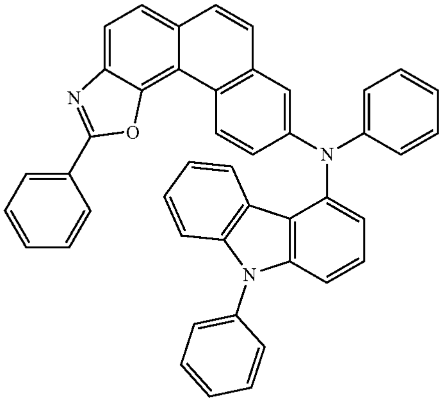
C-82
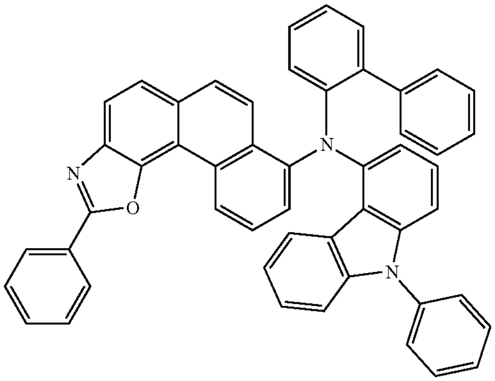
C-83
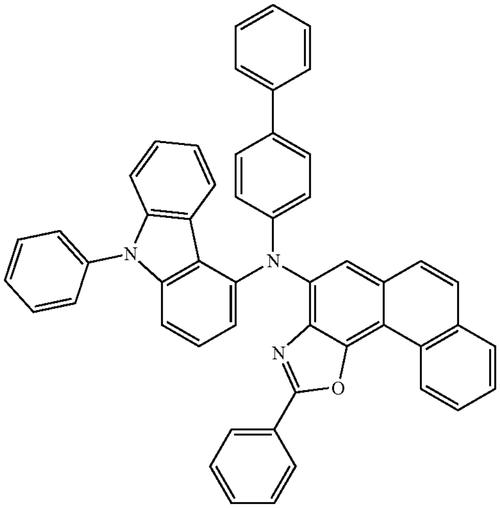

-continued
C-84
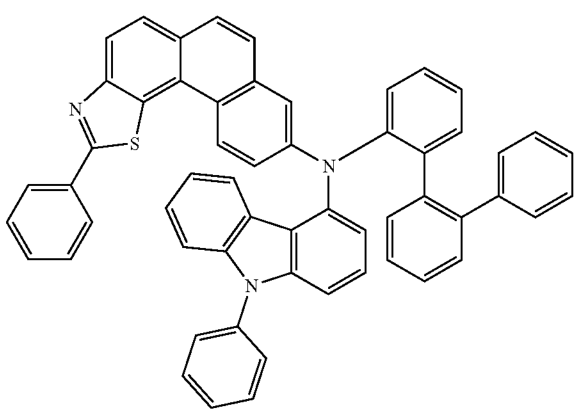
C-85
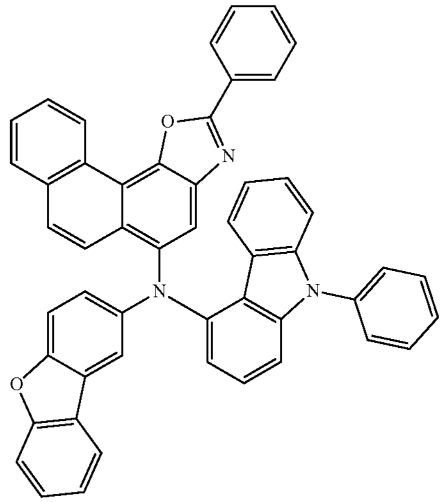
C-86
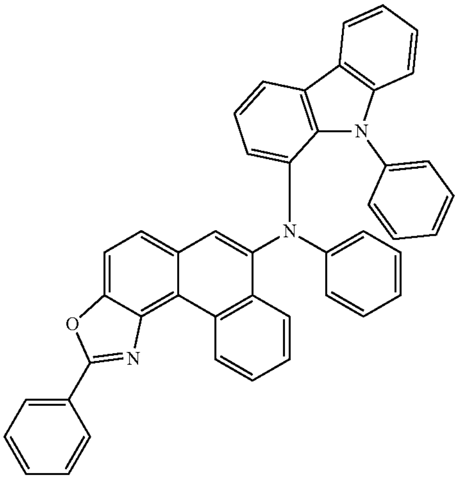
-continued
C-87
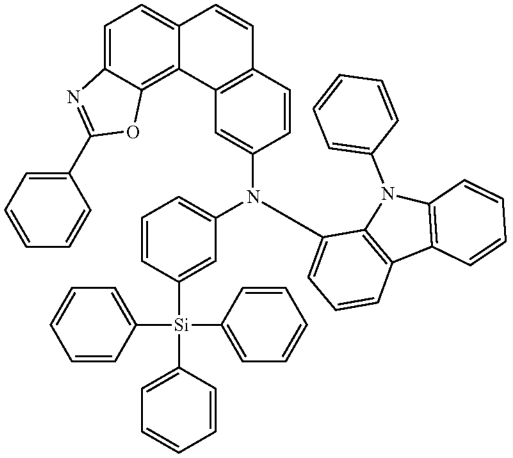
C-88
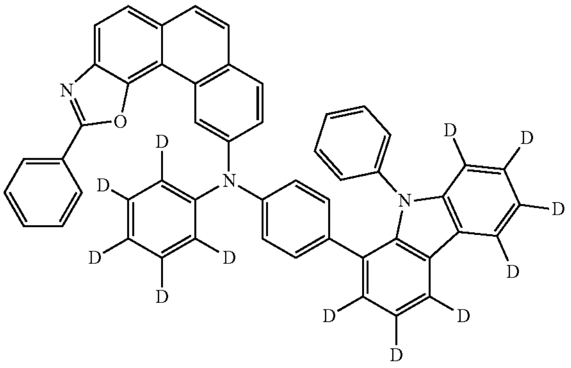
C-89
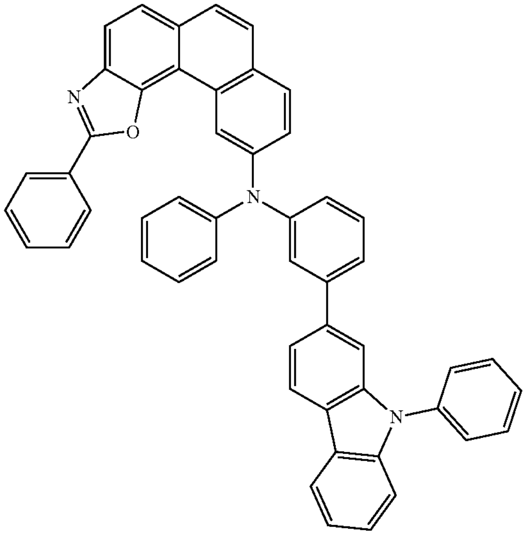

-continued
C-90
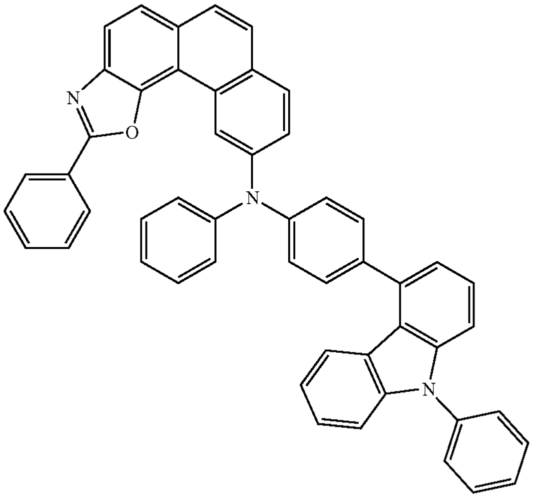
C-91
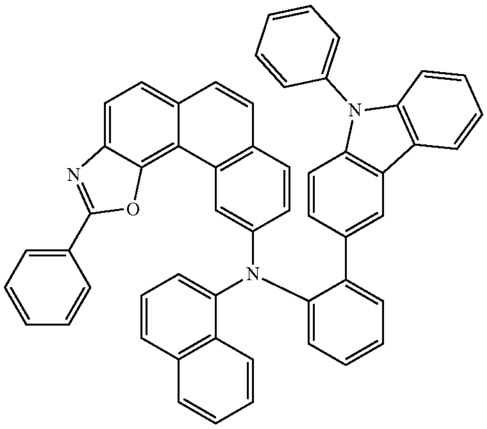
C-92
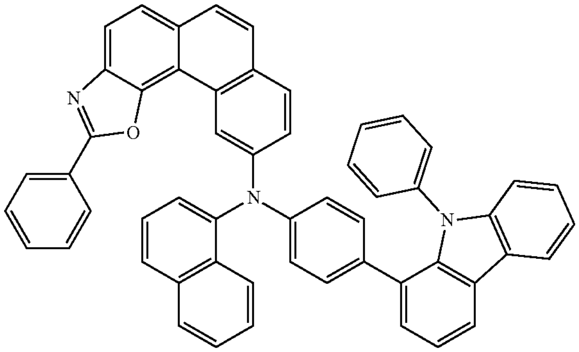
-continued
C-93
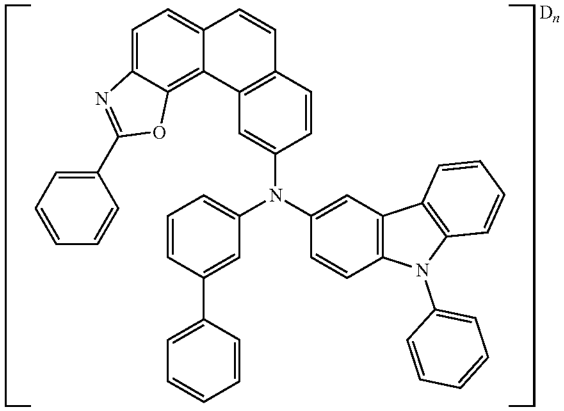
$D_n$: 1-33
C-94
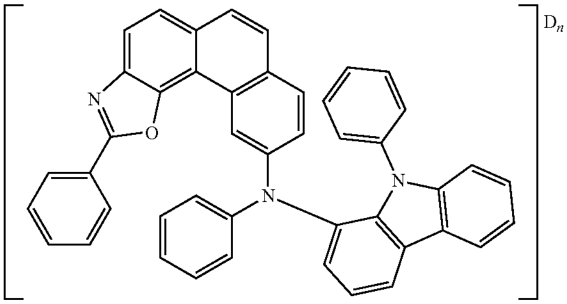
$D_n$: 1-29
C-95
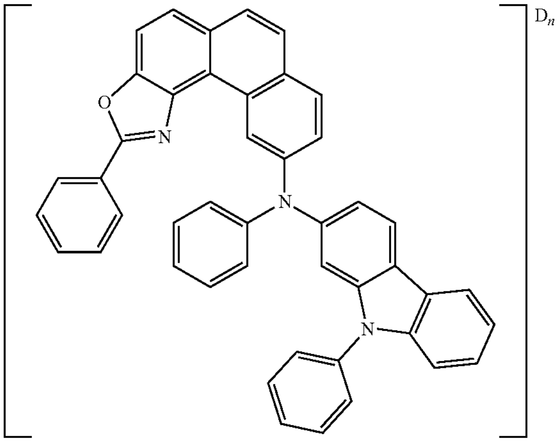
$D_n$ = 1-29

-continued
C-96
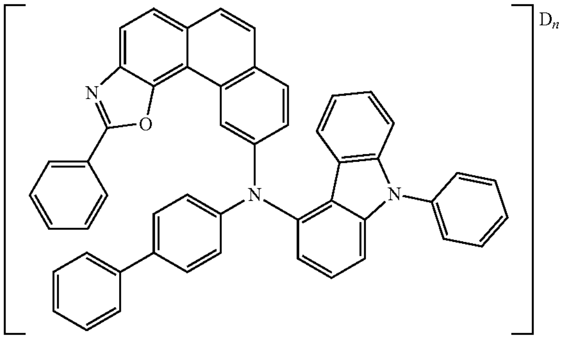
$D_n$ = 1-33
C-97
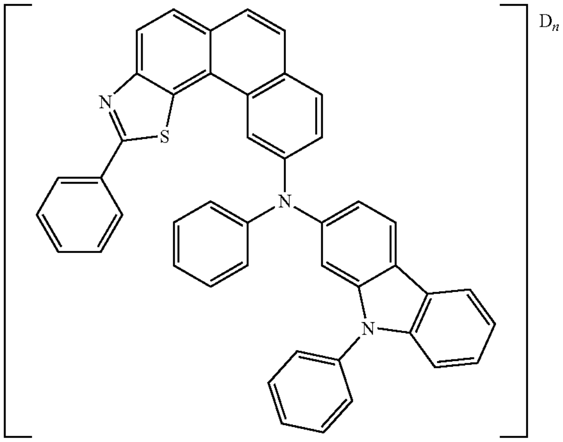
$D_n$ = 1-29
C-98
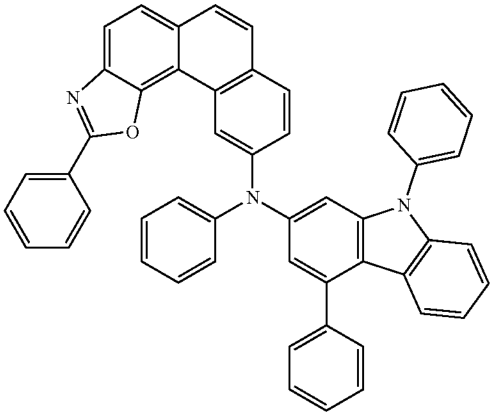
-continued
C-99
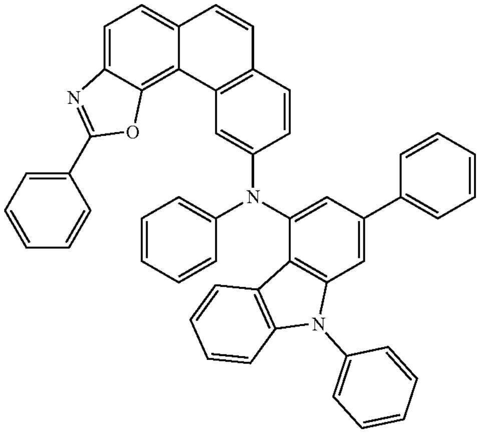
C-100
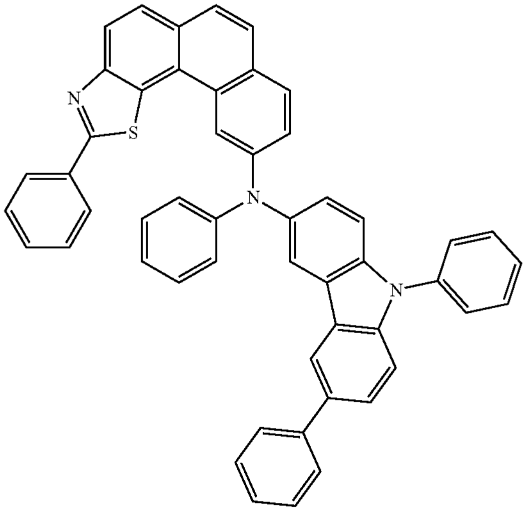
C-101
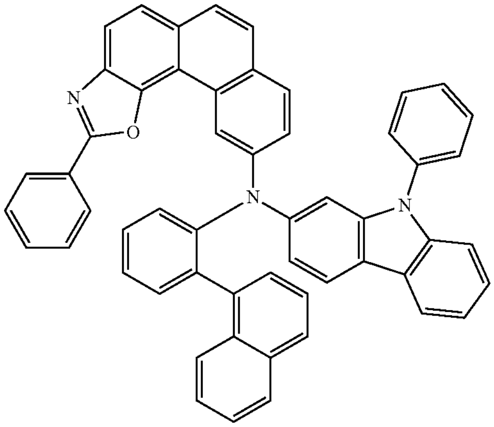

-continued
C-102
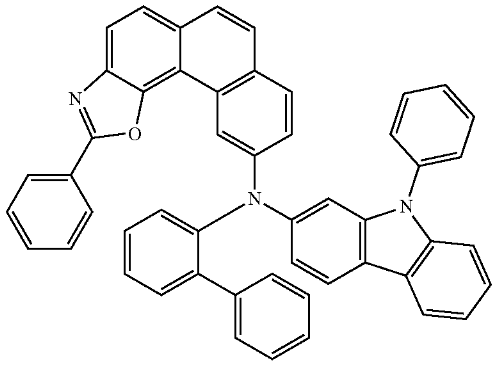
C-103
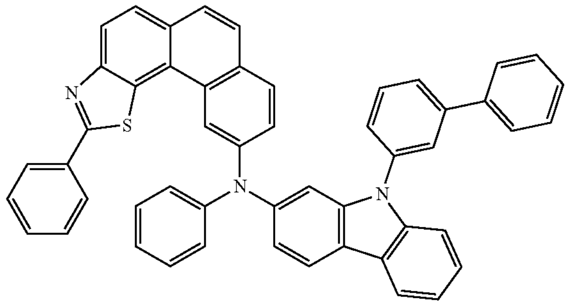
C-104
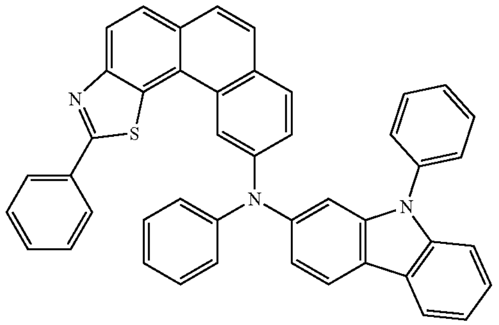
C-105
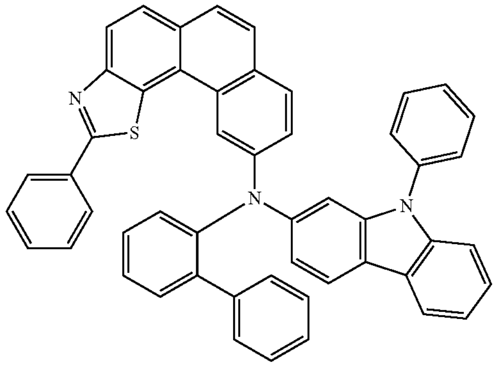
-continued
C-106
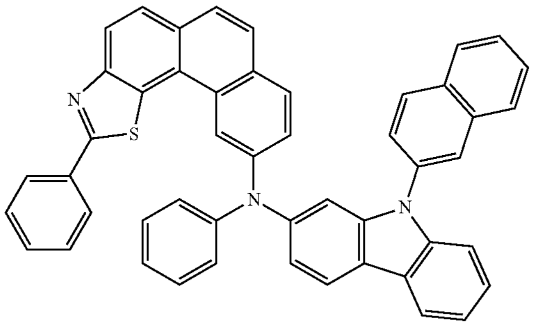
C-107
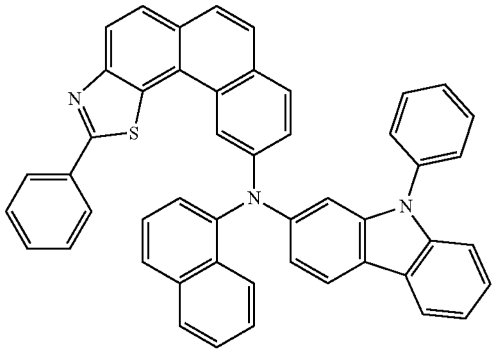
C-108
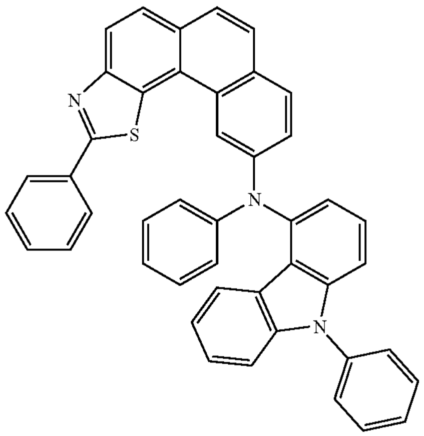

-continued
C-109
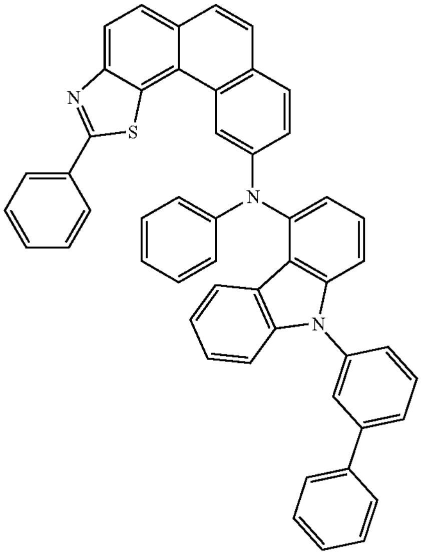
C-110
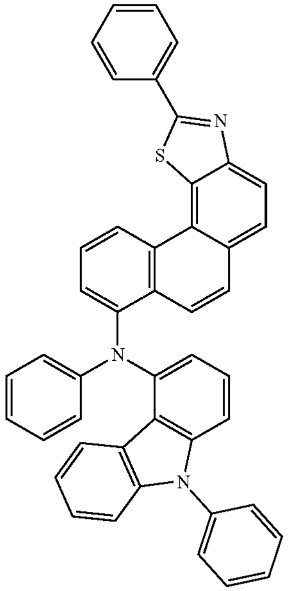
C-111
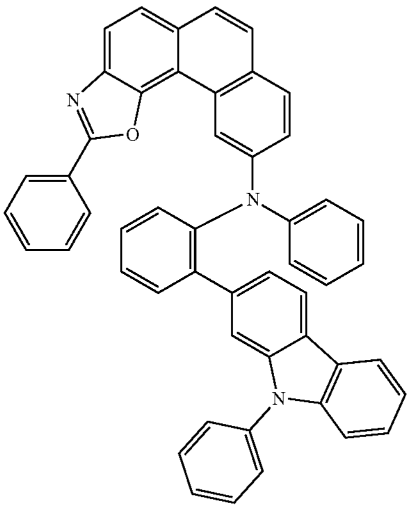
-continued
C-112
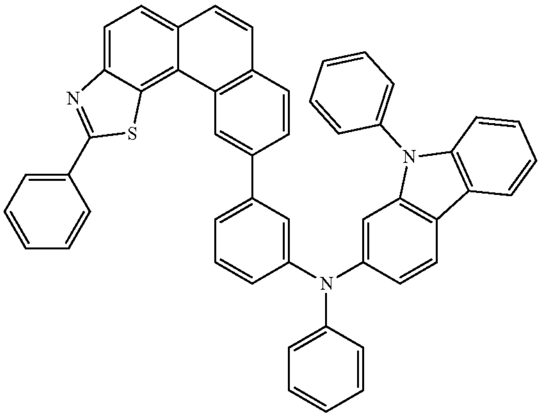
C-113
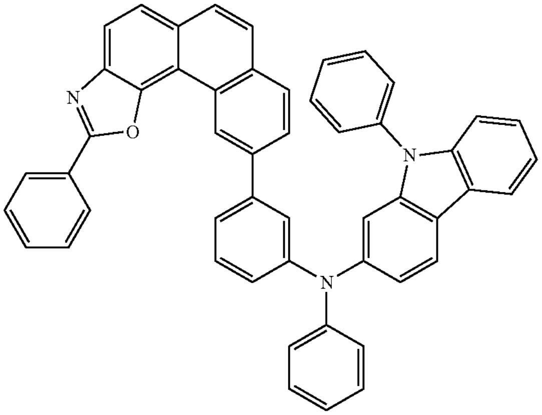
C-114
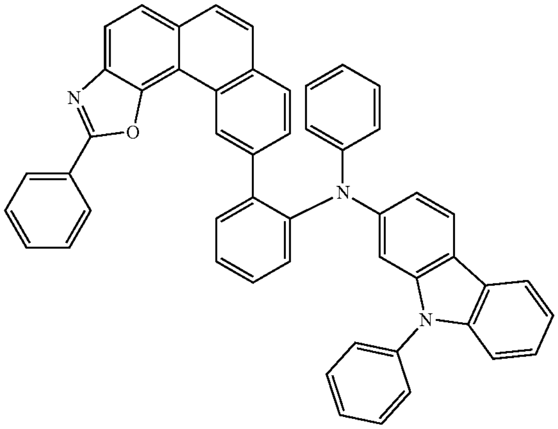

-continued
C-115
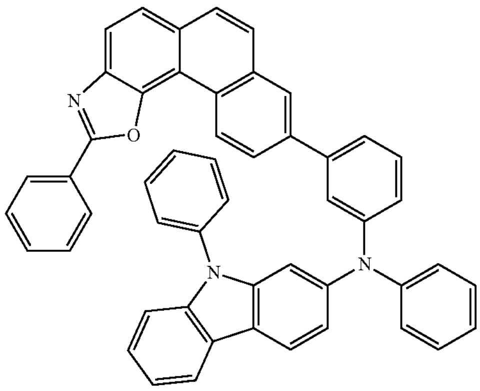
C-116
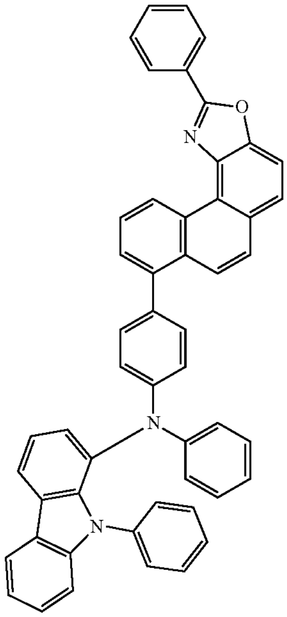
C-117
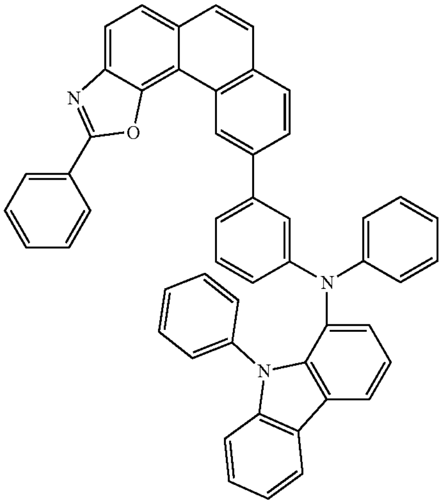
-continued
C-118
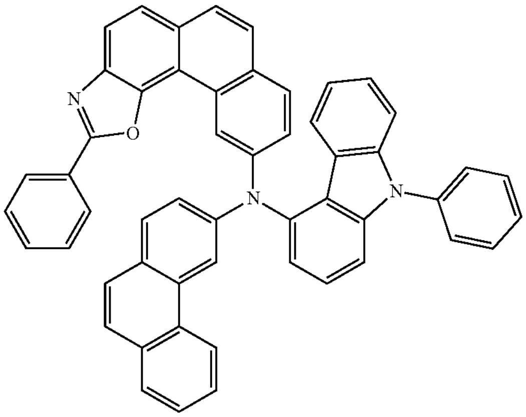
C-119
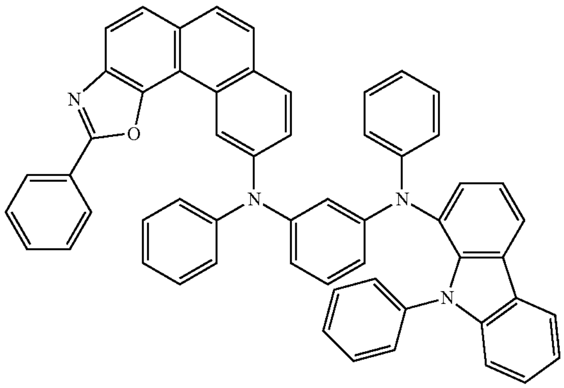
C-120
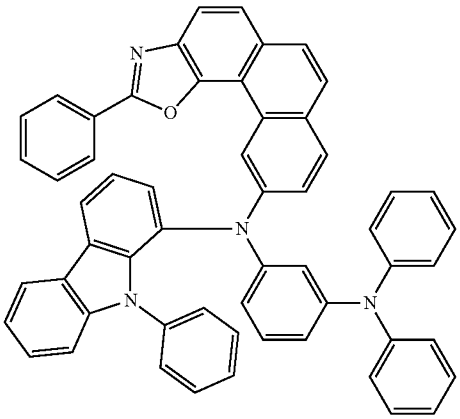
C-121
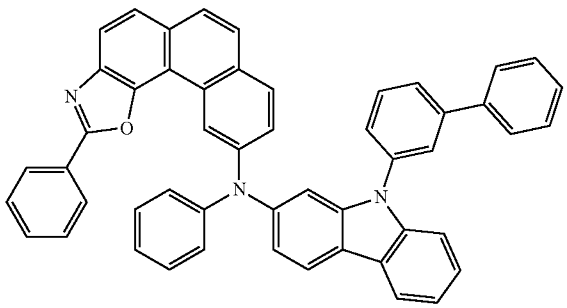

-continued
C-122
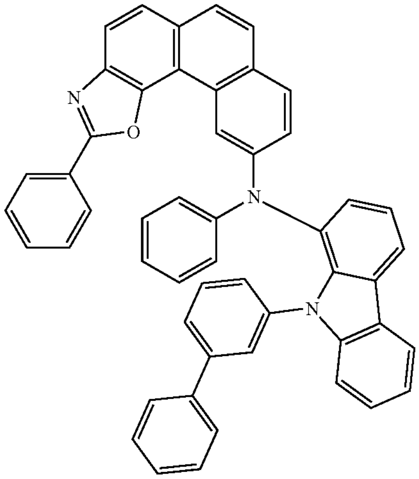
C-123
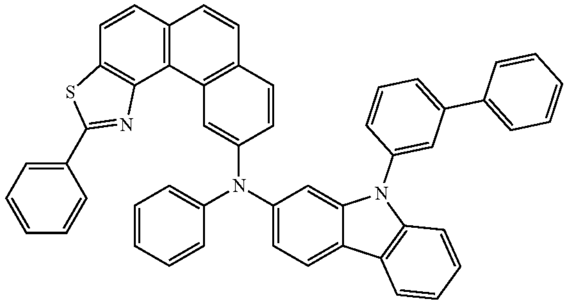
C-124
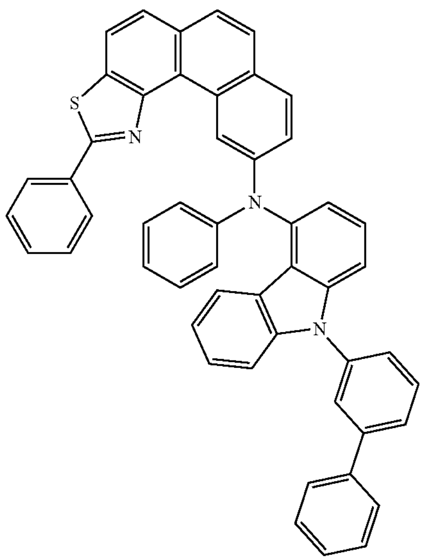
and
-continued
C-125
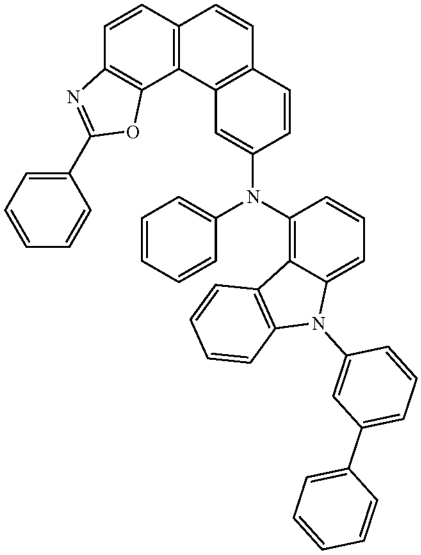
wherein $D_n$: 1-23 and $D_n$: 1-33 in compounds C-93 to C-97 mean that 1 to 29 and 1 to 33 hydrogens may be replaced by deuterium, respectively.
6. The plurality of host materials according to claim 1, wherein the compound represented by formula 2 is selected from the following compounds:
H2-1
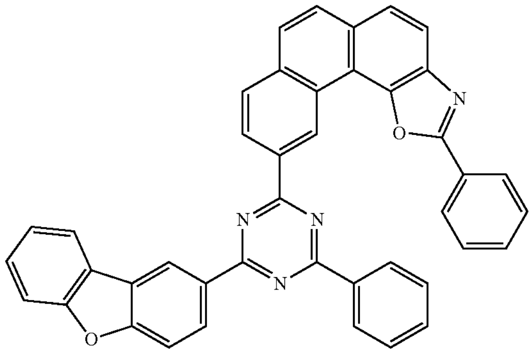
H2-2
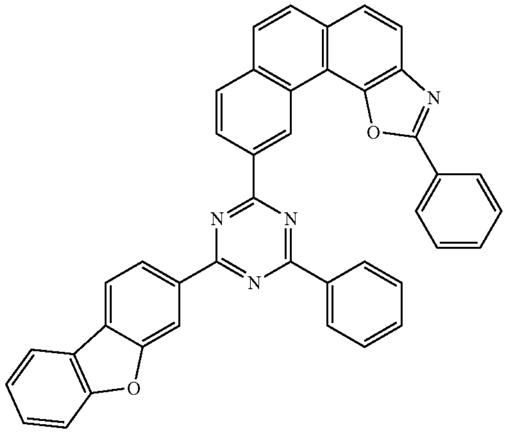

-continued
H2-3
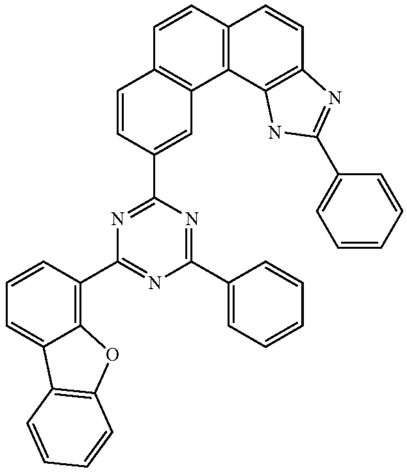
H2-4
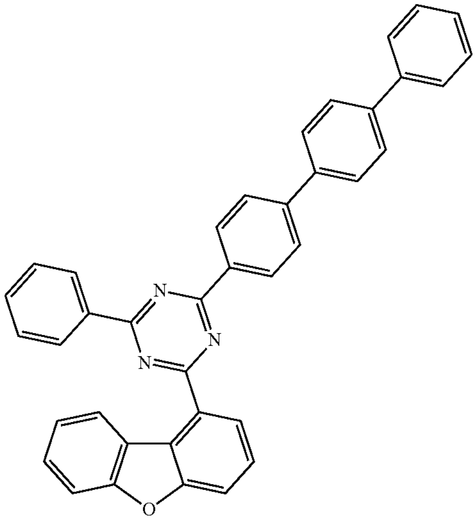
H2-5
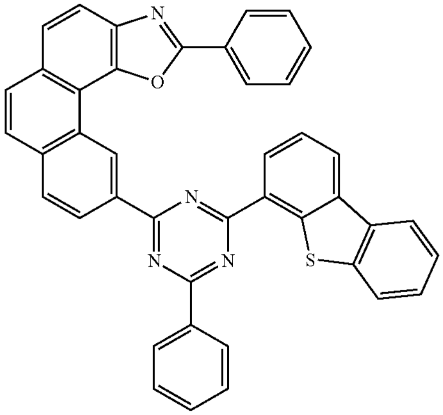
-continued
H2-6
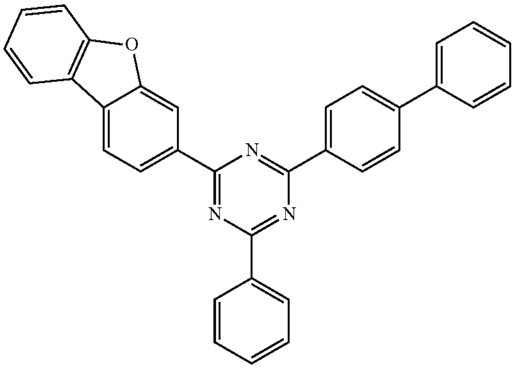
H2-7
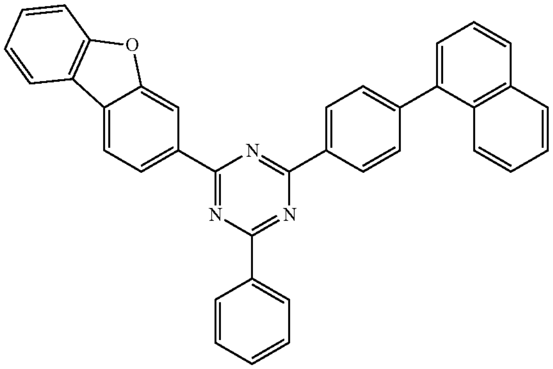
H2-8
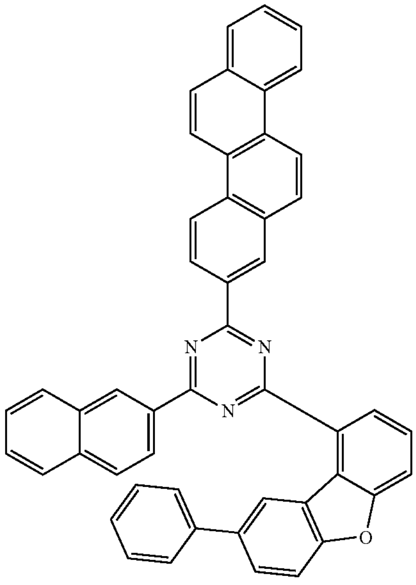

-continued
H2-9
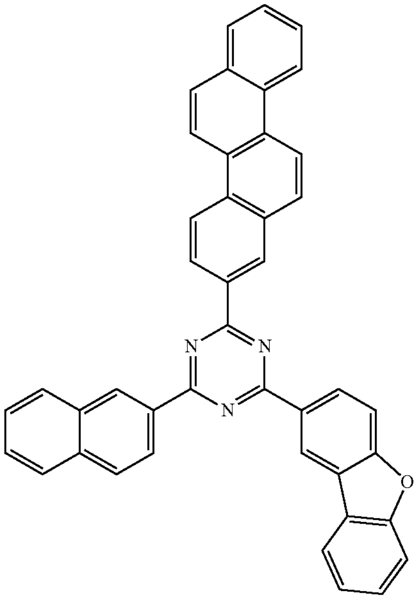
H2-10
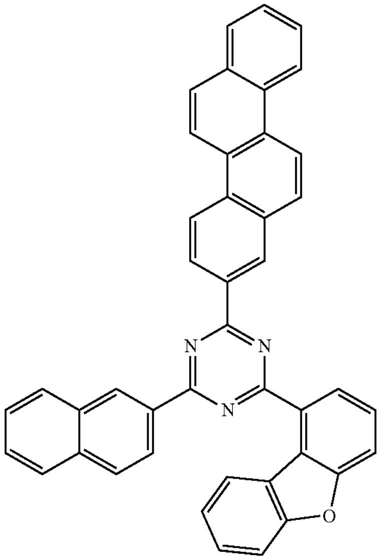
H2-11
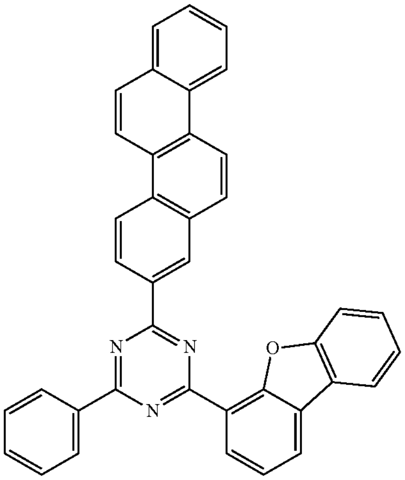
-continued
H2-12
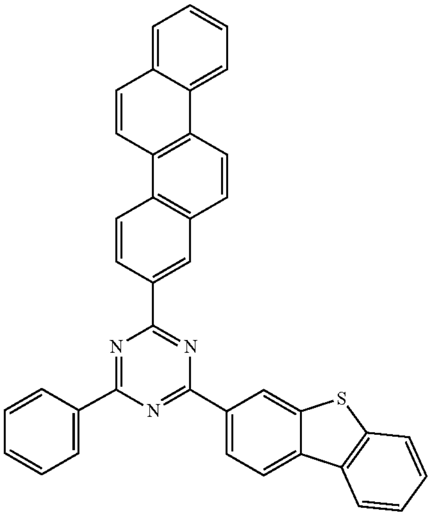
H2-13
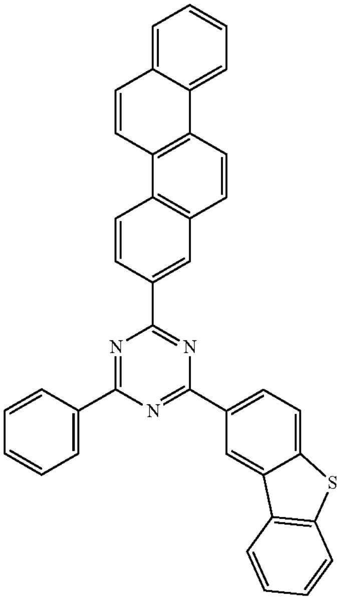

-continued
H2-14
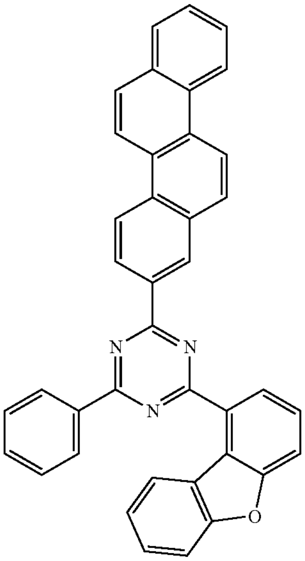
H2-15
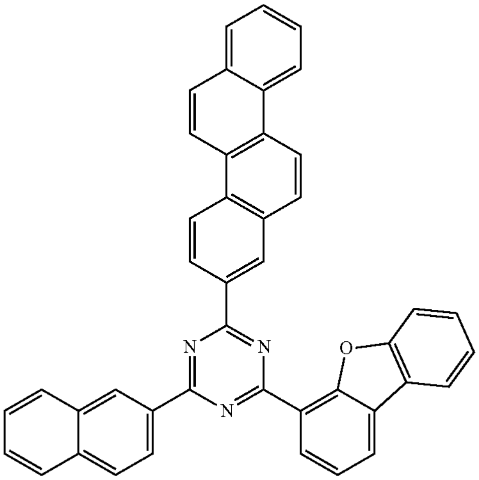
H2-16
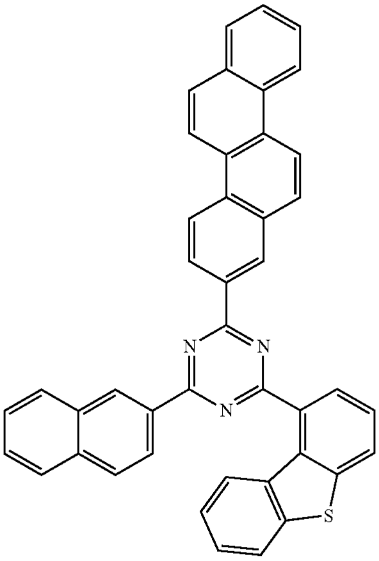
-continued
H2-17
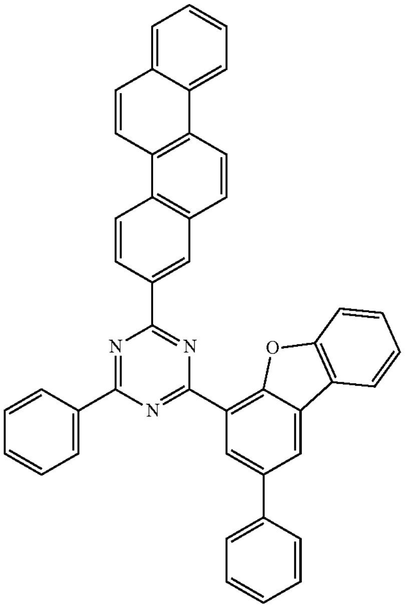
H2-18
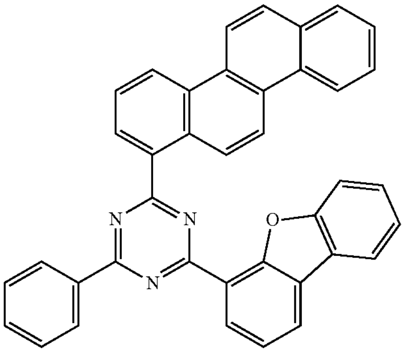
H2-19
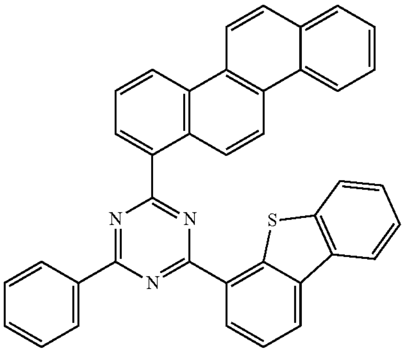

-continued
H2-20
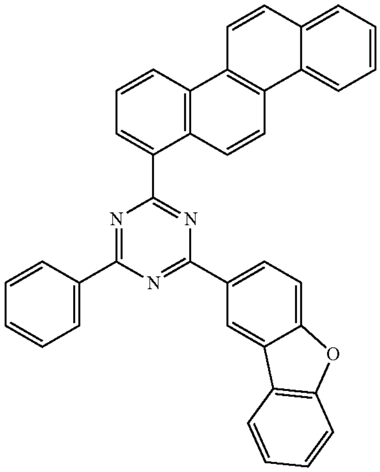
H2-21
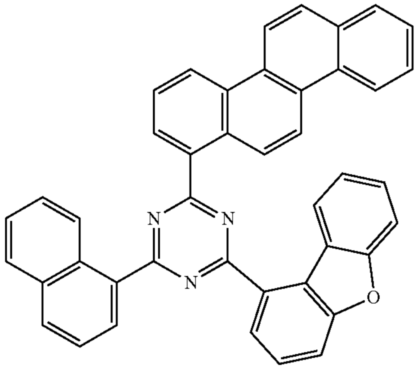
H2-22
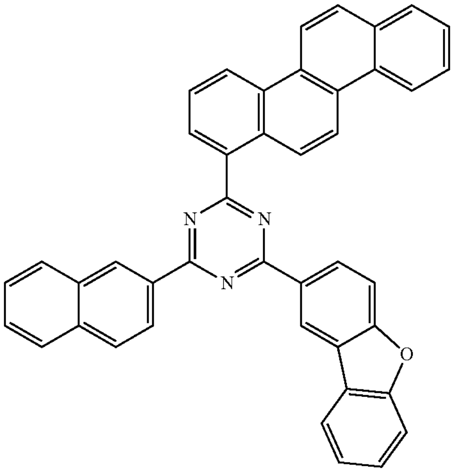
-continued
H2-23
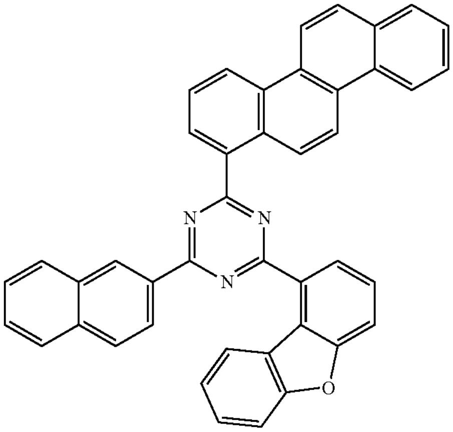
H2-24
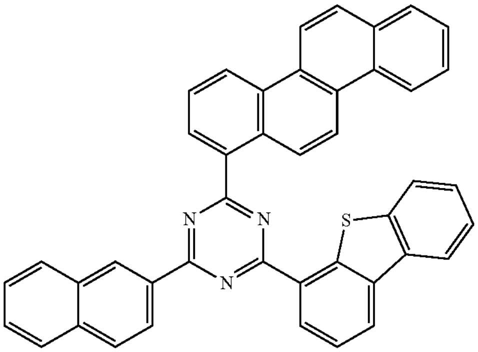
H2-25
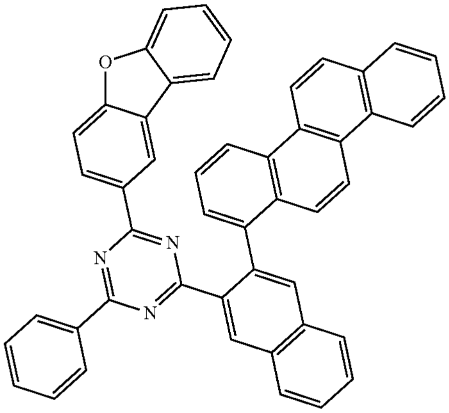
H2-26
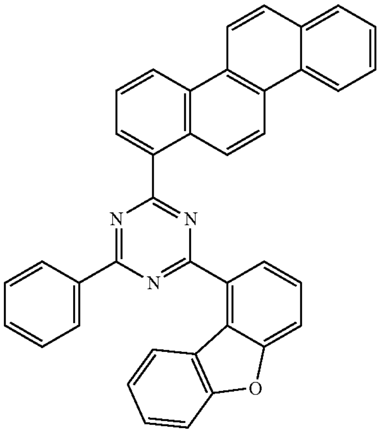

-continued
H2-27
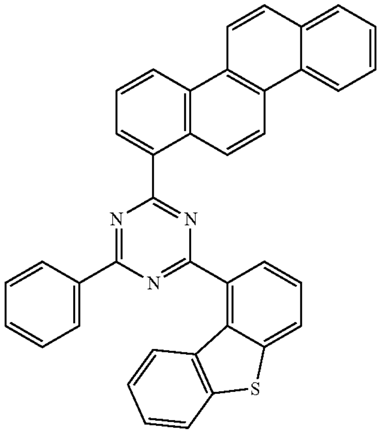
H2-28
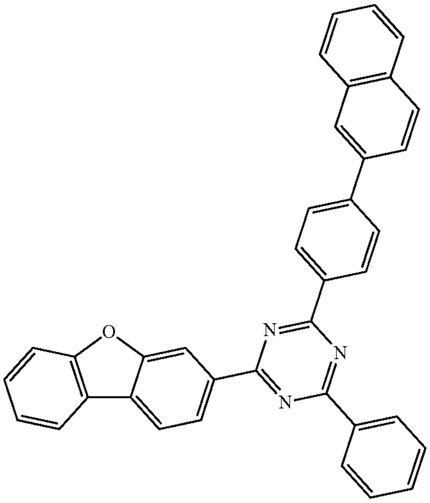
H2-29
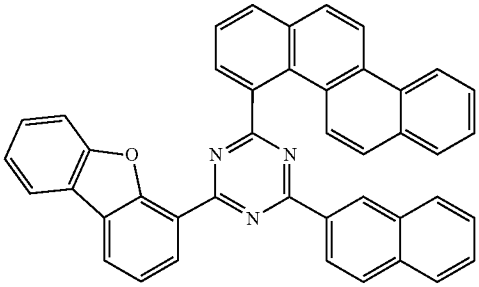
H2-30
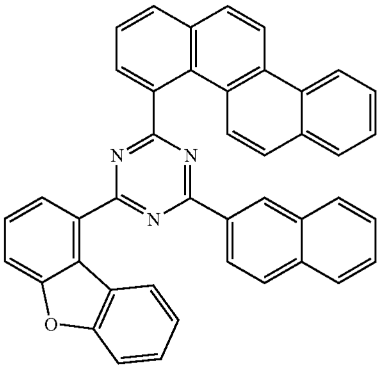
-continued
H2-31
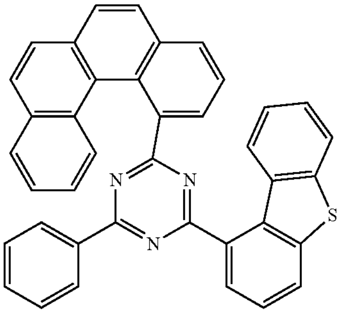
H2-32
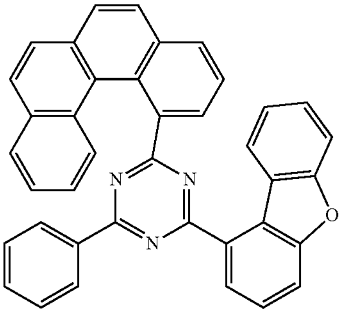
H2-33
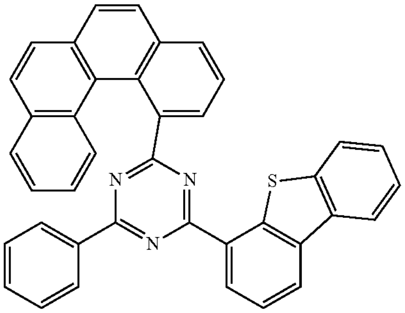
H2-34
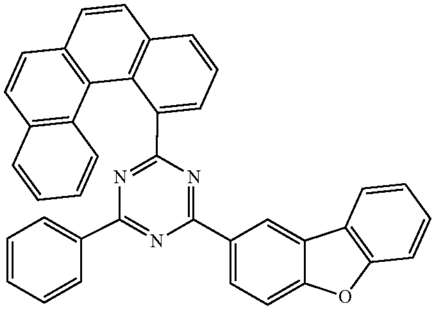
H2-35
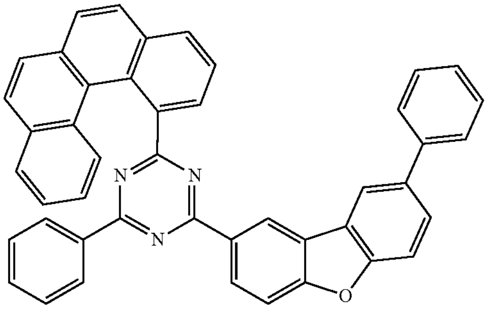

-continued
H2-36
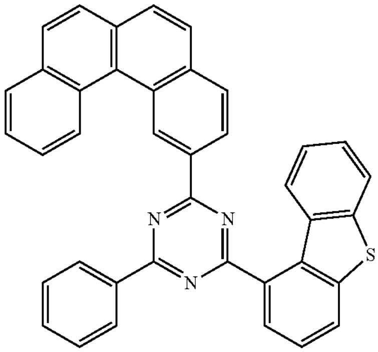
H2-37
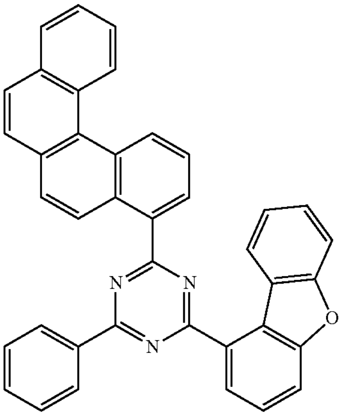
H2-38
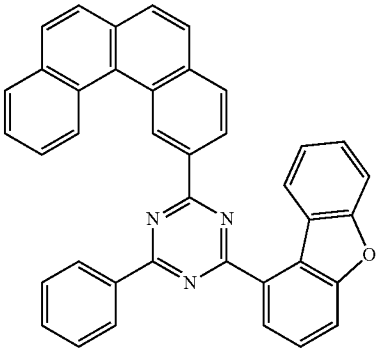
-continued
H2-39
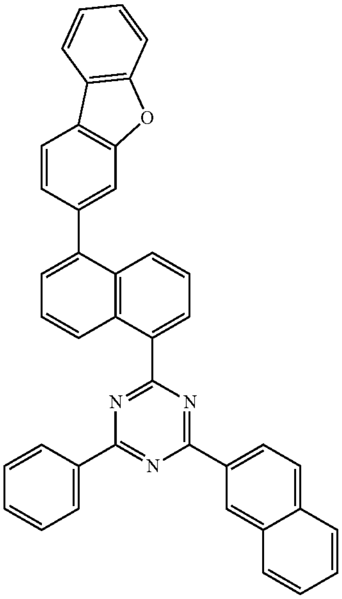
H2-40
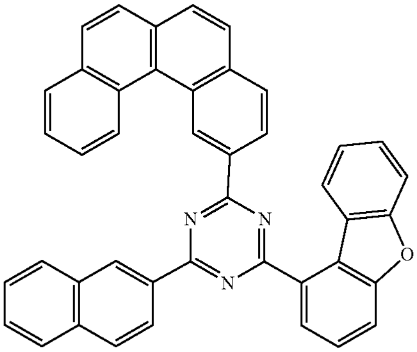
H2-41
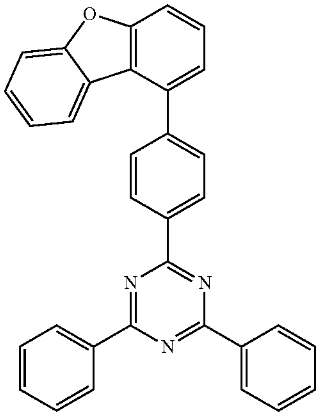

-continued
H2-42
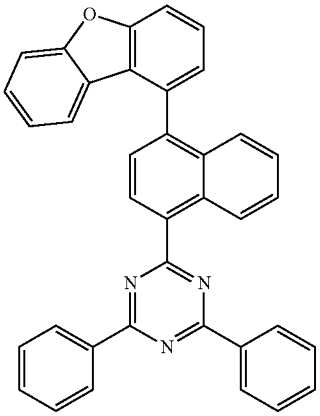
H2-43
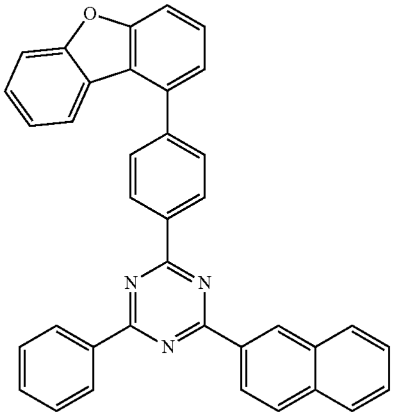
H2-44
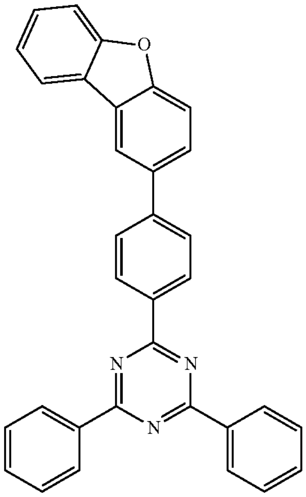
-continued
H2-45
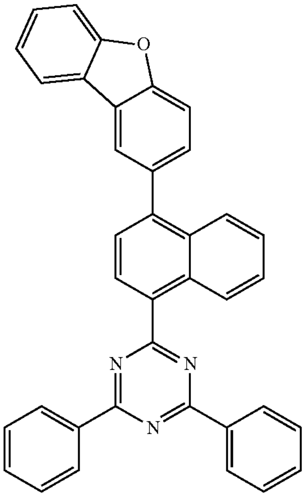
H2-46
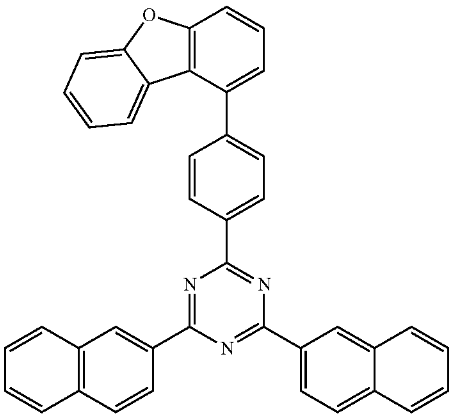
H2-47
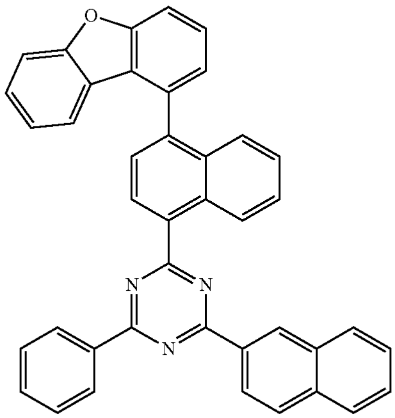

-continued
H2-48
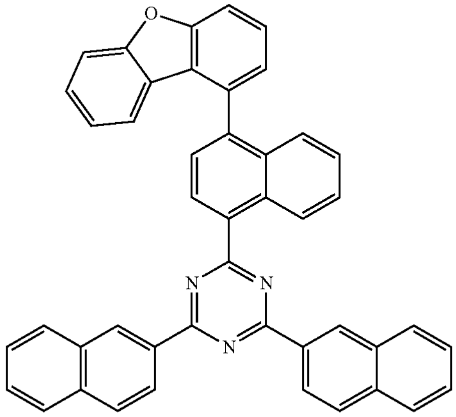
H2-49
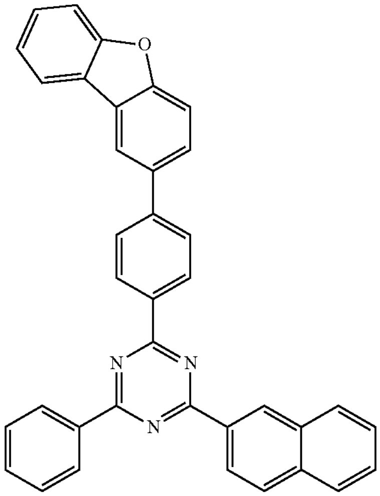
H2-50
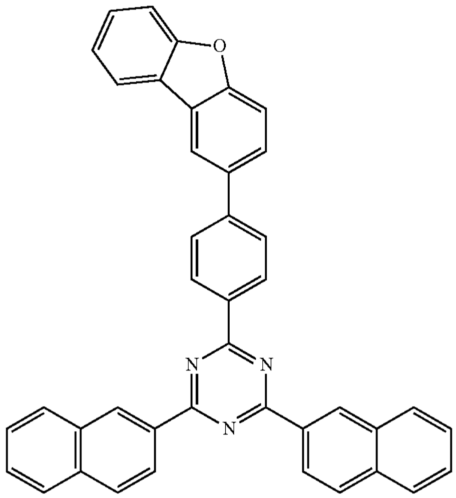
-continued
H2-51
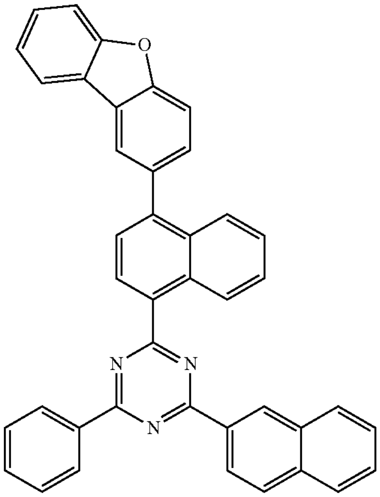
H2-52
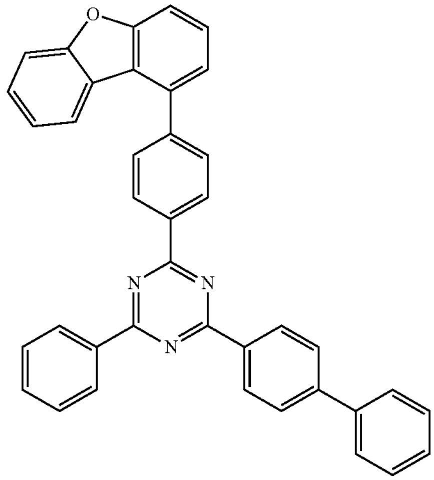
H2-53
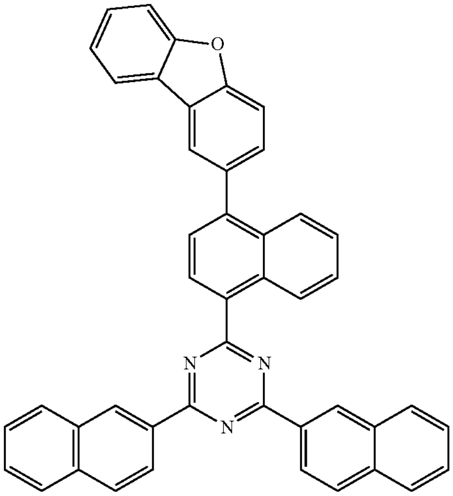

-continued
H2-54
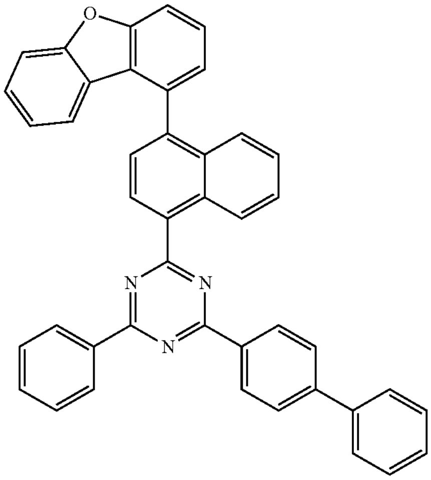
H2-55
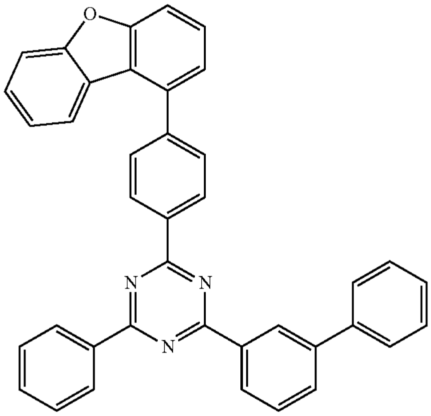
H2-56
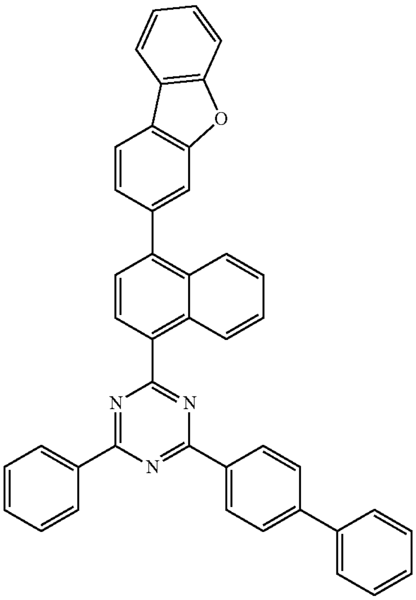
-continued
H2-57
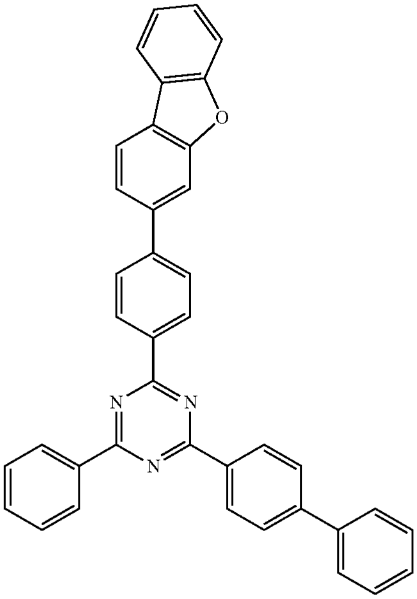
H2-58
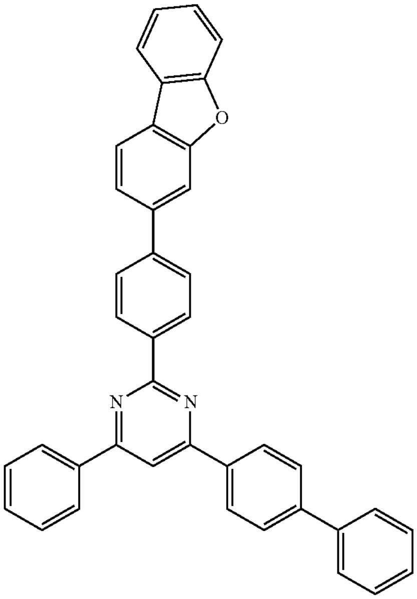

H2-59
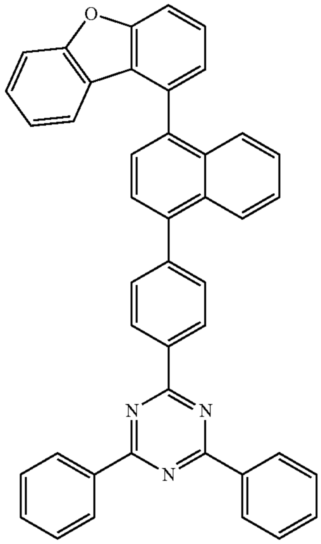
H2-60
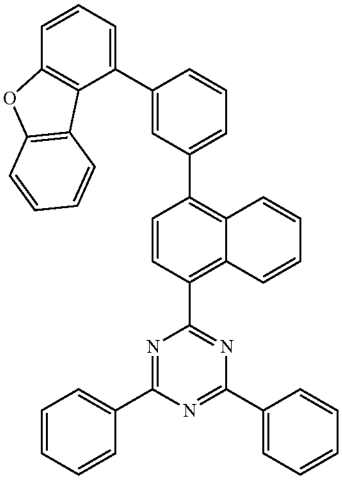
H2-61
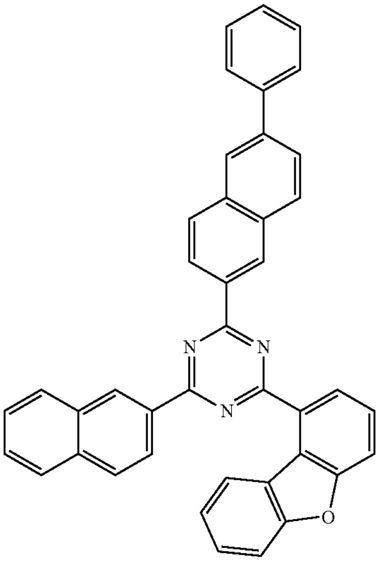
H2-62
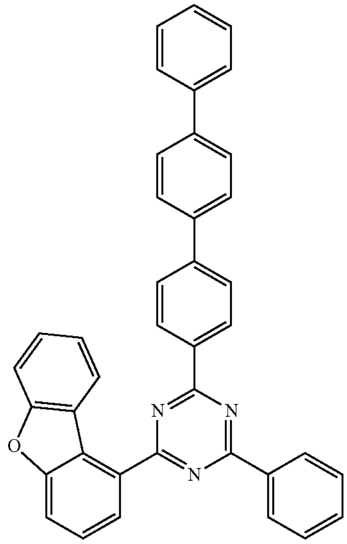
H2-63
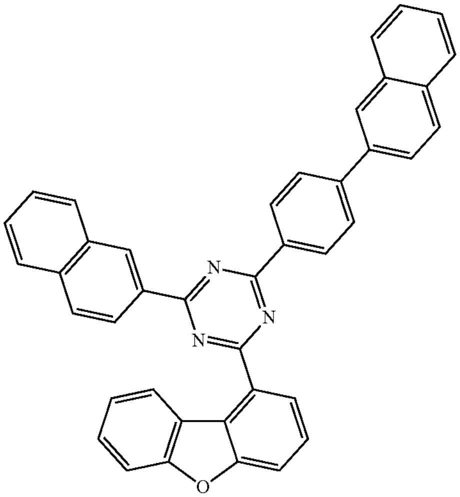
H2-64
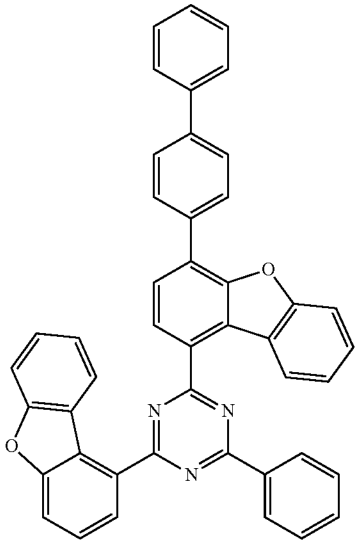

-continued
H2-65
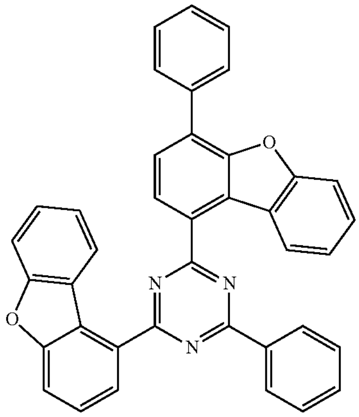
H2-66
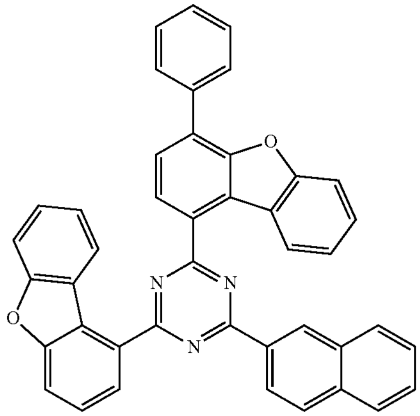
H2-67
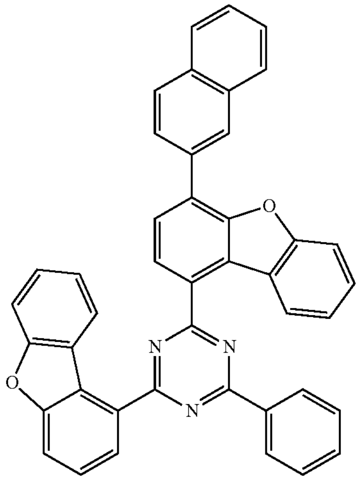
-continued
H2-68
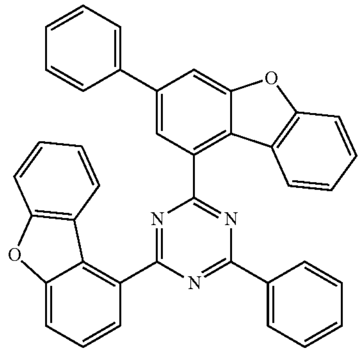
H2-69
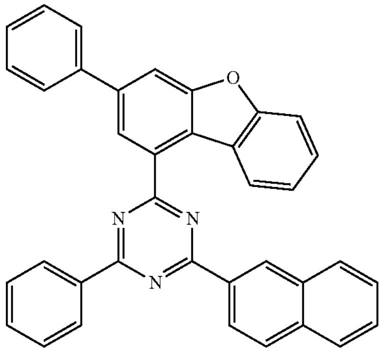
H2-70
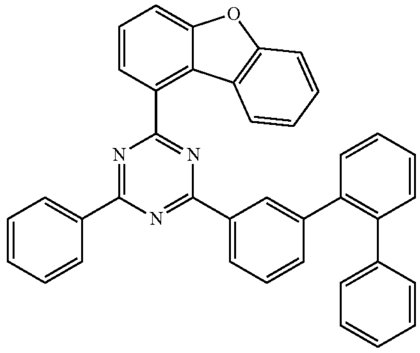
H2-71
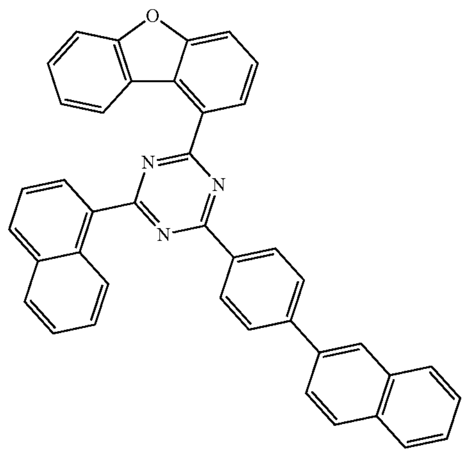

-continued
H2-72
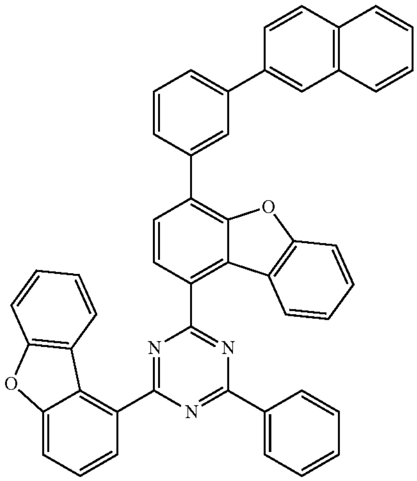
H2-73
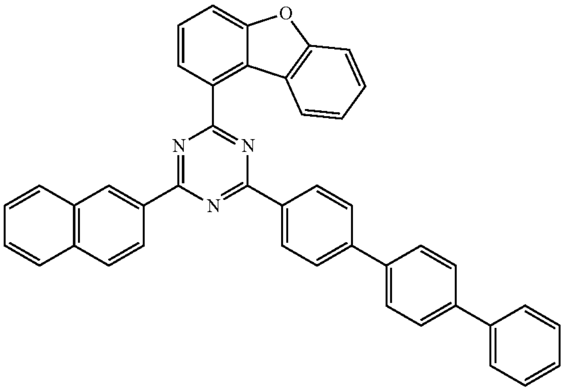
H2-74
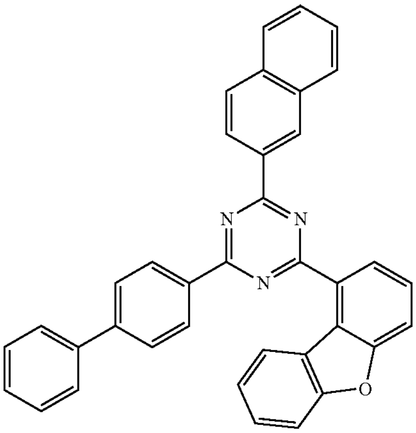
-continued
H2-75
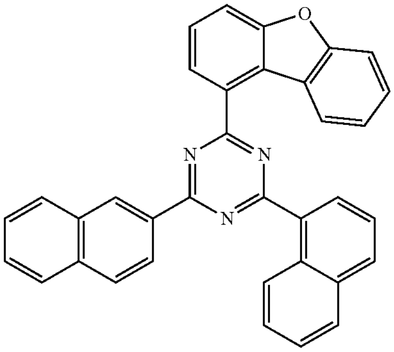
H2-76
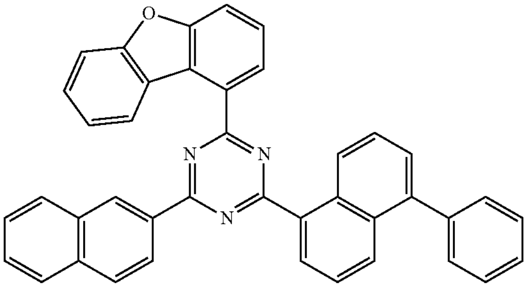
H2-77
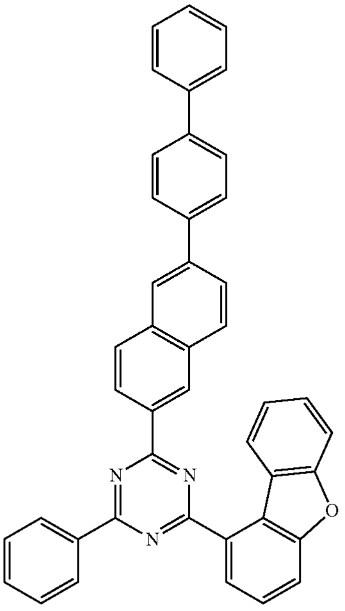

-continued
H2-78
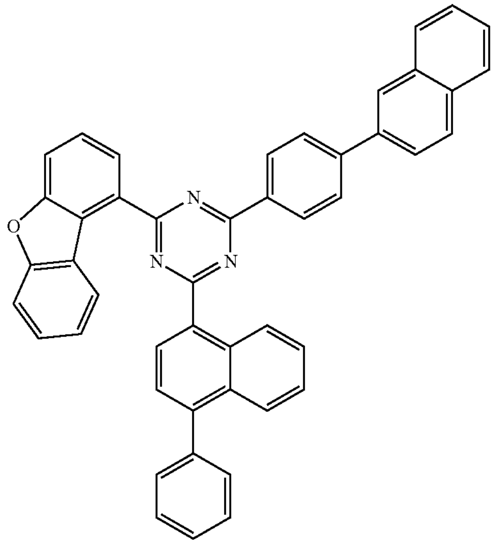
H2-79
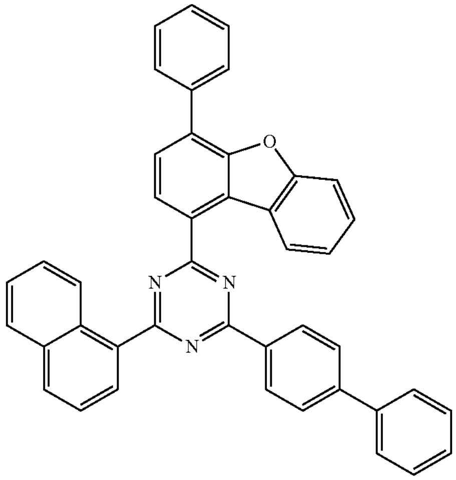
H2-80
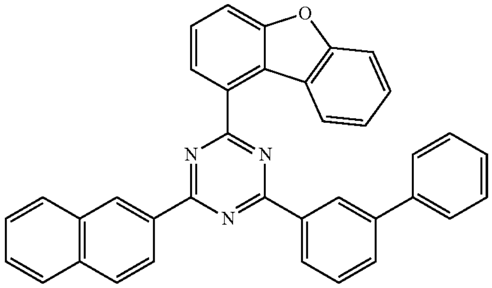
-continued
H2-81
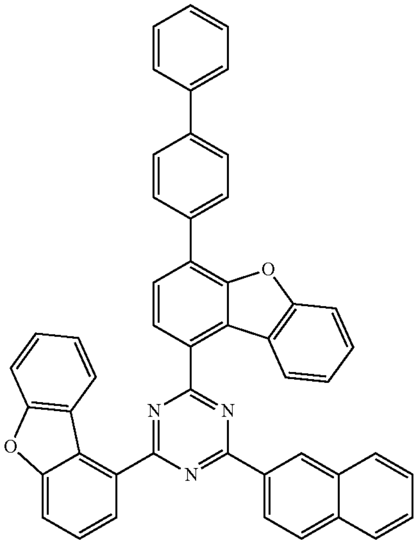
H2-82
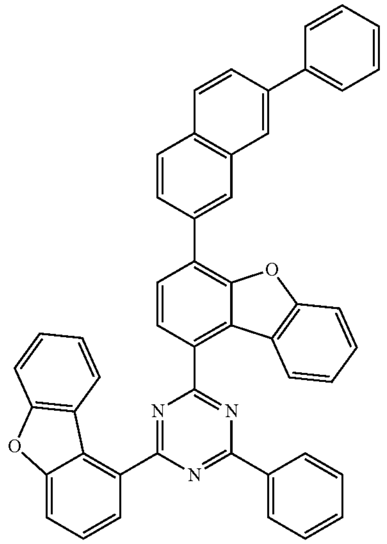
H2-83
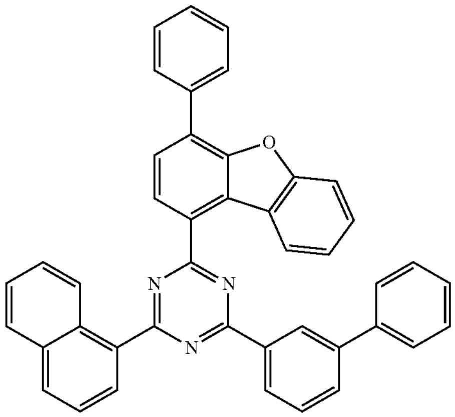

-continued
H2-84
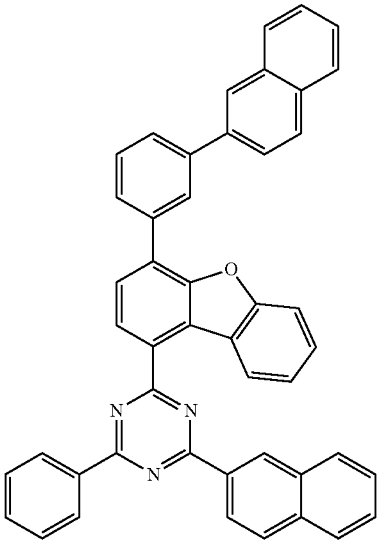
H2-85
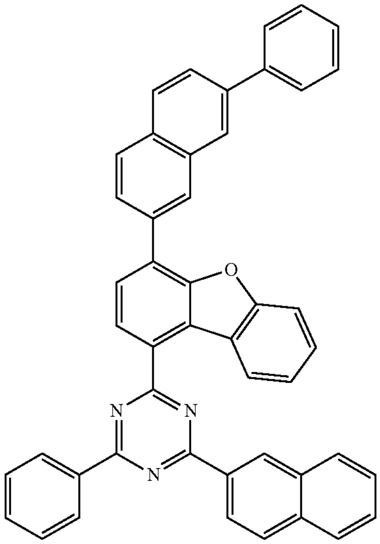
H2-86
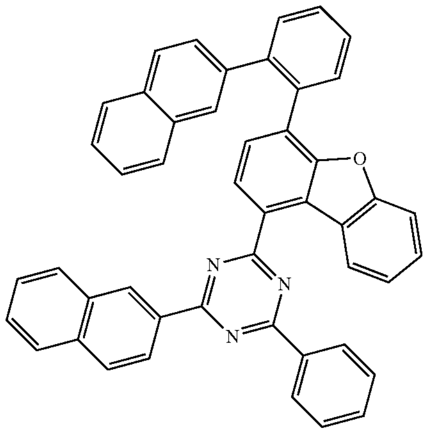
-continued
H2-87
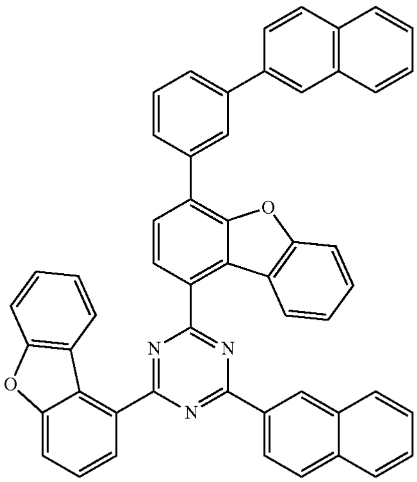
H2-88
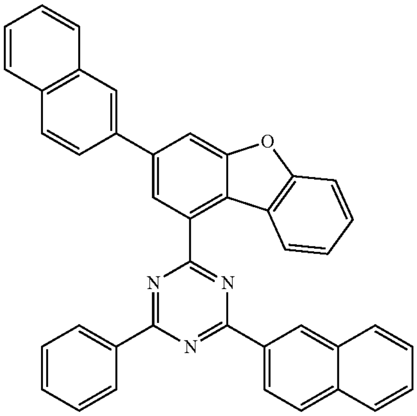
H2-89
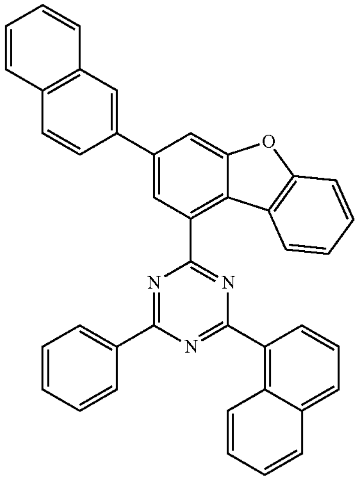

-continued
H2-90
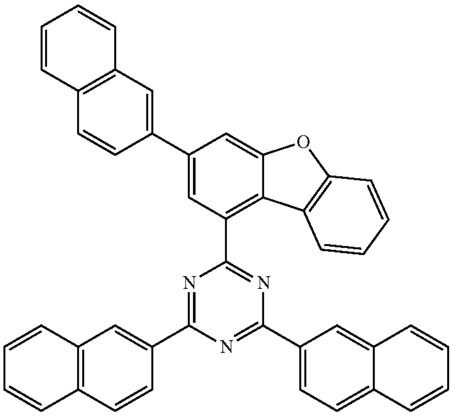
H2-91
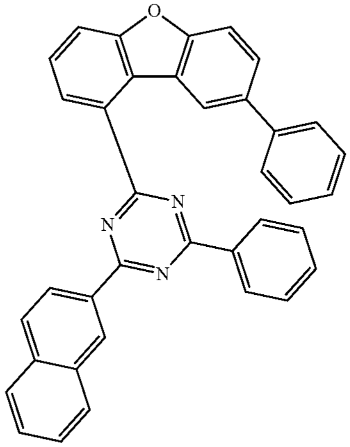
H2-92
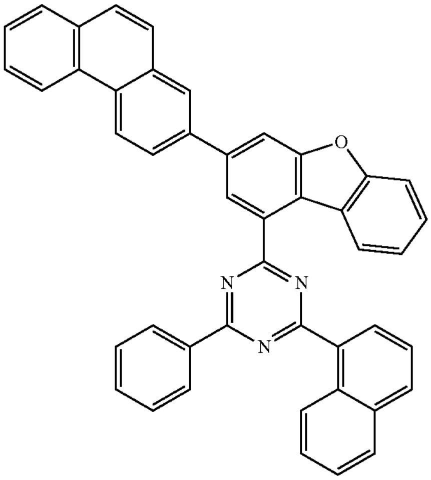
-continued
H2-93
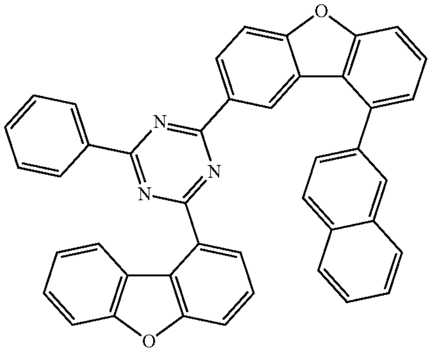
H2-94
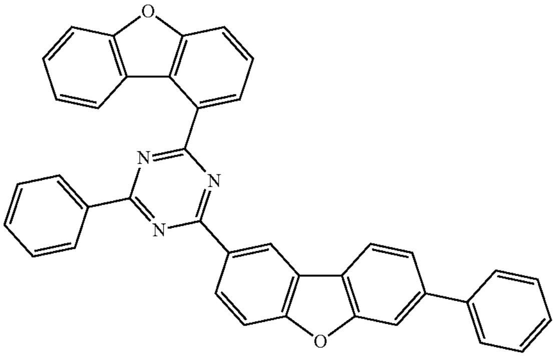
H2-95
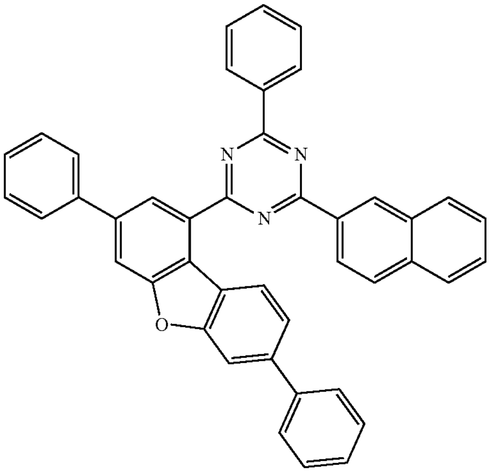
H2-96
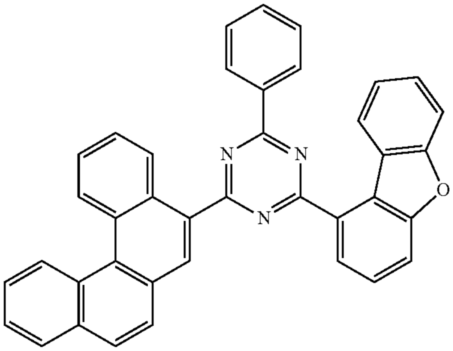

-continued
H2-97
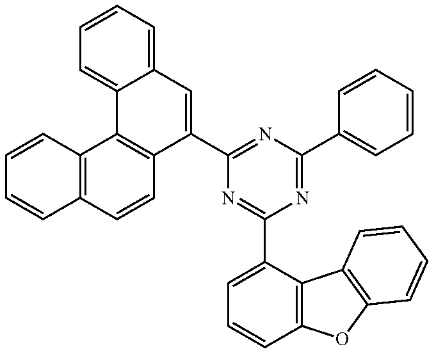
H2-98
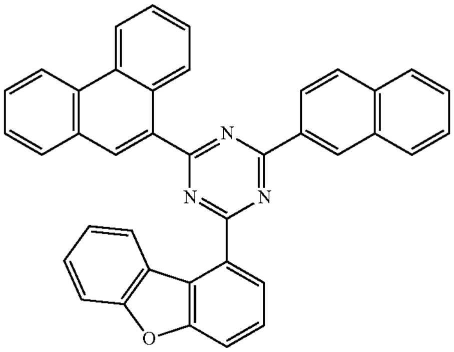
H2-99
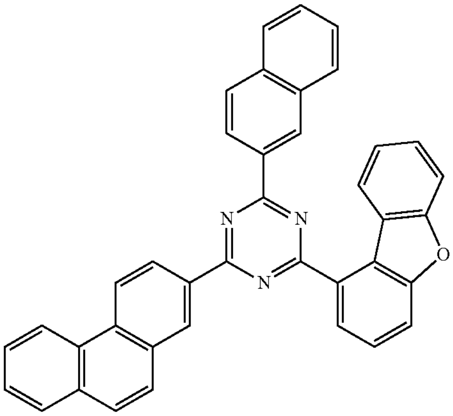
H2-100
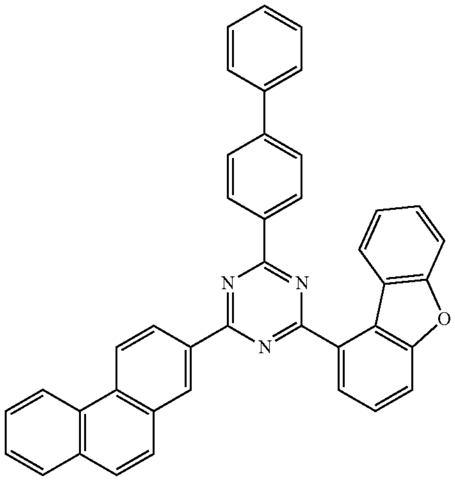
-continued
H2-101
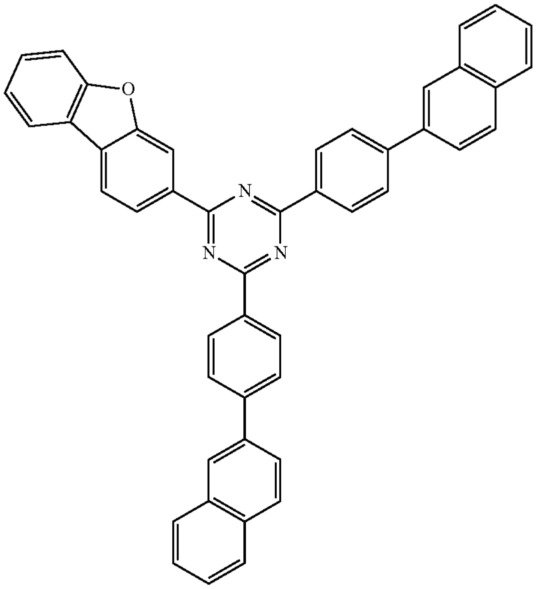
H2-102
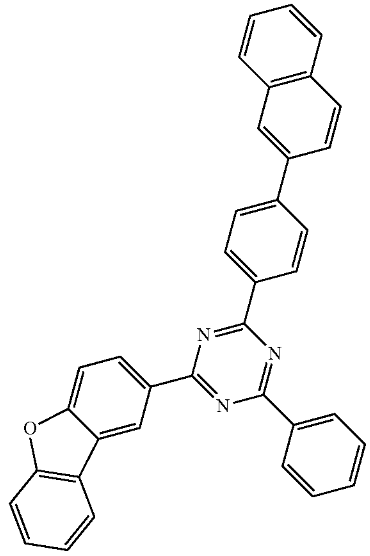
H2-103
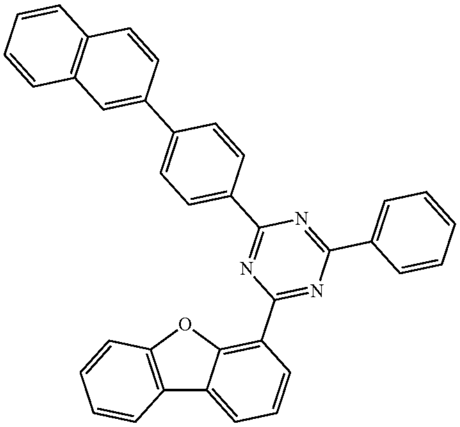

-continued
H2-104
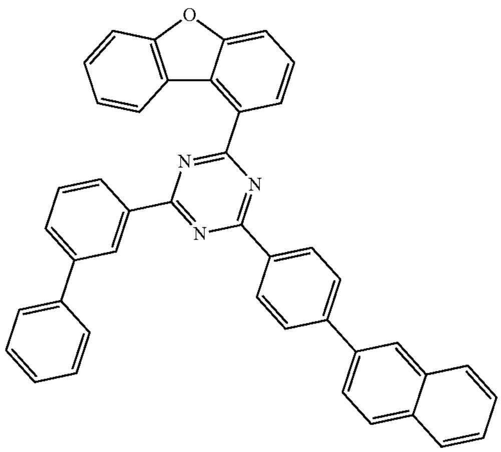
H2-105
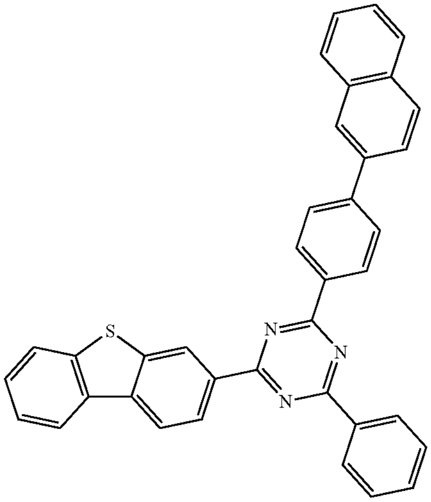
H2-106
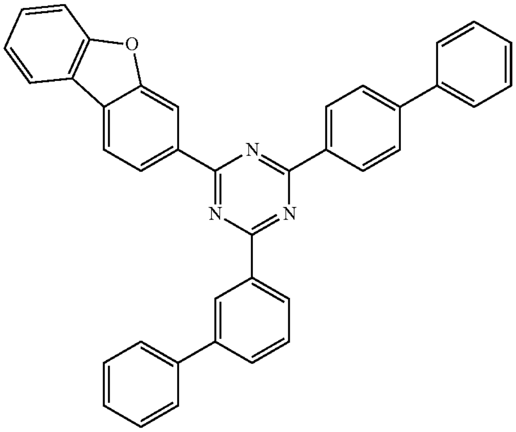
-continued
H2-107
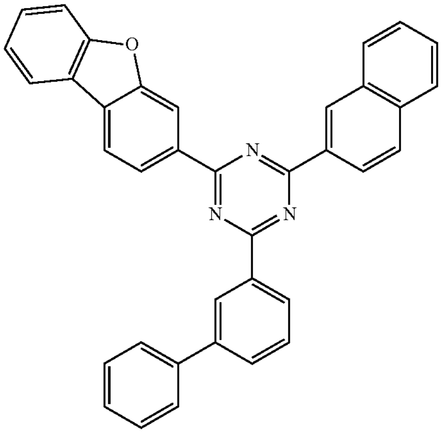
H2-108
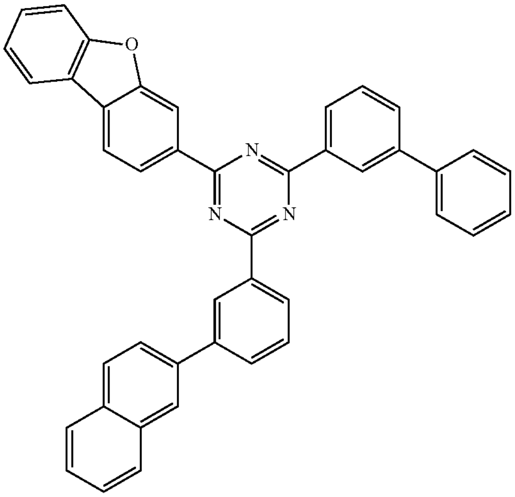
H2-109
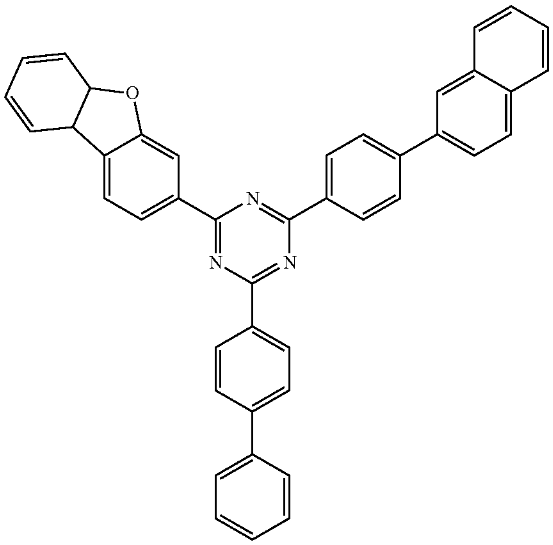

-continued
H2-110
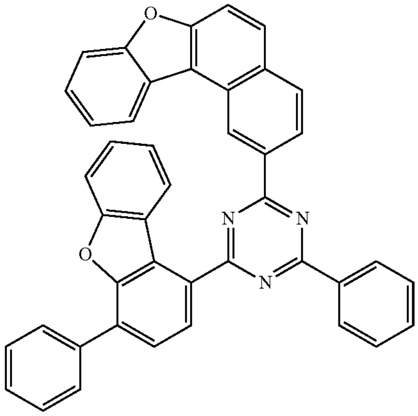
H2-111
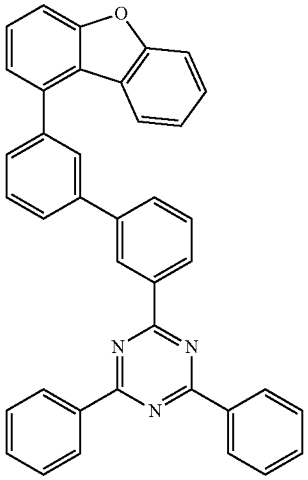
H2-112
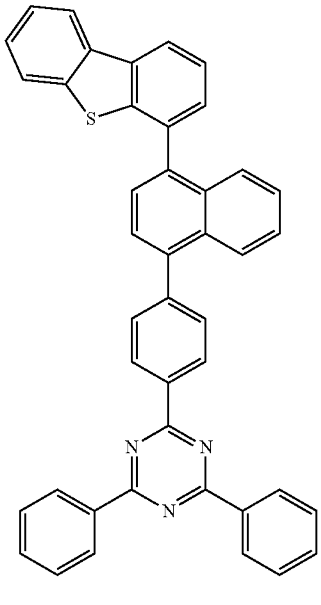
-continued
H2-113
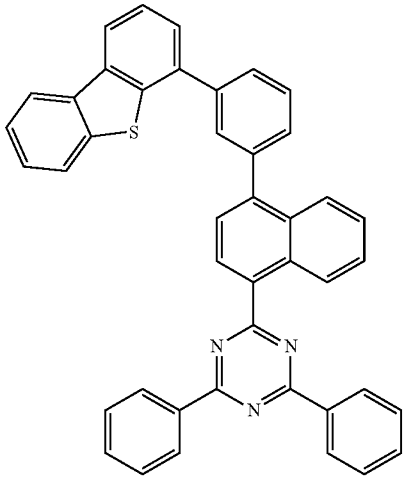
H2-114
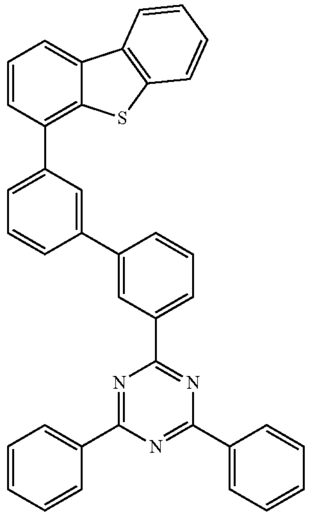
H2-115
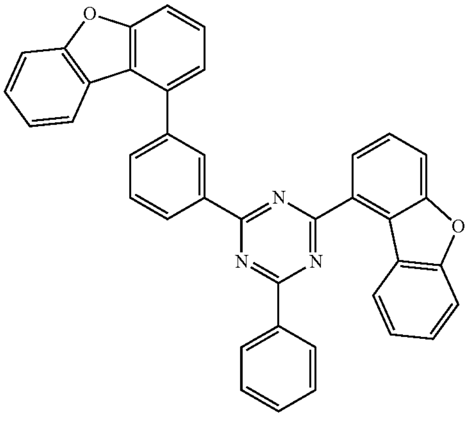

-continued
H2-116
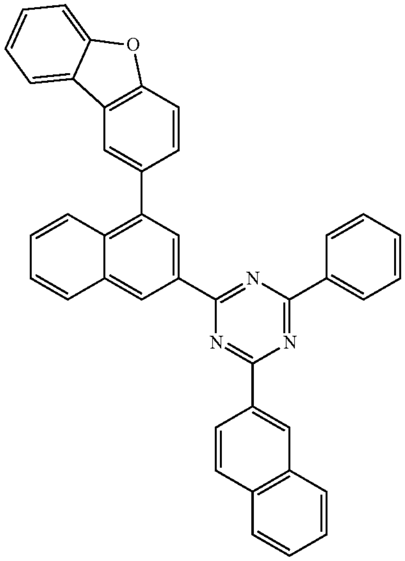
H2-117
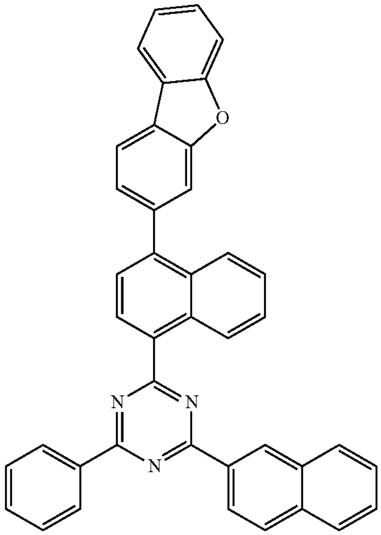
H2-118
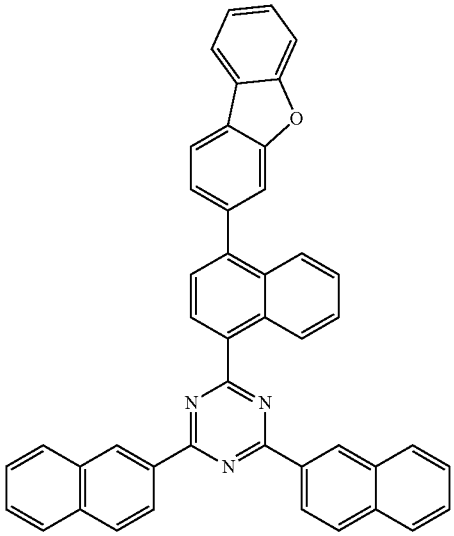
-continued
H2-119
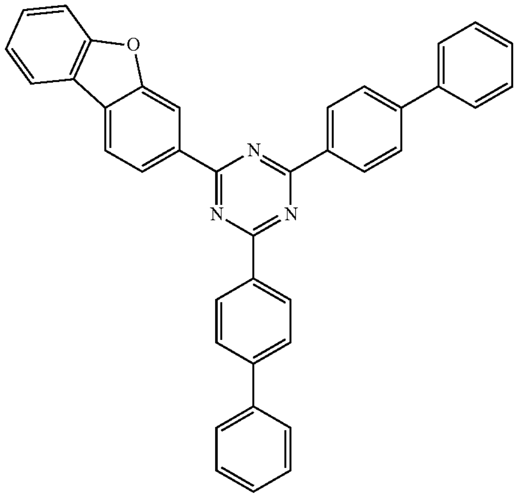
H2-120
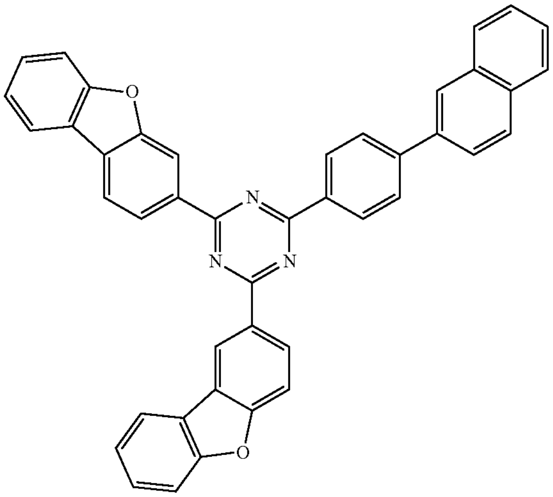
H2-121
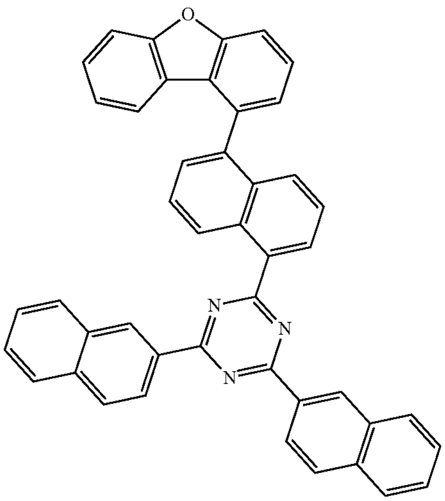

-continued
H2-122
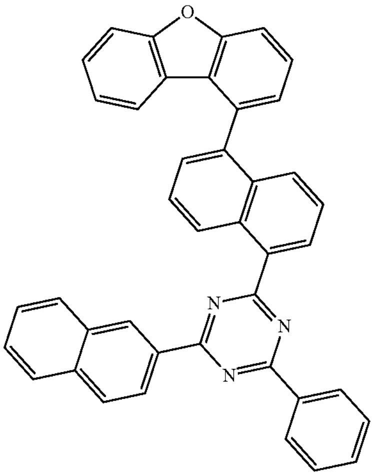
H2-123
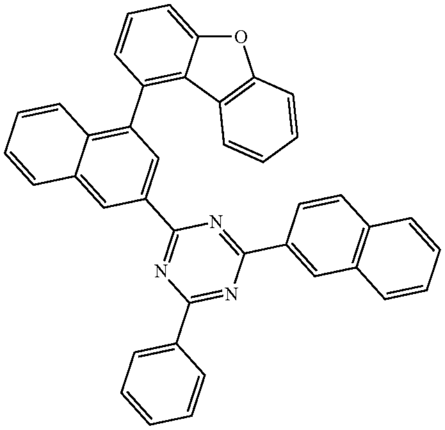
H2-124
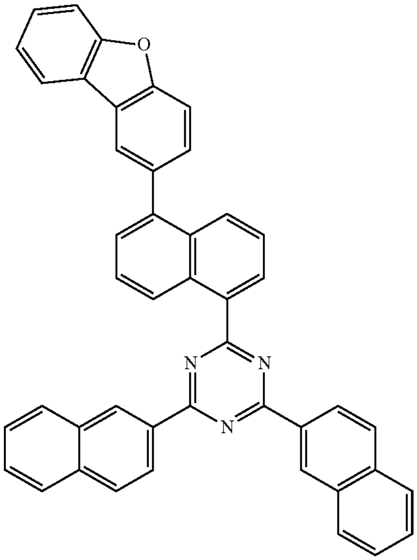
-continued
H2-125
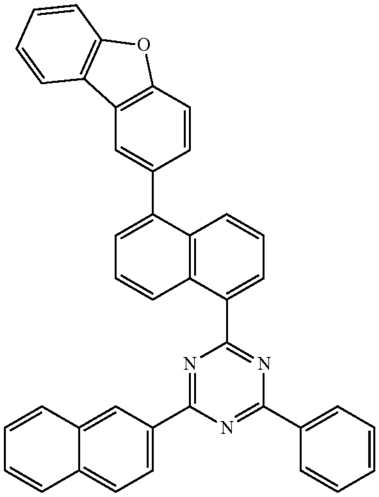
H2-126
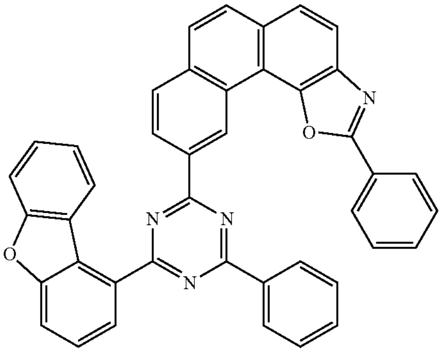
H2-127
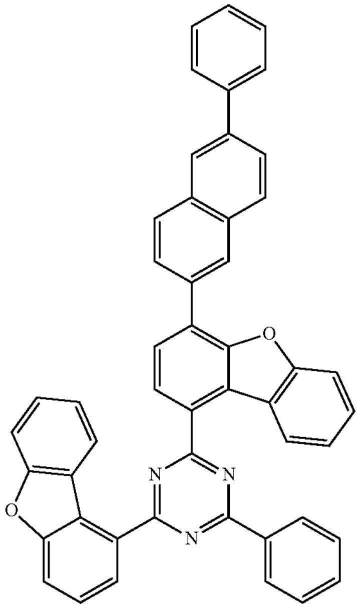

H2-128
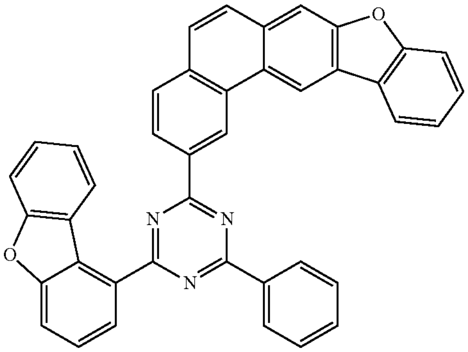
H2-129
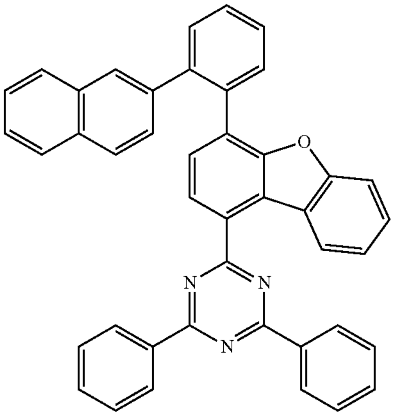
H2-130
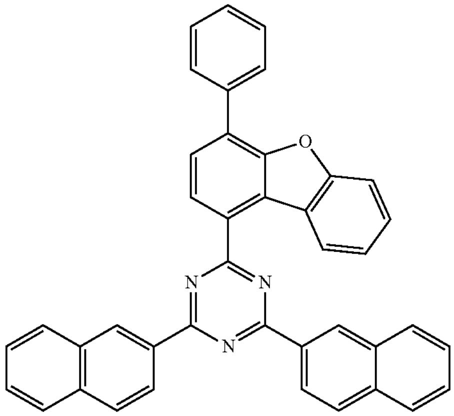
H2-131
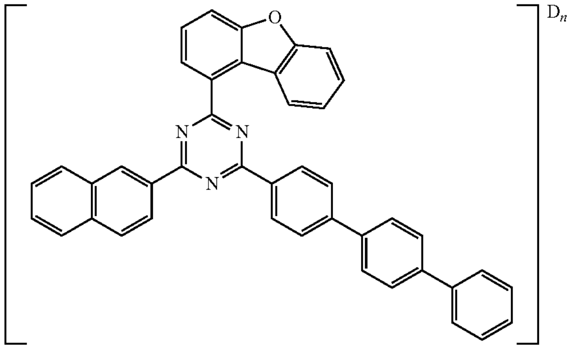
$D_n$: 1-27
H2-132
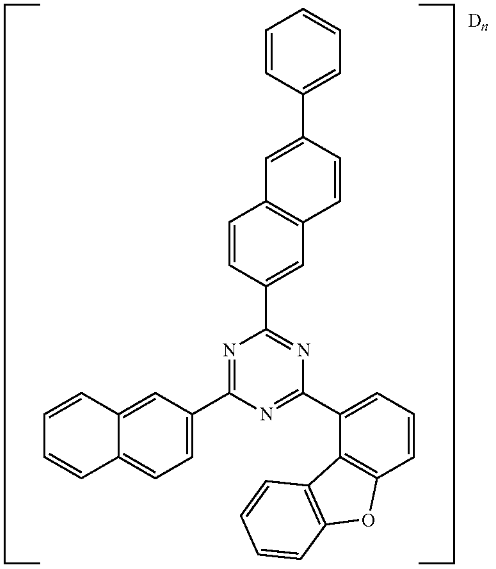
$D_n$: 1-25
H2-133
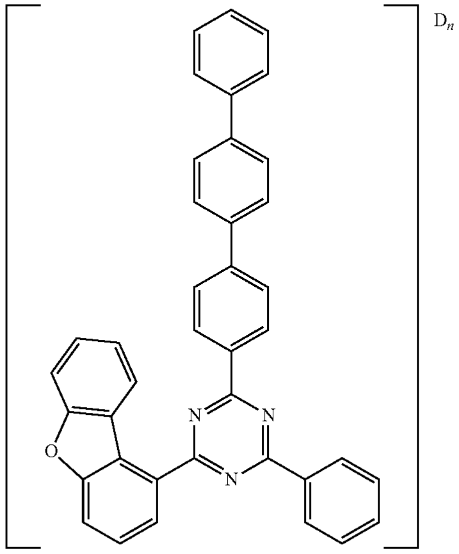
$D_n$: 1-25

-continued

H2-134

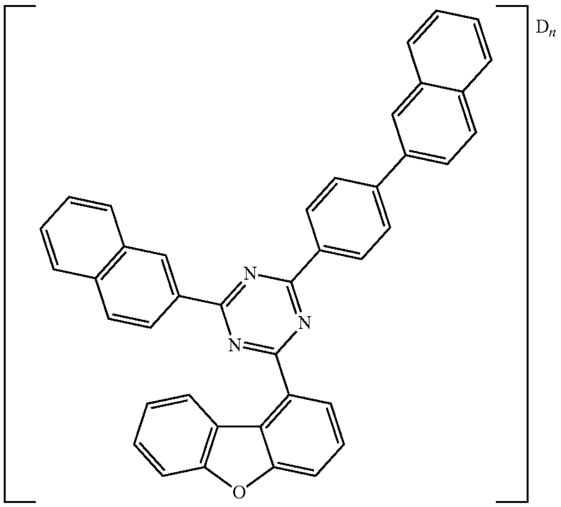

$D_n$: 1-25

H2-135

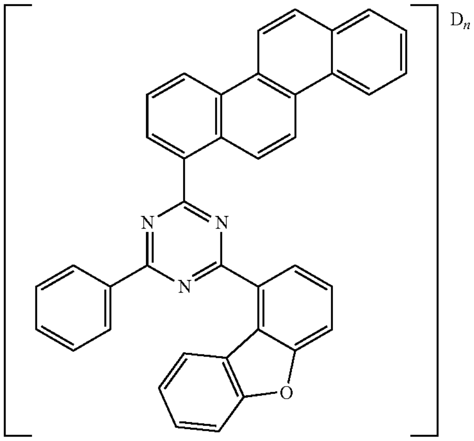

$D_n$: 1-23 and

H2-136

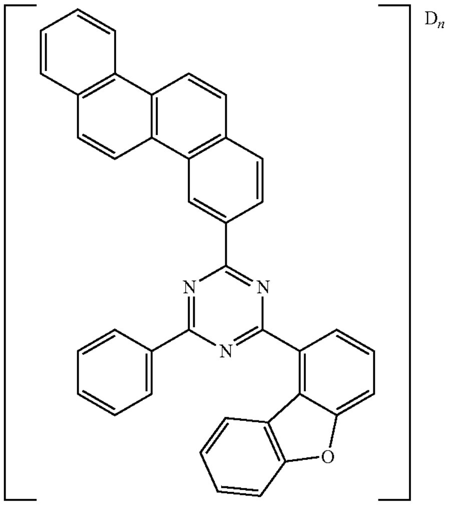

$D_n$: 1-23 wherein $D_n$: 1-23, $D_n$:1-25, and $D_n$: 1-27 in compounds H2-131 to H2-136 mean that 1 to 23, 1 to 25, and 1 to 27 hydrogens are replaced with deuterium, respectively.

7. An organic electroluminescence device comprising: an anode; a cathode; and at least one light-emitting layer between the anode and the cathode, wherein at least one layer of the light-emitting layer comprises the plurality of host materials of claim 1.

8. An organic electroluminescent compound represented by the following formula 1` :

(1')

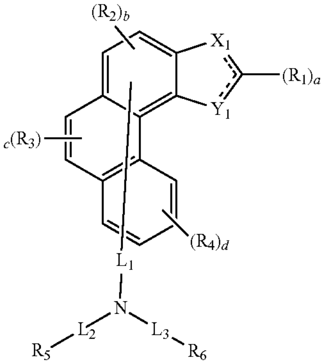

wherein, $X_1$ and $Y_1$ each independently represent, —N═, —$NR_{10}$—, —O— or —S—, provided that any one of $X_1$ and $Y_1$ is —N═, and the other of $X_1$ and $Y_1$ is —$NR_{10}$—, —O— or —S—;

$L_1$, $L_2$ and $L_3$ each independently represent, a single bond, a substituted or unsubstituted (C6-C30)arylene, or a substituted or unsubstituted (3- to 30-membered)heteroarylene;

$R_5$ and $R_6$ each independently represent, a substituted or unsubstituted (C6-C30)aryl, or a substituted or unsubstituted (3- to 30-membered)heteroaryl; with a proviso that at least one of $R_5$ and $R_6$ is selected from carbazole derivatives represented by following formula 1-A or formula 1-B;

(1-A)

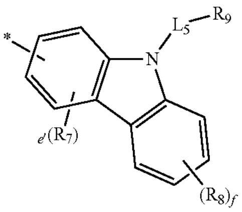

(1-B)

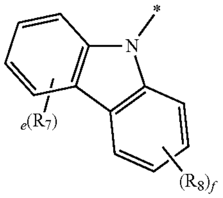

$L_5$ represents a single bond, a substituted or unsubstituted (C6-C30)arylene, or a substituted or unsubstituted (3- to 30-membered)heteroarylene;

$R_1$ represents a substituted or unsubstituted (C6-C30)aryl or a substituted or unsubstituted (3- to 30-membered) heteroaryl;

$R_2$ to $R_4$ and $R_7$ to $R_{10}$ each independently represent, hydrogen, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30)aliphatic ring and (C6-C30)aromatic ring, or -$L_3$`` -N($Ar_3$`` )($Ar_4$`` ); or may be linked to the adjacent substituents to form a ring;

$L_3$`` represents a single bond, a substituted or unsubstituted (C6-C30)arylene, or a substituted or unsubstituted (3- to 30-membered)heteroarylene;

$Ar_3$`` and $Ar_4$`` each independently represent, hydrogen, deuterium, a substituted or unsubstituted (C1-C30) alkyl, a substituted or unsubstituted (C2-C30)alkenyl, a substituted or unsubstituted fused ring of a (C3-C30) aliphatic ring and a (C6-C30)aromatic ring, a substituted or unsubstituted (C6-C30)aryl, or a substituted or unsubstituted (3- to 30-membered)heteroaryl;

a represents 1, b and c each independently represent 1 or 2, d to f each independently represent an integer of 1 to 4, e` represents an integer of 1 to 3, when b to f and e ` are an integer of 2 or more, each of $R_2$ to $R_4$, $R_7$, and $R_8$ may be the same or different;

* indicates a binding site with $L_2$ or $L_3$, provided that the following compounds are excluded in formula 1`

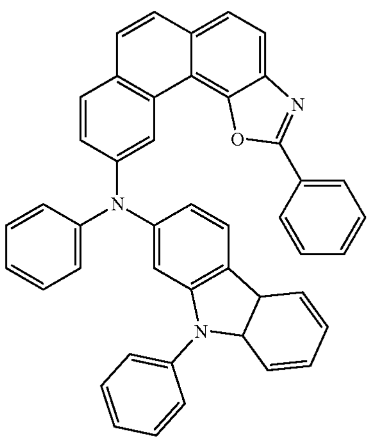

-continued

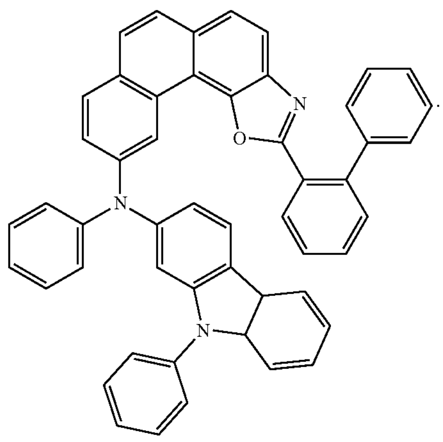

9. The organic electroluminescent compound according to claim 8, wherein the compound represented by formula 1 ` is represented by any one of the following formulas 1-1 to 1-5:

(1-1)

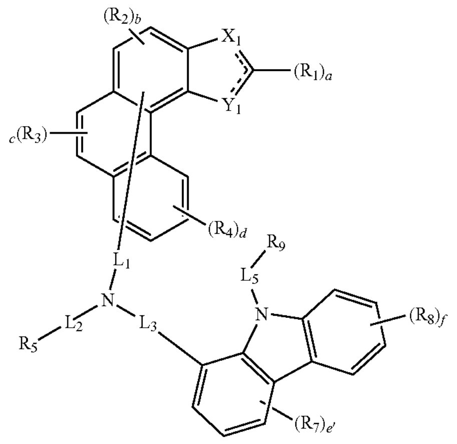

(1-2)

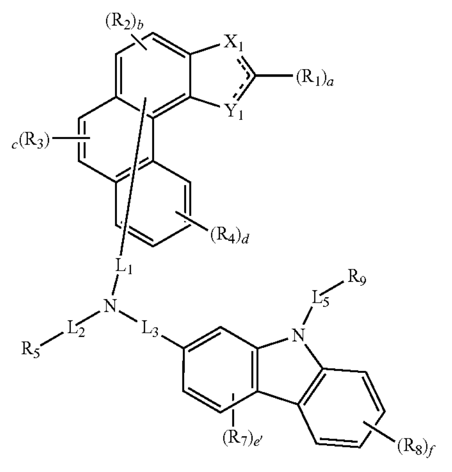

-continued
(1-3)
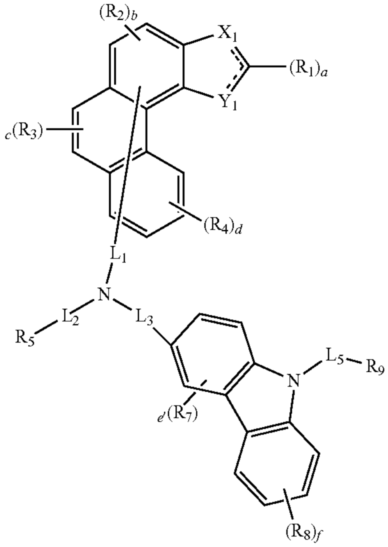
(1-4)
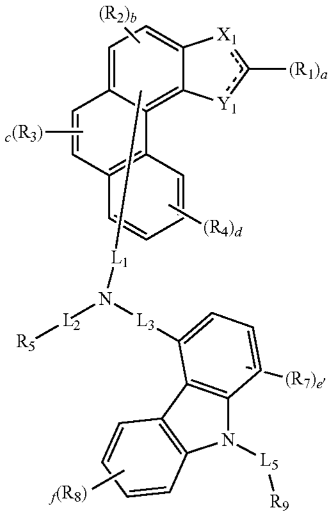
(1-5)
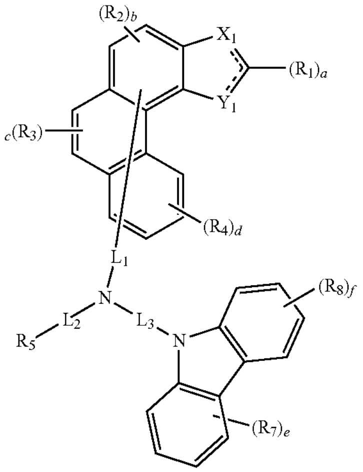
wherein,
$X_1$, $Y_1$, $L_1$ to $L_3$, $L_5$, $R_1$ to $R_5$, $R_7$ to $R_9$, a to f and e` are the same as defined in claim 8.
10. The organic electroluminescent compound according to claim 8, wherein the compound represented by formula 1 ` is selected from the following compounds:
C-1
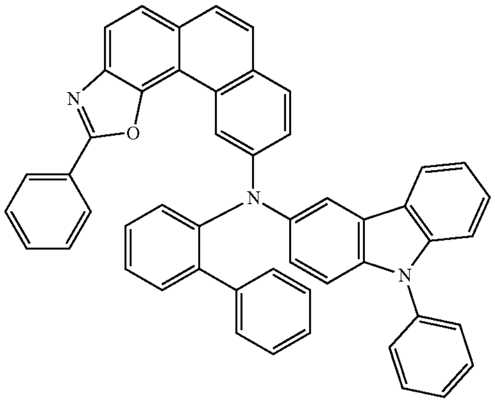
C-2
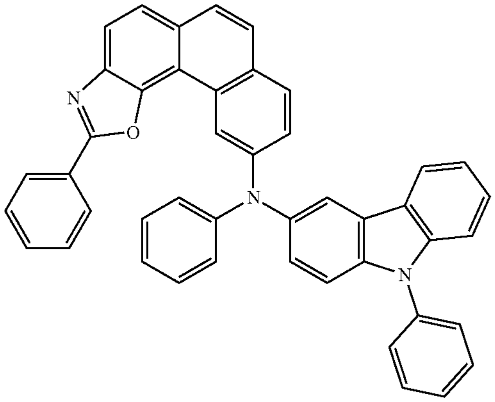
C-3
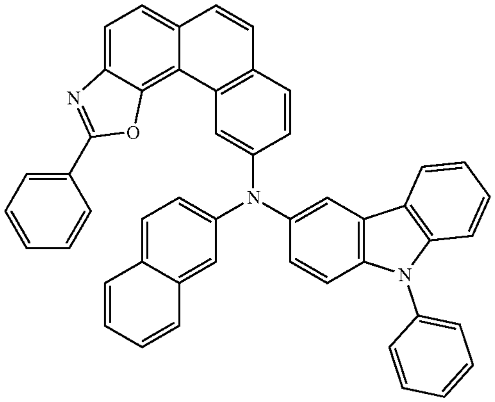

-continued
C-4
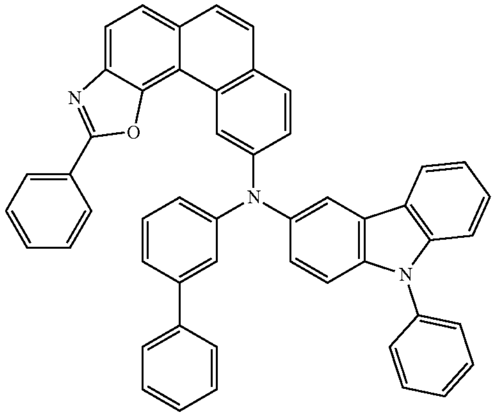
C-5
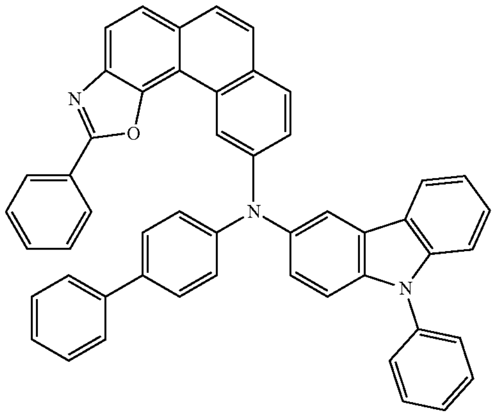
C-6
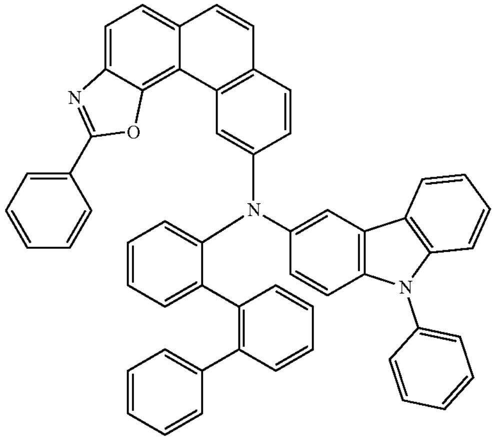
-continued
C-7
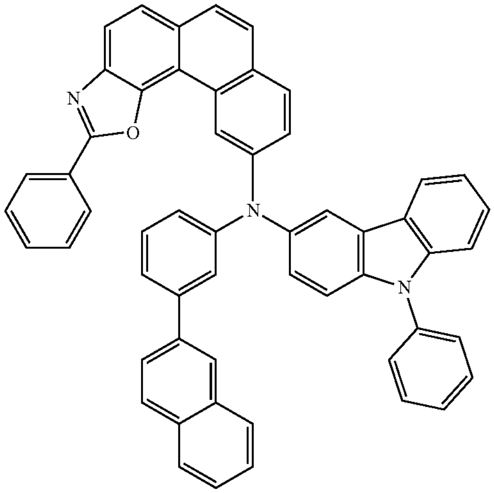
C-8
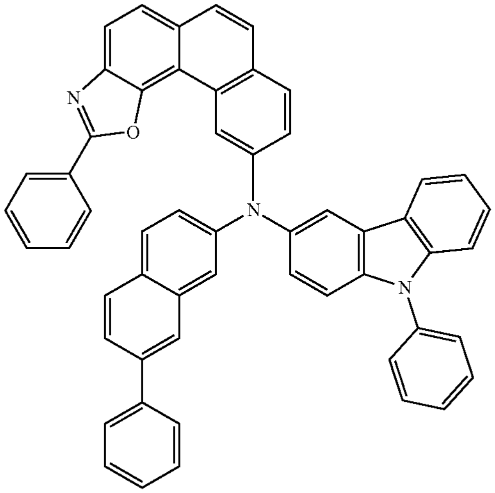
C-9
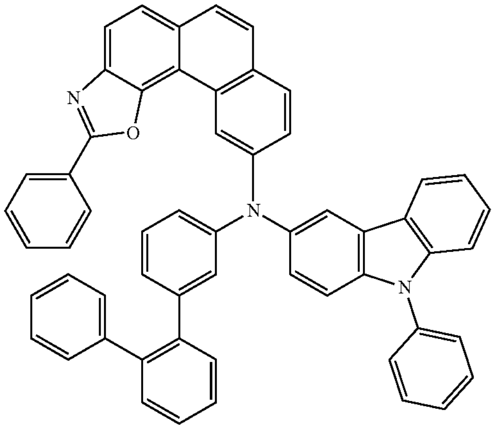

-continued
C-10
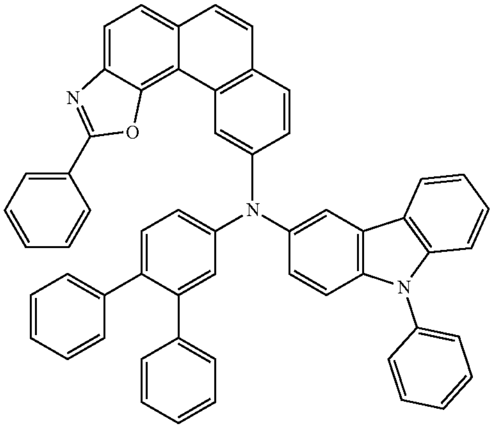
C-11
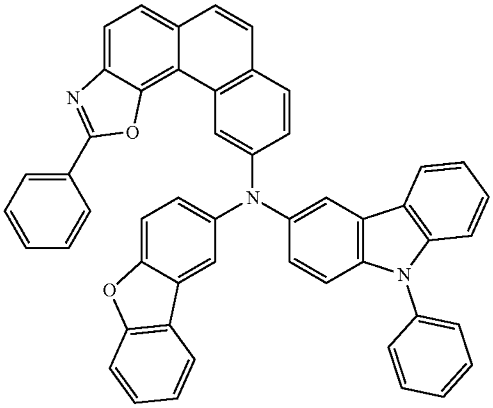
C-12
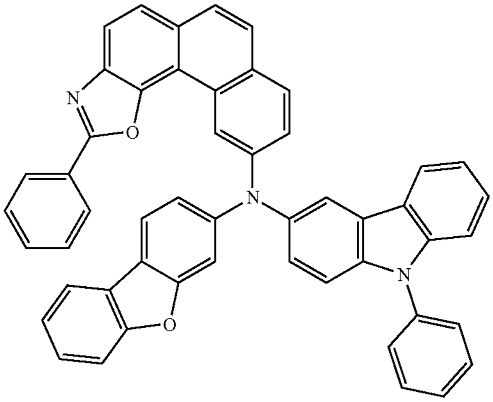
C-13
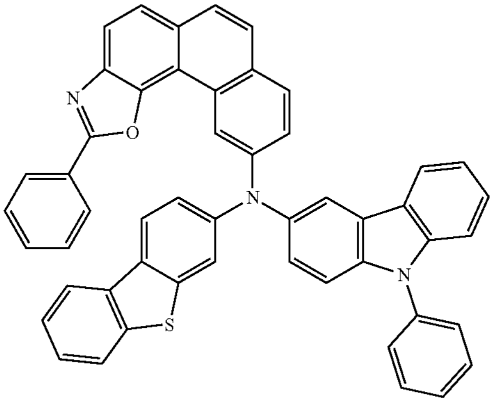
-continued
C-14
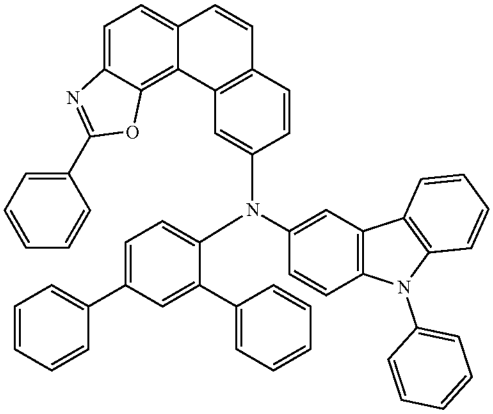
C-15
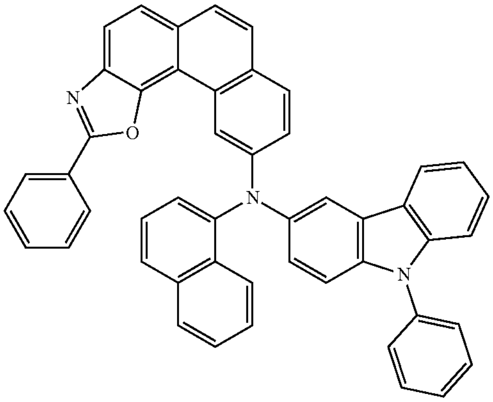
C-16
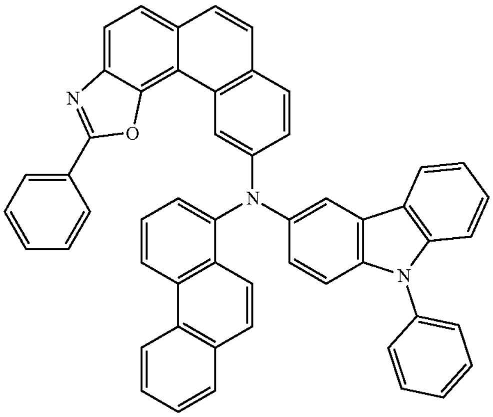

-continued
C-17
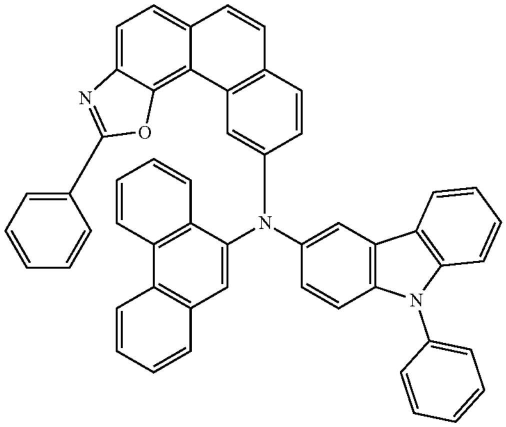
C-18
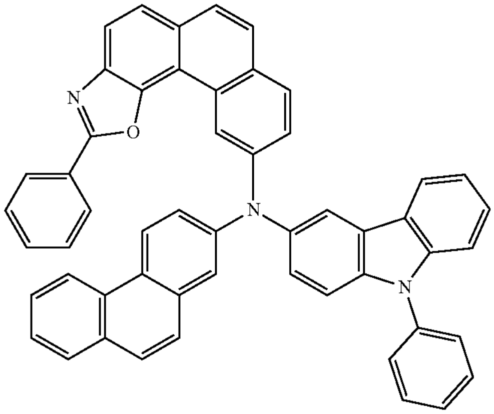
C-19
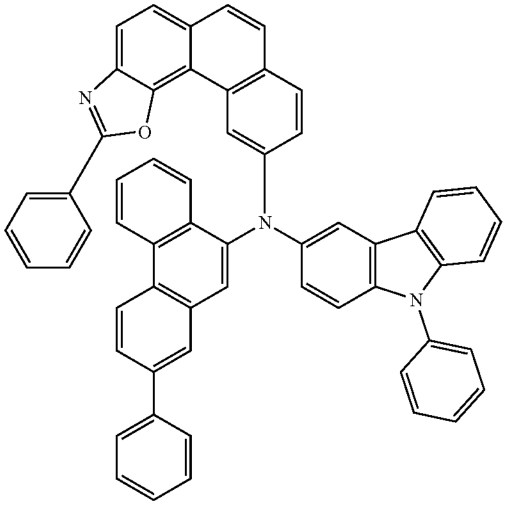
-continued
C-20
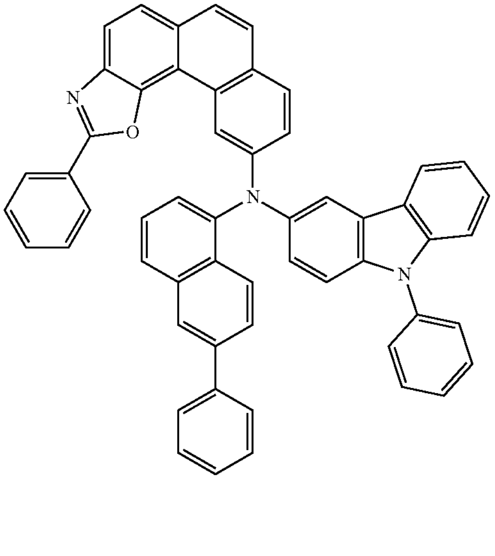
C-21
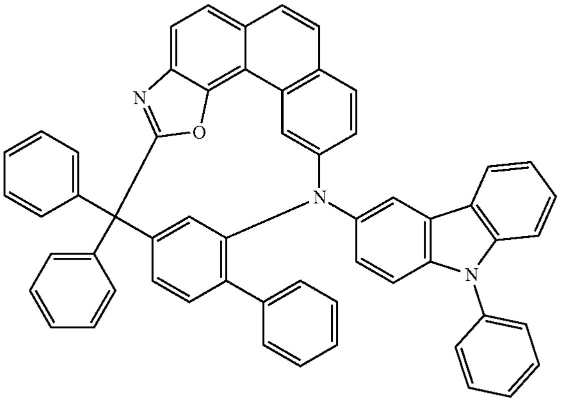
C-22
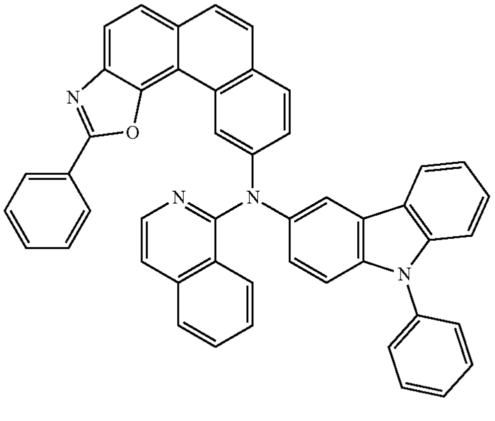

C-23
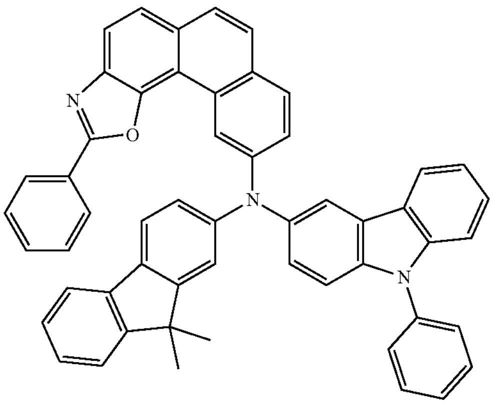
C-24
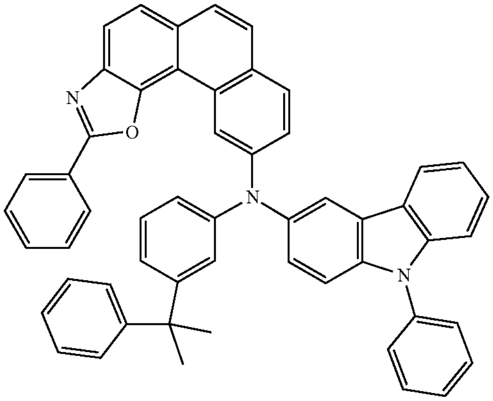
C-25
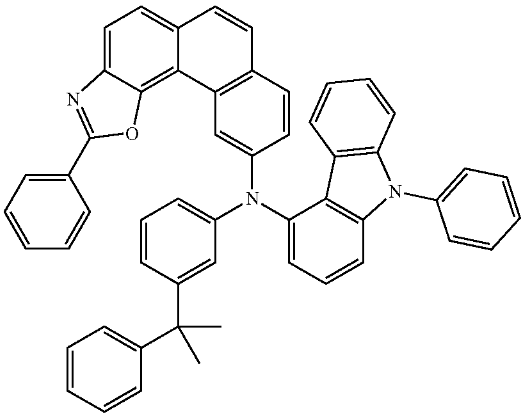
C-26
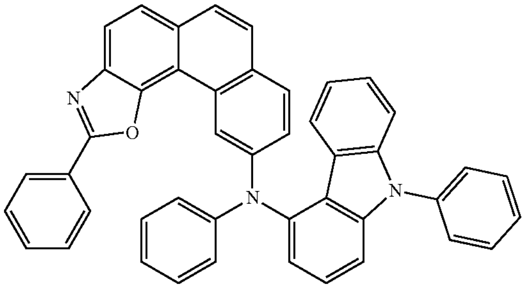
C-27
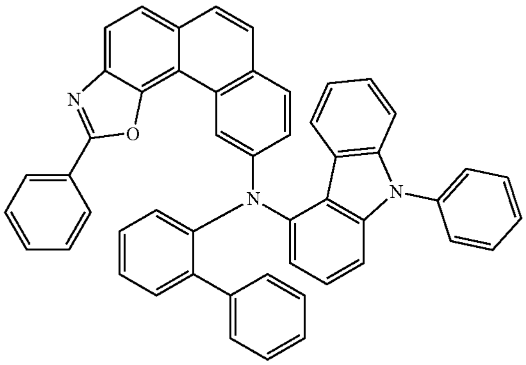
C-28
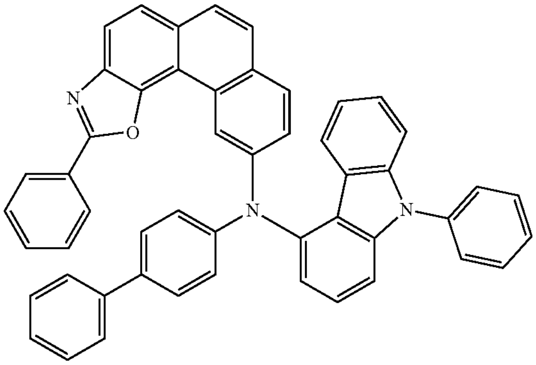
C-29
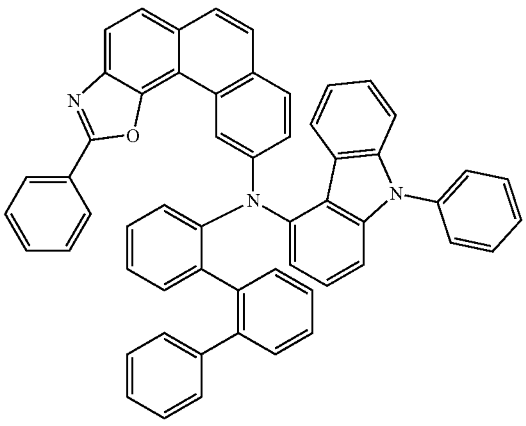
C-30
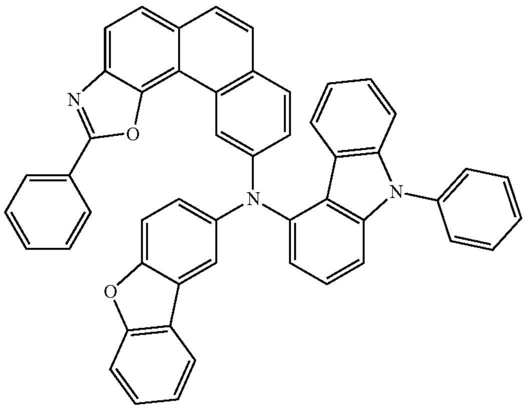

-continued
C-31
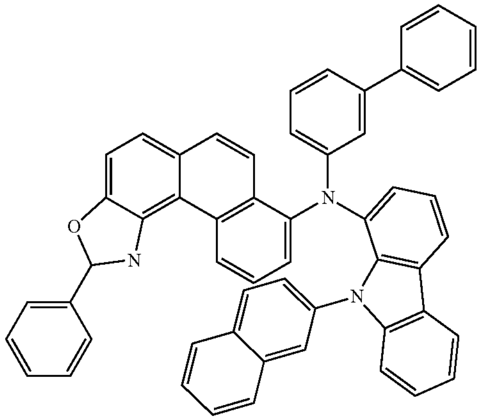
C-32
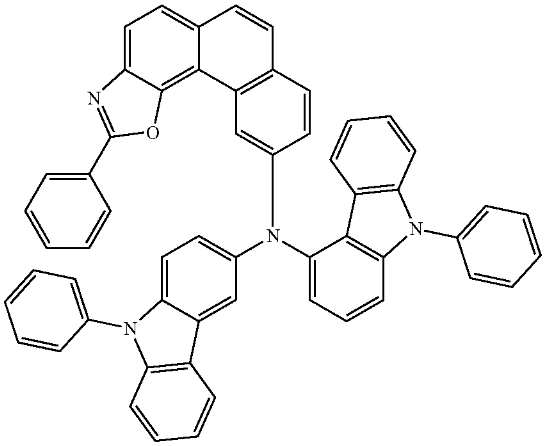
C-33
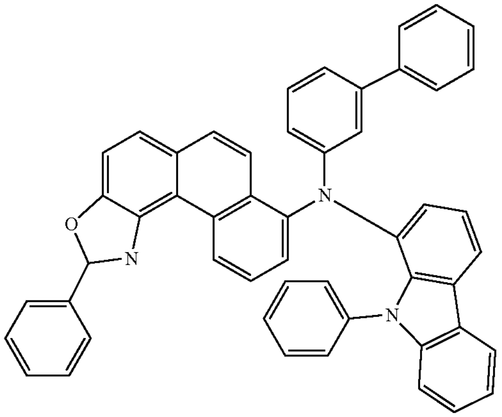
-continued
C-34
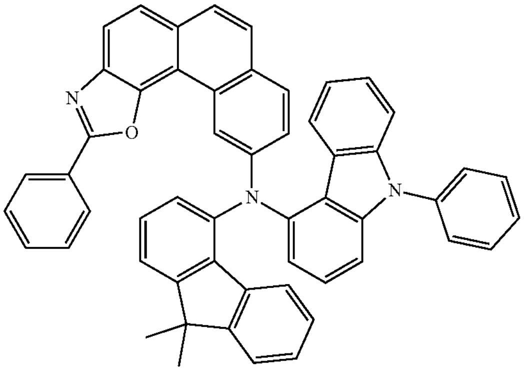
C-35
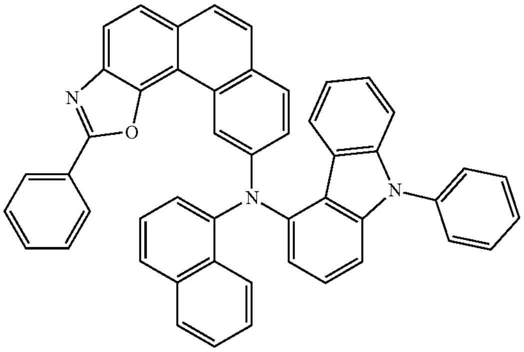
C-36
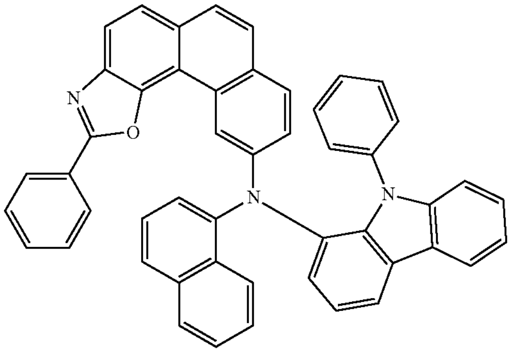
C-37
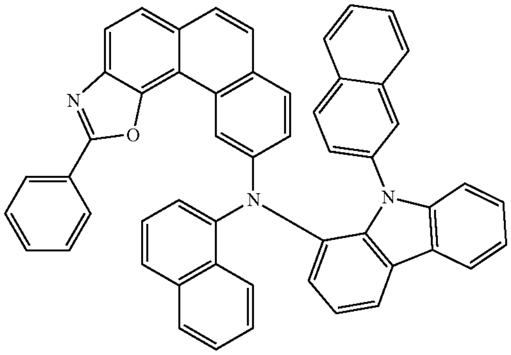

-continued
C-38
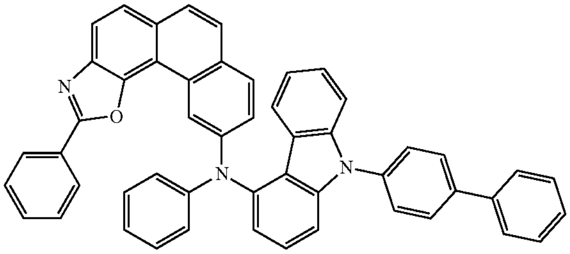
C-39
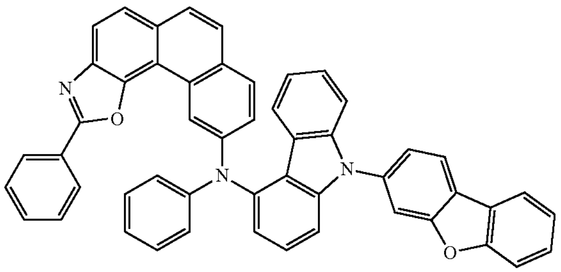
C-40
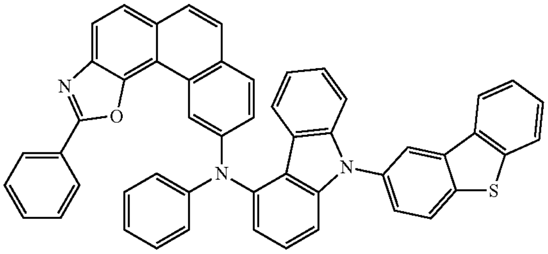
C-41
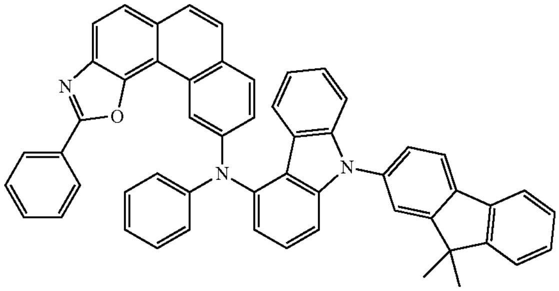
C-42
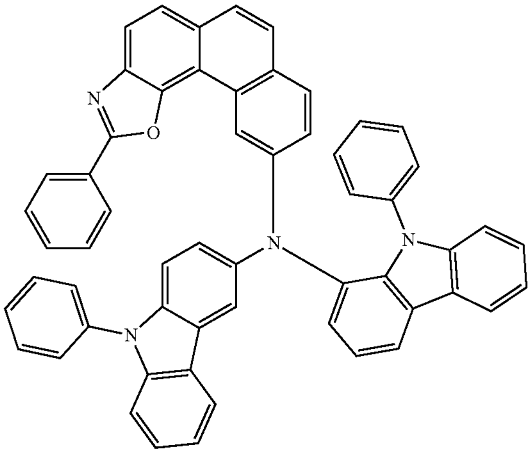
-continued
C-43
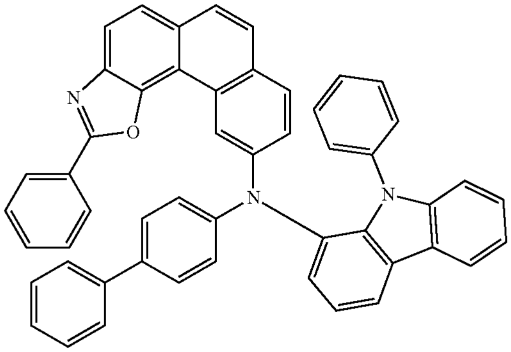
C-44
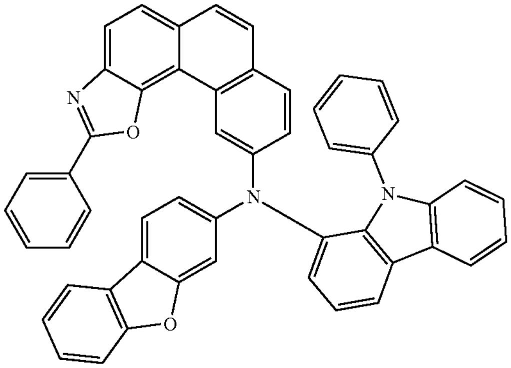
C-45
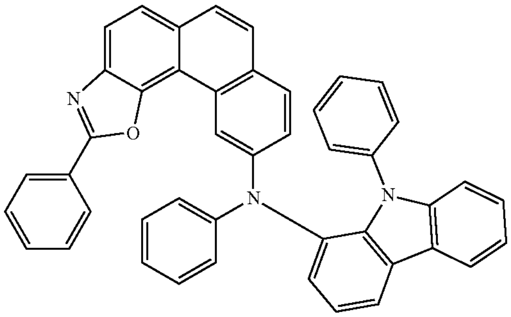
C-46
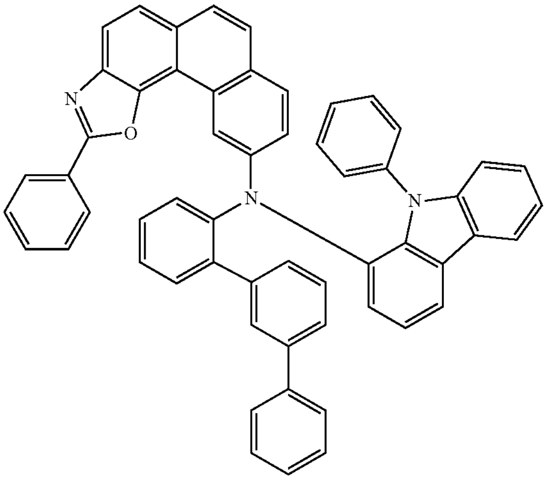

-continued
C-47
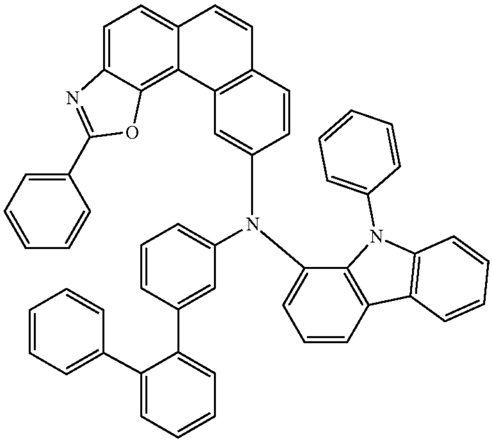
C-48
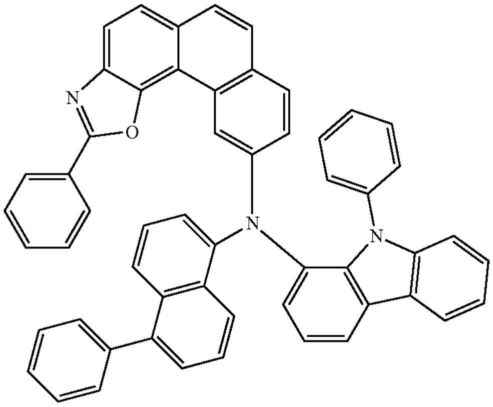
C-49
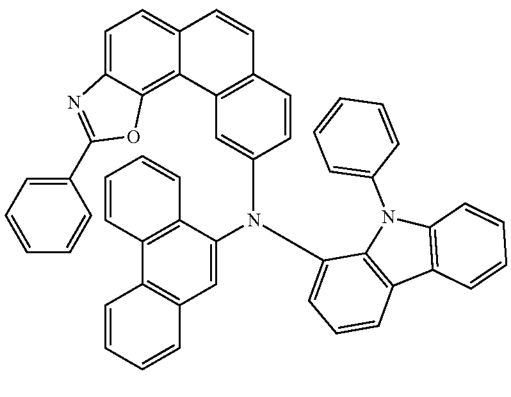
-continued
C-50
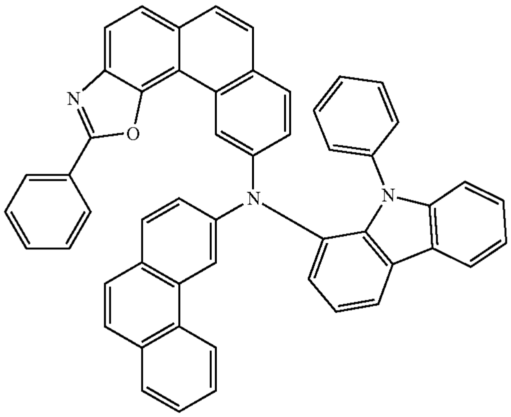
C-51
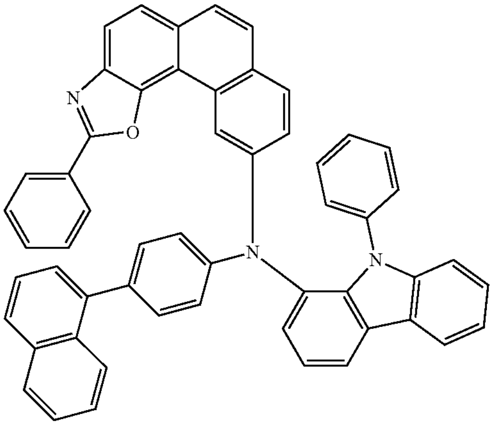
C-52
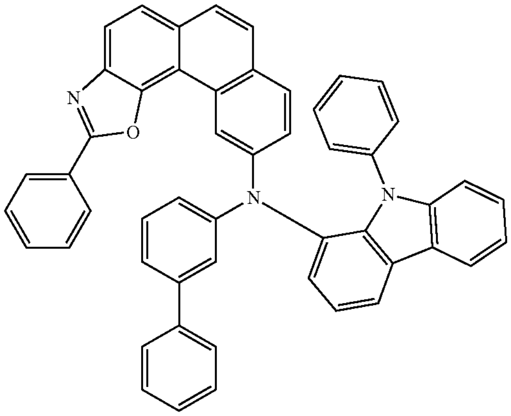

-continued
C-53
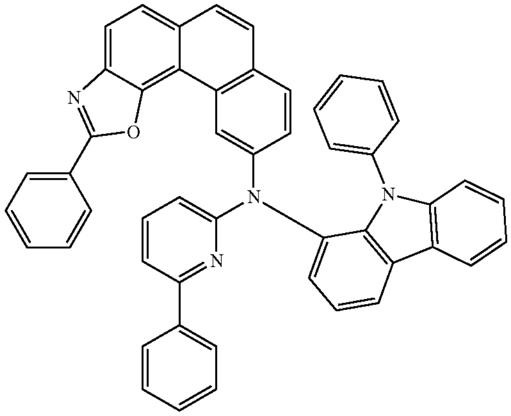
C-54
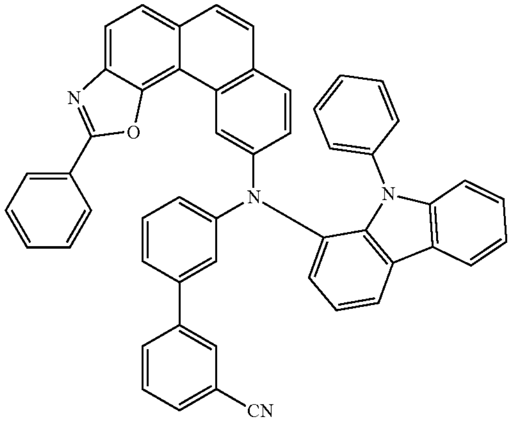
C-55
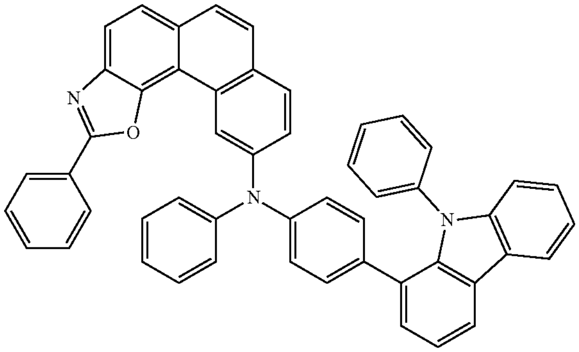
C-56
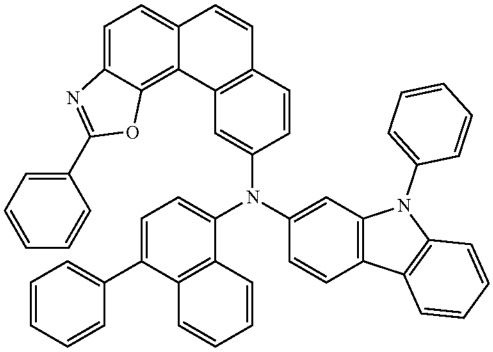
-continued
C-57
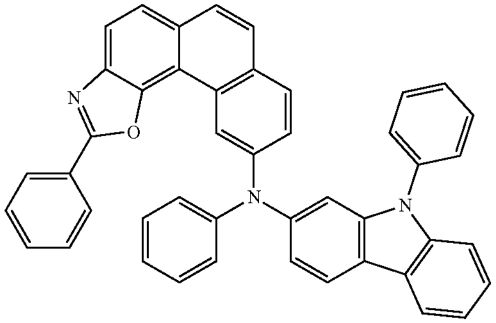
C-58
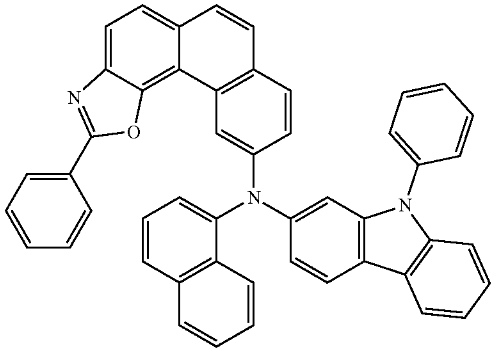
C-59
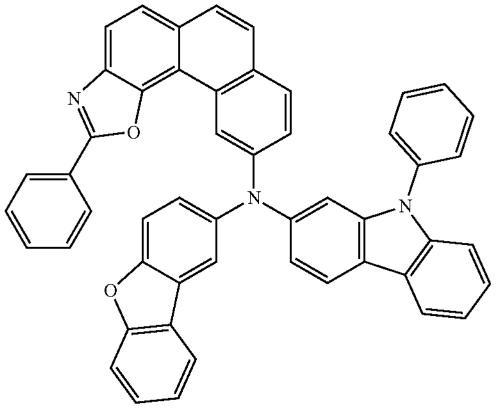
C-60
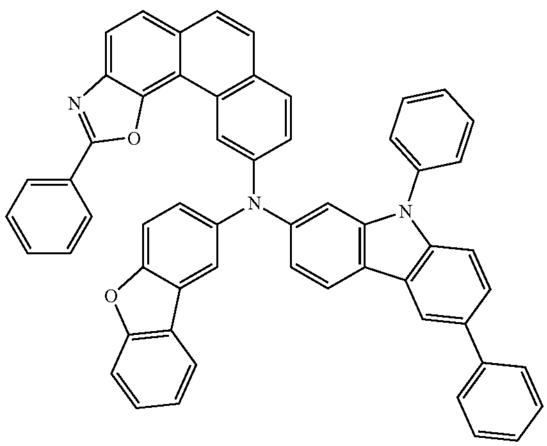

-continued
C-61
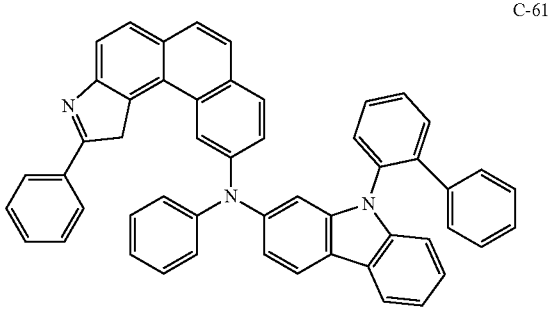
C-62
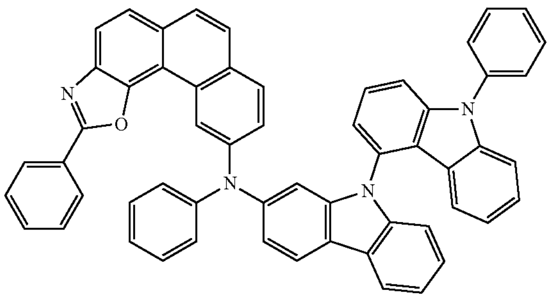
C-63
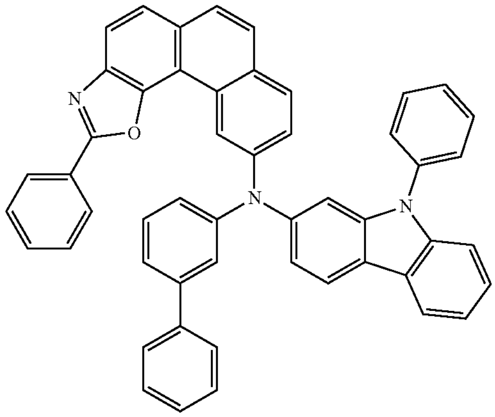
C-64
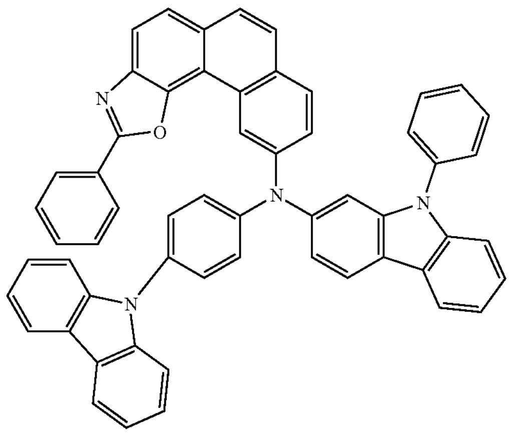
-continued
C-65
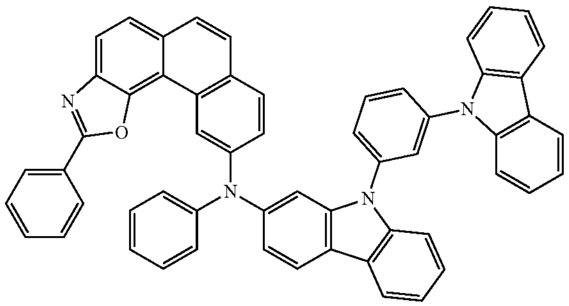
C-66
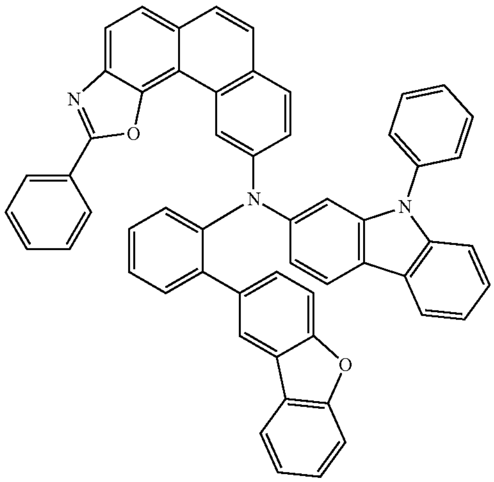
C-67
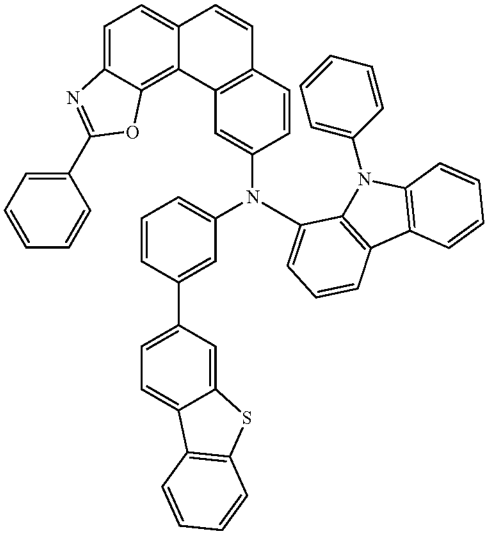

-continued
C-68
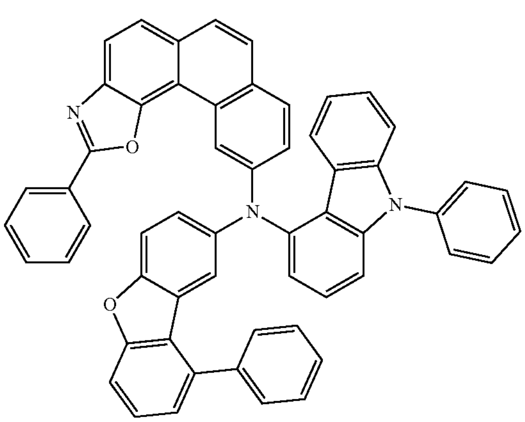
C-69
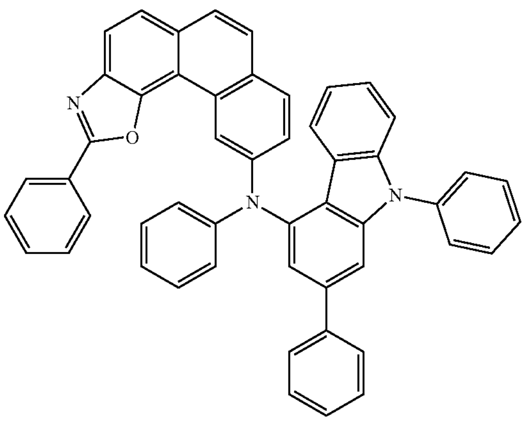
C-70
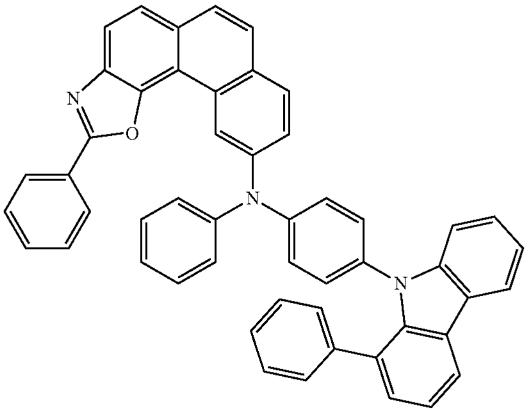
-continued
C-71
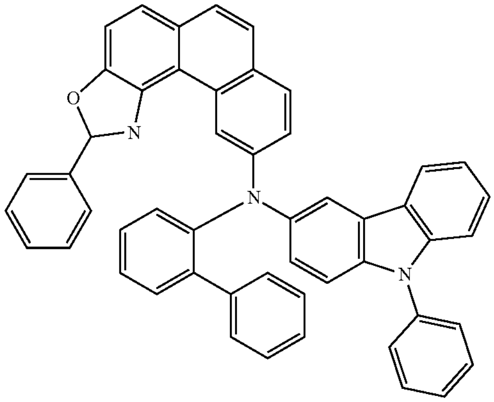
C-72
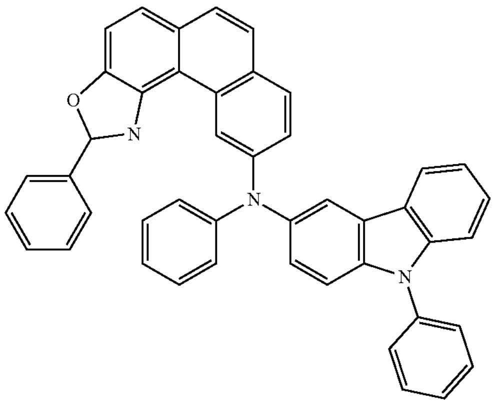
C-73
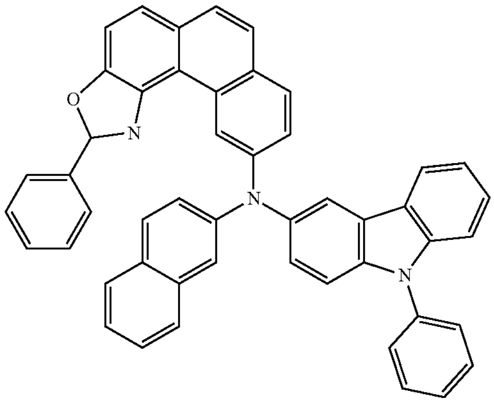
C-74
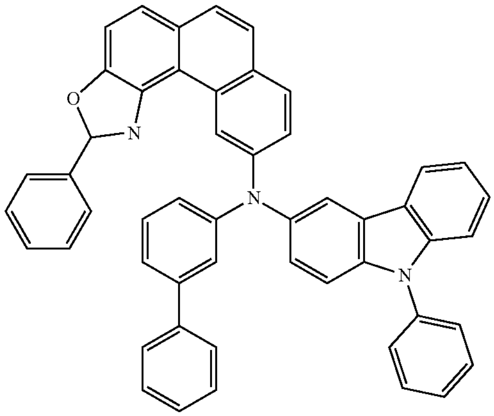

-continued
C-75
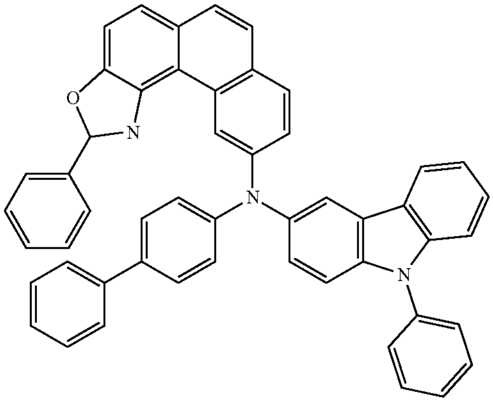
C-76
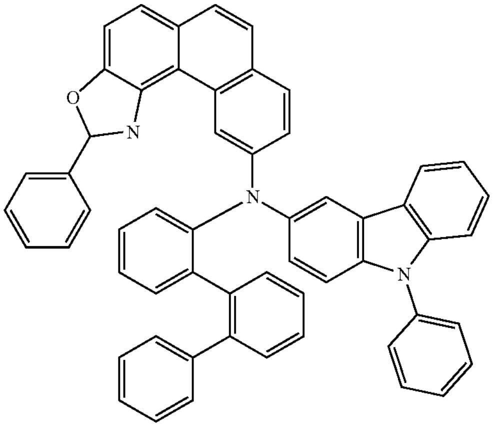
C-77
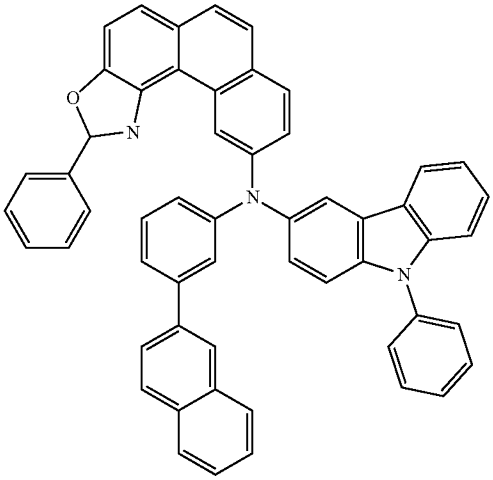
-continued
C-78
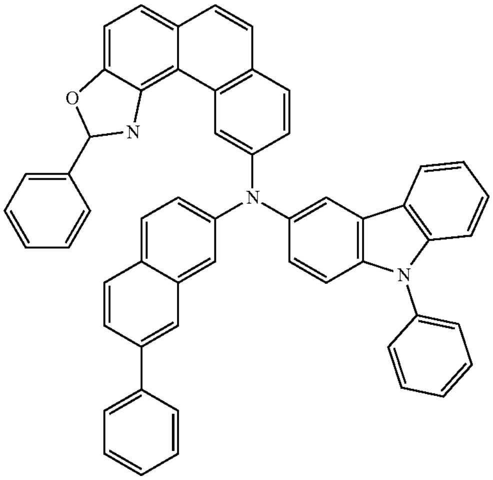
C-79
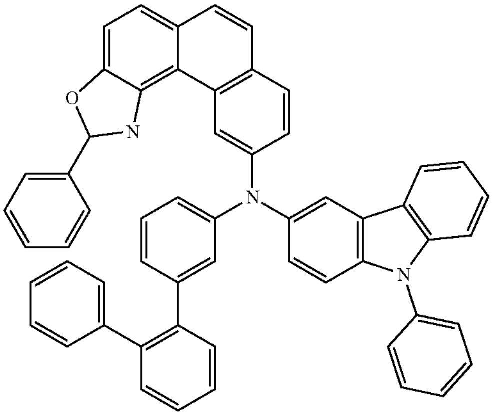
C-80
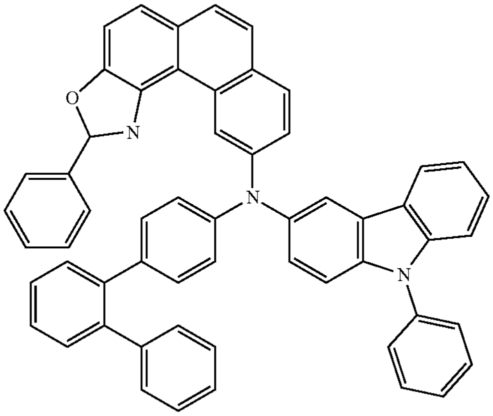

-continued
C-81
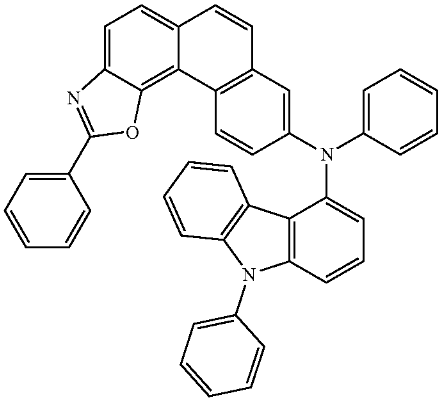
C-82
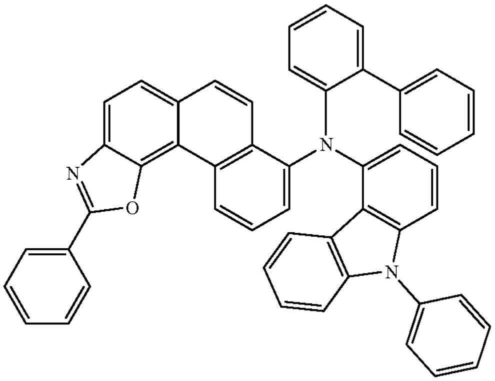
C-83
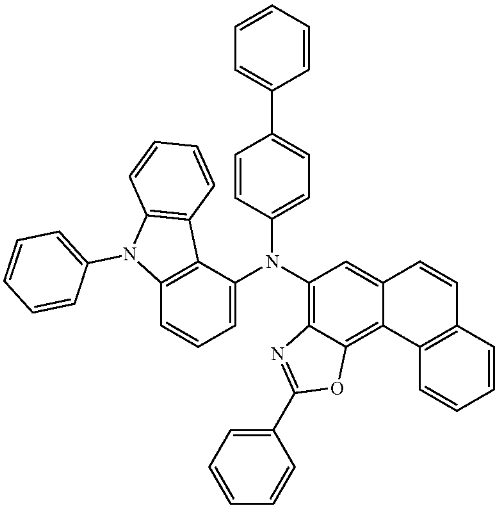
-continued
C-84
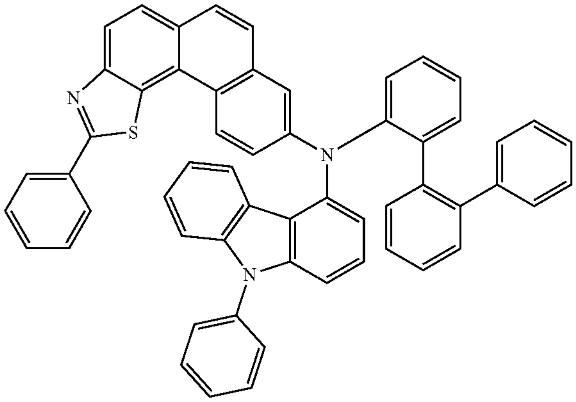
C-85
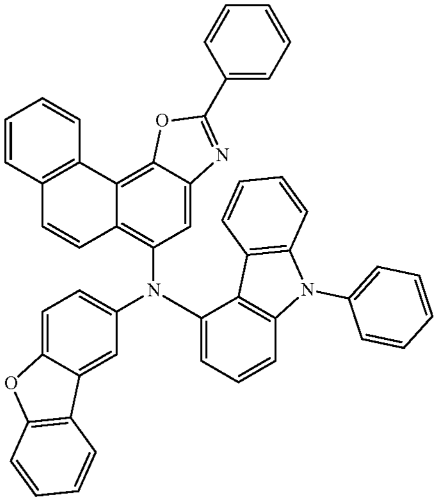
C-86
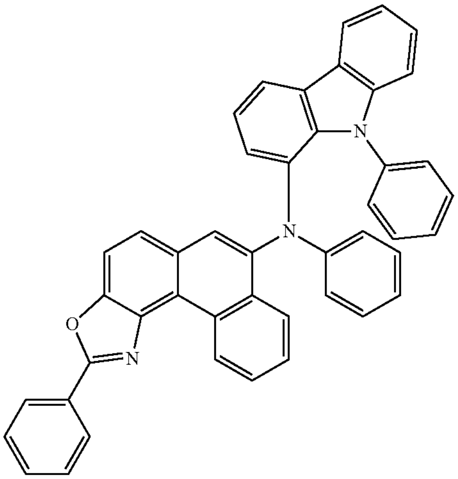

C-87
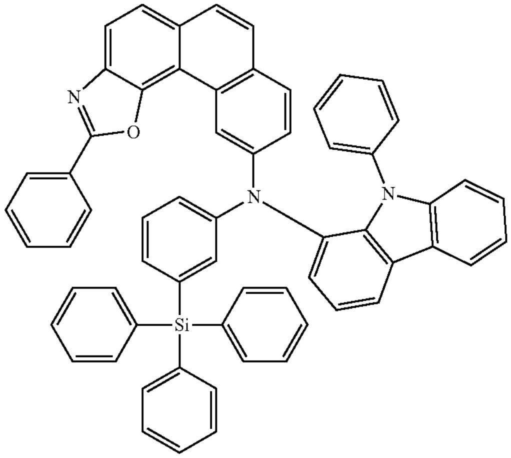
C-88
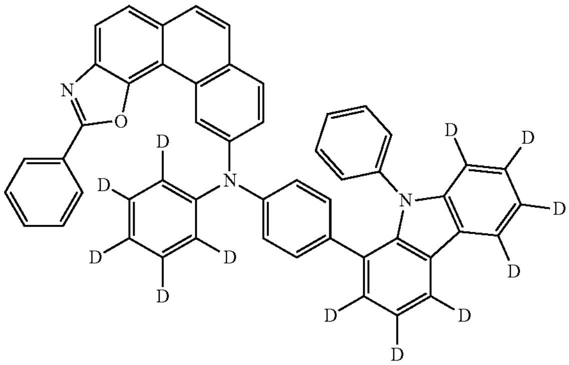
C-89
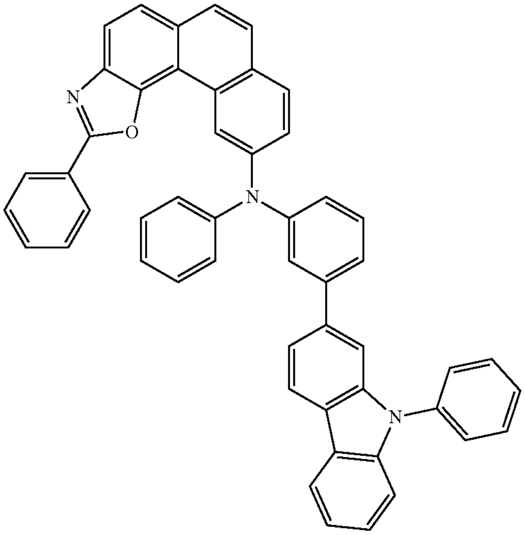
C-90
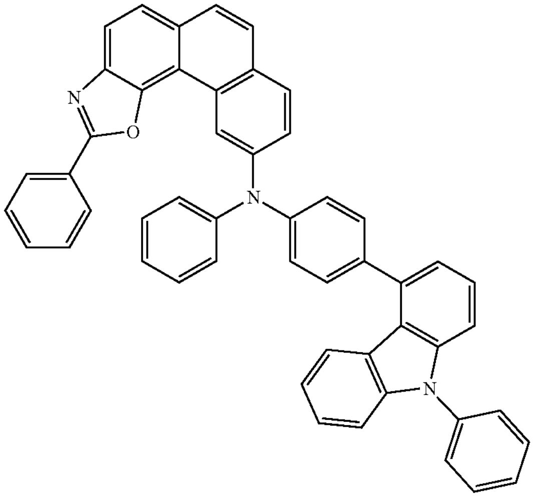
C-91
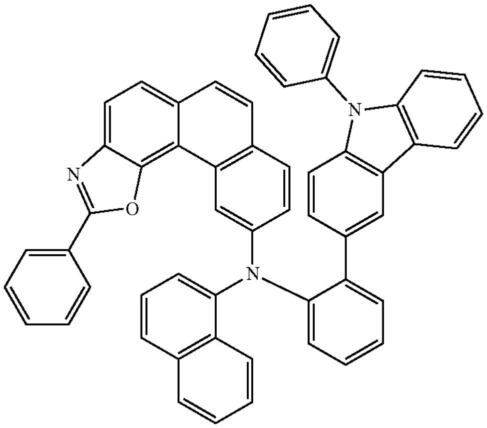
C-92
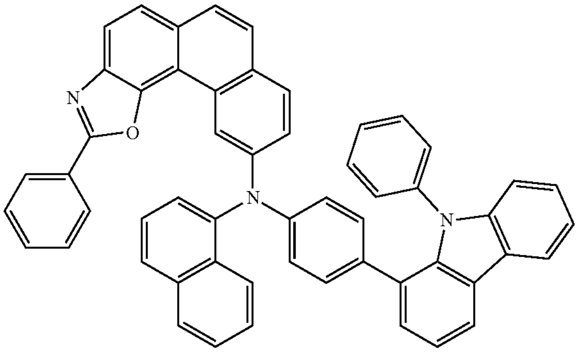

C-93
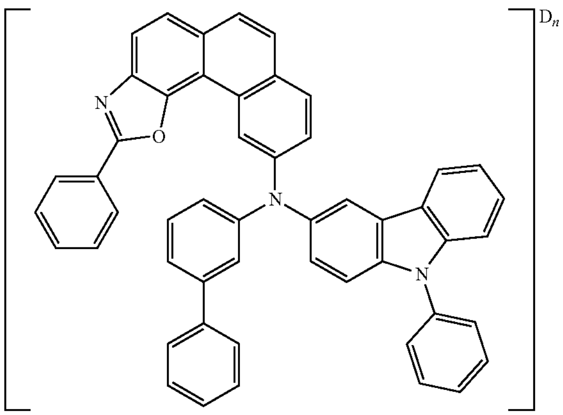
$D_n$: 1-33
C-94
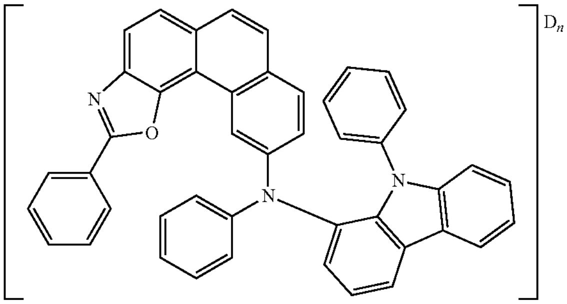
$D_n$: 1-29
C-95
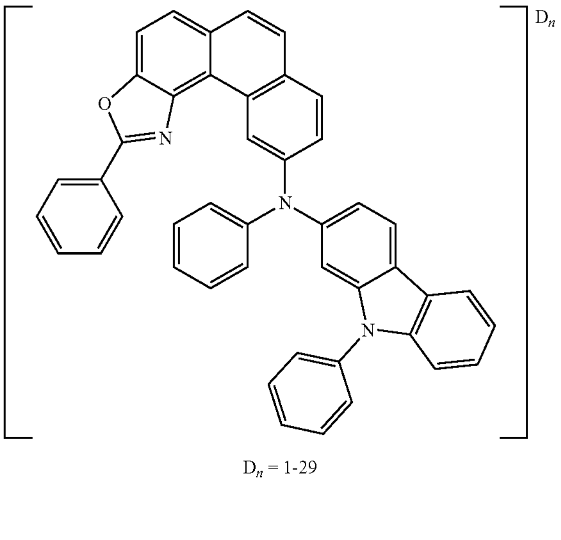
$D_n$ = 1-29
C-96
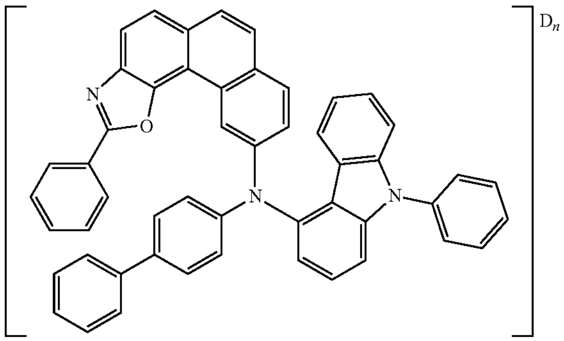
$D_n$ = 1-33
C-97
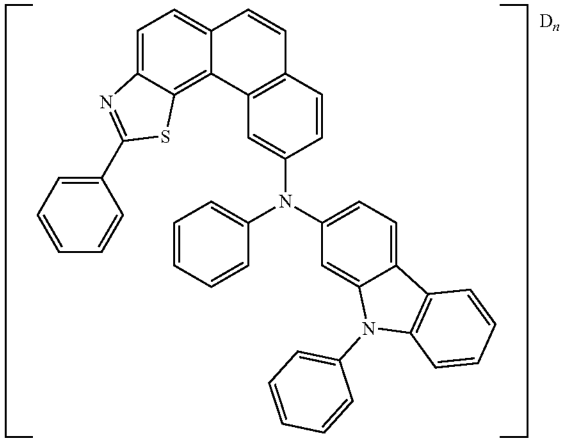
$D_n$ = 1-29
C-98
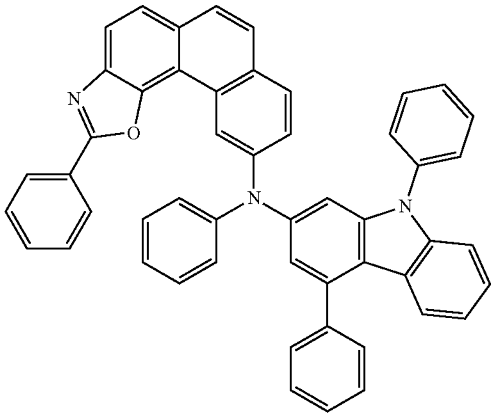

-continued
C-99
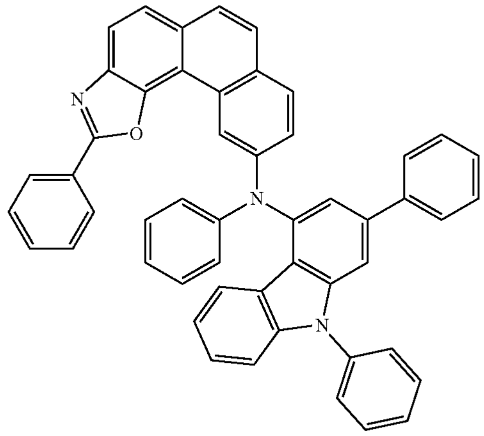
C-100
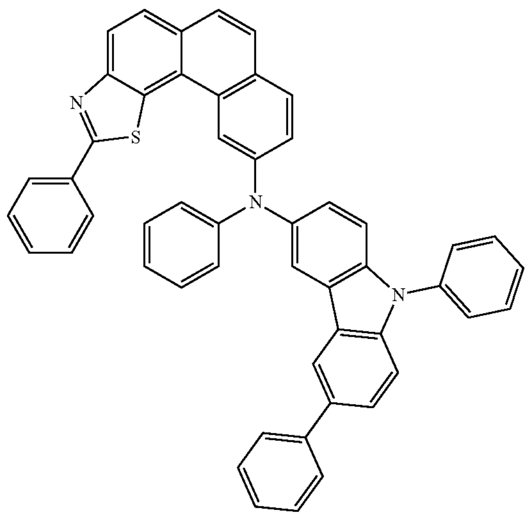
C-101
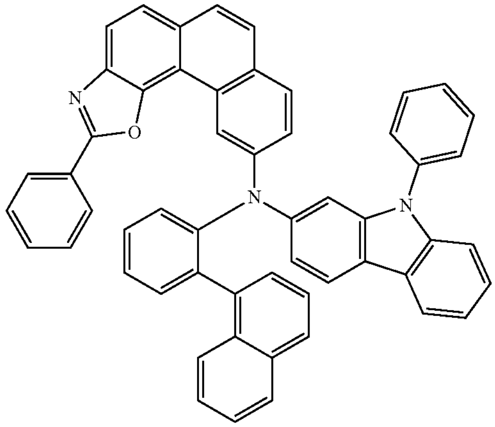
-continued
C-102
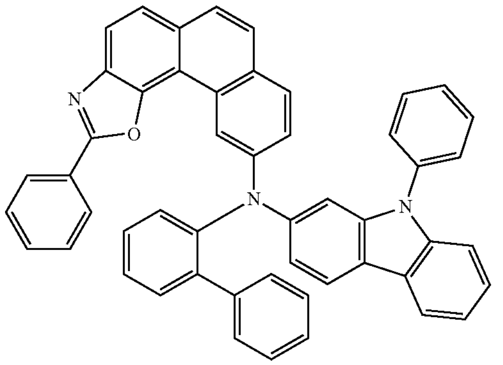
C-103
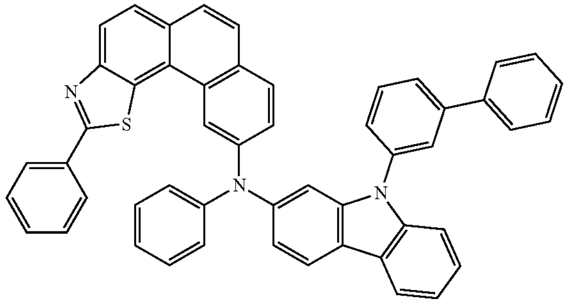
C-104
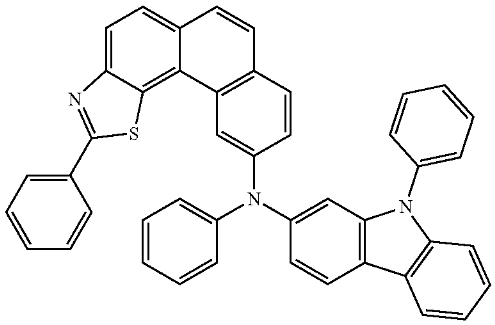
C-105
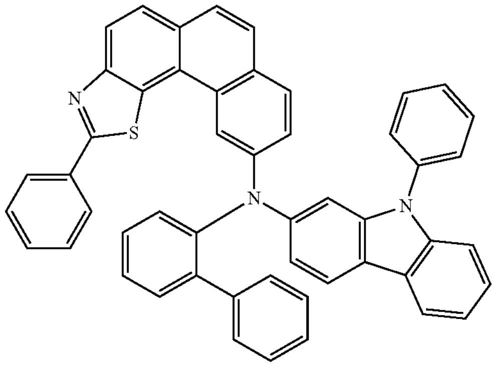

-continued
C-106
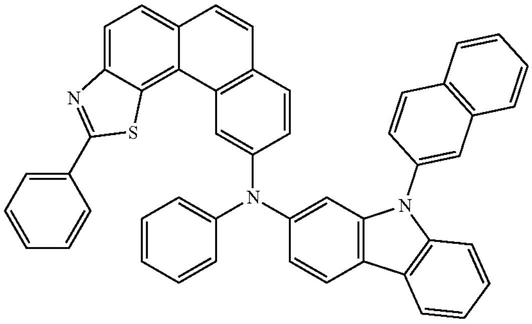
C-107
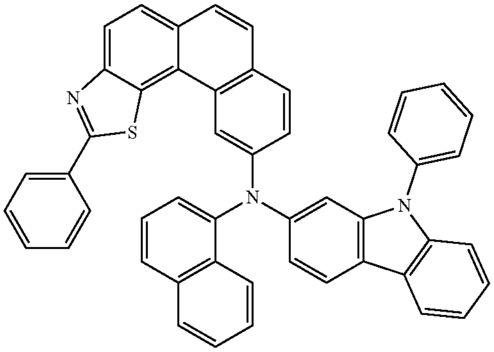
C-108
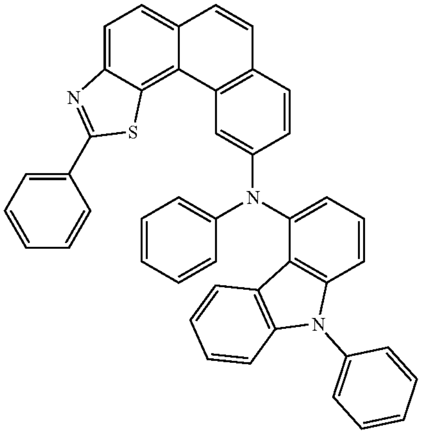
-continued
C-109
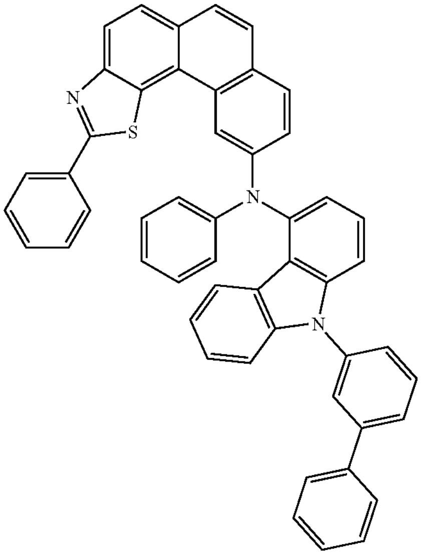
C-110
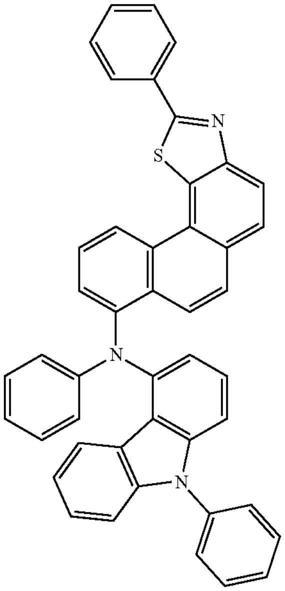
C-111
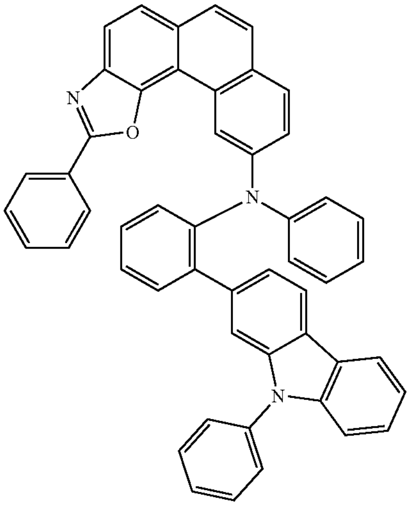

-continued
C-112
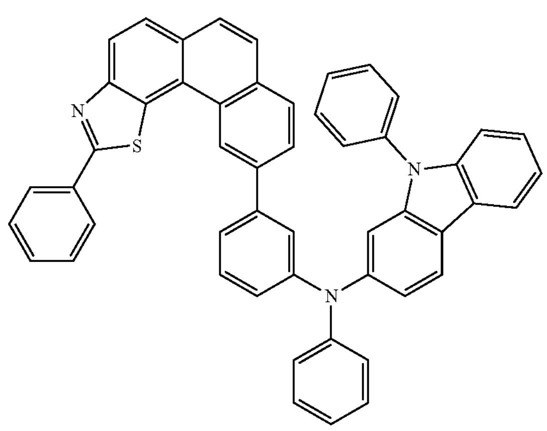
C-113
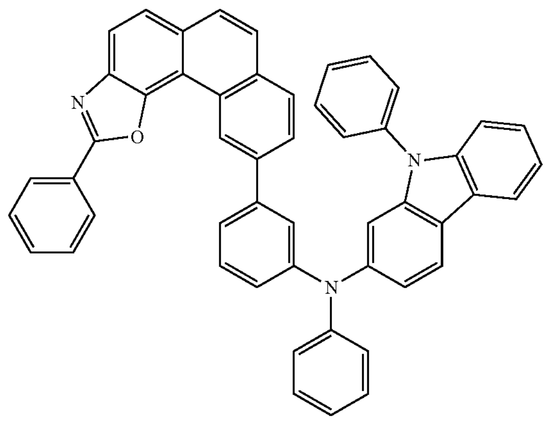
C-114
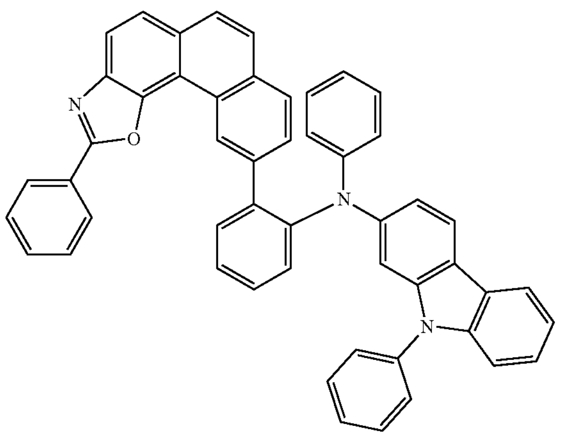
-continued
C-115
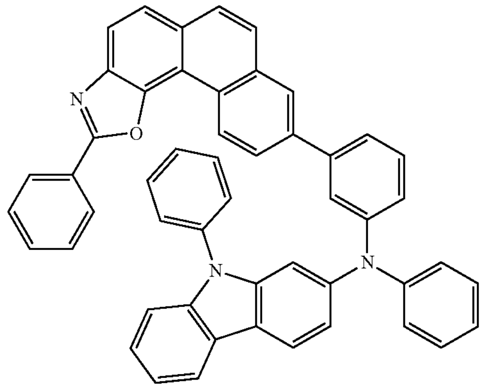
C-116
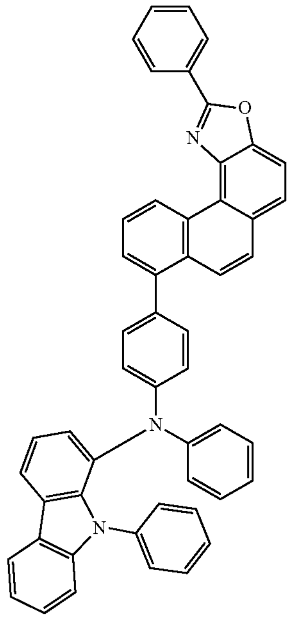
C-117
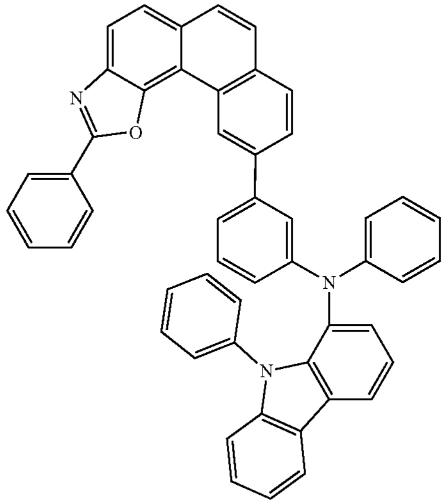

-continued
C-118
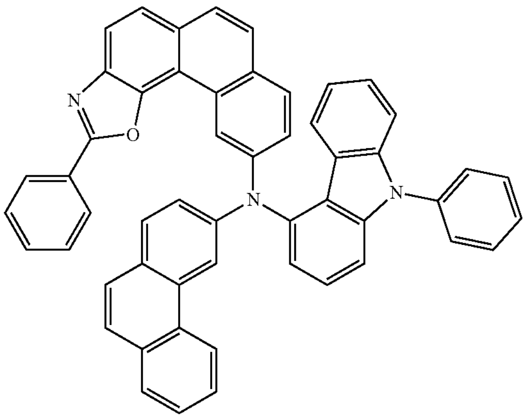
C-119
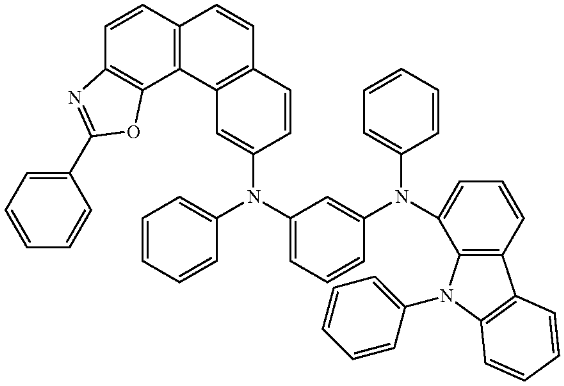
C-120
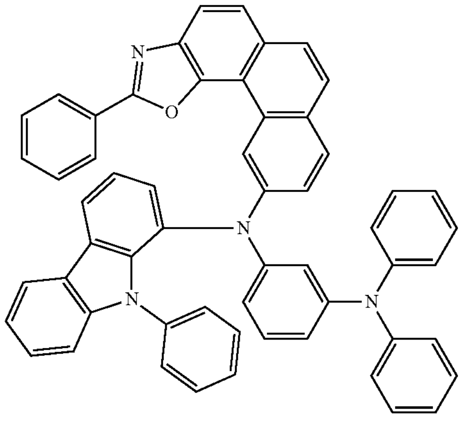
C-121
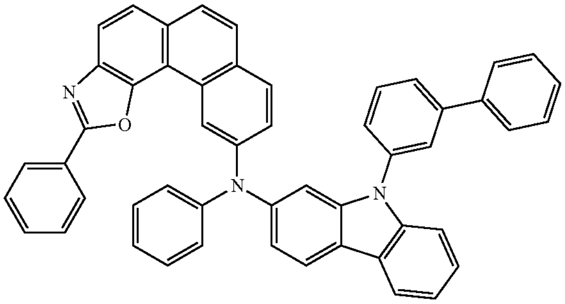
-continued
C-122
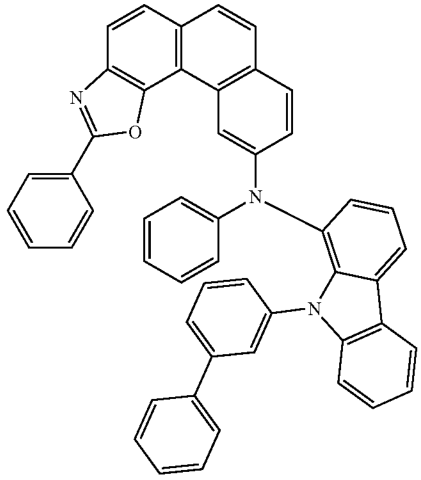
C-123
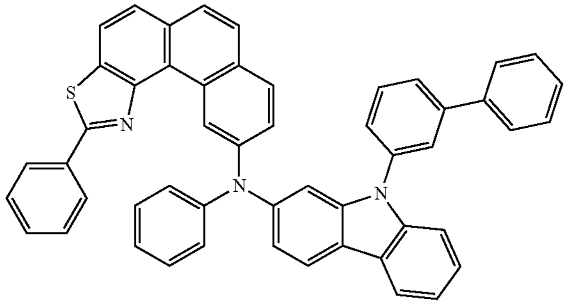
C-124
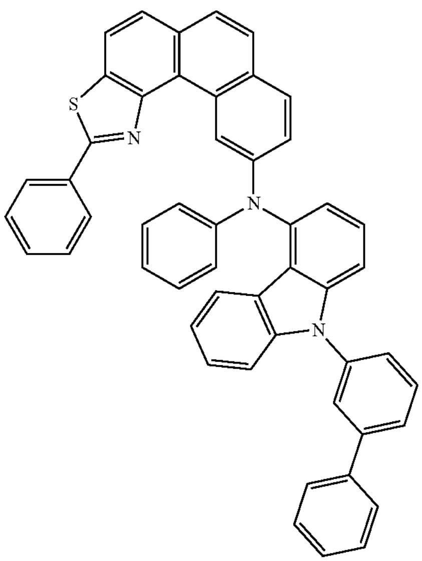
and -continued
C-125
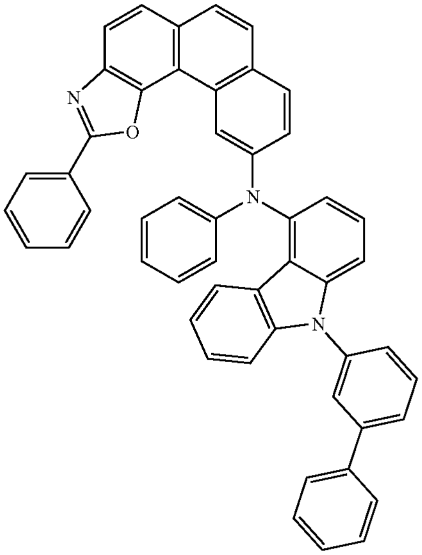
wherein $D_n$: 1-23 and $D_n$: 1-33 in compounds C-93 to C-97 mean that 1 to 29 and 1 to 33 hydrogens may be replaced by deuterium, respectively.
* * * * *